(12) United States Patent
Doshi et al.

(10) Patent No.: US 10,786,652 B2
(45) Date of Patent: Sep. 29, 2020

(54) SUPPORT DEVICES AND METHODS OF MAKING AND USING THEM

(71) Applicant: LightSide MD, LLC, Los Altos, CA (US)

(72) Inventors: Rajiv Doshi, Stanford, CA (US); Kenneth Chou, Oakland, CA (US); Arthur G. Sandoval, San Francisco, CA (US); Robert Charles Lane, San Francisco, CA (US); Gabriel Philip Howles-Banerji, Cupertino, CA (US); Michael Lawrence Favet, San Jose, CA (US); Daejin Ahn, Gyeongsangnamdo (KR)

(73) Assignee: LightSide MD, LLC, Los Altos, CA (US)

( * ) Notice: Subject to any disclaimer, the term of this patent is extended or adjusted under 35 U.S.C. 154(b) by 1119 days.

(21) Appl. No.: 15/029,018

(22) PCT Filed: Oct. 17, 2014

(86) PCT No.: PCT/US2014/061189
§ 371 (c)(1),
(2) Date: Apr. 13, 2016

(87) PCT Pub. No.: WO2015/058114
PCT Pub. Date: Apr. 23, 2015

(65) Prior Publication Data
US 2016/0256665 A1    Sep. 8, 2016

Related U.S. Application Data

(60) Provisional application No. 61/893,095, filed on Oct. 18, 2013, provisional application No. 61/927,943, (Continued)

(30) Foreign Application Priority Data

Aug. 1, 2014    (IN) .......................... 2191/DEL/2014
Aug. 26, 2014   (WO) ................ PCT/US2014/052750

(51) Int. Cl.
*A61M 25/02* (2006.01)
*A61F 5/08* (2006.01)
(Continued)

(52) U.S. Cl.
CPC ........... *A61M 25/02* (2013.01); *A61B 5/6833* (2013.01); *A61B 90/50* (2016.02); *A61F 5/08* (2013.01);
(Continued)

(58) Field of Classification Search
CPC .. A61M 2025/0273; A61M 2025/0266; A61M 2025/028; A61M 25/02;
(Continued)

(56) References Cited

U.S. PATENT DOCUMENTS

| 4,073,610 A | 2/1978 | Cox |
| 4,106,777 A | 8/1978 | Kim |

(Continued)

FOREIGN PATENT DOCUMENTS

| CN | 102448848 A | 5/2012 |
| CN | 102802571 A | 11/2012 |

(Continued)

*Primary Examiner* — Tiffany Legette
(74) *Attorney, Agent, or Firm* — Shay Glenn LLP

(57) ABSTRACT

Described herein are support devices, which may include medical support devices. In particular, three-dimensional medical (and non-medical) devices from a single layer of material, typically by stamping or pressing (including cold pressing) a sheet of the material to form rigid and complex 3D shapes capable of use for a variety of medical and non-medical purposes. These support devices typically also (Continued)

include an adhesive material allowing the device to be attached to a subject's skin and/or mounted on a surface (e.g., wall, etc.). In particular, described herein are methods of manufacturing, assembling, and using adhesive support devices.

16 Claims, 79 Drawing Sheets

Related U.S. Application Data filed on Jan. 15, 2014, provisional application No. 62/026,453, filed on Jul. 18, 2014.

(51) Int. Cl.
| | |
|---|---|
| *A61F 13/00* | (2006.01) |
| *A61F 5/443* | (2006.01) |
| *A61F 5/448* | (2006.01) |
| *A61F 5/445* | (2006.01) |
| *F16M 13/02* | (2006.01) |
| *A61F 13/12* | (2006.01) |
| *A61B 90/50* | (2016.01) |
| *A61F 13/02* | (2006.01) |
| *A61B 5/00* | (2006.01) |
| *A61M 1/00* | (2006.01) |
| *A61B 17/00* | (2006.01) |
| *A61B 17/08* | (2006.01) |

(52) U.S. Cl.
CPC .............. *A61F 5/443* (2013.01); *A61F 5/445* (2013.01); *A61F 5/448* (2013.01); *A61F 13/00063* (2013.01); *A61F 13/0216* (2013.01); *A61F 13/0223* (2013.01); *A61F 13/0226* (2013.01); *A61F 13/126* (2013.01); *A61M 1/0088* (2013.01); *F16M 13/022* (2013.01); *A61B 17/085* (2013.01); *A61B 2017/00561* (2013.01); *A61F 2005/4483* (2013.01); *A61F 2013/00387* (2013.01); *A61F 2013/00412* (2013.01); *A61F 2013/00476* (2013.01); *A61F 2013/00829* (2013.01); *A61F 2013/00859* (2013.01); *A61F 2013/00978* (2013.01); *A61M 2025/024* (2013.01); *A61M 2025/028* (2013.01); *A61M 2025/0246* (2013.01); *A61M 2025/0266* (2013.01); *A61M 2025/0273* (2013.01)

(58) Field of Classification Search
CPC .... A61M 2025/024; A61M 2025/0246; A61B 5/6833; A16B 90/50; A61F 13/00063; A61F 13/0216; A61F 13/0223; A61F 13/0226; A61F 13/126; A61F 2013/00412; A61F 2013/00476; A61F 2013/00829

See application file for complete search history.

(56) References Cited

U.S. PATENT DOCUMENTS

| | | | |
|---|---|---|---|
| 4,516,968 A * | 5/1985 | Marshall | A61M 25/02 |
| | | | 128/DIG. 26 |
| 5,611,333 A | 3/1997 | Johnson | |
| 6,283,945 B1 | 9/2001 | Bierman | |
| 6,361,523 B1 | 3/2002 | Bierman | |
| 6,413,240 B1 | 7/2002 | Bierman et al. | |
| 6,447,485 B2 | 9/2002 | Bierman | |
| 6,737,160 B1 | 5/2004 | Full et al. | |
| 6,808,646 B1 | 10/2004 | Jeans | |
| 6,827,705 B2 | 12/2004 | Bierman | |
| 6,872,439 B2 | 3/2005 | Fearing et al. | |
| 7,014,627 B2 | 3/2006 | Bierman | |
| 7,175,723 B2 | 2/2007 | Jones et al. | |
| 7,542,301 B1 | 6/2009 | Liong et al. | |
| 8,025,643 B2 | 9/2011 | Bierman | |
| 8,197,447 B2 | 6/2012 | Wright | |
| 8,333,736 B2 | 12/2012 | Wright et al. | |
| 8,394,065 B2 | 3/2013 | Bierman | |
| 2006/0247577 A1* | 11/2006 | Wright | A61M 5/158 |
| | | | 604/174 |
| 2008/0033377 A1* | 2/2008 | Kauth | A61F 13/00987 |
| | | | 604/304 |
| 2010/0121282 A1* | 5/2010 | Propp | A61M 25/02 |
| | | | 604/180 |
| 2010/0318052 A1 | 12/2010 | Ha et al. | |
| 2010/0324511 A1 | 12/2010 | Dove et al. | |
| 2011/0106113 A1* | 5/2011 | Tavakkolizadeh | A61B 17/064 |
| | | | 606/151 |
| 2011/0126972 A1 | 6/2011 | Frerot | |
| 2011/0218451 A1 | 9/2011 | Lai et al. | |
| 2011/0254205 A1 | 10/2011 | Inamiya et al. | |
| 2012/0046582 A1* | 2/2012 | Hopman | A61B 17/1322 |
| | | | 602/4 |
| 2012/0071566 A1 | 3/2012 | Kelly et al. | |
| 2013/0075959 A1 | 3/2013 | Ohya et al. | |
| 2013/0231698 A1 | 9/2013 | Smith | |
| 2015/0320606 A1 | 11/2015 | Kawahara et al. | |
| 2016/0199230 A1 | 7/2016 | Doshi et al. | |

FOREIGN PATENT DOCUMENTS

| | | |
|---|---|---|
| EP | 806210 A2 | 11/1997 |
| EP | 643420 B1 | 8/2004 |
| EP | 2497449 A2 | 9/2012 |
| WO | WO2006/042430 A1 | 4/2006 |
| WO | WO2015/179869 A2 | 11/2015 |

* cited by examiner

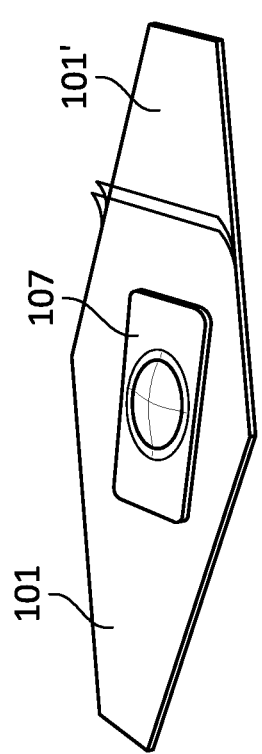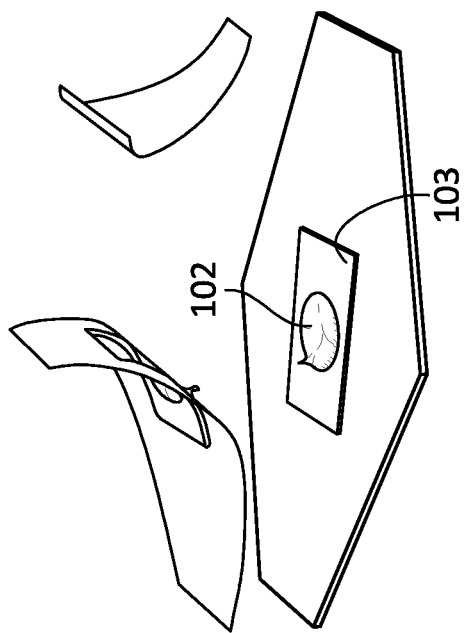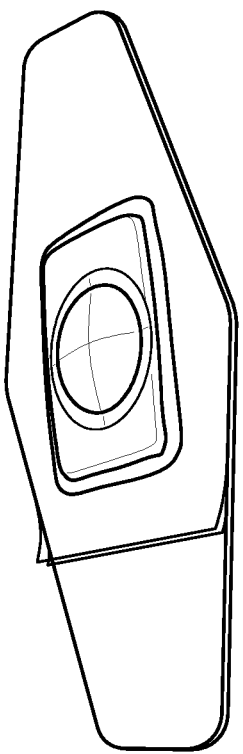
FIG. 4A
FIG. 4B
FIG. 4C

CAP AS PART OF PACKAGING

CAP AS PART OF LINER

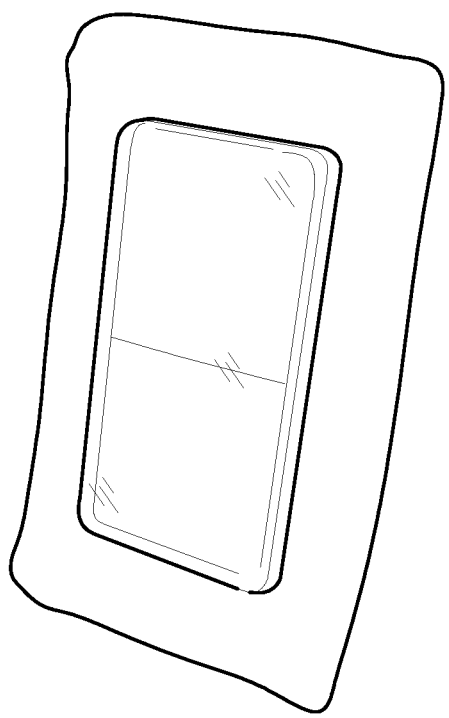
FIG. 9L
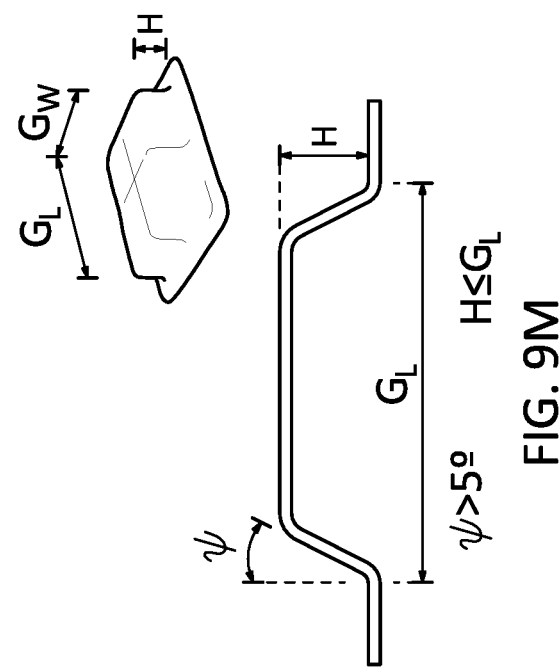
FIG. 9M
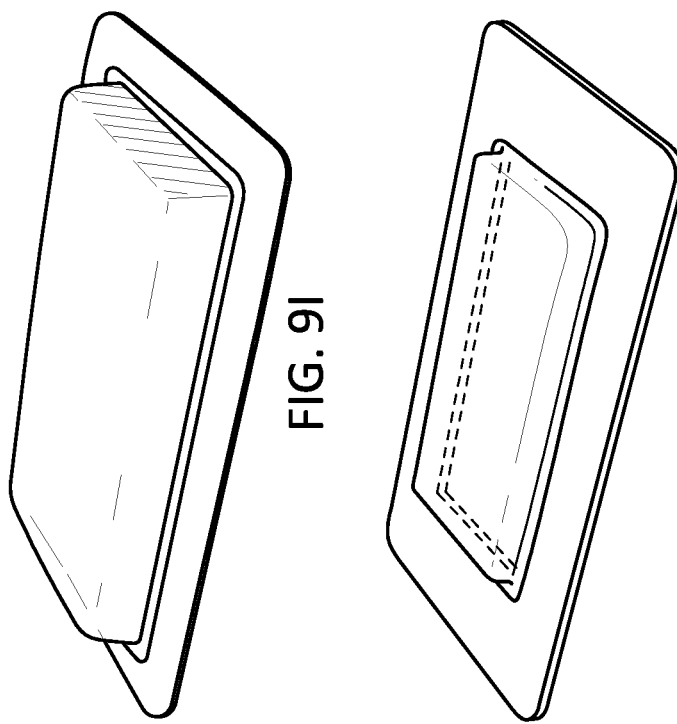
FIG. 9I
FIG. 9J
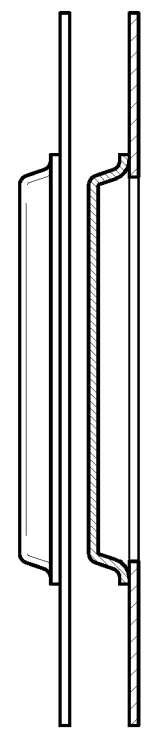
FIG. 9K

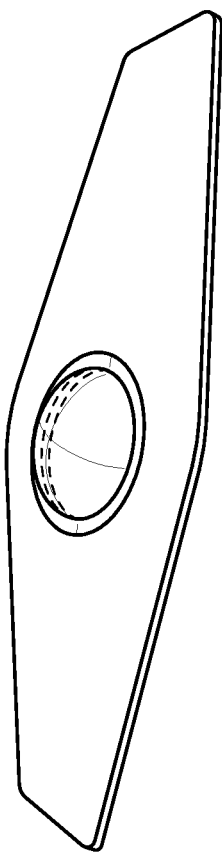
FIG. 9N
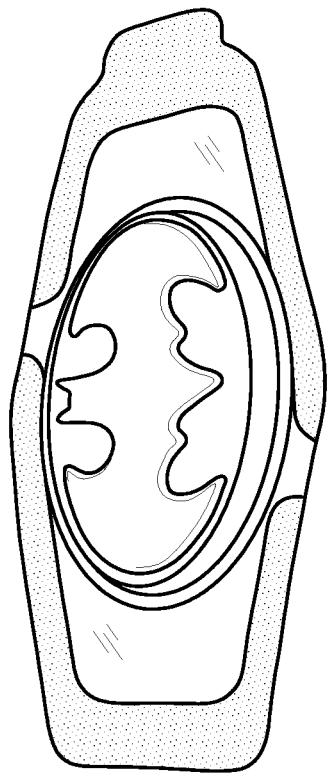
FIG. 9O
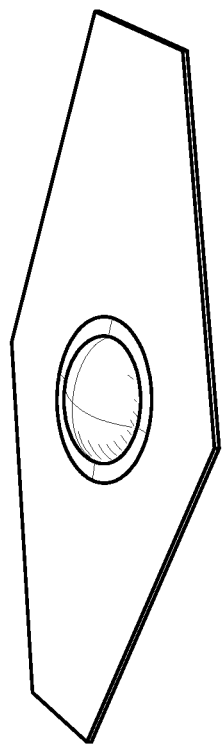
FIG. 9P
FIG. 9Q
FIG. 9R

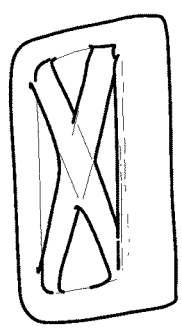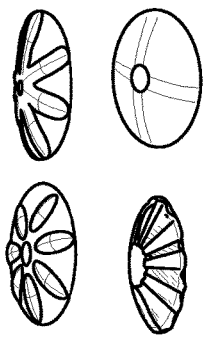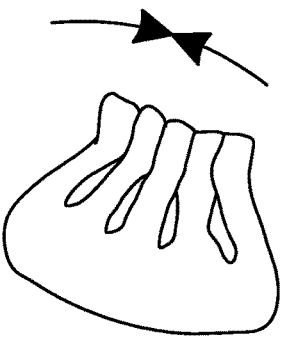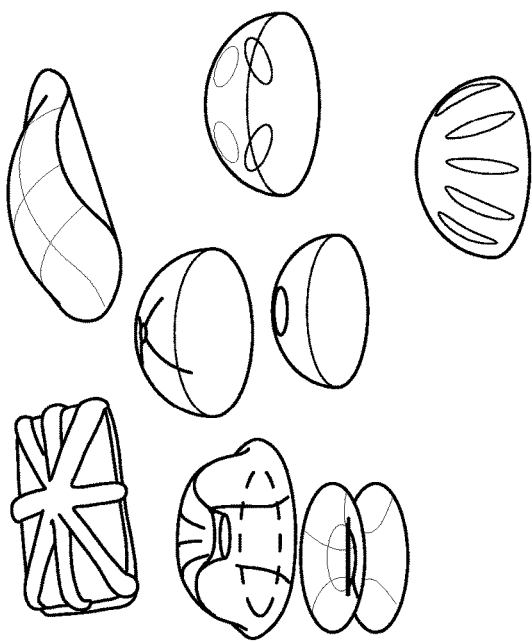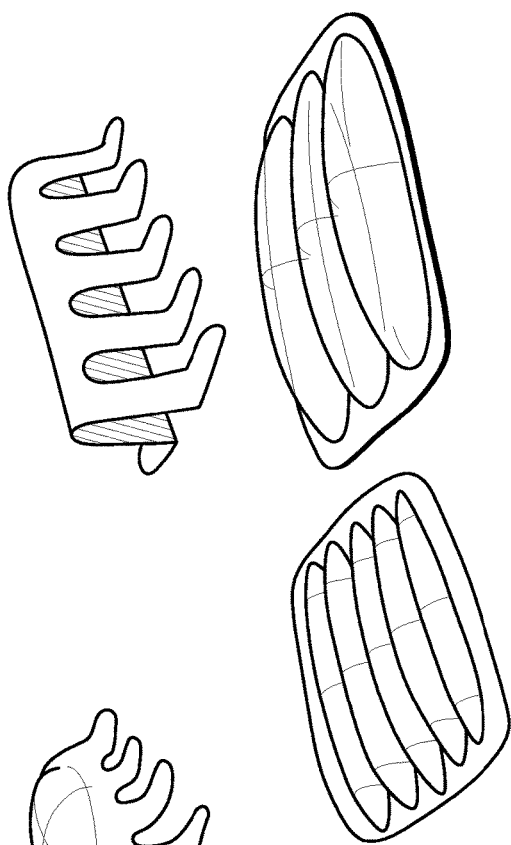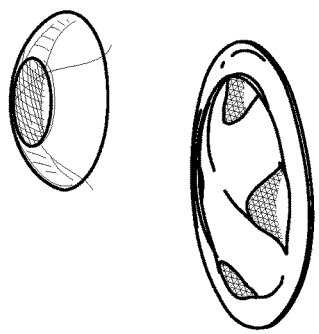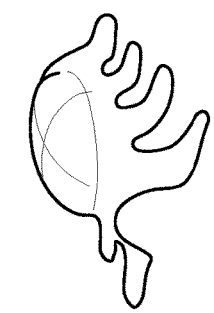
FIG. 9U
FIG. 9V

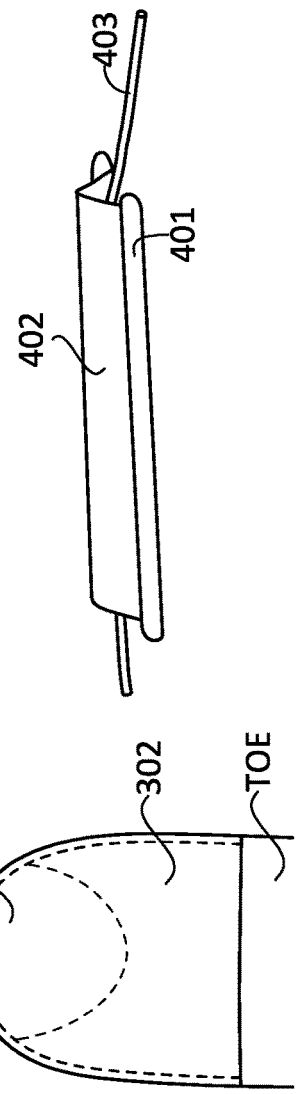
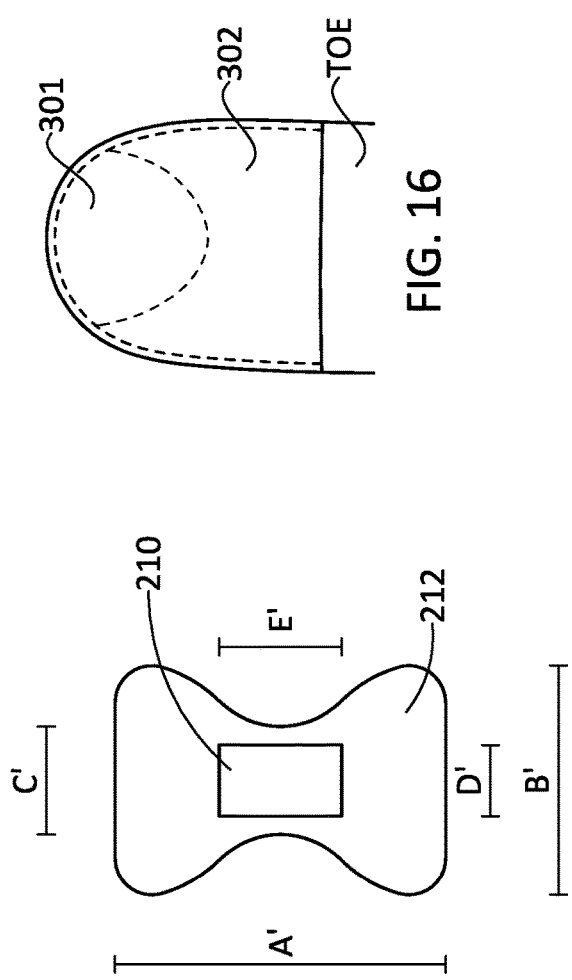
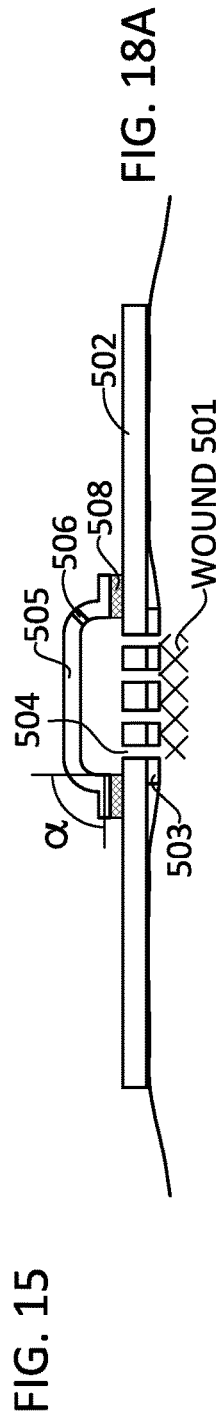
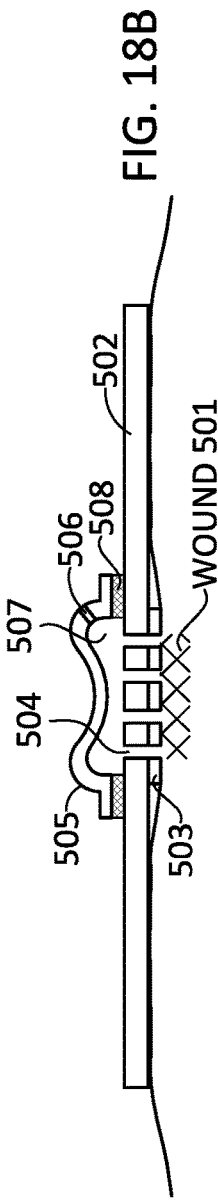

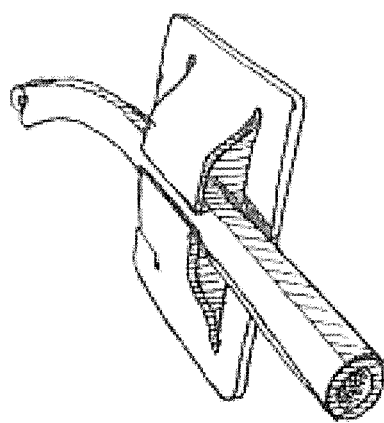
Fig 18O
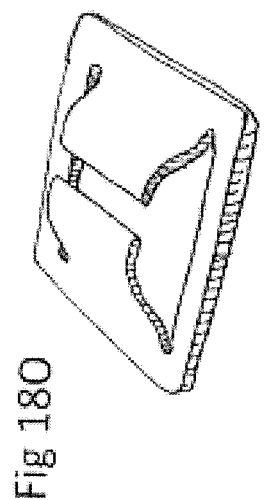
Fig 18P
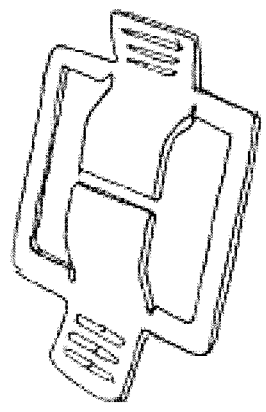
Fig 18Q
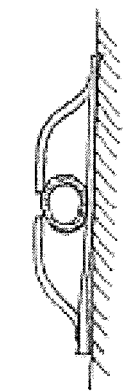

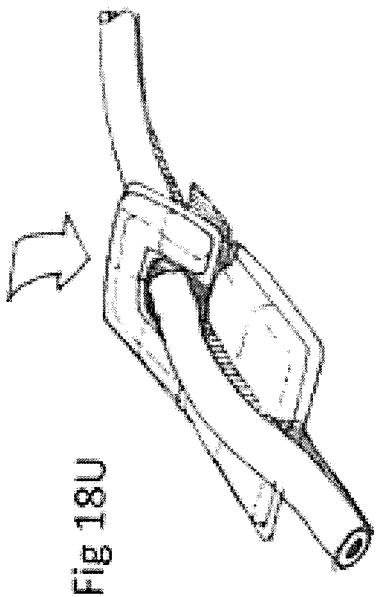
Fig 18S
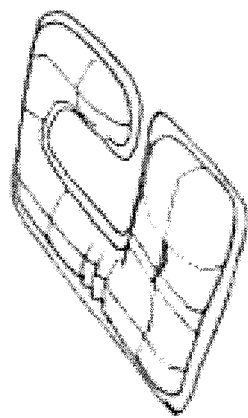
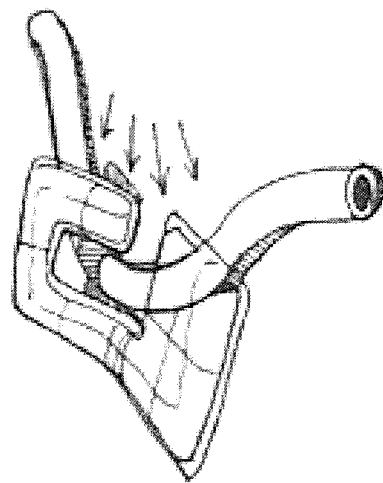
Fig 18U
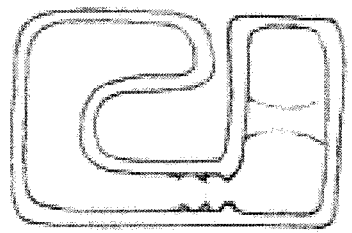
Fig 18R
Fig 18T

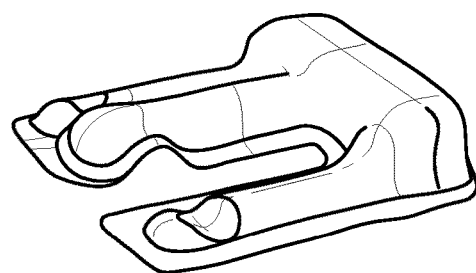
FIG. 18W
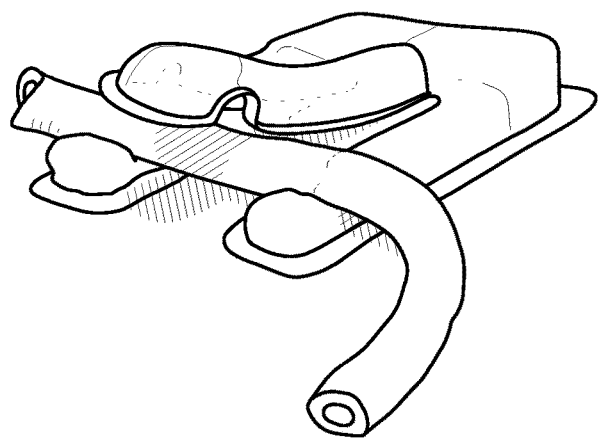
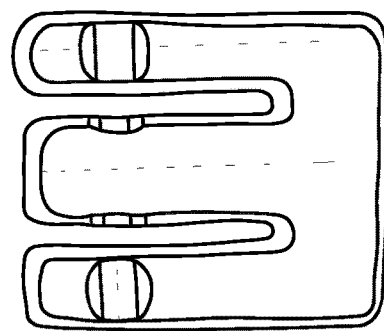
FIG. 18X
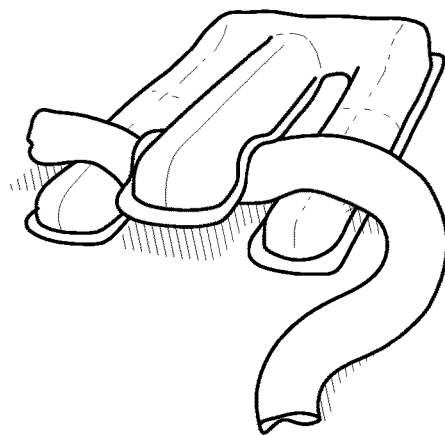
FIG. 18V

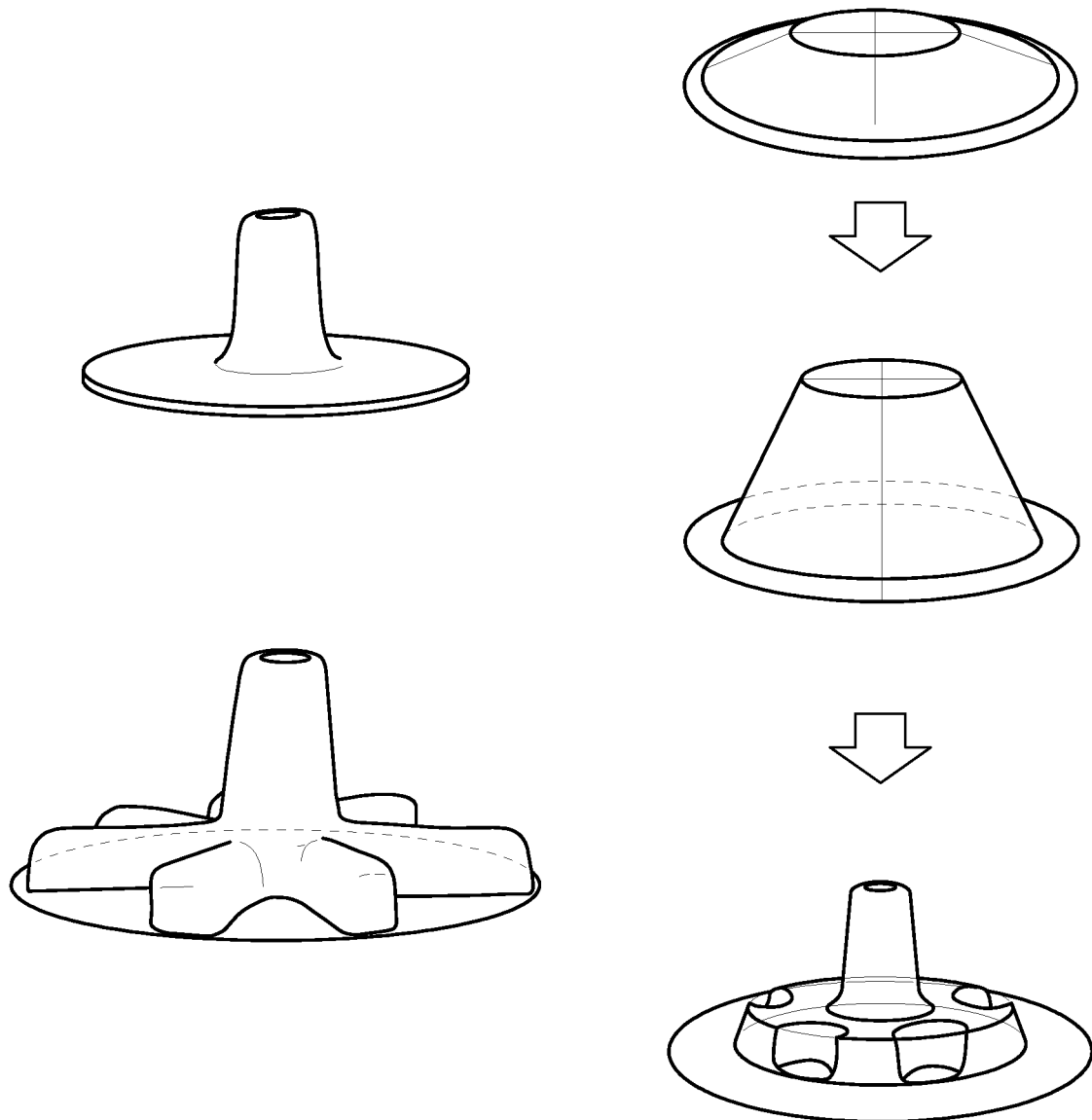
FIG. 18Y                    FIG. 18Z

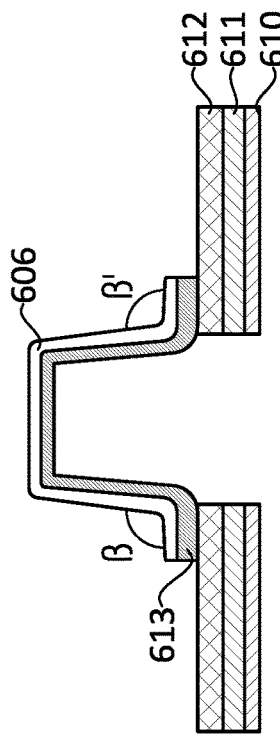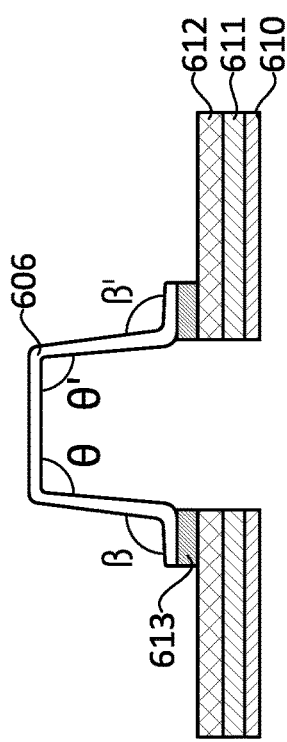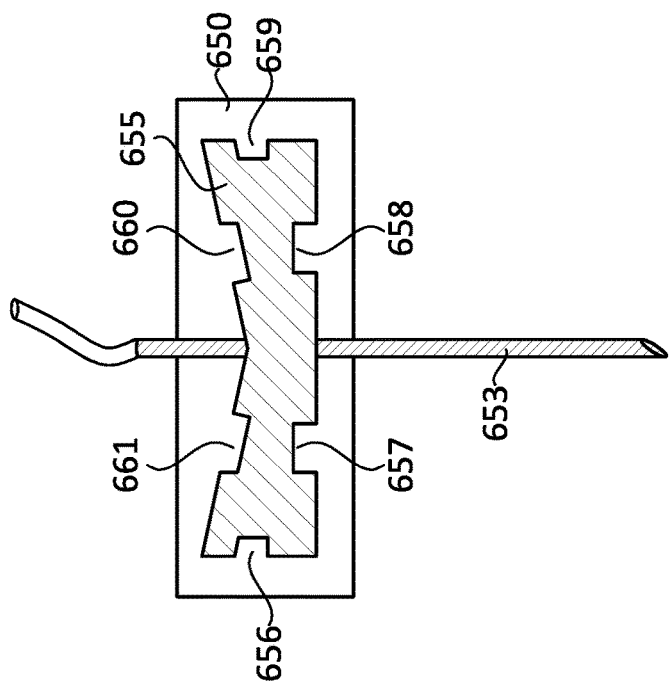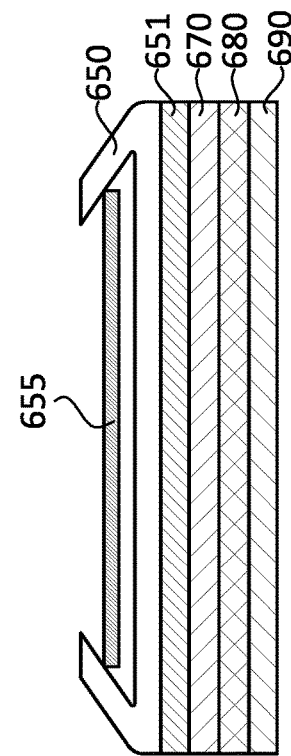
FIG. 21A
FIG. 21B
FIG. 21C
FIG. 21D

R1<R2 TO CONSTRAIN AXIAL MOTION

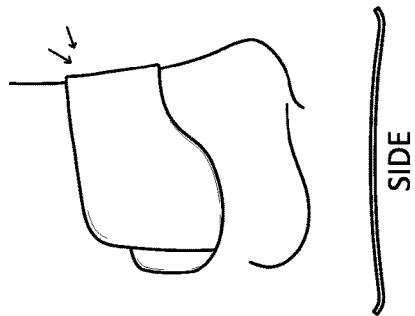
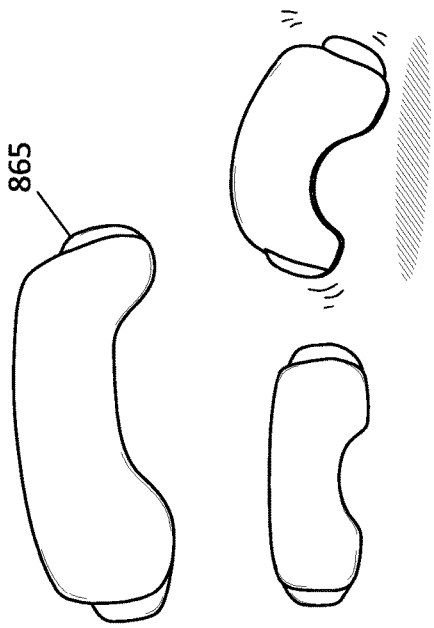
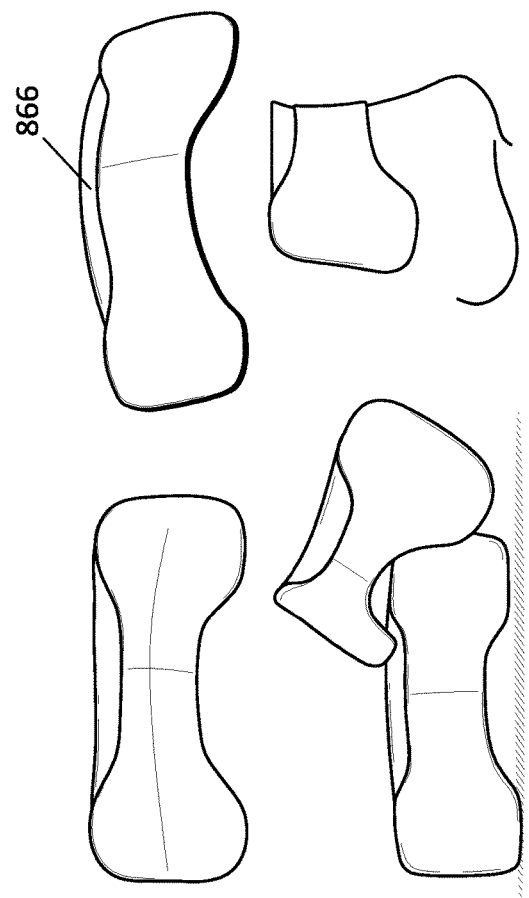
FIG. 24N
FIG. 24O
FIG. 24M

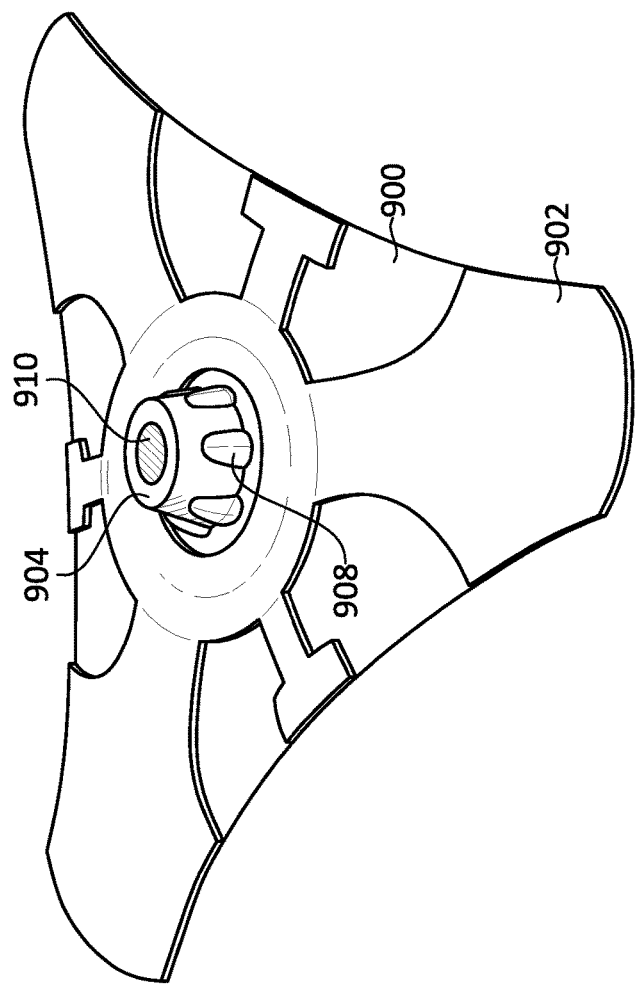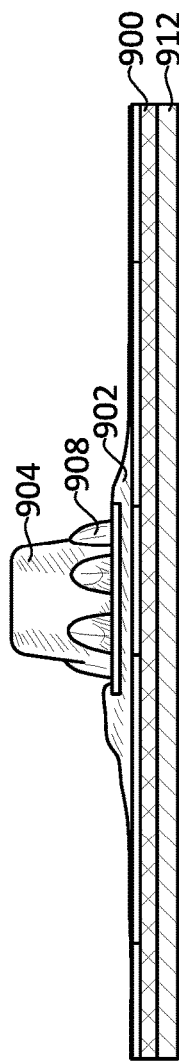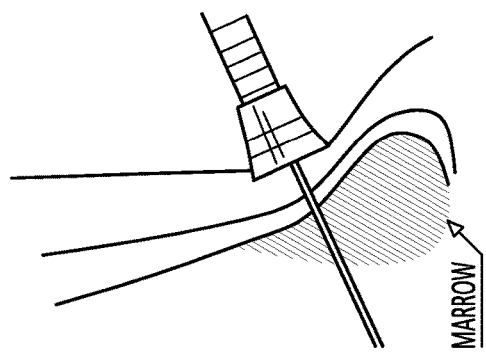
FIG. 26B
FIG. 26C
FIG. 26A

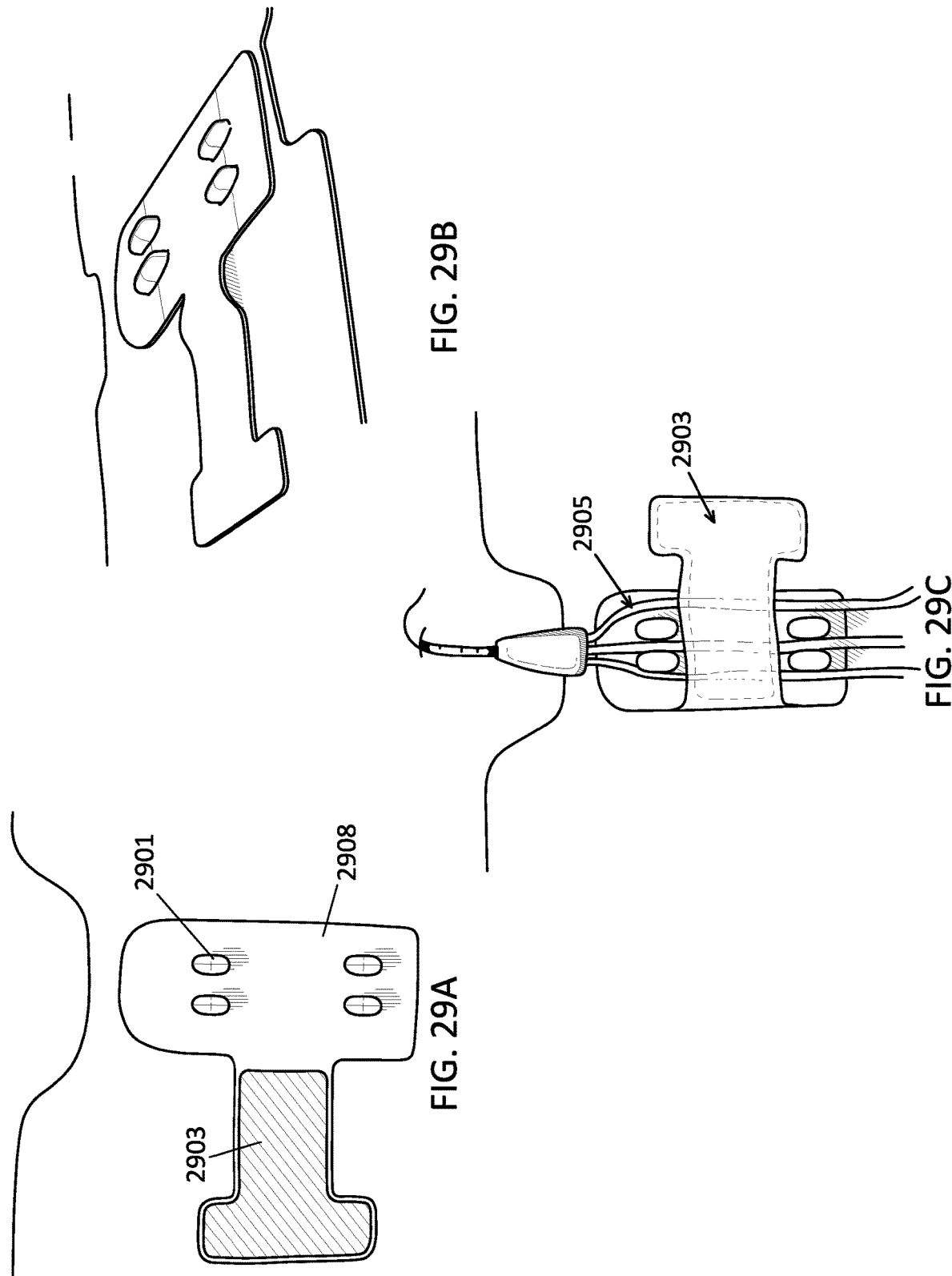

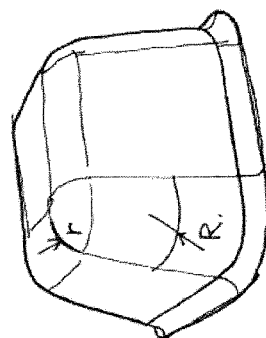
Fig 34
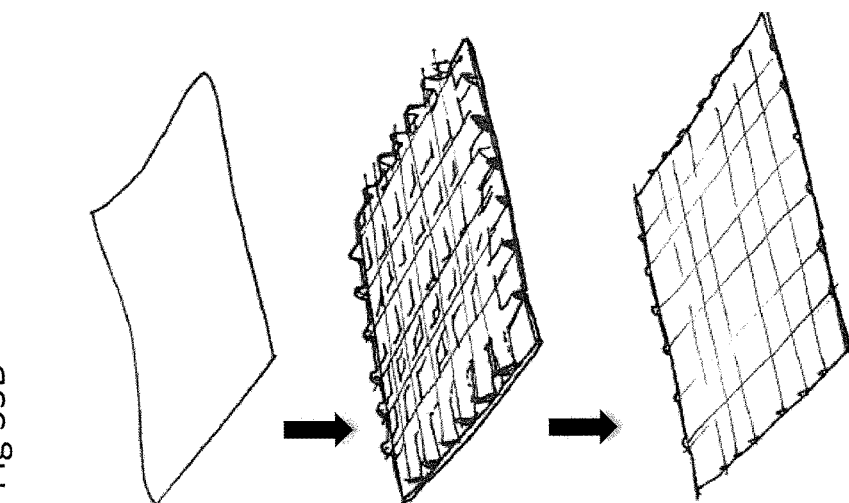
Fig 33D
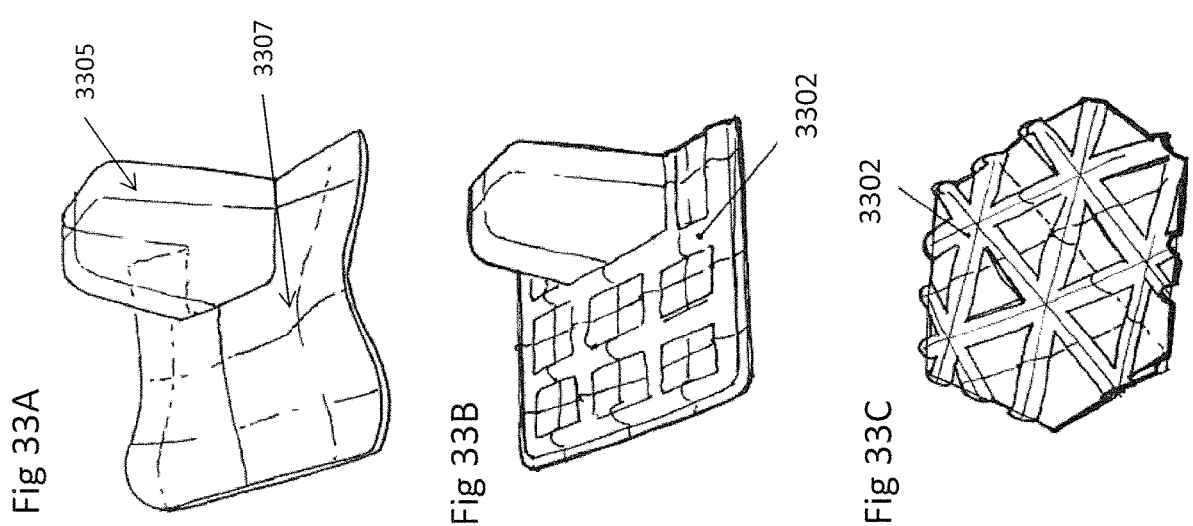
Fig 33A
Fig 33B
Fig 33C

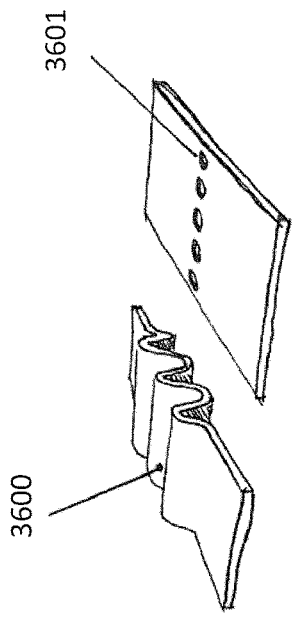
Fig 36A
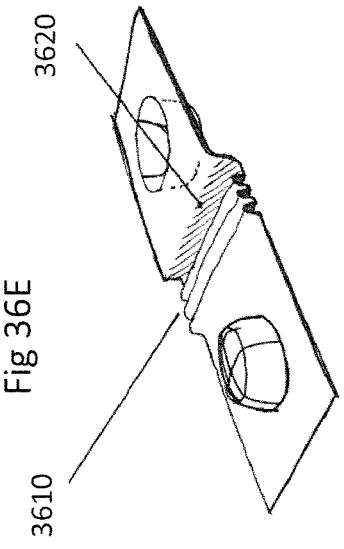
Fig 36D
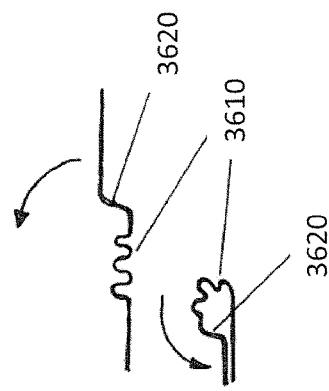
Fig 36F
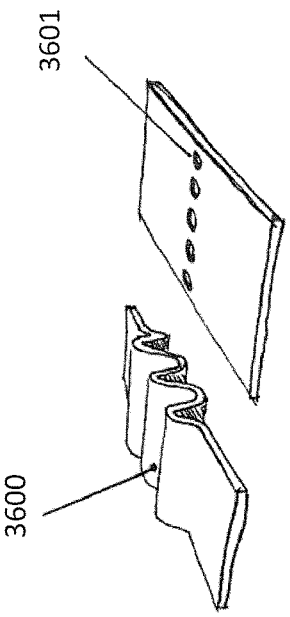
Fig 36B
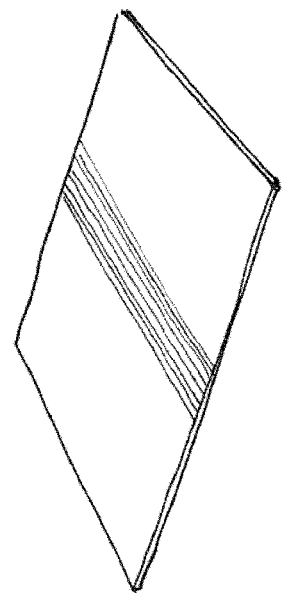
Fig 36E
Fig 36C
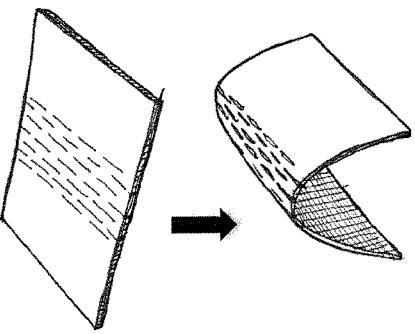

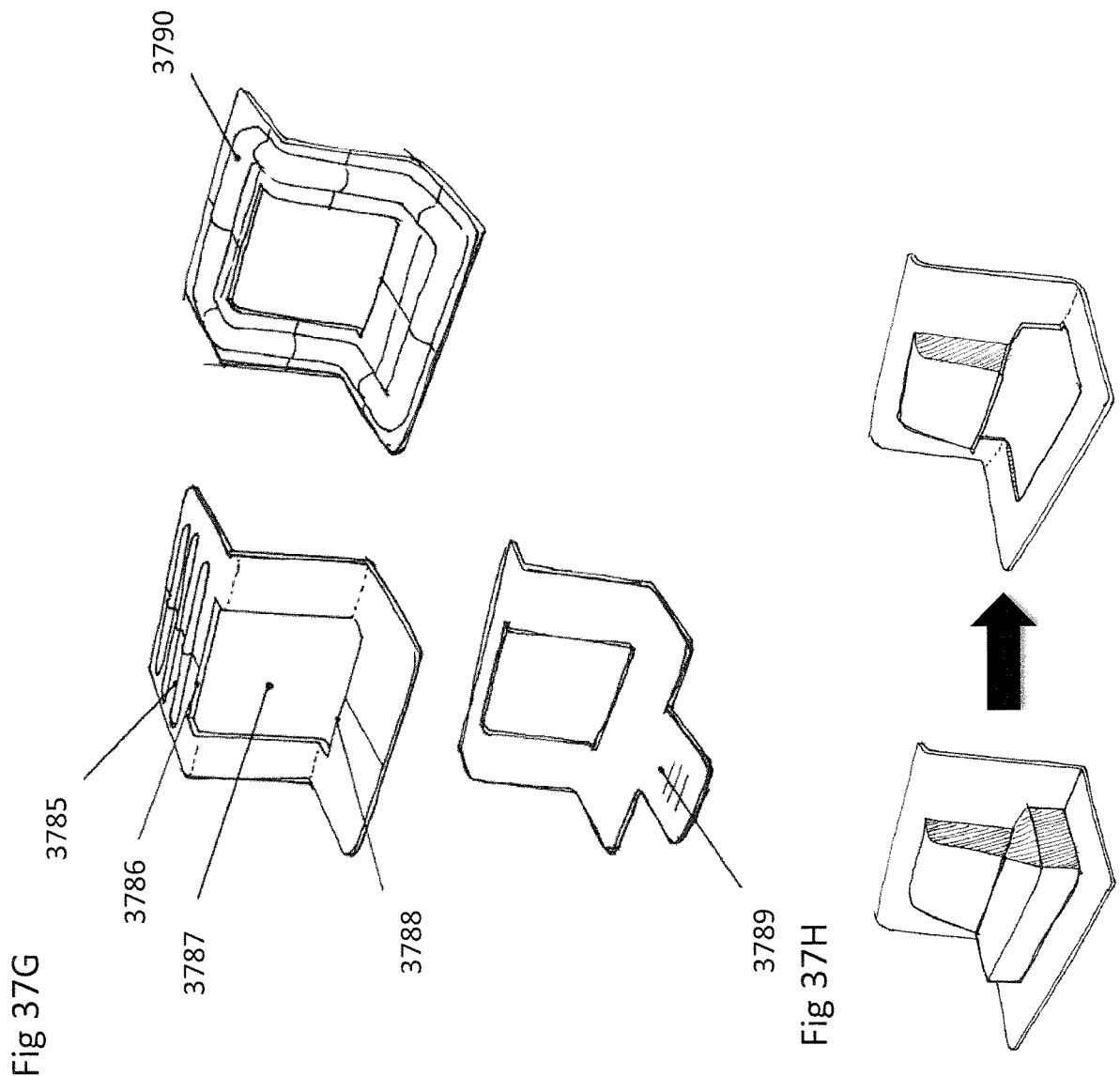

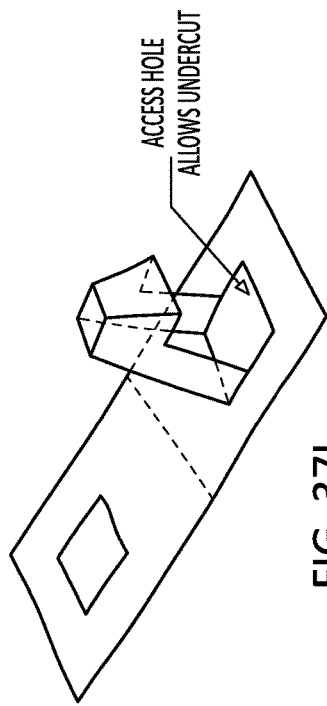
FIG. 37L
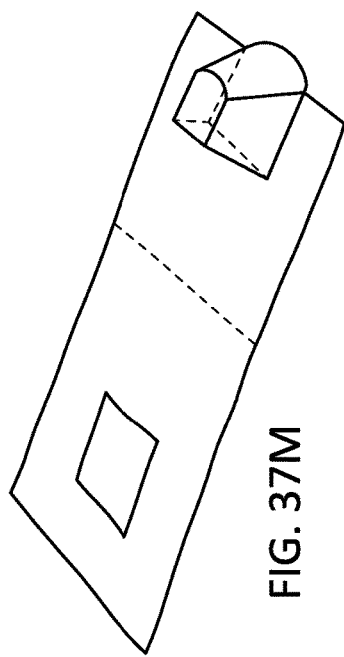
FIG. 37M
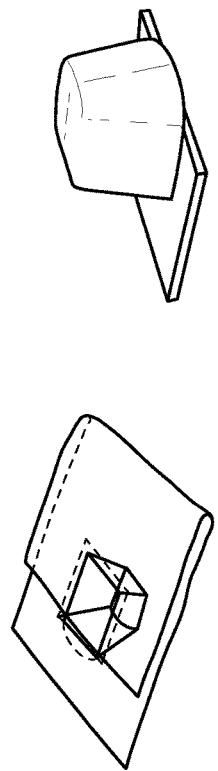
FIG. 37O
FIG. 37N
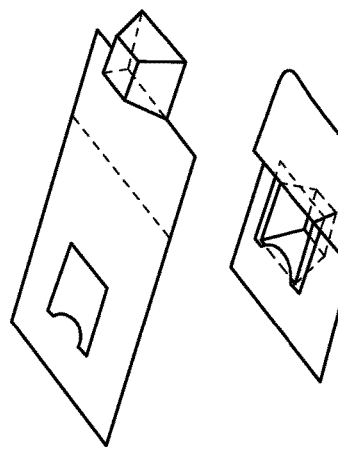
FIG. 37I
FIG. 37J
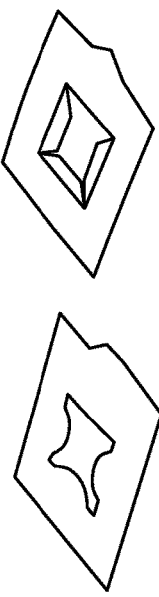
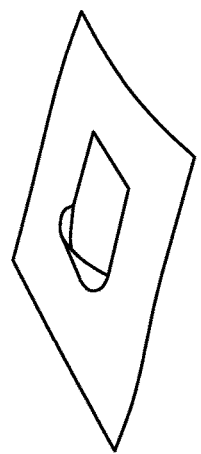
FIG. 37K

FIG. 39
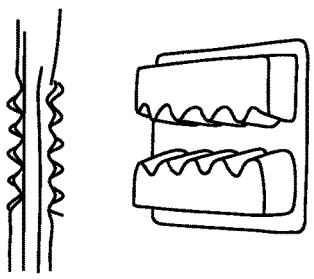
FIG. 40
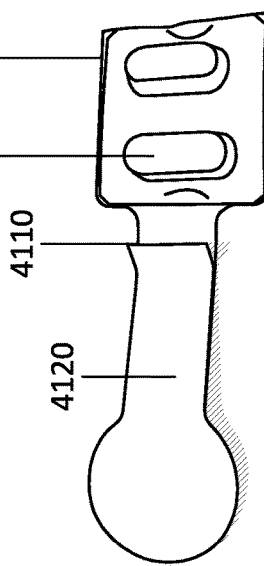
FIG. 41
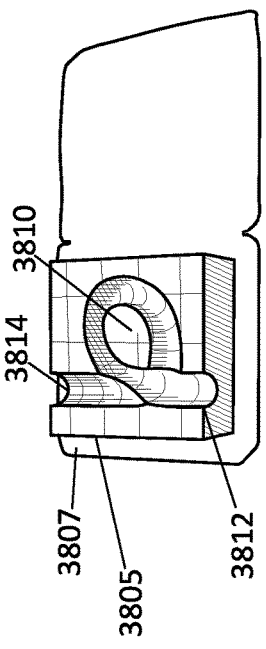
FIG. 38A
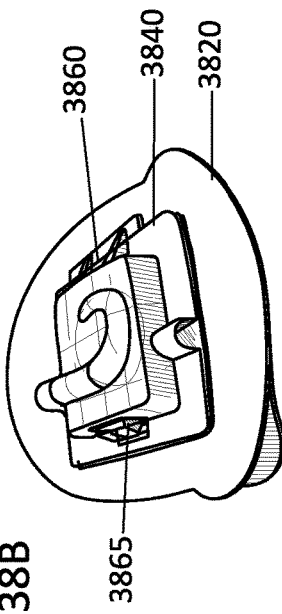
FIG. 38B
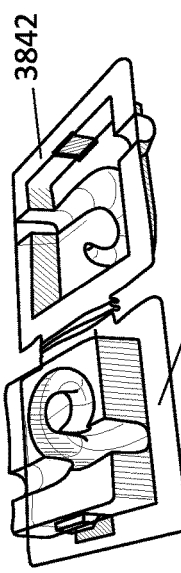
FIG. 38C
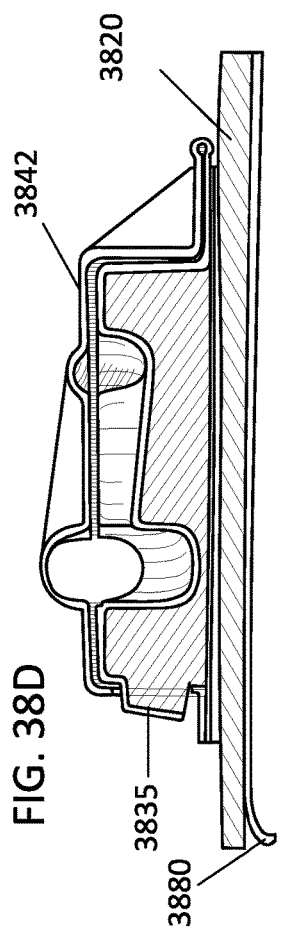
FIG. 38D

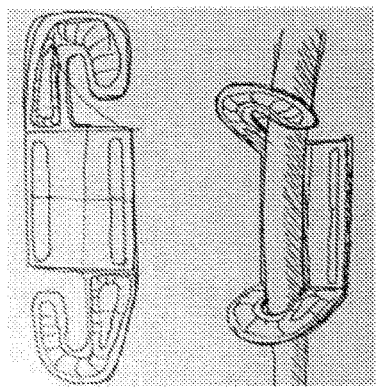
Fig 46C
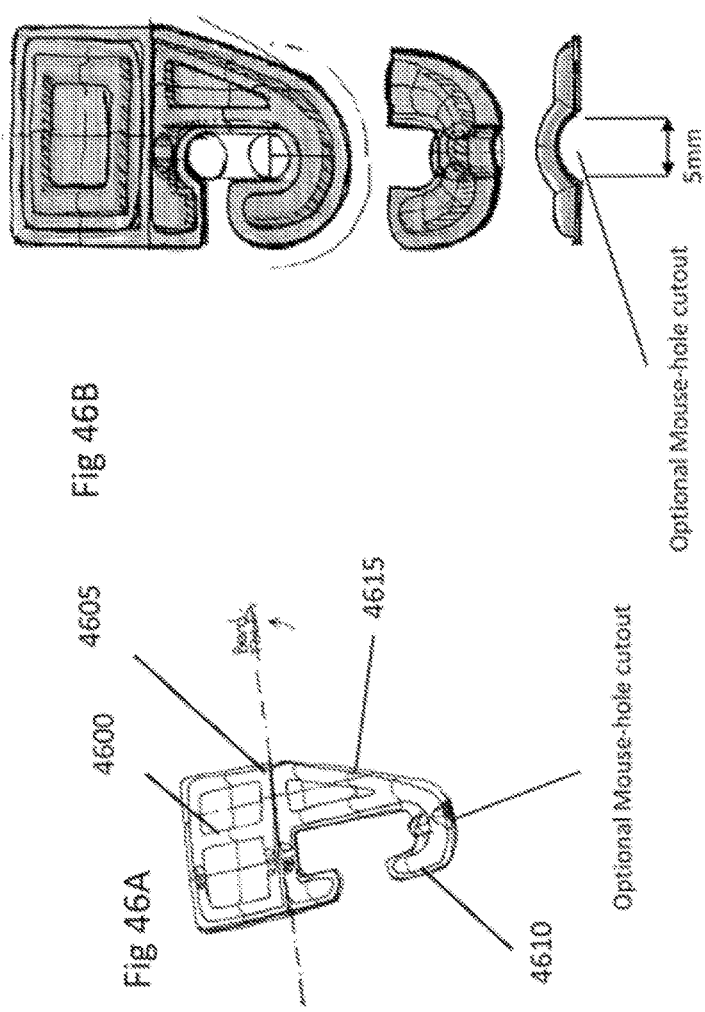
Fig 46B
Fig 46A
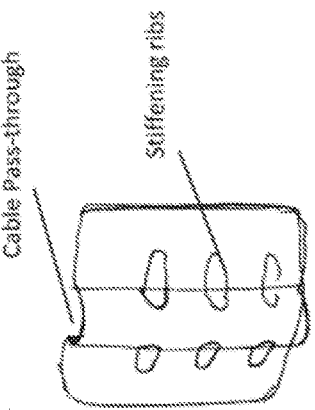
Fig 48
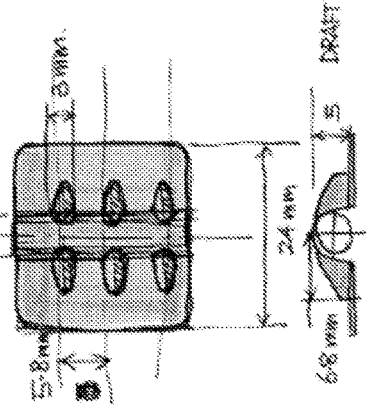
Fig 47

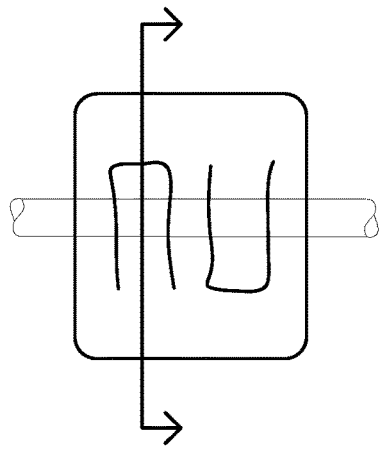
FIG. 52A
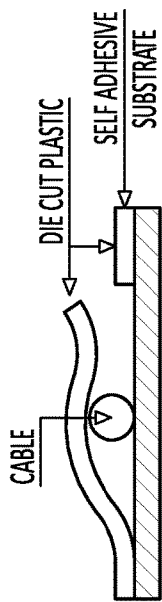
FIG. 52B
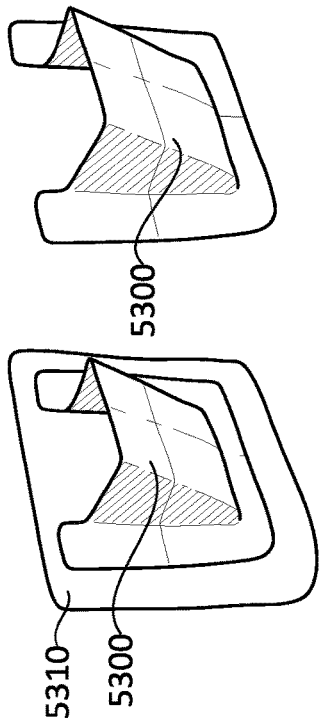
FIG. 53A
FIG. 53B
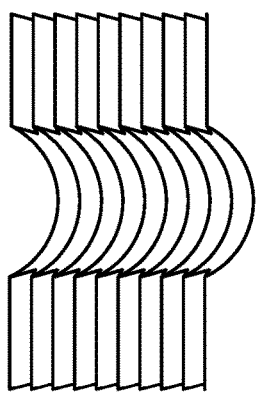
FIG. 49
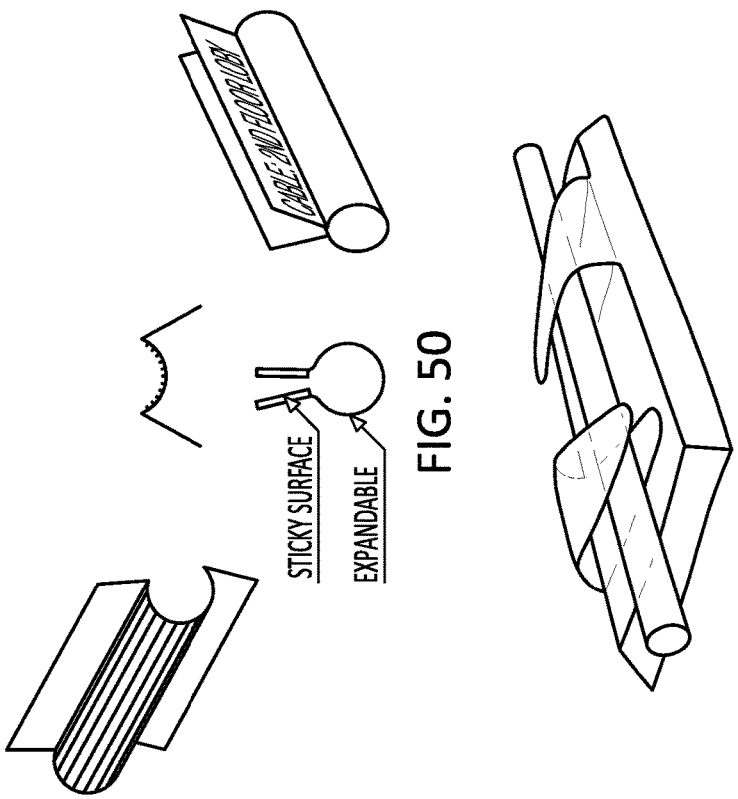
FIG. 50
FIG. 51

WIRE SECUREMENT

WEB CONNECT

STEEL

LIVING HINGE

WALL

VERTICAL SUPPORT

USE POSITION

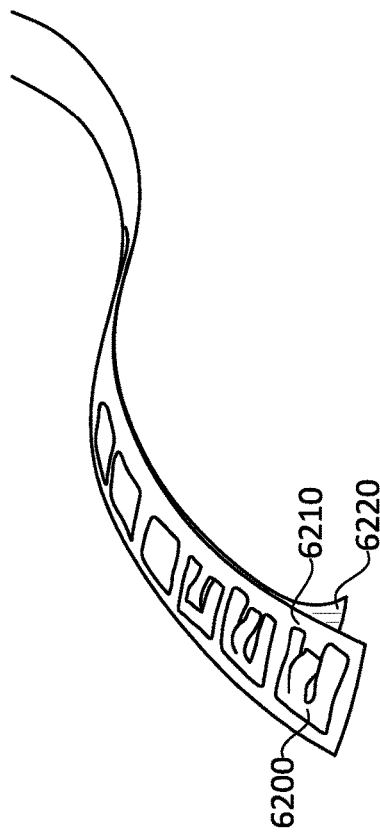
FIG. 62
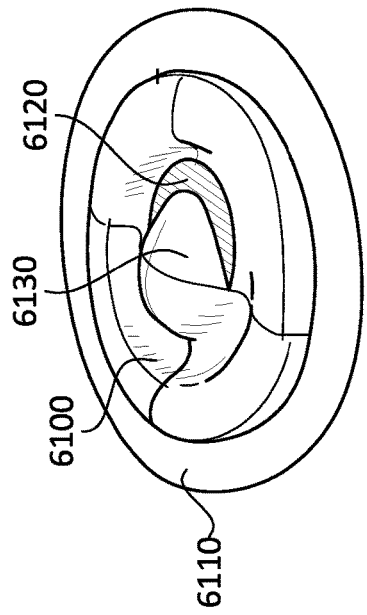
FIG. 61
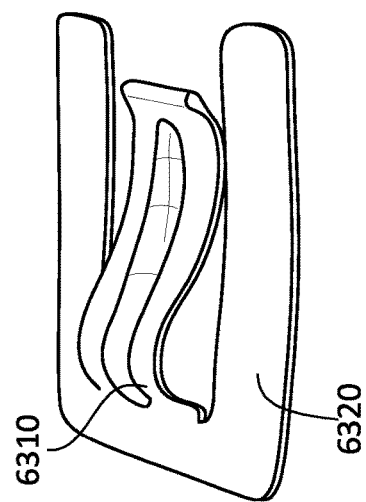
FIG. 63
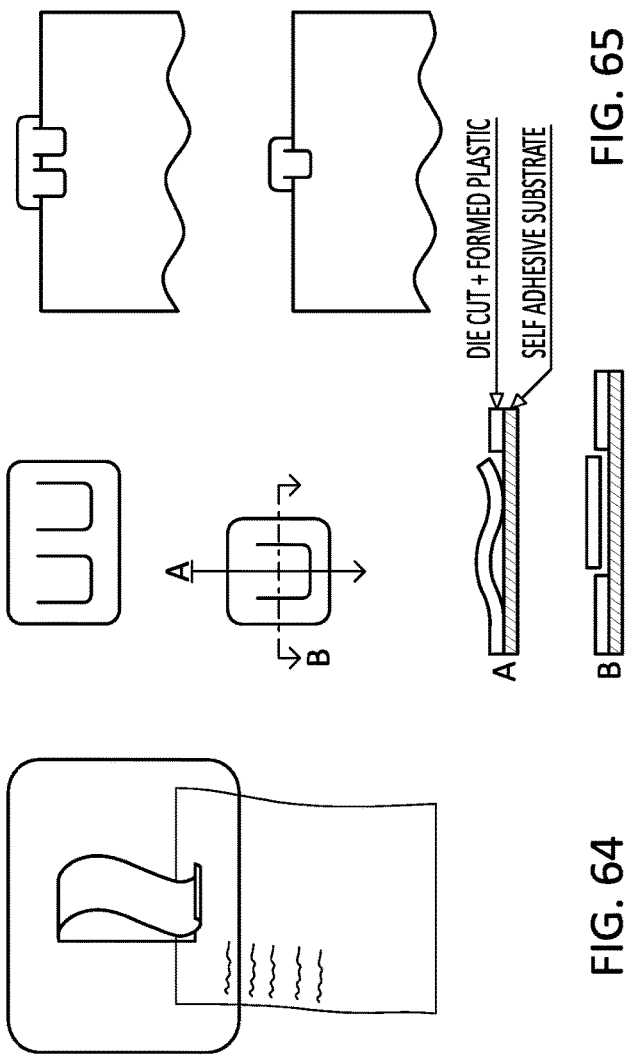
FIG. 64
FIG. 65

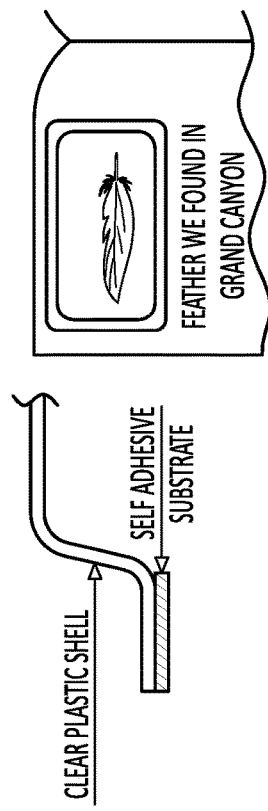

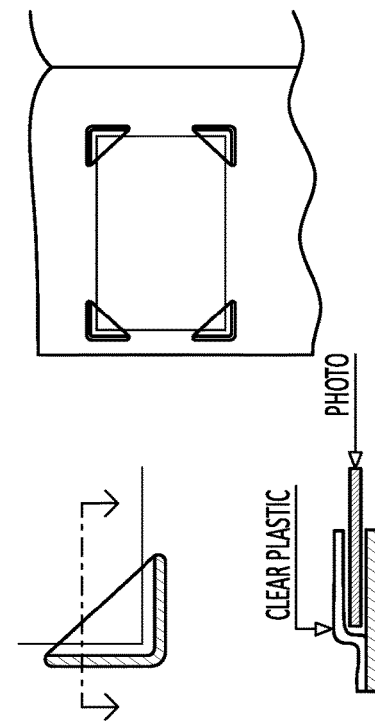

SELF ADHESIVE SHELL FOR MOUNTING LOOSE OBJECTS
- e.g., HOLD SMALL OBJECTS IN A SCRAPBOOK
- MANY DIFFERENT SHAPES + THICKNESSES (DEPH)

CLEAR PLASTIC SHELL
SELF ADHESIVE SUBSTRATE
FEATHER WE FOUND IN GRAND CANYON

FIG. 67

CORNER MOUNTS
- INEXPENSIVE PICTURE CORNER HOLDERS FOR SCRAPBOOK, WALL MOUNT, TACKBOARD.
- BETTER QUALITY - PRICE RATIO THAN CURRENT

CLEAR PLASTIC
PHOTO
SUBSTRATE ADHESIVE

FIG. 68

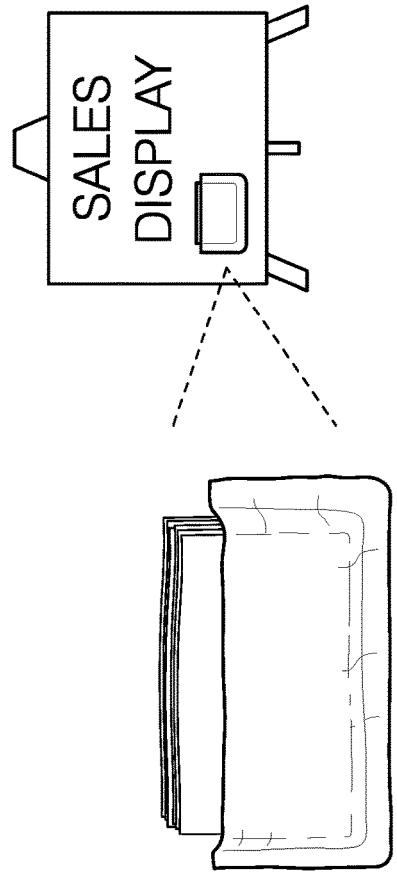

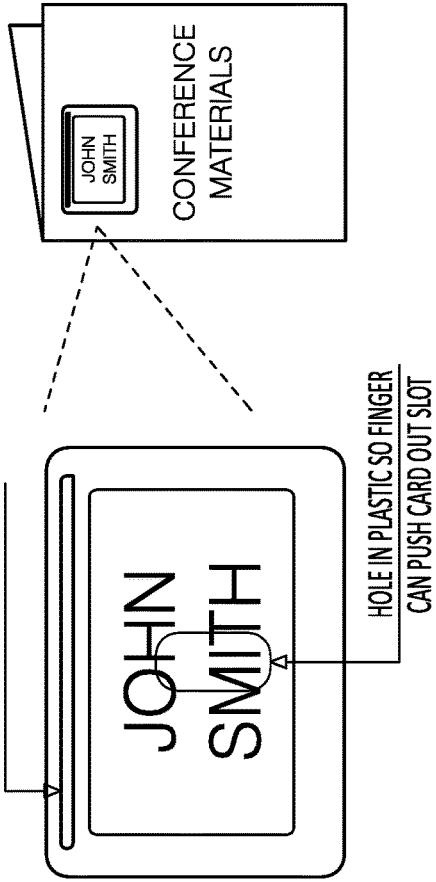

SINGLE CARD VERSION

SLOT IN TOP TO INSERT CARD
HOLE IN PLASTIC SO FINGER CAN PUSH CARD OUT SLOT

FIG. 66

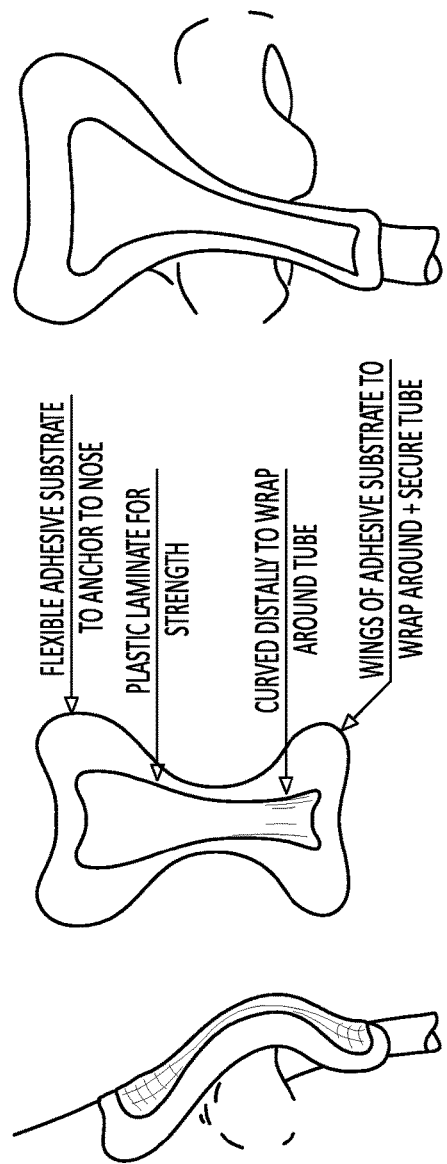
FIG. 69
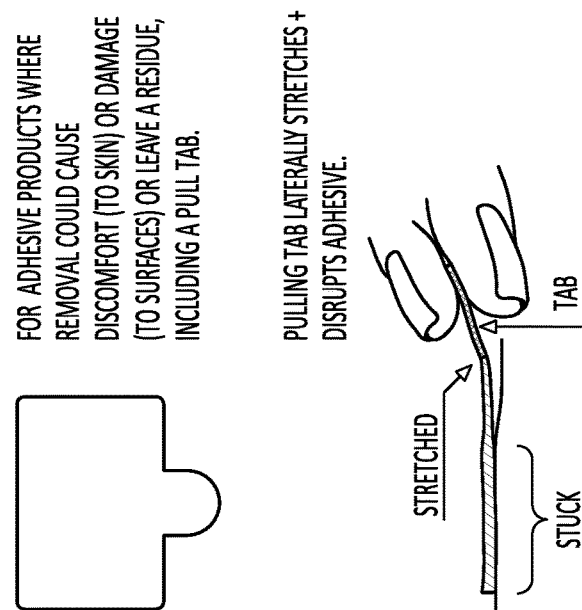
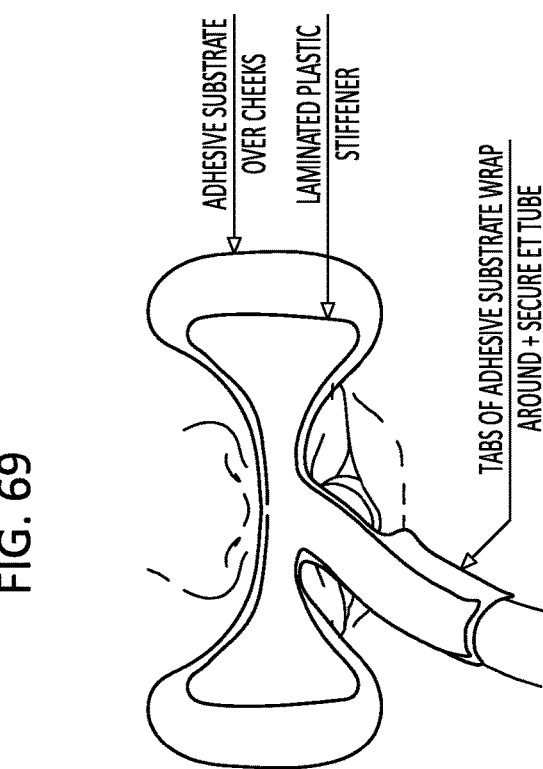
FIG. 70
FIG. 71

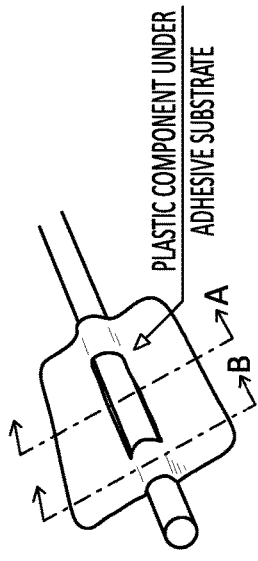
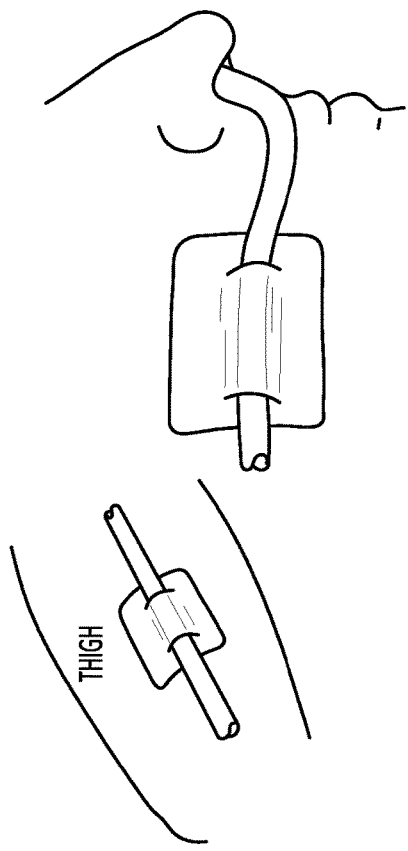
FIG. 84
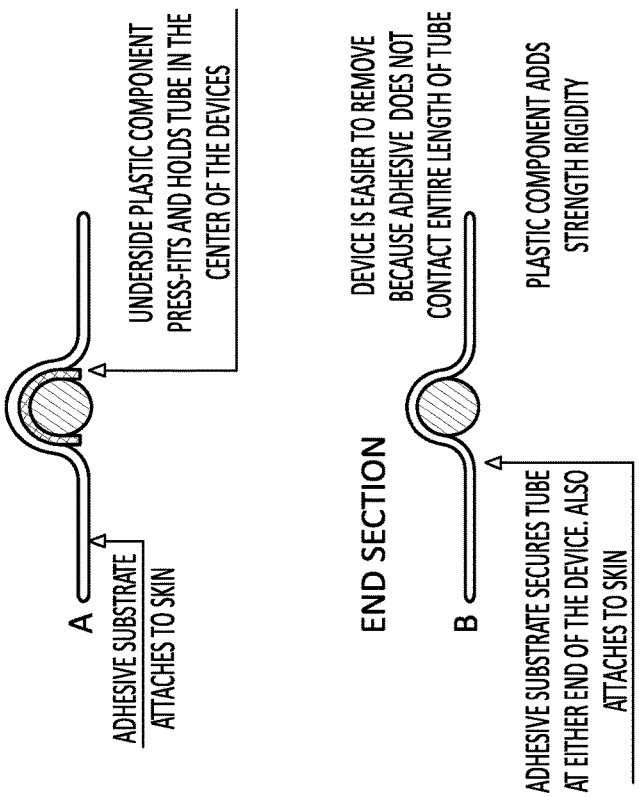
FIG. 86
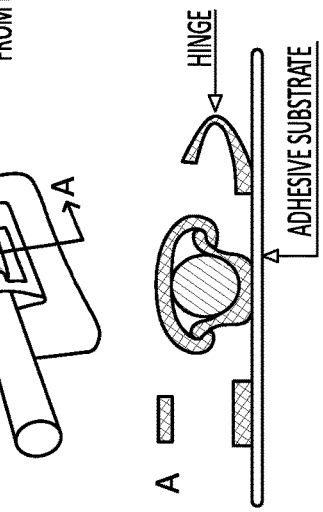
FIG. 85

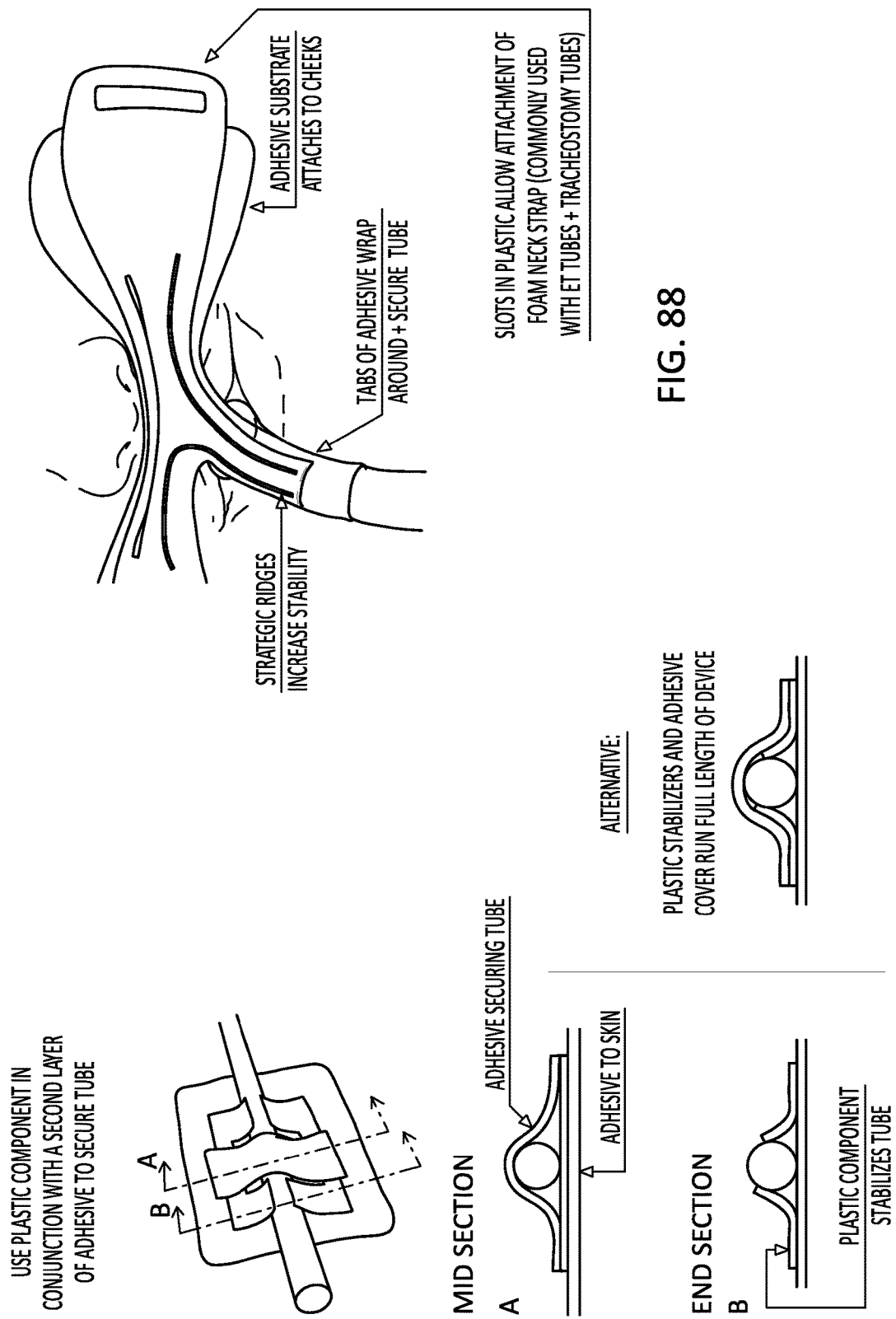

SUPPORT DEVICES AND METHODS OF MAKING AND USING THEM

CROSS REFERENCE TO RELATED APPLICATIONS

This patent application claims priority to the following provisional patent applications: U.S. provisional patent No. 61/893,095, filed on Oct. 18, 2013, and titled "ADHESIVE MEDICAL DEVICES"; U.S. provisional patent No. 61/927,943, filed on Jan. 15, 2014, and titled "ADHESIVE MEDICAL DEVICES"; U.S. provisional patent No. 62/026,453, titled "ADHESIVE DEVICES", and filed on Jul. 18, 2014; and Indian provisional patent application 2191/DELNP/2014, filed on Aug. 1, 2014, and titled "ADHESIVE DEVICES". This patent also claims priority to the PCT application filed 26 Aug. 2014, as International Application No. PCT/US2014/052750. Each of these patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to three-dimensional support products, including adhesive support devices such as adhesive medical devices, formed of a sheet of rigid or semi-rigid material into a 3D shape to which an adhesive material is attached, as well as methods of making and using these apparatuses.

BACKGROUND

Support products including medical devices and household consumer products can be used for many purposes. For example, adhesive medical devices are used to treat various medical and non-medical conditions or to supplement the use of other medical and consumer devices. These adhesive devices include, but are not limited to, adhesive bandages, ostomy devices, catheter stabilization devices, finger splints, nasal strips, wound therapy devices, ECG leads and drug delivery patches.

Many adhesive products including medical devices that are made through web converting manufacturing methods, are generally flat or planar (mostly two dimensional). For example, adhesive medical bandages may not have significant thickness, though they consist of multiple layers of materials, and typically are mostly flat. There is a need for adhesive products including medical devices that are three dimensional, which will enable a large number of new uses for such devices, uses that are not possible to achieve with traditional flat, planar devices. These new uses may include but are not limited to stabilization of other medical devices, wound care, treatment of burns, ostomy devices, application of antibiotic or antifungals, stabilization of joints, and treatment of other skin and nail conditions.

Fabrication of layered devices, and particularly layered medical device by continuous processes, such as web converting, work well for flat structures (layers), but may not be used to create devices with three-dimensional structures. Instead, such three dimensional (3D) structures must be separately placed/positioned, which may be expensive and time consuming, limiting rate of production and increasing manufacturing costs and cost of goods. Thus, there is also a need for automated processes or methods for manufacture of layered devices including 3D structures.

SUMMARY

Described herein are specific variations of support devices, accessories for support devices, methods of using support devices and kits including support devices. In particular, described herein are adhesive support devices configured as adhesive medical devices. Examples of such medical devices may include bandages carrying (e.g., pre-applied) liquid, gel, or paste medicines, bandages forming a protected chamber over a wound when applied to the patient, and the like. The adhesive medical devices described herein may be used for various medical, non-medical and consumer health applications, including OTC (over-the-counter) products that treat medical, non-medical or cosmetic conditions and/or promote wellness or other tangible or intangible benefit. The term "medical" does not exclude devices and therapies that do not treat diagnosed medical conditions. These adhesive medical devices are thus intended to treat any health condition. Further, adhesive medical devices may be worn by a subject to enhance or supplement some body function, to treat a medical condition or facilitate the use of another medical device. Other adhesive devices described herein may be purely ornamental or designed to provide amusement (e.g., toys) or be used for fashion or aesthetic purposes. In still other cases, adhesive products may be used to hang other items (e.g., serve as hooks) or manage cords, or serve other household purposes. As described in more detail below, an adhesive device may be secured to any part of the user's body, and may attached to the skin of any part of the body, including the face.

The adhesive devices described herein may be completely flexible, partially flexible, partially rigid, or completely rigid. For example, the devices described herein may include an adhesive region (e.g., configured as a holdfast region) that is at least partially flexible and may also include another region that serves a medical or non-medical purpose or function. In other embodiments, the adhesive devices described herein may have a flexible portion (such as a holdfast) and another portion or region which is more rigid, which may help provide the intended function of the adhesive device. In other embodiments, a rigid layer may extend over all or substantially all, of the adhesive device to provide structure to the device including the holdfast region. This rigid layer may enable the device to support other devices (such as holding a tube, catheter or other medical product or to support or hang other items (thereby serving as a hook or fastener).

In general, an adhesive support devices described herein may be secured in communication with a subject's skin. The adhesive region (e.g., holdfast) may comprise a biocompatible adhesive and a flexible substrate configured to conform to the subject's skin. Materials for the holdfast may be chosen to attach the device to the skin or other body part and/or to serve an intended therapeutic or non-therapeutic function.

As used herein, rigid or semi-rigid structures, and particular 3D structures forming the cover, protective cap, barrier cap, protective cover, vacuum cap, or other formed plastic component may use similar materials and thickness, share similar geometries, and utilize similar manufacturing processes including in line forming using rotary dies or step and repeat forming processes. Any description of a material, geometry, etc. for one rigid or semi-rigid 3D structure may be used for any other rigid or semi-rigid 3D structure described herein. For example, draft angles, relative thicknesses or sequential forming processes described for a barrier cap may be applicable for the vacuum cap or securement doors (including living hinges), etc.

As used herein, rigid or semi-rigid structures, and particular 3D structures forming the cover, protective cap, barrier cap, protective cover, vacuum cap, or other formed plastic component, etc. described herein, may have a material and/or structural stiffness that is above a predetermined threshold. For example, in some variations a rigid or semi-rigid structure is formed of a material having an elastic modulus that is relatively high, so that the material resists deformation (e.g., a rod or sheet of material resists deformation). For example, a material forming a 3D structure to be included in any of the apparatuses (including systems and devices) described as a stiff or rigid material and may be a material that has an elastic modulus (e.g., Young's modulus) value in a range of greater than about 0.4 GPa, e.g., from 0.4 to 200 GPa, such as from 0.8 to 200 GPa, for example from 1.0 to 200 GPa, etc. Semi-rigid materials may have an elastic modulus (e.g., Young's modulus) of between about 0.04 and about 4 GPa, for example. Material having a range of Young's modulus such as 0.5 GPa to 100 GPa, 0.9 GPa to 100 GPa, etc., may also be preferred.

A 3D structure as described herein may also be rigid or semi-rigid based on the structural stiffness. Stiffness is understood to refer to resistance to deformation in response to applied force, and may be described in terms of force per unit length (e.g., newtons per meter or pounds per inch). Stiffness, particularly of three-dimensional structures may be described a deflections in a particular dimension (e.g., degree of freedom); for simplicity, stiffness (rigidity) may refer to stiffness in the direction(s) opposing crushing forces, of the 3D structure when applied to a subject. As described herein, structural elements may be formed into the 3D structure to increase the rigidity (stiffness) of the material, including ridges, ribs, and the like, which may buttress and support the structure, increasing its relative rigidity.

As examples, 3D structures may use materials with tensile strength of 70-80 N/mm$^2$, notched impact strength of 60-80 Kj/m$^2$, thermal coefficient of expansion 65×10$^{-6}$, maximum continuous use temperature of 125° C., and density 1.20 g/cm$^3$. In other cases, materials may have a tensile strength of 0.20-0.40 N/mm$^2$, thermal coefficient of expansion 100-220×10$^{-6}$, maximum continuous use temperature of 65° C. and density 0.944-0.965 g/cm$^3$. In other cases, tensile strength may be approximately 9500 psi, flexural modulus of approximately 345,000 psi and a coefficient of linear thermal expansion of 3.8 in/in/° F.×10$^{-5}$ though these values may be increased or decreased by +/−30% depending on the exact material chosen.

The adhesive devices described herein may be composed of layers. Layered devices (which may also be referred to as layered adhesive devices or layered adhesive medical devices) may be completely or partially flexible, as previously mentioned. For example, a layered device may include a pad and medicament and an adhesive holdfast layer that secures the adhesive device in communication with the skin. The adhesive holdfast layer may itself include a flexible substrate that includes a biocompatible adhesive.

Any of the devices described herein may also include an anatomic guide, such as a ring, a conical alignment guide, a tactile alignment guide, or a visual alignment guide, which enables or facilitates placement of the device on or around an anatomic site on the subject's body.

In some variations, the device may further include a support frame. The support frame may be removable and/or removably attached to another portion of the device including the adhesive substrate, the adhesive layer or another portion of the device including rigid portions of the device that may be made from plastic. For example, the support frame may support the device, including the holdfast region of the device, and be completely or partially removable after the device has been applied to the subject. In some variations, the support frame remains on the device after application. The support frame may serve to make application of the device easier or to prevent the holdfast from unintentionally attaching to itself, to another portion of the device or to the subject. As mentioned, any of these devices may also include a support frame. In some variations, the support frame is a support frame layer.

Also described herein are methods of treating a subject that include the steps of removing a protective cover or liner from a layered adhesive holdfast of an adhesive device and placing the layered device in communication with the subject's skin.

Also described are methods of fabricating a layered medical device, including the steps of forming an adhesive layer comprising a biocompatible adhesive and forming a rigid three dimensional layer, cutting the rigid three dimensional layer (including laser cutting) and accurately attaching this rigid layer to the layered device.

The adhesive devices described herein may be fabricated by batch or continuous fabrication methods, and may include the use of web converting to enable the production of very large volumes of product at low cost. The layered devices described herein may be contrasted with previously described adhesive devices that were made by other methods that required more assembly time, required "pick-and-place" assembly of injection molded parts, or were not able to be produced at low cost.

An adhesive device may be adapted to be removably secured in communication with a subject's skin and configured to provide a medicament (which may be a liquid, semi-liquid, paste, ointment, gel, liquid matrix, liquid/solid mix, solid, fluid or semi-fluid) to a subject's skin or nails for a sustained duration to provide a benefit to the subject. Medicaments may include various OTC and prescription medications, antibiotics, antifungals or other active ingredients. Adhesive devices that deliver antibiotics may be beneficial in preventing bacterial infection, promoting healing or reducing scar formation. Adhesive devices that deliver antifungals may be used to treat toenail fungus or other fungal skin conditions. Other adhesive devices described herein deliver medicaments that may deliver tar (for example to treat psoriasis), petroleum jelly, moisturizers, oils, extracts, minerals or vitamins to the skin or nails (e.g., to make them stronger, healthier or to improve appearance), and may include other active ingredients as described herein. The medicament may comprise an odorant, such as a fragrance. In some versions, the active agent comprises menthol, eucalyptus oil, and/or phenol. Such devices may be applicability in treating humans and in some cases may have veterinary applications for the treatment of cats, dogs, horses, alpacas and the like.

In some cases, a protective cap is removably attached to the holdfast (and more specifically at least partly attached to the adhesive layer of the holdfast) which serves to protect and/or seal a medicament prior to use by the subject. This protective cap is generally a rigid or semi-rigid three dimensional structure that has been optimized for the purpose of protecting the medicament. As such the protective cap provides a physical barrier that may prevent or minimize migration or movement of the medicament off the pad, especially during storage and transport. This protective cap may serve to reduce evaporation of components of the medicament, thereby maintaining the medicament in a more preferred liquid or fluid state. In other cases, the protective cap may have one or more holes, which may enable evaporation thereby hardening or making more solid the medicament on the pad of the adhesive medical device. The protective cap (or cover, barrier cap, protective cover, vacuum cap, etc.) may also include a selectively compressible region that can be activated by applying force (e.g., from a hand or finger) to deform the region. Such elements may be bistable, so that deformation of this activatable region may be achieved by applying force above some threshold to "snap" the structure from a first configuration to a second configuration. Bistable sub-structures may be useful for protecting, then delivering upon user activation, a medicament as illustrated and described below.

In some cases, a barrier cap is removably attached to the holdfast (and more specifically at least partly attached to the adhesive layer of the holdfast) and serves to protect the wound or other treatment site of the subject. This barrier cap is generally a rigid or semi-rigid three dimensional structure that has been optimized for the purpose of protecting a wound. The barrier cap may also contain a medicament and/or gauze or foam or another hemostatic agent.

In some devices, the shape of the adhesive holdfast may be optimized to comfortably fit an anatomic body site, such as parts of the face, hands, wrists, fingers, legs, ankles, toes, toe or finger nails, ostomy sites, breast, ear, earlobe, arm, chest, thorax, pelvis and the like. In some cases, the adhesive holdfast is designed to be sufficiently flexible to enable comfortable movement of the user, especially when the adhesive device is located on or close to a joint. In other cases, the device may be used to stabilize a joint or prevent motion of a joint.

In other cases, the adhesive device is designed to help support the function of another body part or another medical device, including intravenous (IV) catheters, peripherally inserted central catheters (PICC) or central venous catheters (CVC), urinary catheters, other types of catheters, endotracheal tubes, nasogastic/orogastric tubes, activity monitors as a few examples. For example, an adhesive medical device that comprises an adhesive holdfast that surrounds and securely and releaseably attaches to a portion of an IV catheter may provide stabilization of the IV catheter, preventing its motion which is a can cause pain or injury to the vein. A similar design can used to stabilize urinary catheters or PICC/CVC lines, in which an adhesive holdfast is attached to a more rigid, plastic structure on the adhesive medical device which removeably attaches to and secures an indwelling catheter. In other cases, the adhesive medical device may be useful in the management of stoma sites. For example, ostomy devices with integrated, rigid or semi-rigid rings that are fixed on an adhesive substrate (such as a hydrocolloid) may find use. In this case, the ostomy device (or ostomy "wafer") may be attached to an ostomy or urostomy bag.

Additionally, adhesive devices are described in which the patient is treated with negative pressure wound therapy, in which an adhesive holdfast creates a seal against the subject's skin and a chamber provides negative pressure to the subject's wound to promote more rapid healing. The negative pressure within the chamber may be created by one or more of several means including patient actuation of a small vacuum chamber or by an external bulb or similar device that creates negative pressure and is attached to a tube. A negative pressure wound therapy device and methods of manufacturing and using said device are described and illustrated herein. The device may include a wound dressing, a plastic cover including an integrated adapter, tubing, and a vacuum source.

As mentioned, an adhesive holdfast may include a flexible adhesive substrate, and/or a protective cover or liner (configured to be removed, for example, by peeling off to expose the adhesive of the adhesive layer). The device may also include a tab or handle configured to be grasped by a subject applying the device. In some variations, this tab or handle is formed from a region of the layered adhesive holdfast.

The various components of the device may be made of any appropriate materials, as described in greater detail below. For example, various components of the device (e.g., protective or barrier cap regions) may be made of medical grade plastic, such as Acrylonitrile Butadiene Styrene (ABS), polypropylene, polyethylene, polycarbonate, polyurethane or polyetheretherketone. The adhesive holdfast may include an adhesive substrate made of silicone, polyurethane or polyethylene. Examples of biocompatible adhesive on the adhesive holdfast may include hydrocolloids, hydrogels or acrylics.

Also described herein are methods of making any of the adhesive support devices described herein. For example, described herein are methods of making an adhesive support device having a three-dimensional shape, the method comprising: placing a planar sheet of material between a first tool and a second tool, wherein the sheet of material extends in a first plane and wherein the material has an elastic modulus of greater than 0.4 GPa; stamping the planar sheet of material between the first tool and the second tool to deform a portion of the material so that it forms a cavity portion extending out of the first plane that is surrounded by a base region extending in the first plane; and securing an adhesive substrate to at least a portion of the base region.

Any of the methods of making an adhesive support device having a three-dimensional shape may include: placing a planar sheet of material between a first tool and a second tool, wherein the sheet of material extends in a first plane and wherein the material has an elastic modulus of greater than 0.4 GPa; stamping the planar sheet of material between the first tool and the second tool to deform a portion of the material so that it forms a cavity portion extending out of the first plane, wherein a wall of the cavity portion comprises one or more ridges increasing the rigidity of the cavity portion; and securing an adhesive substrate to a base region extending in the first plane wherein the base region is a portion of the planar sheet peripheral to the cavity portion.

For example, a method of making an adhesive support device having a three-dimensional shape, the method comprising: placing a planar sheet of material between a first tool and a second tool, wherein the sheet of material extends in a first plane, wherein the material has an initial thickness, and wherein the material has an elastic modulus of greater than 0.4 GPa; stamping the planar sheet of material between the first tool and the second tool to deform a portion of the material so that it forms a cavity portion extending out of the first plane that is surrounded by a base region extending in the first plane, wherein a ratio of a maximum length of the cavity portion in the first plane to a maximum depth of the cavity portion out of first plane is greater than 2:1, further wherein a wall thickness of the cavity portion is less than the initial thickness while the thickness of the base region is approximately the same as the initial thickness; and securing an adhesive substrate to at least a portion of the base region.

Securing an adhesive substrate to at least a portion of the base region may comprise securing the adhesive substrate so that the adhesive substrate is covered on a face opposite from the base region by a liner.

Because of the manner in which the devices described herein are fabricated, e.g., by stamping, pressing, cold pressing, etc. an initially flat piece of rigid or semi-rigid material into a 3D shape, any of the structures described may have structural features that are characteristic of this formation process; these features may have functional benefits. For example, a wall thickness of the cavity portion may generally be less than an initial thickness of the planar sheet of material, while the thickness of the base region may be approximately the same as the initial thickness. Similarly, a ratio of a maximum length of the cavity portion in the first plane to a maximum depth of the cavity portion out of first plane may be greater than 2:1 (e.g., the depth may be much less than the length).

In general, a wall of the cavity portion may comprise one or more ridges increasing the rigidity of the cavity portion.

The angles of all walls of the cavity portion relative to adjacent portions of the base region extending in the first plane may be greater than 90° and less than 180°. This angle (e.g., non-normal) wall, may be useful for cutting, particularly when cutting the device from above (perpendicular to the plane of the base region). For example, the method of forming may include laser cutting one or more walls of the cavity portion using a laser that is oriented perpendicular to the first plane. In general, the method may include cutting around the base region to release the adhesive support device from the planar sheet of material.

Multiple stamping/forming steps may be performed as part of the formation. For example, the method may include stamping the planar sheet of material between a third tool and a fourth tool to further deform the cavity portion so that it extends further out of the first plane.

As mentioned above, in general, the method of forming any of these device may be performed with the tool at room temperature (e.g., "cold" stamping).

Stamping the planar sheet of material between the first tool and the second tool may comprise compressing the planar sheet of material between complementary sides of a die, wherein the first tool forms an upper side of the die and the second tool forms lower side of the die.

In any of the variations described herein, any of the stamped projections formed in the material may then be flattened (e.g., flattening the cavity region) which may increase support and reduce the device profile.

Stamping a material (having the appropriate Young's modulus) may comprise forming a cavity region having a lattice pattern extending in parallel to the first plane; the lattice may enhance stiffness. The material may have a Young's modulus of great than 0.4 GPa, greater than 0.5 GPa, greater than 0.6 GPa, greater than 0.7 GPa, greater than 0.8 GPa, greater than 0.9 GPa, greater than 1.0 GPa, between 0.4 GPa and 100 GPa, between 0.4 GPa and 80 GPa, etc. Exemplary materials that may be used generally include a polycarbonate material (having a Young's modulus/modulus of elasticity of between about 2.0-2.6 GPa), a polyethylene material (having a Young's modulus/modulus of elasticity of between about 0.11-1 GPa, e.g., approximately 0.11 to 0.45 GPa for low density polyethylene, about 0.7-1.0 GPa for high-density polyethylene), or a polyethylene terephthalate material (having a Young's modulus/modulus of elasticity of between about 2-2.7 GPa). In general, the Young's modulus can be used to predict the elongation or compression of an object as long as the stress is less than the yield strength of the material.

In general, placing comprises placing the planar sheet between projecting surfaces of the first and second tool that have only rounded edges. This may also result in device having projecting regions (e.g., cavity regions, hub regions, etc.) having rounded edges on all projecting surfaces.

Stamping the planar sheet of material between the first tool and the second tool to deform the material may comprise stamping an elongate hinge region in the material, and further comprising forming a living hinge by folding the material along the elongate hinge region.

In forming the devices, one or more regions may be cut (e.g., die cut, laser cut, etc.). For example the methods may include die cutting one or more openings through the material.

The material of the initial sheet may comprise a polycarbonate, a polyethylene, or polyethylene terephthalate.

For example, described herein are adhesive support devices having a three-dimensional shape, the device comprising: a body portion comprising a sheet of material, the material having an elastic modulus of greater than 0.4 GPa, wherein the sheet has been deformed from a flat plane to form: a base region extending in the flat plane, the base region having a first thickness; and a cavity region having a thickness that is less than the first thickness, the cavity region at least partially surrounded by the base region, wherein the cavity region extends out of the flat plane at an angle that is greater than 90° relative to an adjacent base region; and an adhesive substrate portion coupled to at least a portion of the base region, wherein the adhesive substrate comprises a liner on a face opposite from the base region.

An adhesive support device having a three-dimensional shape may include: a body portion comprising a sheet of material, the material having an elastic modulus of greater than 0.4 GPa, wherein the sheet has been deformed from a flat plane to form: a base region extending in the flat plane, the base region having a first thickness; and a cavity region having a thickness that is less than the first thickness, the cavity region at least partially surrounded by the base region, wherein the cavity region extends out of the flat plane, wherein a volume of material in any section of a continuous portion of the base region bounded by an arbitrary shape projected from a plane that is parallel to the flat plane is approximately equal to a volume of material in any section of a continuous portion of the cavity region bounded by the arbitrary shape projected from the plane that is parallel to the flat pane; and an adhesive substrate portion coupled to at least a portion of the base region.

An adhesive support device having a three-dimensional shape may include: a body portion comprising a sheet of material, the material having an elastic modulus of greater than 0.4 GPa, wherein the sheet has been deformed from a flat plane to form: a base region extending in the flat plane, the base region having a first thickness, a cavity region at least partially surrounded by the base region, wherein the cavity region extends out of the flat plane, and one or more ridges in a wall of the cavity region increasing the rigidity of the cavity portion, wherein the volume of material in any section of a continuous portion of the base region bounded by a shape projected from a plane that is parallel to the flat plane is approximately equal to the volume of material in any section of a continuous portion of the cavity region bounded by the shape projected from the plane that is parallel to the flat pane; and an adhesive substrate portion coupled to at least a portion of the base region, wherein the adhesive substrate comprises a liner on a face opposite from the base region.

In general, because of the manner in which the devices described herein are formed (e.g., by cold pressing) any of these device may include different regions, such as the base region and the cavity region (or hub region), and the volume of material in any section of a continuous portion of the base region bounded by a shape projected from a plane that is parallel to the flat plane is approximately equal to the volume of material in any section of a continuous portion of the cavity region bounded by the shape projected from the plane that is parallel to the flat pane. This is illustrated in FIG. 72. In this example, a section through a device 7200 formed as described herein is shown. A projection of an arbitrary shape 7202 is made up from a plane parallel to the plane of the base region. The volume of material contained within the portion of the base region enclosed within the projected shape is shown 7210 in this cross-section as a darker region. This volume of material is equivalent to the volume of material 7212 within a portion of non-base (e.g., a cavity region or hub region) region that is contained within a non-base portion enclosed by same projected shape 7205, when it is projected up from the same plane.

As mentioned, any of these devices may include one or more ridges in a wall of the cavity region increasing the rigidity of the cavity region. The devices may include one or more cut-out sections on a wall of the cavity region, wherein the wall is angled greater than 90° relative to an adjacent base region.

A ratio of a maximum length of the cavity portion in the flat plane to a maximum depth of the cavity portion perpendicular to the flat plane is greater than 1:1 (e.g., 2:1, 3:1, 4:1, etc.). The angle of all walls of the cavity portion relative to the first plane are greater than 90° and less than 180° relative to an adjacent base region. The base region may form a lip of greater than 0.5 mm around the cavity portion. The cavity region may comprise a lattice pattern extending in parallel to the first plane to enhance stiffness. As mentioned, in general, all projecting surfaces of the cavity region have rounded edges.

Any of these devices may include an elongate hinge region in the material, forming a living hinge by folding the material along the elongate hinge region.

In general, the cavity (or hub) region may extend up from the base region by between about 1 mm and about 50 mm.

Any 3D structure may be formed of any appropriate thin layer (sheet) or material having the requisite Young's modulus as described herein. For example, the material may comprise a polycarbonate, a polyethylene, a polyethylene terephthalate, etc.

An example of a device as described herein configured as a medical device is an intraosseus needle securement device stamped from a sheet of material into a three-dimensional shape. In this example, the device may include: a body portion comprising a sheet of material having an elastic modulus of greater than 0.4 GPa, wherein the sheet has been stamped from a flat plane to form: a base region extending in the flat plane, the base region having a first thickness, and a hub region surrounded by the base region, the hub region having a maximum wall thickness that is equal to or less than the first thickness, wherein the hub region extends from the flat plane at an angle that is greater than 90° relative to an adjacent base region, the hub region having an opening configured to secure an intraosseus needle, and a plurality of ridges in the hub region extending from the base region towards the opening and configured to increase stability of the hub relative to the base region; and an adhesive substrate coupled to the base region and configured to secure the device to a patient's skin.

For example, an intraosseus needle securement device stamped from a sheet of material into a three-dimensional shape may include: a body portion comprising a sheet of material having an elastic modulus of greater than 0.4 GPa, wherein the sheet has been stamped from a flat plane to form: a base region extending in the flat plane, the base region having a first thickness, and a hub region surrounded by the base region, the hub region having a maximum wall thickness that is equal to or less than the first thickness, wherein each wall of the hub region extend up from the flat plane at an angle that is greater than 90° relative to a nearest portion of the base region, the hub region having a central opening configured to secure an intraosseus needle, and a plurality of ridges in the hub region extending up toward the opening and configured to increase stability of the hub relative to the base region; and an adhesive substrate coupled to the base region and configured to secure the device to a patient's skin.

As mentioned above, the base region comprises a raised pattern extending in parallel to the first plane to enhance stiffness. The hub region may comprise a generally cylindrical shape (e.g., a cylinder with an outer wall that slopes or tapers slightly inward (forming a flattened cone or bullet shape, for example).

In general, the device described are adhesive devices. These devices may generally include a flat (planar) region having a back side to which the adhesive material is attached. The opposite (e.g., front) side of the device typically includes a three-dimensional structure stamped from a planar sheet of material so that the 3D structure extends out from the front side.

As mentioned above, the volume of material in any section of a continuous portion of the base region bounded by a shape projected from a plane that is parallel to the flat plane is approximately equal to the volume of material in any section of a continuous portion of the hub region bounded by the shape projected from the plane that is parallel to the flat pane.

The ratio of a maximum length of the hub portion in the flat plane to a maximum depth of the hub portion perpendicular to the flat plane is greater than 1:1.

The base region may form a lip of greater than 0.5 mm adjacent to the hub portion.

All surfaces of the hub region projecting from the flat plane may have rounded edges. The hub region may extend up from the base region by between about 1 mm and about 50 mm.

In general, the hub region may be continuous with the base region, or it may be separated from the base region by one or more intermediate regions.

As mentioned above, the material forming the base and hub region (from the initially planar sheet) may comprise a polycarbonate, a polyethylene, or polyethylene terephthalate.

BRIEF DESCRIPTION OF THE DRAWINGS

FIGS. 4A-4D are other variations of the adhesive medical device shown in FIG. 1.

FIGS. 9I-9R are various adhesive medical devices with barrier caps.

FIGS. 9U and 9V illustrate various shapes and sizes of protective caps for adhesive medical devices.

FIG. 15 shows the adhesive medical device shown in FIG. 11.

FIG. 16 illustrates the adhesive medical device of FIG. 11 after application to a user.

FIG. 17 shows another adhesive medical device that protects wires on a user.

FIGS. 18A and 18B show cross-section views of another adhesive medical device designed to create negative pressure wound therapy.

FIGS. 18M-18Q show the dressing and tubing of a negative pressure wound therapy device and a small device that may help stabilize the tube.

FIGS. 18R-18U show top (18R) and side perspective views (18S-18U) of another variation of a tubing holder.

FIGS. 18V-18X illustrate another variation of a tubing holder.

FIG. 18Y shows one variation of a plastic cap.

FIG. 18Z illustrates a method of forming a plastic cap.

FIGS. 21A and 21B illustrate cross-sectional views of variants of the medical device of FIG. 20.

FIG. 21C illustrates cross-sectional views of another adhesive medical device designed to stabilize an IV catheter.

FIG. 21D illustrates top down view of the adhesive medical device shown in FIG. 21C.

FIGS. 24L-24S illustrate variations of nasal splint devices as described herein.

FIG. 26A illustrates the placement of an intraosseous access device into the bone.

FIB. 26B illustrates the top view of an intraosseous access device being stabilized by an adhesive medical device.

FIG. 26C illustrates the side view of the device of FIG. 26B.

Figure 27A:
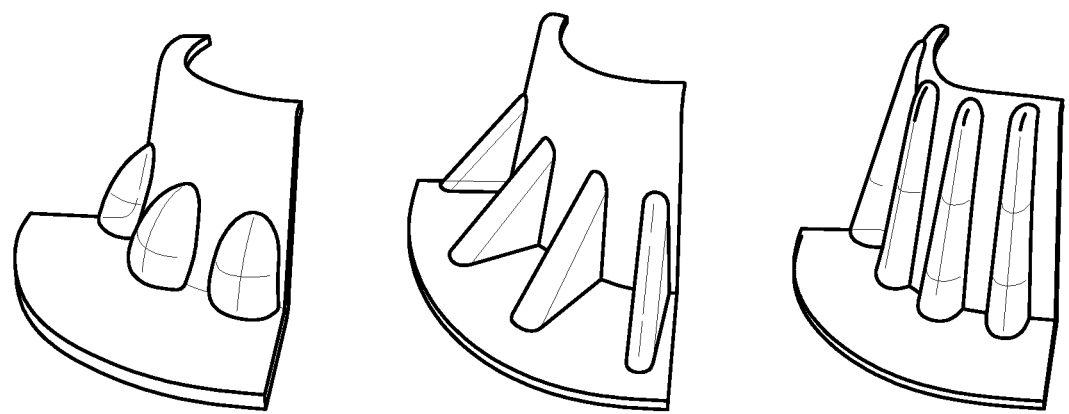
Figure 27B:
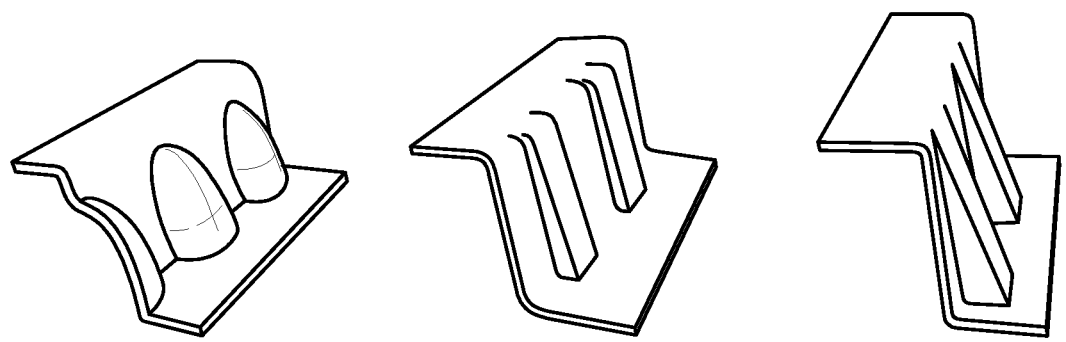

FIGS. 27A and 27B are various ridge or rib designs that offer increased stability to any plastic cone design of any product described herein.

FIGS. 28A-28G illustrate a series of novel ostomy products, including an ostomy wafer that snaps onto an ostomy bag.

Figure 29D:
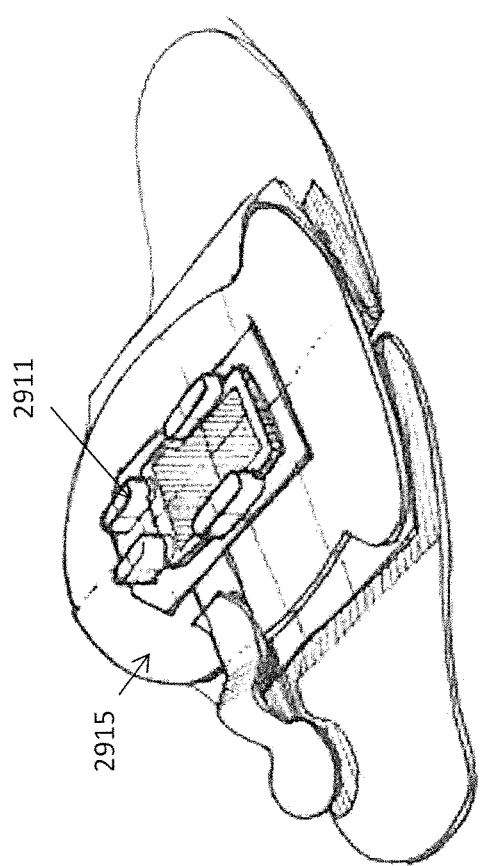
Figure 29E:
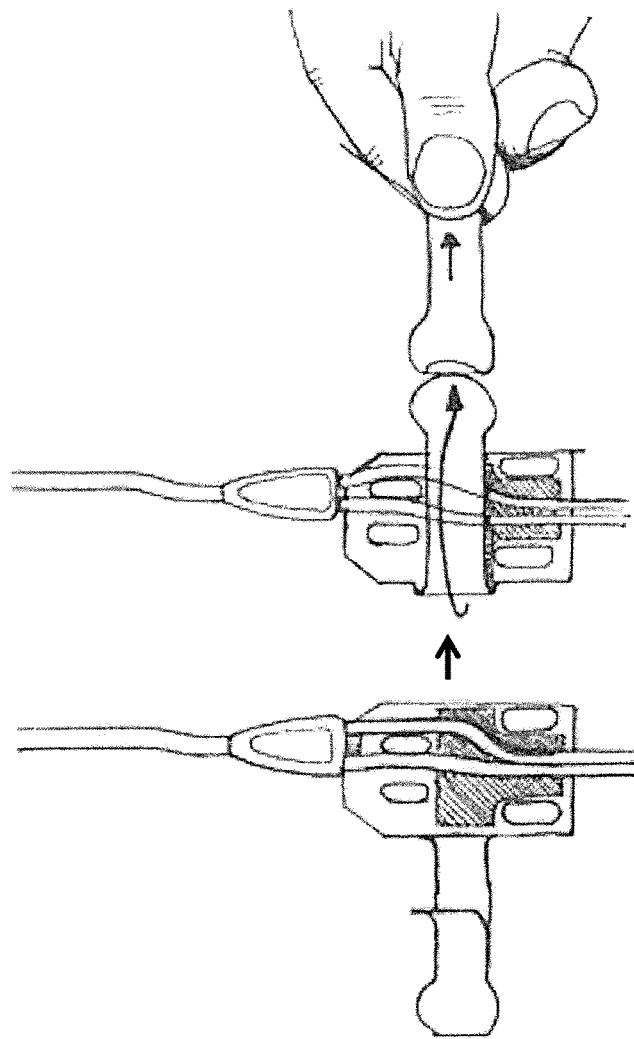
Figure 29G:
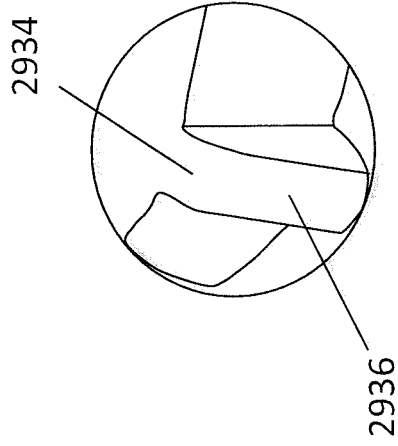
Figure 29H:
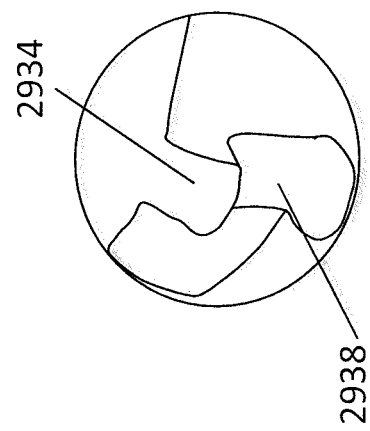
Figure 29F:
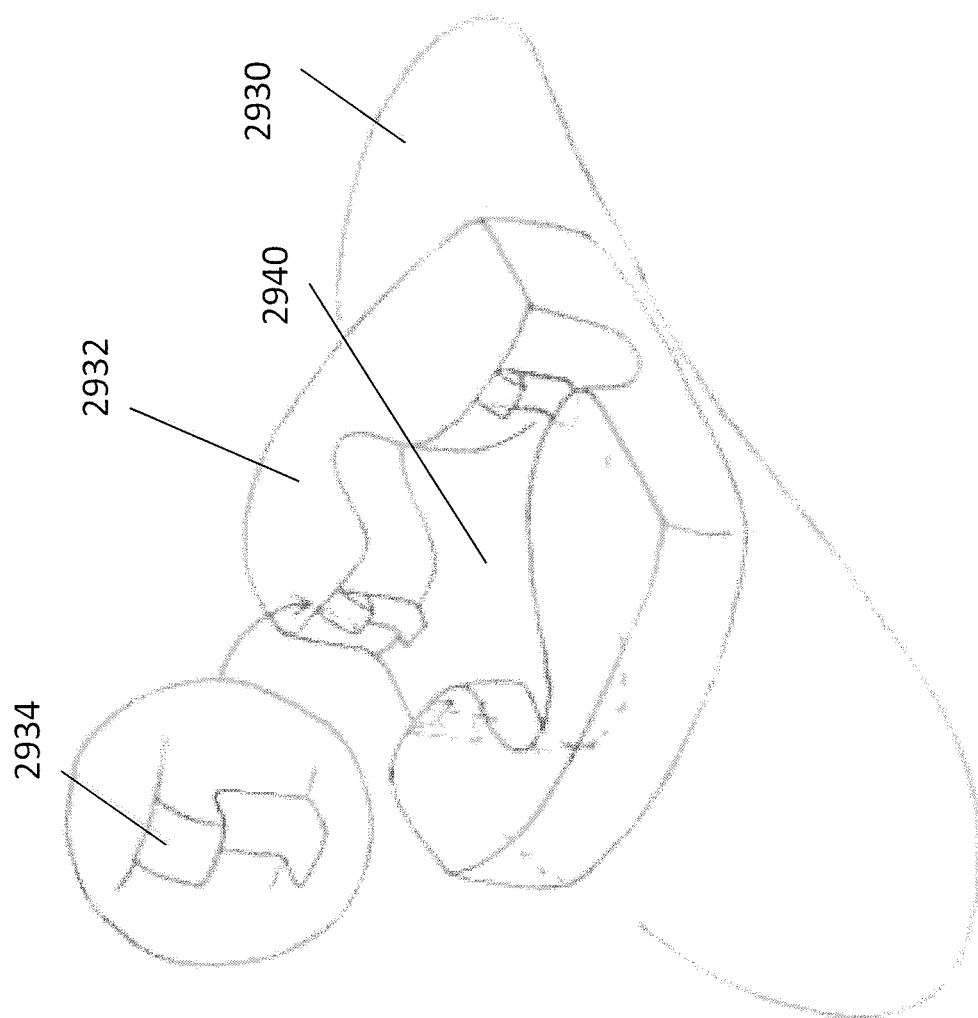

FIGS. 29A-29C illustrate top, side and top views, respectively, of a PICC line securement device. FIGS. 29D-29E show another variation of a PICC line guide device. FIG. 29F illustrates a PICC securement device. FIGS. 29G and 29H illustrate the formation of a snap region from a sheet of material using laser cutting.

Figure 30:
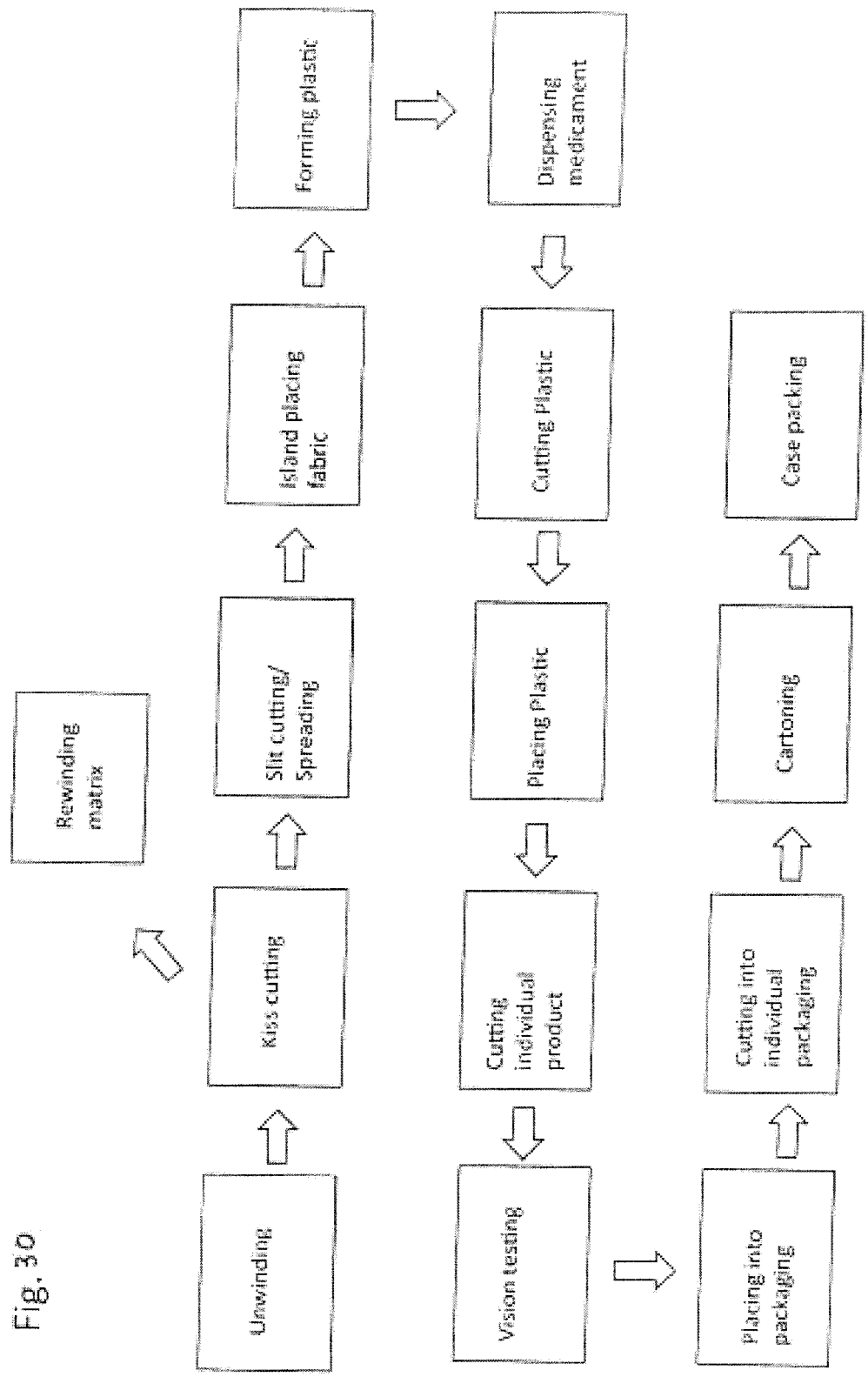

FIG. 30 illustrates the web-converting and packaging process that would be used to make any product with a 3D features attached to the adhesive holdfast.

Figure 31B:
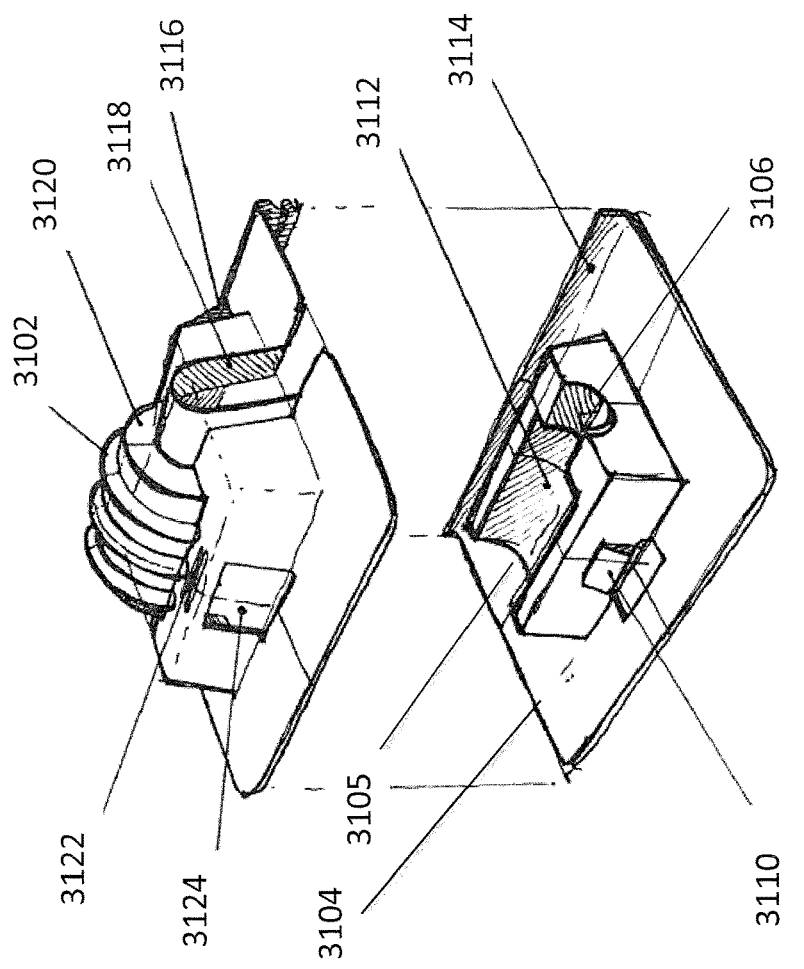
Figure 31A:
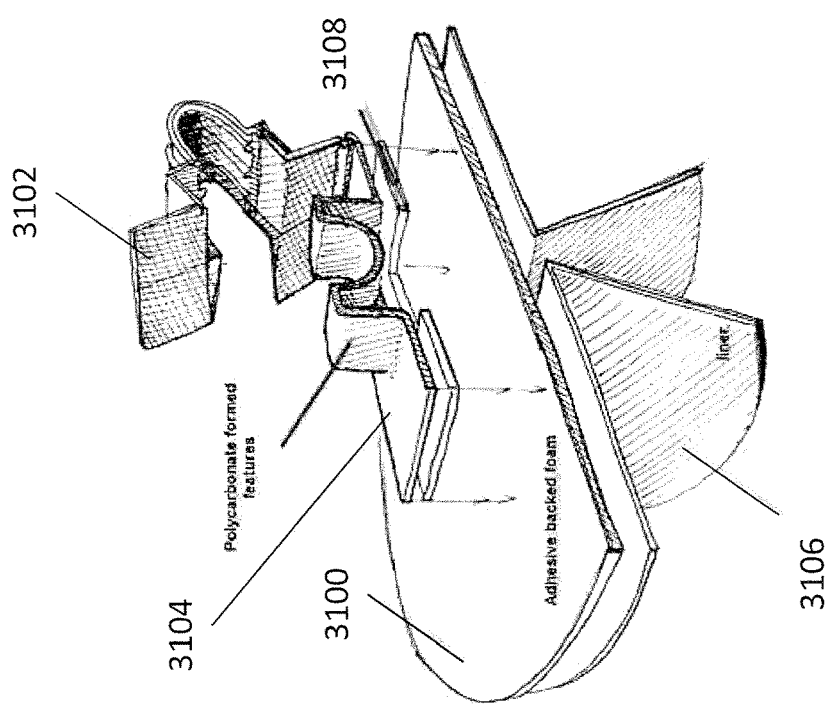
Figure 31E:
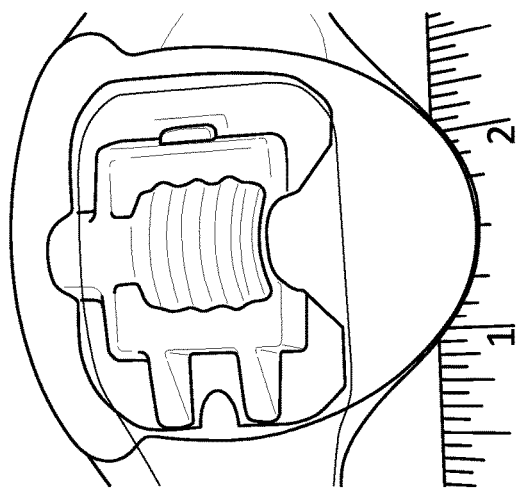
Figure 31F:
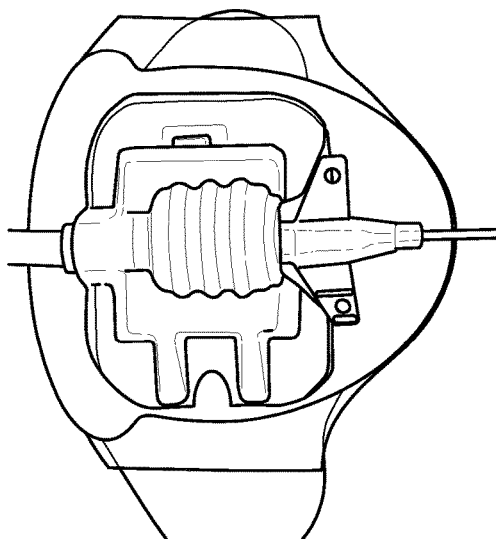
Figure 31C:
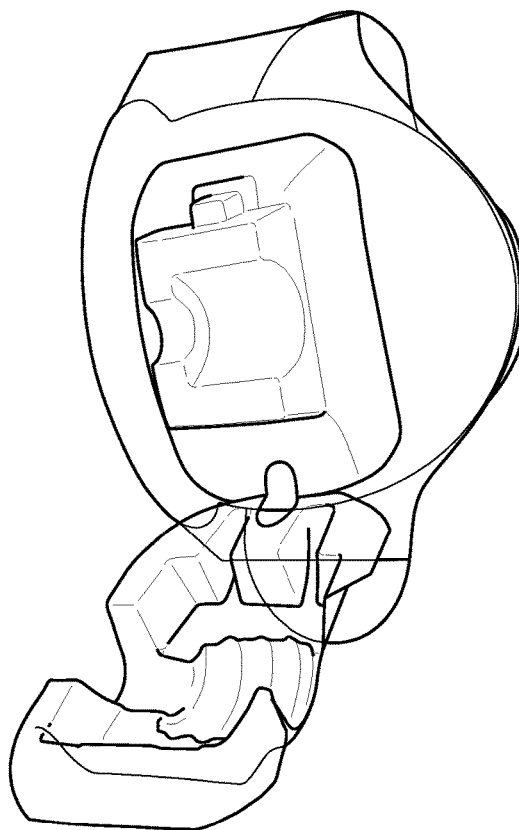
Figure 31D:
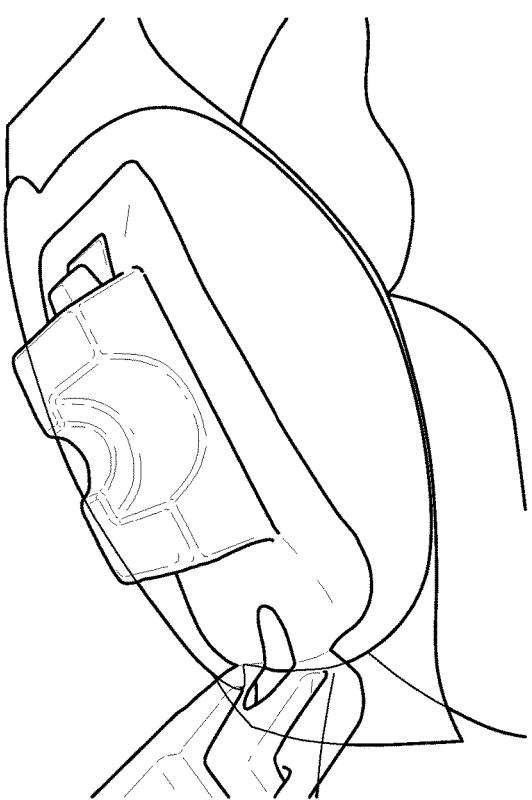

FIG. 31A shows a view of an IV securement device featuring a living hinge. FIG. 31B shows an exploded view of the device shown in FIG. 31A.

FIGS. 31C-31F show additional views of an IV securement device.

Figure 32C:
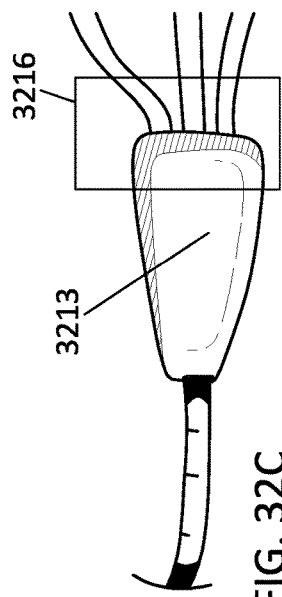
Figure 32D:
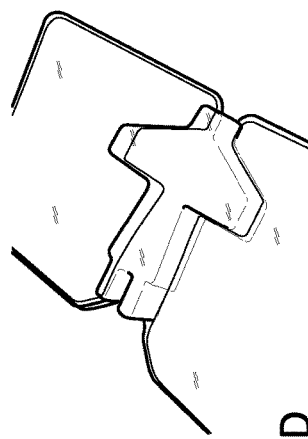
Figure 32E:
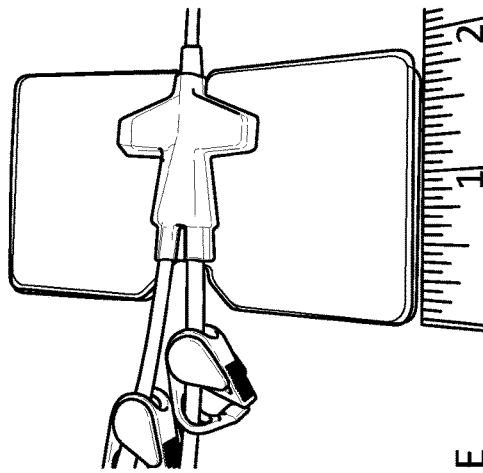
Figure 32A:
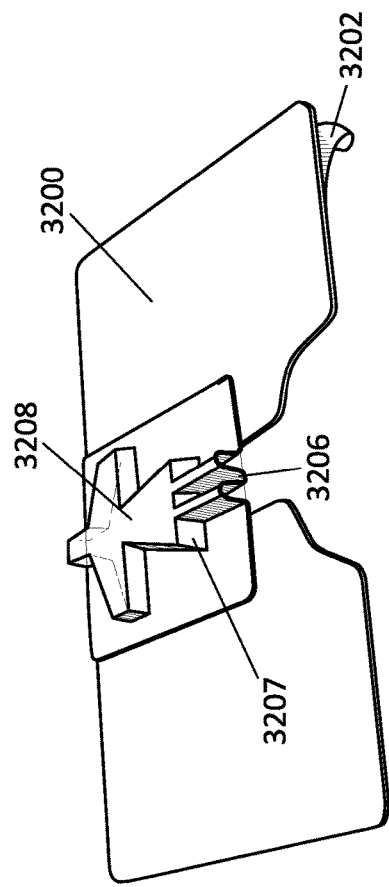
Figure 32B:
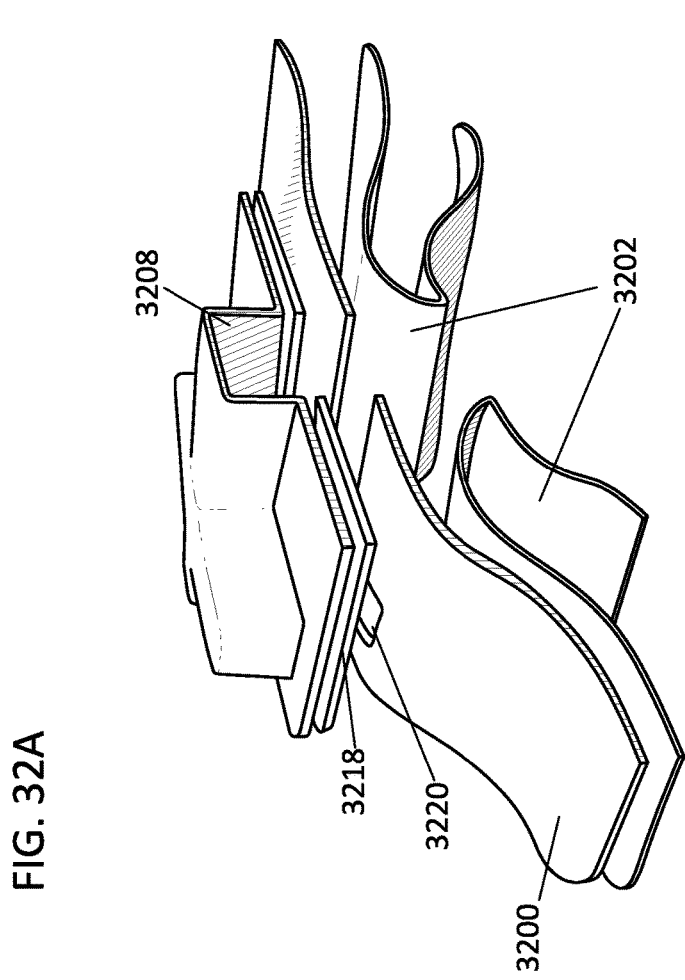

FIG. 32A illustrates a top down view of PICC securement device. FIG. 32B shows an exploded view of the device shown in 32A.

FIG. 32C illustrates a relatively rigid portion of a PICC device.

FIGS. 32D and 32E provide additional views of the PICC securement device shown in FIG. 32A.

FIGS. 32F-32K illustrate a PICC securement device with a living hinge.

FIG. 33A shows an example of warping of plastic that can occur during the forming process. FIGS. 33B and 33C show lattice structures that can minimize warping.

FIG. 33D shows a multi-step process that can minimize warping.

FIG. 34 illustrates various radii of curvatures for shapes created during the forming process.

Figure 35A:
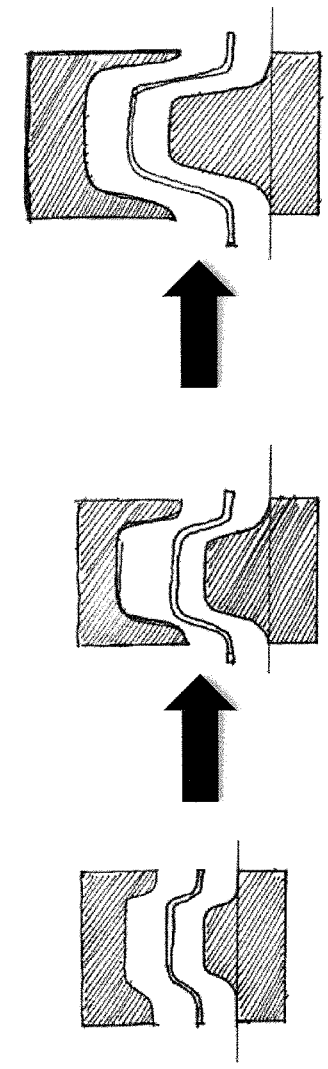
Figure 35B:
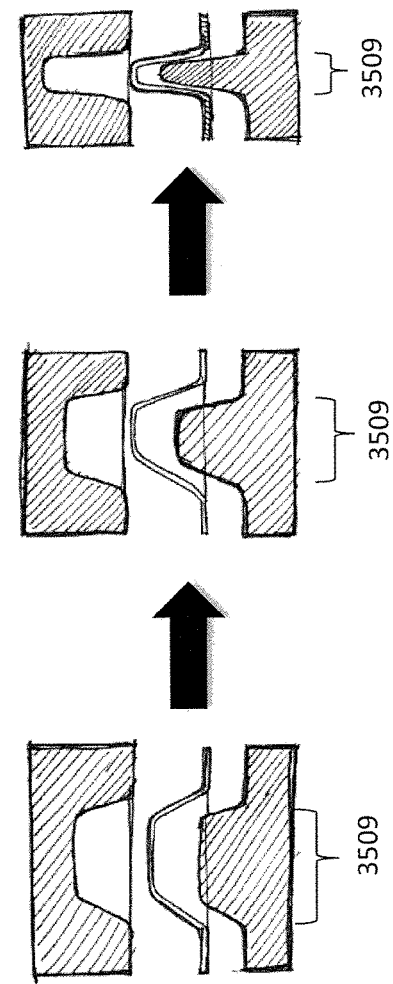
Figure 35C:
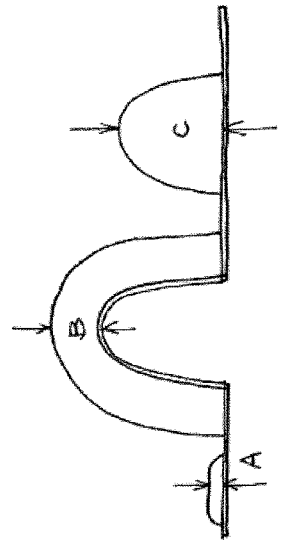

FIGS. 35A and 35B show the multi-step process of forming a 3D shape. FIG. 35C shows various shapes that have been formed to various depths.

FIGS. 36A-F illustrate different designs of living hinges that can be used in the subject devices.

Figure 37D:
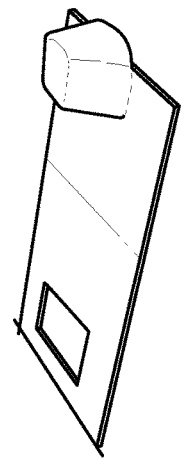
Figure 37E:
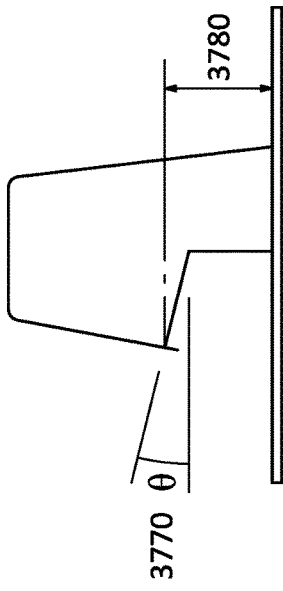
Figure 37F:
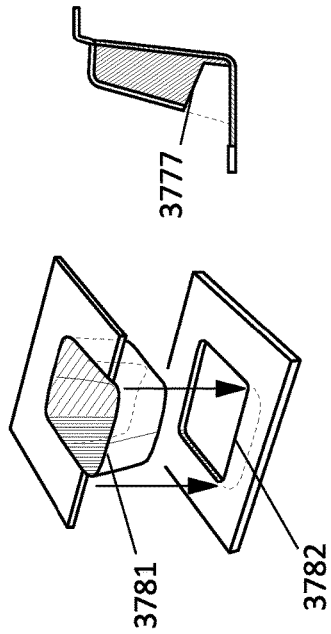
Figure 37A:
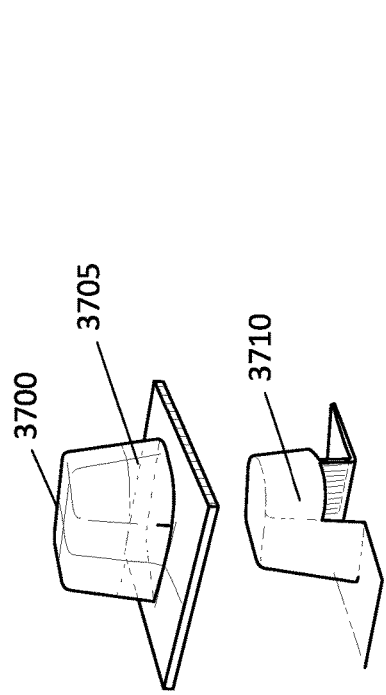

FIGS. 37A-O illustrate different designs of snap hooks that can be used in the subject devices.

FIGS. 38A-D show devices that secure a catheter and creates a loop of catheter within the device.

FIGS. 39, 40 and 41 illustrate devices that can be secure a tube or catheter having one of many thicknesses.

FIGS. 42A-D shows securement devices of activity monitors.

Figure 43:
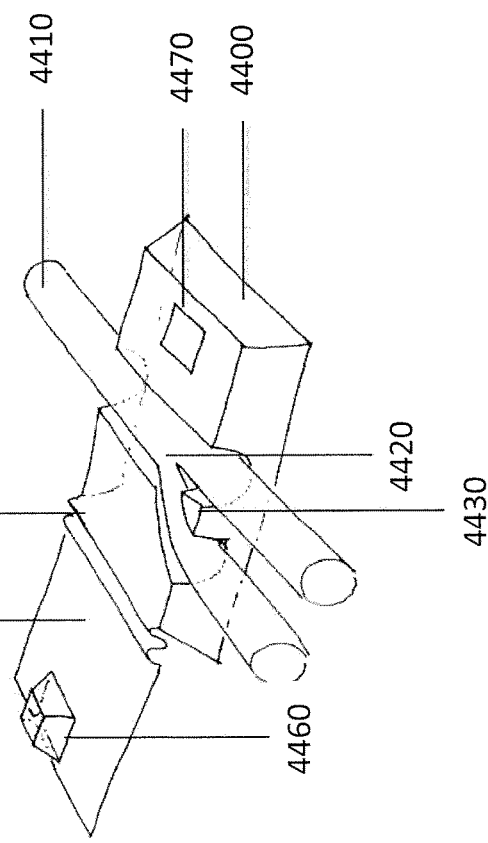
Figure 44:
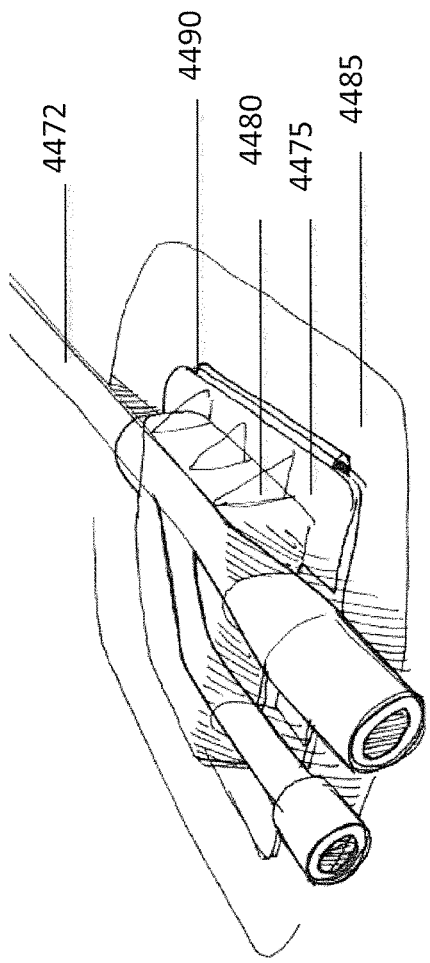

FIGS. 43 and 44 illustrate a urinary catheter securement device featuring a living hinge mechanism.

FIGS. 45A-45F illustrate hooks that can be used to secure household items.

FIGS. 46A and 46B illustrate hooks that can be used to secure household or medical items.

FIG. 46C, FIGS. 47-51 and FIGS. 52A and 52B each show a cord management device.

FIGS. 53A and 53B illustrates a household mini-storage device.

Figure 54:
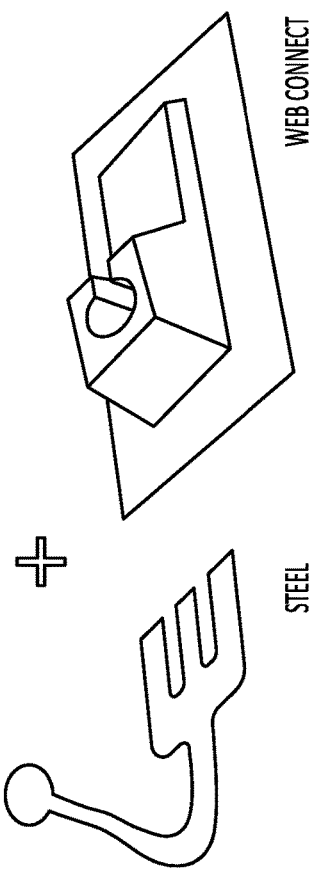

FIG. 54 shows a hook device.

Figure 56:
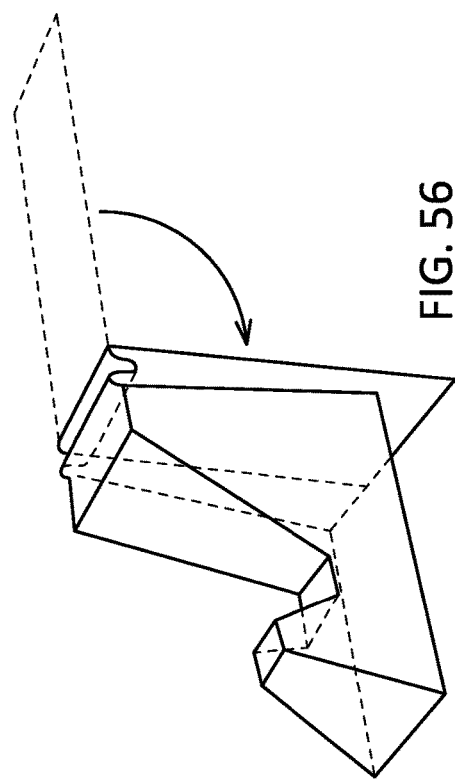
Figure 55:
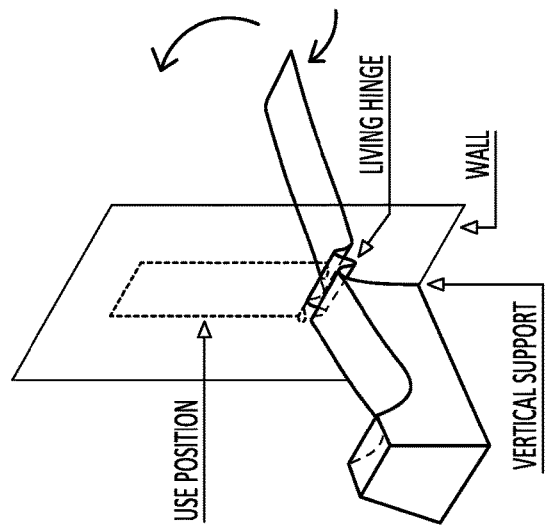

FIGS. 55 and 56 show hook devices with living hinge mechanisms.

Figure 57:
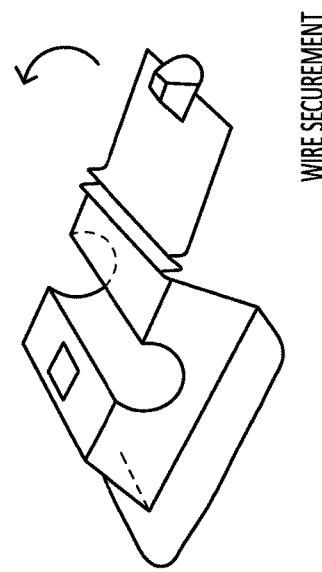
Figure 58:
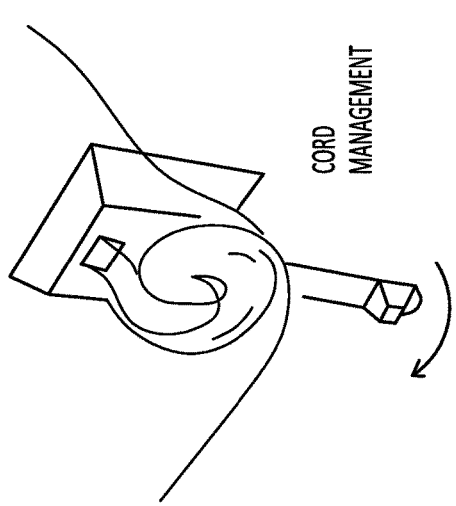

FIGS. 57 and 58 illustrate cable securement devices with living hinge mechanisms.

Figure 59:
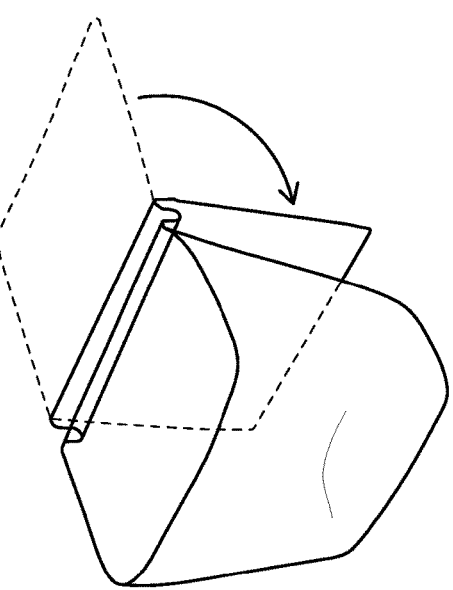

FIG. 59 shows a mini-storage device with a living hinge mechanism.

Figure 60A:
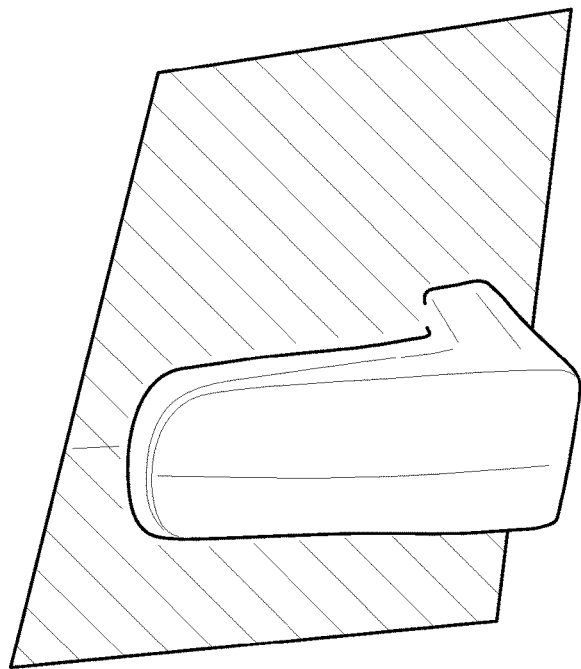
Figure 60B:
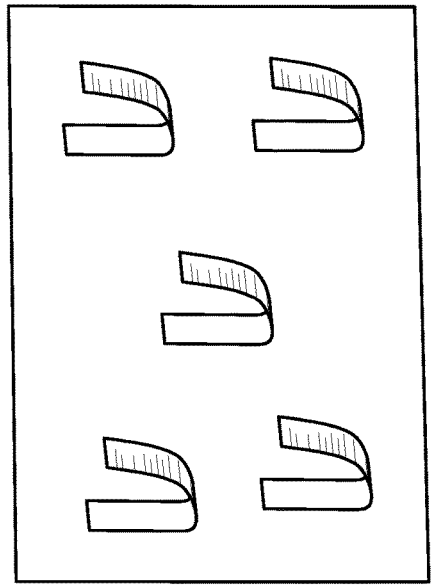

FIGS. 60A and 60B show hook devices.

FIGS. 61, 62, 63-65 show simple devices capable of holding objects.

FIGS. 66 and 67 illustrates a simple holder of household items such as business cards and souvenirs.

FIG. 68 shows devices that can mount a photograph or other graphic materials.

FIG. 69 illustrates a nasogastric tube holder.

FIG. 70 shows an endotracheal tube holder.

FIG. 71 illustrates an adhesive removal device.

Figure 72:
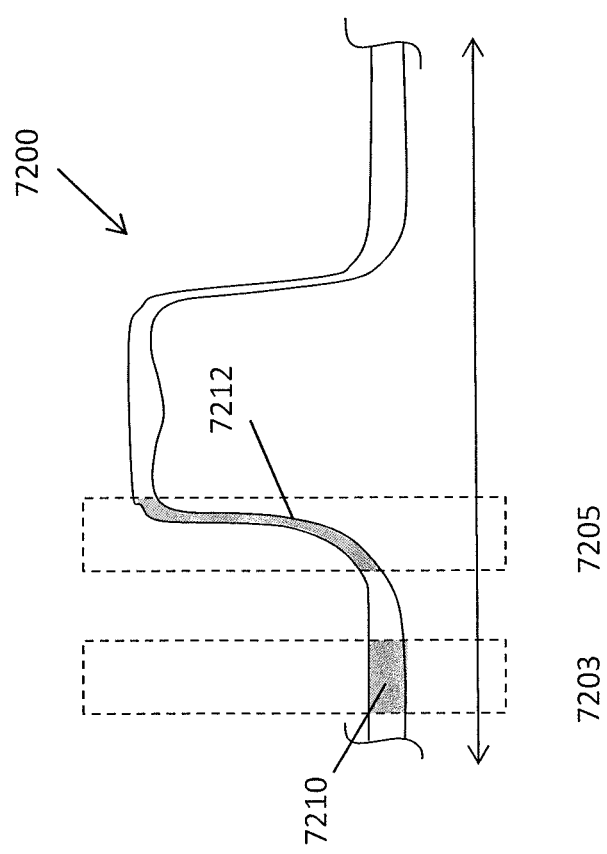

FIG. 72 illustrates volumes of material in section of different regions of an exemplary device formed as described herein.

Figure 73:
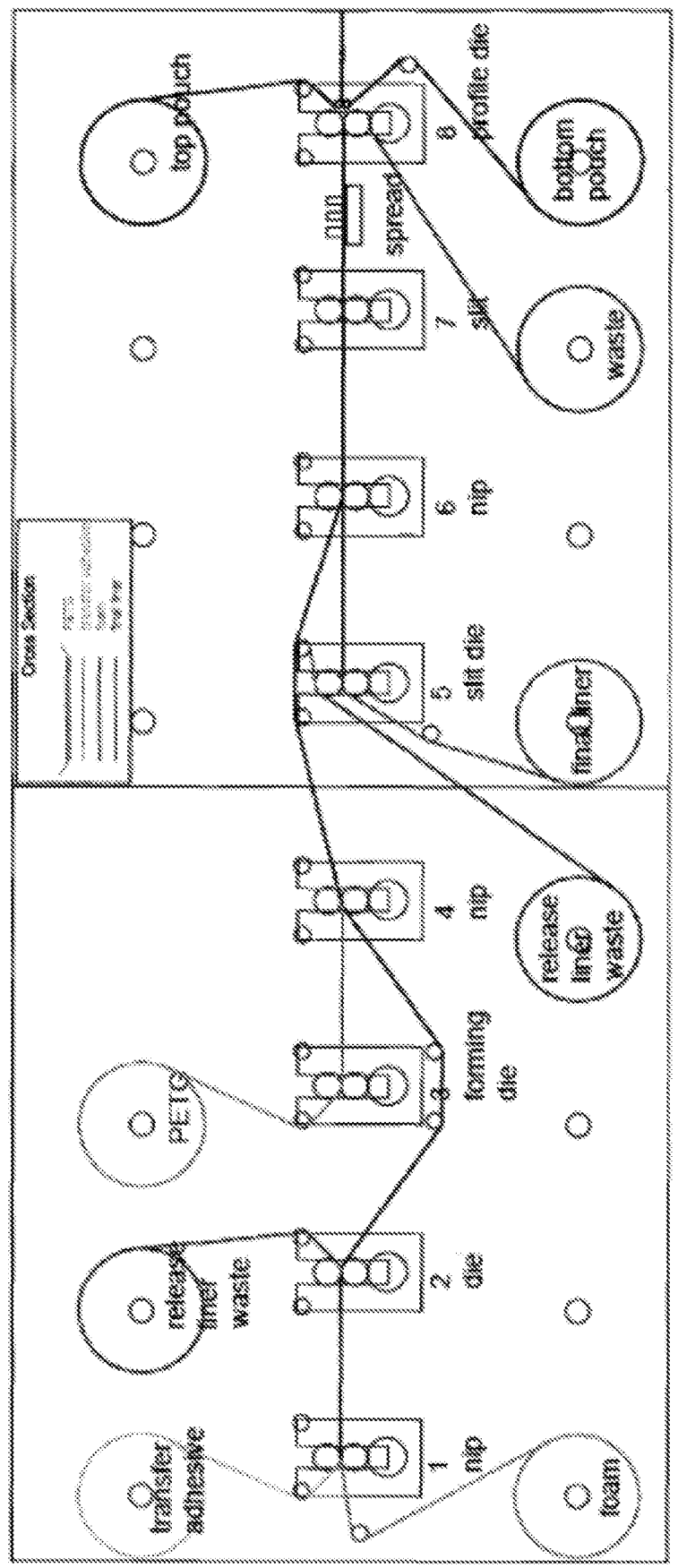

FIG. 73. illustrates one example of a manufacturing process diagram to make the devices described herein.

Figure 76:
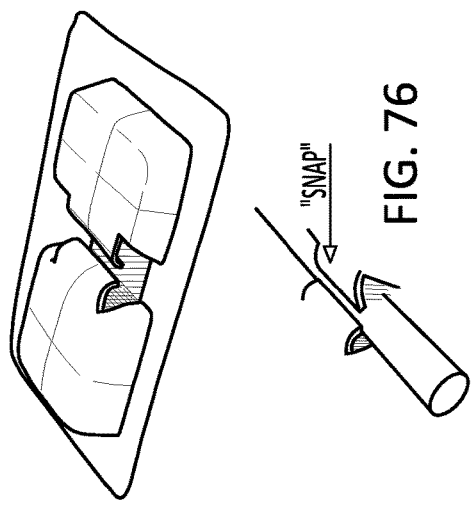
Figure 74:
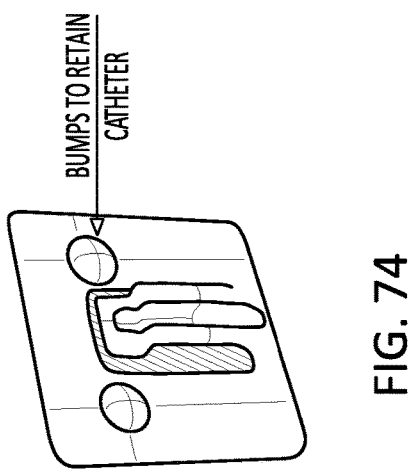
Figure 75:
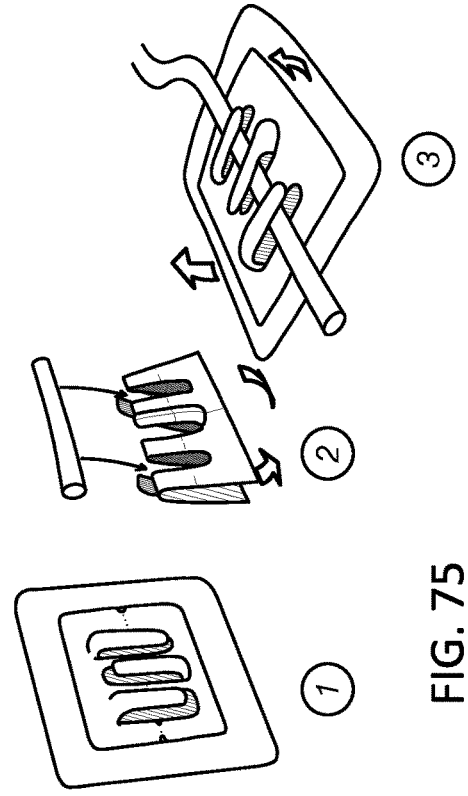

FIGS. 74-76 illustrate devices that can be used to secure tubing in place.

Figure 77:
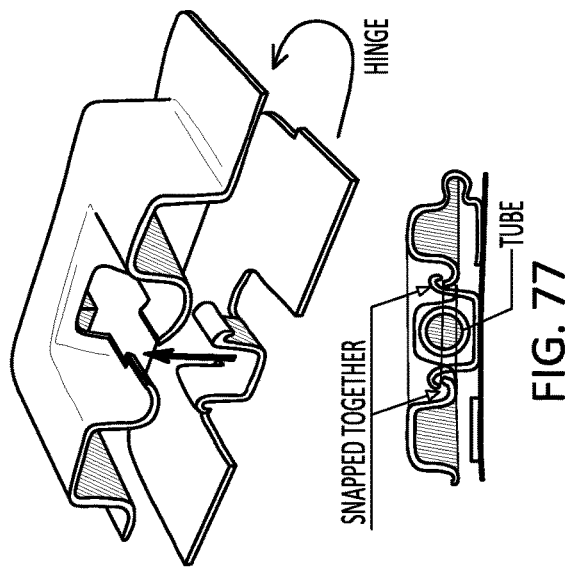

FIG. 77 illustrates a device featuring a living hinge mechanism to secure tubing.

Figure 78:
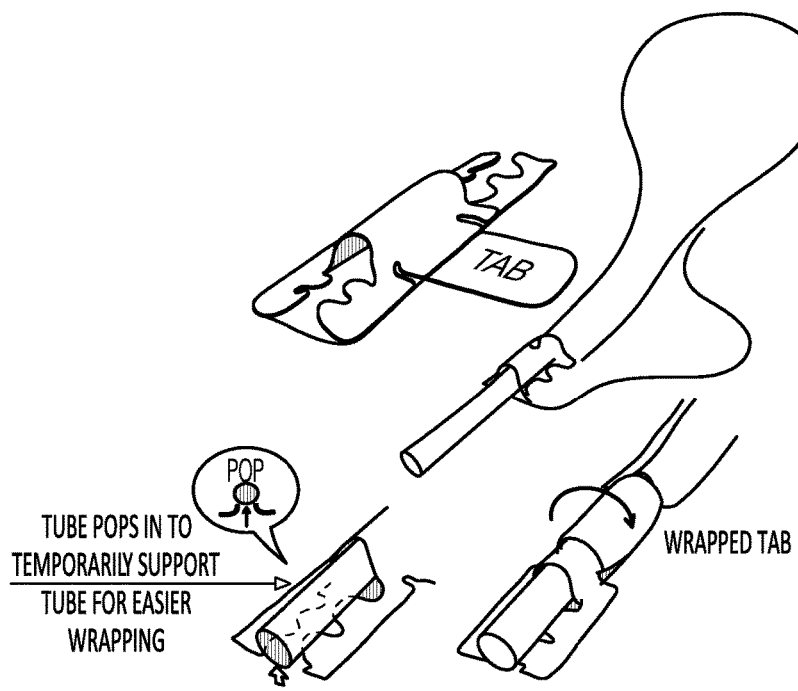
Figure 80:
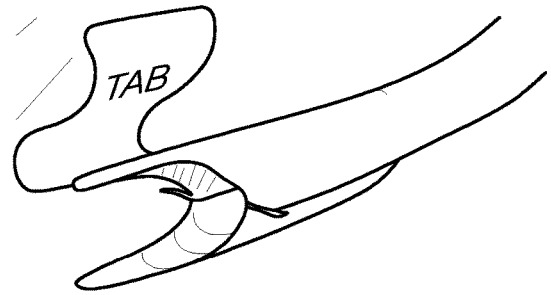
Figure 79:
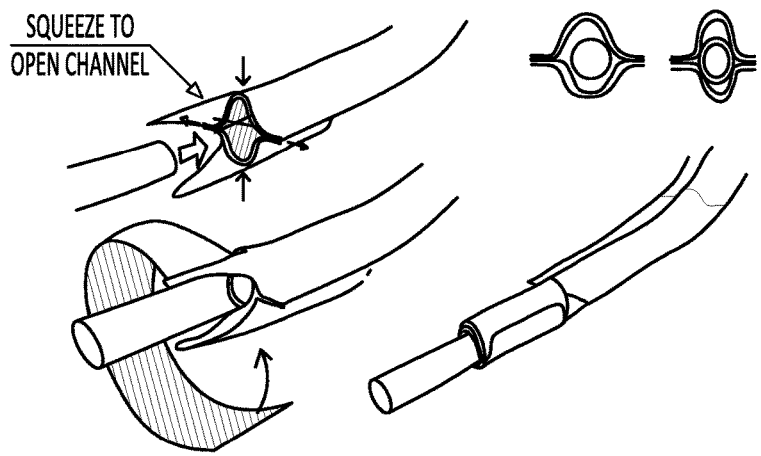

FIGS. 78-80 illustrate various embodiments of devices that secure tubing.

Figure 82:
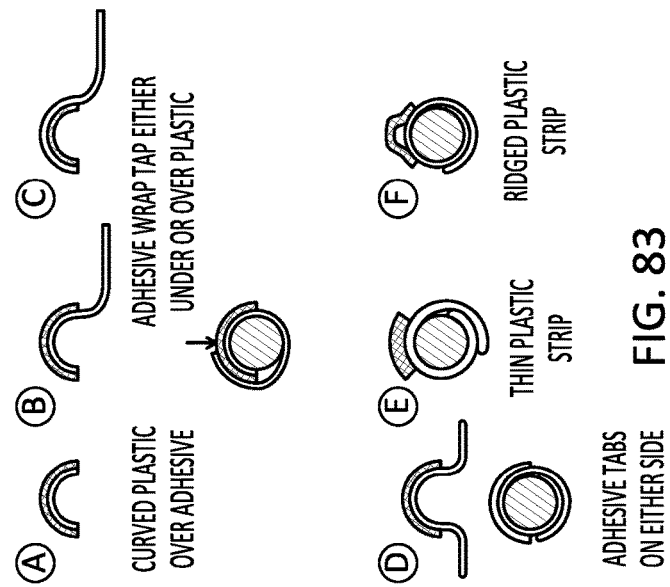
Figure 81:
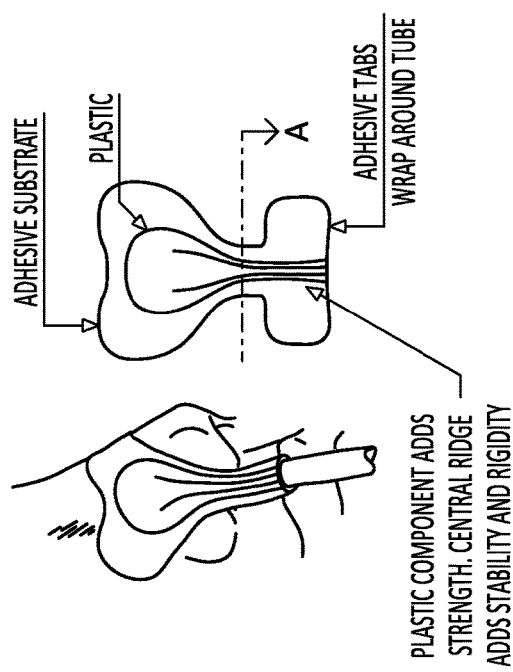

FIGS. 81-82 illustrate securement devices to hold a nasogastric tube in place.

FIGS. 83-87 illustrate devices that can be used to secure tubing in place.

FIG. 88. illustrates an endotracheal tube securement device.

DETAILED DESCRIPTION

Described herein are devices and household products, including adhesive medical devices having a three-dimensional structure configured to be adhesively secured to a patient or other object. Although this disclosure describes various different structures, any of which may be referred to as an adhesive device, any of these devices or variations of devices may incorporate any of the features or elements described in any of the other device or variations of devices. Features and elements illustrated and described for the various figures and exemplary embodiments described herein may, unless the context indicates otherwise, be applied to any of the embodiments described.

For example, any of the devices described herein may be layered adhesive devices that include a three-dimensional structure extending from an adhesive base (or substrate) that may be attached to a patient or other surface. The three-dimensional structure may generally be formed of a lightweight, relatively durable material. In any of the embodiments described herein, the structure may be formed by a press, e.g., as part of a web converting process. The 3D structure or component may be formed from an initially planar material (e.g., a thin polymeric material) that is pressed (e.g., cold pressed, hot pressed, stamped, etc.) one or more times (sequentially) during fabrication and concurrent assembly. Thus, the resulting structure may include features that reflect this forming technique, such as the thickness, dimensions, orientation, vertical wall angle, and the like, as described in greater detail below. For example, the 3D structures may include an outer edge having a wall thickness that is greater than the thickness of any of the more radially inward walls. This outer edge wall thickness may also provide improved stability and strength.

The structures described herein may also include one or more cutting, and particularly laser cutting, steps to be formed. As described in greater detail below, a laser cutter may be used and mounted above the manufacturing line to cut materials, including the 3D structures formed by the pressing/stamping techniques described above, including making cut outs. Thus, in general, when laser cutting is performed, the walls to be cut may all have outwardly sloping walls, so that the laser cutter will be able to project its beam on the wall to be cut. A vertically oriented laser cutter may typically emit a beam that is parallel to the vertical wall, hence for precise cutting, the wall should be sloping. For example, the walls to be cut may be sloping relative to a direction that is perpendicular from a base region, at an angle of (relative to an outer 'flat' base region) greater than 90° and less than 180° (e.g., greater than 91°, 92°, 93°, 94°, 95°, 96°, 97°, 98°, 99°, 100°, 101°, 102°, 103°, 104°, 105°, 110°, 115°, etc.).

An adhesive device is one variation of a medical device in which an adhesive holdfast region is used to secure the device in communication with a body part of the subject such as the skin. The devices and methods described herein are not limited to the particular embodiments described. Variations of the particular embodiments described may be made and still fall within the scope of the disclosure. Examples and particular embodiments described are not intended to be limiting.

Layered devices are of particular interest, and are described more fully below. Layered adhesive medical devices may include two or more layers. For example, a layered medical device may include an adhesive holdfast layer (which itself is made from a single or multiple layers) and a functional component (which may include a three dimensional rigid or semi-rigid structure). These various layers may be composed of separate layers, and these layers may be separated by other layers, or they may be adjacent. The adhesive holdfast layer may be itself formed of layers (optionally: a substrate layer, a protective covering layer (or liner), an adhesive layer, etc.), and thus may be referred to as a layered adhesive holdfast. Similarly, the functional component may be formed of multiple layers including layer(s) that may be rigid and be comprised of thin plastic, for example. In some variations, the layered adhesive holdfast and the functional component may have one or more layers. For example, the liner layer and protective cap may be the same layer.

As used herein, a "layer" may be generally planar geometry (e.g., flat), although it may have a thickness, which may be uniform or non-uniform in section.

The following descriptions including various design parameters or goals, and methods and devices which fit the design parameters or goals. The devices and methods described herein (and recited by any claims) are not limited to any particular theory of operation.

In general, the adhesive medical devices described herein include a holdfast region (or layer) and at least one functional layer that provides a therapeutic or non-therapeutic function. As will be apparent from the figures, many of these devices may be removable and insertable by a user without special tools. In some variations, a subject may use an applicator to apply the device (e.g., to help align it). Adhesive medical devices may also be packaged in various ways, including pouches or boxes that may be designed to create a seal around each device or around more than one device. In some cases, the packaging will be airtight to prevent evaporation of any parts of the device (including the medicament). In other cases, the packaging may not be airtight or may be partly or completely permeable to air or gaseous components.

It may also be beneficial for a subject to wear an adhesive device over an extended period of time (several minutes to an hour to several hours, for approximately 4, 6, 8 or 12 hours, a day or more than one day, several days or a week). Some devices may be reused while others are single use and disposable. A user may be required to wear the device (or multiple new devices) over the course of days, week, months or years depending on the condition being treated.

Described below are variations of adhesive devices that may be comfortably worn by the subject. In some variations, a grip (e.g., a tab, handle, strap, or other additional interface region) may be included to help secure the device to the subject's face or body, and may additionally or alternatively be helpful in positioning or manipulating (e.g., gripping) the device, particularly when it is being applied. This additional interface region may be formed of the same material as the adhesive holdfast region, or it may be a separate region, as described in more detail below.

Other materials of interest include any materials that can serve as filters. This filter may be part of the device. Any suitable filtering material known to those skilled in the art may be used. Such materials include, but are not limited to, activated carbon charcoal filters, hollow-fiber filters, and the like.

Adhesive Holdfast

The adhesive devices described herein generally include an adhesive holdfast for securing the device in communication with a subject's body or in communication with another surface such as a wall or furniture. The adhesive holdfast may include one or more adhesive surfaces that are suitable for use against a subject's body (e.g., skin, mucous membranes, wounds). Thus, the adhesive holdfast may include a biocompatible adhesive. The adhesive holdfast may facilitate the positioning and securing of the device in a desired location with respect to the subject's body. In some cases, the adhesive device may be removable and worn again, depending on the choice of adhesive layer (which may include silicone for example).

The adhesive holdfast may be flexible so that it conforms to the surface of the subject's skin, which may be relatively irregularly shaped and may include hair, wounds and the like. In some variations, the adhesive holdfast is made of a material that permits the passage of water vapor, liquid water, sweat and/or oil, which may enhance comfort. In other variations, the adhesive holdfast (and the entire device) may be completely, mostly or somewhat occlusive, or impermeable to these substances, in order to provide a moist healing environment for the wound. A fully occlusive material may help promote transport of the medicament into the skin. Any commonly used occlusive wound materials may be used as a component of the adhesive medical device. The adhesive holdfast may also include a texture or patterned relief surface (either on the later directly touching the skin or any other layer including the adhesive substrate) to enhance bonding to the subject's skin.

The adhesive holdfast may be made of layers. Thus, the adhesive holdfast may be referred to as a layered holdfast (or layered adhesive holdfast). For example, the adhesive holdfast may include a substrate (also known as adhesive substrate) layer to which a biocompatible adhesive is applied. The substrate is typically a substantially flat (predominantly 2-sided) material that is flexible. An adhesive may be present on at least one surface of the substrate. In some variations, the substrate layer is itself adhesive without needing an additional adhesive. An additional protective cover or liner may also be removably attached to the adhesive of the adhesive layer. The protective cover or liner may allow the device (and particularly the adhesive holdfast) to be manipulated without inadvertently sticking the device to the fingers or other parts of the body and it may also prevent contamination of the adhesive. The liner may be a removable paper or other film that can be peeled off or otherwise removed to expose the adhesive. In some variations, the adhesive of the adhesive holdfast is activatable. For example, the adhesive may become 'sticky' only after exposure to an activator (e.g., water, air, light, etc.) or may increase its "stickiness" after application (for example after exposure to heat from the subject's body or skin). In some variations, an adhesive could be applied to the skin in a liquid form first, than the device is applied. In other variations, the skin of the subject is prepped through normal or vigorous cleaning which may involve the use of solvents or other cleaning substances or fluids. In some variations, a protective cover is not used. As already mentioned, in some variations, the substrate and adhesive are a single layer, so that the substrate comprises an adhesive material, or a material that can be activated to become adhesive.

The adhesive holdfast may comprise any appropriate material. For example, the adhesive substrate may be a biocompatible material such as silicone, fabric, cloth, polyethylene, or polyethylene foam. Other appropriate biocompatible materials (that may be part of the holdfast or any part of the device) may include some of the materials previously described, such as biocompatible polymers and/or elastomers. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art. Structurally, the substrate may be a film, foil, woven, non-woven, foam, or tissue material (e.g., poluelofin non-woven materials, polyurethane woven materials, polyethylene foams, polyurethane foams, polyurethane film, etc.). In some cases, a pad maybe attached to the any portion of the adhesive holdfast and may be made from woven or non-woven materials, gauze, foam (open or close cell) or other material that may provide hemostasis. In some cases, the pad also comprises a medicament that can promote clotting, healing or repair, or provide other medical or non-medical benefit.

In variations in which an adhesive is applied to the substrate, the adhesive may comprise a medical grade adhesive such as a hydrocolloid or an acrylic. Medical grade adhesives may include foamed adhesives, acrylic co-polymer adhesives, porous acrylics, synthetic rubber-based adhesives, silicone adhesive formulations (e.g., silicone gel adhesive), and absorbent hydrocolloids and hydrogels.

In some variations, the adhesive is a structural adhesive. For example, the adhesive may adhere based on van der Walls forces. U.S. Pat. Nos. 7,011,723, 6,872,439, 6,737,160, and 7,175,723 describe setal-like structures whose shape and dimension provide adhesive force. These patents are herein incorporated by reference in their entirety.

The removable liner layer may be made of any appropriate matter that may be released from the adhesive. For example, the liner material may comprise craft paper. In some variations, the liner material comprises polyethylene film, or polyethylene coated paper (e.g. kraft paper) or any plastic or other material described herein. In some cases, different types of liner material may be used in the same device. For example, one liner material may be used as part of a protective cap and another liner material may be used to protect other parts of the adhesive layer (i.e. not in the area of the protective cap. In general, any of the materials commonly used in the manufacture of bandages (particularly disposable bandages such as Band-Aids™), ostomy kits, and wound care products may be used in any or all components of devices described herein.

The following materials may be used in any part of the adhesive devices (including the protective and barrier caps or any other 3D form component) described herein: fabric, cloth, latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), sodium polyacrylate, paper batteries, and thermosetting resins (such as a hard urethane, phenolic resins, and a melamine resins), and injection moldable materials such as polyether block amide (e.g., PEBAX®), and the like.

An adhesive layer (or an adhesive holdfast layer) may be formed using any appropriate method, particularly those described herein. For example, an adhesive layer may be formed by cutting (stamping, punching, die cutting, laser cutting, etc.) the adhesive substrate, biocompatible adhesive, and protective cover into the desired shape. Multiple steps may be used to form the adhesive layer. For example, the adhesive layer may be formed by cutting (or otherwise forming) the outer perimeter, then by cutting (or otherwise forming) an inner opening. Any of these steps may be combined, as appropriate.

It is not necessary that the entire adhesive holdfast region include an adhesive, although many of the substantially flat holdfast regions described in the figures may have a biocompatible adhesive over much of the skin-contacting surface (although it may be covered by a protective cover that can be at least partially removed later). In some variations only a subset of the holdfast region (including the outer layer) includes an adhesive. For example, the region beneath the tabs or grips may not include an adhesive. In some variations, the adhesive medical devices described herein are adapted to fit different users having a diversity of sizes and shapes. In other cases, there is an adhesive layer on both sides of the adhesive substrate. For example, the side of the device that is attached to patient's skin may have adhesive on part or all of its skin-contacting surface, and there may be adhesive applied to part or all of the other side of the holdfast or device to attach various 3D plastic pieces (or other components as described herein).

The adhesive devices may be formed by sequentially layering onto a backing layer (or liner) that protects one side of double-sided adhesive (forming the adhesive holdfast), and cutting out (e.g., die-cutting) one or more openings through this adhesive holdfast substrate.

Medicament

In some versions, the device includes a medicament. As used herein, a medicament includes any substance that may be applied or delivered to the subject by the device. A medicament may provide a health benefit, including treating a certain health condition. In some versions, the medicament may be an active agent that comprises a drug. In other versions, the active agent is not a drug and does not serve a medicinal purpose. For example, the active agent may only provide fragrance. In some cases, the active agent may be embedded or impregnated in the device or components of the device. In some cases the active agent is a coating. A medicament may comprise any compound that is in some way useful or desirable for the subject. For example, the active agent may be any odorant, including: menthol, phenol, eucalyptus, tea tree oil, or any agent that provides a fragrance. Alternatively, a medicament may comprise a drug with beneficial effects, such as beneficial vasculature effects. For example, a medicament may comprise a drug that affects the blood vessels (oxymetazoline or any other vasoactive compound), nasopharynx, airways or lungs (albuterol, steroids, or other bronchoconstriction or bronchodilation compounds). A medicament may comprise, for example, an antibiotic or a steroid. Other medicaments may be topical anesthetics (which may be helpful to numb an area prior to a medical or surgical intervention), and imiquimod and fluorouracil for various skin conditions including cancer. The above list of active agents is not meant to be limiting.

Any medicament, whether therapeutic or non-therapeutic, may be used. The medicament can take the form of an ointment, balm, cream, salve, liquid, paste, gel, solid, or near solid. Agents that change from solid to liquid (or change from a more viscous liquid to a less viscous liquid) when applied to the subject or when exposed to higher temperatures may find use. The medicaments may have medicinal benefit and may be prescription, non-prescription or OTC (over the counter).

A medicament may be placed in or on any portion of the device. Furthermore, the location of the medicament within the device may specifically guide the delivery of the active agent. For example, in versions of the device, the holdfast comprises a medicament (e.g., coated, embedded or otherwise part of the holdfast). In another example, a medicament may be included as a powder or releasable coating. Thus, a medicament may be on an internal or external surface of the device (e.g., pad, holdfast, cap, etc.) or embedded within or on any surface of the device. A separate drug-containing region may also be included in the device. In some cases, a flux enhancer may be used. As an example, for veterinary use, a fragrance such as bitter apple may be applied or deposited to any portion of the subject devices. Such a fragrance may deter the animal from removing or chewing on the device.

In some embodiments, one or more components of the device are impregnated with, contain or are coated with one or more compounds that may be inhaled during use. The presence of airflow, heat or other conditions may facilitate the release of the compound into the air or surrounding tissues. The compound may be herbal (such as menthol or lavender), chemical or pharmaceutical (such as an antihistamine or anti-asthma drug) in nature. Depending on the compound, the user might experience a pleasant aroma (which may soothe or promote sleep or activity) or medical benefits, such as nasal decongestion or asthma relief. The compound may be inhaled during all or at least a portion of the time the user is wearing the device.

Active ingredients that may find use include: isotretinoin, alclometasone, doxycycline, erythromycin, iodoquinol, hydrocortisone, imiquimod, alefacept, sodium sulfacetamide, sulfur, tretinoin, muprirocin, clindamycin, benzoyl peroxide, fluocinolone, fluorouracil, clocortolone, clobetasol, fluticasone, prednicarbate, adapalene, calcipotriene, minocycline, pimecrolimus, mometasone, sertaconazole, famciclovir, azelaic acid, urea, terbinafine, lidocaine, acetate, ciclopirox, metronidazole, minocycline, naftifine, oxiconazole, finasteride, tacrolimus, tretinoin, itraconazole, diclofenac, tazarotene, desoximetasone, fluocinolone, hydroquinone (including 2 and 4%), valacyclovir, doxepin cetirizine, salicylic acid, silver sulfadiazine, zinc oxide, silver nitrate, aloe vera, benzalkonium chloride, dyclonine, LMX or other topical anesthetic, steroids, Aldera, Efudex, phenol, tar (to treat psoriasis), petroleum jelly, Vicks VaporRub, moisturizers, oils, extracts, minerals or vitamins and combinations of more than one of the above compounds. Other medicaments and inactive ingredients include persea gratissima oil (avocado), ethylhexyl Palmitate, Vitis vinifera seed oil, Helianthus annuus seed oil (sunflower), isopropyl palmitate, lecithin, Sesamum indicum seed oil (sesame), capric/caprylic stearic triglyceride, aleurites moluccana (kukui nut) seed oil, tocotrienol, alcohol, glyceryl stearate, oleic acid, vitamin C, tocopherol, BHT, methylparaben, benzyl alcohol, benzyl salicylate, geraniol, hexylcinnamal, hydroxyisohexyl 3 cyclohexene carboxaldehyde, butylphenyl methypropional, onion extract, limonene, linalool, terbinafine, butenafine, amorolfine, and tonalftate.

Other compounds that may be used include other antiobiotic and antimicrobials including bacitracin, polymixin B, neomycin and various double or triple combinations of various antimicrobials including Neosporin. These include but are not limited to: bacitracin ointment containing, in each gram, 500 units of bacitracin, bacitracin zinc ointment containing, in each gram, 500 units of bacitracin zinc, chlortetracycline hydrochloride ointment containing, in each gram, 30 milligrams of chlortetracycline hydrochloride, neomycin sulfate ointment containing, in each gram, 3.5 milligrams of neomycin in a suitable water soluble or oleaginous ointment base, neomycin sulfate cream containing, in each gram, 3.5 milligrams of neomycin, tetracycline hydrochloride ointment containing, in each gram, 30 milligrams of tetracycline hydrochloride.

Alternatively, combinations of antibiotic active ingredients may include. (1) bacitracin-neomycin sulfate ointment containing, in each gram, 500 units of bacitracin and 3.5 milligrams of neomycin in a suitable ointment base. (2) bacitracin-neomycin sulfate-polymyxin B sulfate ointment containing, in each gram, in a suitable ointment base the following: (i) 500 units of bacitracin, 3.5 milligrams of neomycin, and 5,000 units of polymyxin B; or (ii) 400 units of bacitracin, 3.5 milligrams of neomycin, and 5,000 units of polymyxin B; (3) bacitracin zinc-neomycin sulfate ointment containing, in each gram, 500 units of bacitracin and 3.5 milligrams of neomycin in a suitable ointment base. (4) bacitracin zinc-neomycin sulfate-polymyxin B sulfate ointment containing, in each gram, in a suitable ointment base the following: (i) 400 units of bacitracin, 3 milligrams of neomycin, and 8,000 units of polymyxin B; or (ii) 400 units of bacitracin, 3.5 milligrams of neomycin, and 5,000 units of polymyxin B; or (iii) 500 units of bacitracin, 3.5 milligrams of neomycin, and 5,000 units of polymyxin B; or (iv) 500 units of bacitracin, 3.5 milligrams of neomycin, and 10,000 units of polymyxin B; (5) bacitracin zinc-polymyxin B sulfate ointment containing, in each gram, 500 units of bacitracin and 10,000 units of polymyxin B in a suitable ointment base. (6) bacitracin zinc-polymyxin B sulfate topical powder containing, in each gram, 500 units of bacitracin and 10,000 units of polymyxin B in a suitable (7) neomycin sulfate-polymyxin B sulfate ointment containing, in each gram, 3.5 milligrams of neomycin and 5,000 units of polymyxin B in a suitable water miscible base. (8) neomycin sulfate-polymyxin B sulfate cream containing, in each gram, 3.5 milligrams of neomycin and 10,000 units of polymyxin B in a suitable vehicle. (9) oxytetracycline hydrochloride-polymyxin B sulfate ointment containing, in each gram, 30 milligrams of oxytetracycline and 10,000 units of polymyxin B in a suitable ointment base.

Additionally, combinations of first aid antibiotic active ingredients and local anesthetic active ingredients may be used: (1) bacitracin ointment containing, in each gram, 500 units of bacitracin and any amine or "caine"-type local anesthetic active ingredient in a suitable ointment base. (2) bacitracin-neomycin sulfate-polymyxin B sulfate ointment containing, in each gram, in a suitable ointment base the following: (i) 500 units of bacitracin, 3.5 milligrams of neomycin, 5,000 units of polymyxin B, and any amine or "caine"-type local anesthetic active ingredient; or (ii) 400 units of bacitracin, 3.5 milligrams of neomycin, 5,000 units of polymyxin B, and any single generally recognized as safe and effective amine or "caine"-type local anesthetic active ingredient. (3) bacitracin zinc-neomycin sulfate-polymyxin B sulfate ointment containing, in each gram, in a suitable ointment base the following: (i) 400 units of bacitracin, 3 milligrams of neomycin, 8,000 units of polymyxin B, and any amine or "caine"-type local anesthetic active ingredient; or (ii) 400 units of bacitracin, 3.5 milligrams of neomycin, 5,000 units of polymyxin B, and any amine or "caine"-type local anesthetic active ingredient; or (iii) 500 units of bacitracin, 3.5 milligrams of neomycin, 5,000 units of polymyxin B, and any amine or "caine"-type local anesthetic active ingredient; or (iv) 500 units of bacitracin, 3.5 milligrams of neomycin, 10,000 units of polymyxin B, and any single amine or "caine"-type local anesthetic active ingredient; (4) bacitracin zinc-polymyxin B sulfate ointment containing, in each gram, 500 units of bacitracin, 10,000 units of polymyxin B, and any amine or "caine"-type local anesthetic active ingredient in a suitable ointment base. (6) neomycin sulfate-polymyxin B sulfate cream containing, in each gram, 3.5 milligrams of neomycin, 10,000 units of polymyxin B, and any amine or "caine"-type local anesthetic active ingredient in a suitable vehicle.

Antifungals that may be used include: clioquinol (including 3 percent formulations), haloprogin (including 1 percent formulations), miconazole nitrate (including 2 percent formulations), povidone-iodine (including 10 percent formulations), clotrimazole (including 1 percent formulations) and tolnaftate (including 1 percent formulations). Additionally, undecylenic acid, calcium undecylenate, copper undecylenate, and zinc undecylenate may be used individually or in any ratio that provides a total undecylenate concentration of 10 to 25 percent.

Acne medications may also be used including: benzoyl peroxide (including 2.5 to 10 percent formulations), resorcinol (including 2 percent formulations), resorcinol monoacetate (including 3 percent formulations which may be combined with sulfur), salicylic acid (including 0.5 to 2 percent formulations-which may also be used for the treatment of warts), sulfur, (including 3 to 10 percent formulations), and sulfur (including 3 to 8 percent formulations which may be combined with resorcinol or resorcinol monoacetate.)

The volume of medicament in each device may be approximately 0.1 ml, 0.2 ml, 0.3 ml, 0.4 ml, 0.5 ml, 0.6 ml, 0.7 ml, 0.8 ml, 0.9 ml, 1.0 ml, 1.1 ml, 1.2 ml, 1.3 ml, 1.4 ml, 1.5 ml, 1.6 ml, 1.7 ml, 1.8 ml, 1.9 ml, 2.0 ml, 2.1 ml, 2.2 ml, 2.3 ml, 2.4 ml, 2.5 ml, 2.6 ml, 2.7 ml, 2.8 ml, 2.9 ml, 3.0 ml, 3.1 ml, 3.2 ml, 3.3 ml, 3.4 ml, 3.5 ml, 3.6 ml, 3.7 ml, 3.8 ml, 3.9 ml, 4.0 ml, 4.1 ml, 4.2 ml, 4.3 ml, 4.4 ml, 4.5 ml, 4.6 ml, 4.7 ml, 4.8 ml, 4.9 ml, or 5.0 ml.

The viscosity of the medicament may vary from 1 cps to 200,000 cps. Generally medium to higher viscosity medicaments may find use include those with viscosities between 25,000-35,000 cps, between 35,000-45,000 cps, between 45,000-55,000 cps, between 55,000-65,000 cps, between 65,000-75,000 cps, between 75,000-85,000 cps, between 85,000-95,000 cps, between 95,000-105,000 cps, between 105,000-120,000 cps, between 120,000-135,000 cps, between 135,000-150,000 cps and above 150,000 cps in some cases.

A medicament (such as an ointment or the like) may have the tendency to seep or wick through a gauze, pad, or other substrate that it contacts, especially if the ointment has a relatively low viscosity. This effect may be worsened if the substrate has holes within it. Ointment that is too viscous may have a tendency to stick to the protective cap. In some cases, a hydrophobic or hydrophilic pad is used. In some cases, a portion of the device (e.g., a pad) may be treated or covered so as to prevent absorption or wicking of materials. In some cases, paraffin wax or similar materials may be used as a layer under the medicament, under the pad, under the adhesive, etc.

Materials

Exemplary materials that may be used for use any portion of the adhesive devices described herein include: metals, plastics, rubbers, ceramics, wood, chrome, or combinations thereof. Other materials may include acrylics, latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), sodium polyacrylate, thermochromatic plastic, and thermosetting resins (such as a hard urethane, phenolic resins, and a melamine resins).

Biocompatible materials may be used, particularly for those portions of the device which may contact a user. In addition to some of the materials described above, biocompatible materials may also include a biocompatible polymer and/or elastomer. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art. Teflon, Mylar, PFA, LDPE, Hytrel, HDPE and polyester may also find use in any components of the devices. Materials that are biocompatible and/or sterilizable may also be preferred, for example, medical grade plastics such as Acrylonitrile Butadiene Styrene (ABS), latex, polypropylene, polycarbonate, and polyetheretherketone. The forgoing materials are intended as illustrations only.

In general, the materials used for any of the adhesive devices described herein may be appropriate for in-line fabrication, for example, using a web conversion technique. For example, the materials used to form the various layers (adhesive substrate, adhesive, 3D rigid/semi-rigid structure, etc.) may be an appropriate material selected from those described above. Further, the dimensions (e.g., thickness) of such materials may be within an appropriate range to accommodate this fabrication technique. Examples of such materials and fabrication techniques are provided herein.

For example, an exemplary class of adhesive devices described herein includes negative pressure wound therapy systems Traditional negative pressure wound therapy often requires vacuum sources that are bulky, complex, and/or expensive. There is a need for devices that are more portable, simpler and less expensive. Currently available devices are generally manufactured with a hybrid method, involving some steps that are performed by machine, and other steps that are performed by hand. The instant invention may utilize a manufacturing method such as web converting that can be fully or partially automated, can be easily scaled and is cost-effective. Web converting can involve die cutting, island placement, heat seal packaging, printing, conveying, inspecting, and rejecting parts not within set tolerances. With respect to negative pressure wound therapy systems, the instant invention may use a web converting method in order to co-manufacture the absorbent pad/dressing and the vacuum interface (e.g., plastic cap hat attaches to the vacuum tubing) simultaneously. Rather than using slower and relatively expensive "pick and place" processes, web converting enables the invention to be manufactured with less human labor and less cost and increased speed.

Negative pressure wound therapy devices enable controlled application of negative pressure to a wound. A dressing that is sealed against the skin surrounding the wound is placed on the user and connected to a vacuum pump which pulls negative pressure. The pressure draws out fluid from the wound and increases blood flow to the area, facilitating healing and minimizing scar tissue. Large wounds, chronic wounds, pressure sores and diabetic ulcers may all benefit from negative pressure therapy.

The wound dressing is typically placed directly on the wound. It may be a flexible material to shape to the contours of the wound area, or it may be a more rigid material in order to better support a seal for negative pressure. The wound dressing may be impermeable to fluids, or may be absorbent. It may contain an absorbable matrix. In some embodiments, the wound dressing may contain, or work in communication with, another absorbent material, such as open cell or polyurethane foam, medical gauze or fabric pad. In some embodiments, the wound dressing may contain a layer designed to evenly distribute pressure over the wound. This layer may contain one or more materials that in some way deform under negative pressure, such as open cell foam, medical gauze, sponges, other matrix-like materials, etc. In some embodiments, an airlock layer may additionally be added to the wound dressing. In some embodiments, a hydrophilic layer that interacts with any fluid to form a gel may be used. In some embodiments, a moisture wicking material may be used. The wound dressing may additionally contain an adhesive for the purposes of adhering to patient skin around the wound and may be made out of hydrocolloid. The pad can be cut to size, or can be different size and shapes according to the type of wound. Saline or antibiotics or growth factors may be dispensed into the wound or dressing. Any of the parts of the device described herein may be impregnated with antibiotics or other medicines.

Figure 1:
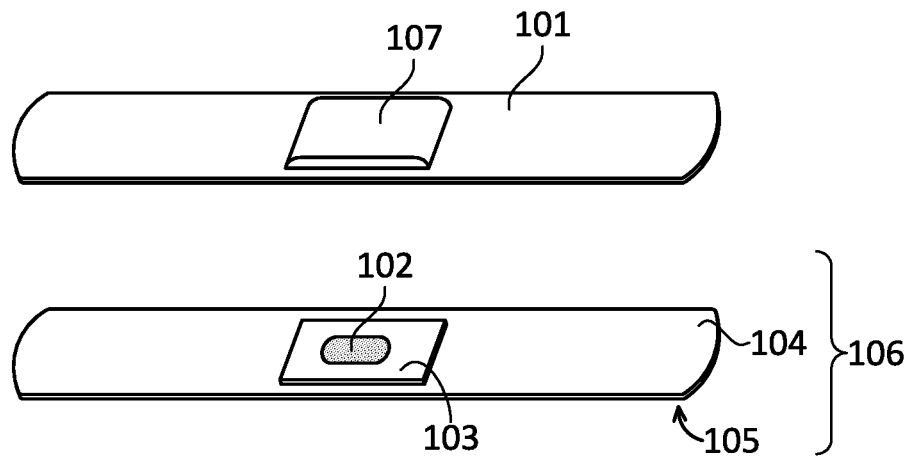
FIG. 1 shows one variation of an adhesive medical device with a protective cap in an exploded view.

Turning to the figures, additional exemplary devices, systems and methods of manufacturing and using them are described. For example, FIG. 1 shows a top perspective view of a layered adhesive medical device that includes a liner 101 and a medicament 102 that is located on a pad 103. The device is shown in two parts, the liner 101 and cover 107 is shown above the holdfast with medicament and pad 103; the two parts may be combined so that the liner covers the adhesive surface of the holdfast and the pad. The two parts may be separated to apply to a user. The layered adhesive device has an adhesive (also known as adhesive layer) 104 that is planar and attached to the adhesive substrate 105 (which may be referred to as the backing). Together, the adhesive and adhesive substrate comprises the holdfast 106 (which may be referred to as a holdfast layer). The device also has a protective cap 107 that serves to physically protect and prevent the migration of medicament 102 beyond the area of pad 103 prior to application of the adhesive device to the body of a user. The protective cap 107 may also serve to seal the medicament so it is not exposed to the outside air, which may harden or otherwise alter the composition or viscosity of the medicament. The liner 101 (which may also be referred to as a protective cover or cover) can be removed to expose the adhesive before application of the device by the subject. Thus, the holdfast layer 106 of the device secures it to the subject. The adhesive substrate 105 may be made of fabric, foam or another spongy material, either open or close cell, or may be made of non-spongy materials or other materials, such as plastic. This adhesive substrate 105 may act as a substrate for the layer of adhesive 104. In some variations, the adhesive substrate is itself adhesive, such as when hydrocolloid or hydrogel or the like is used within the adhesive device. The holdfast (and any or all of its components namely the adhesive layer and the adhesive substrate may have holes or perforations along their entire length, or may have no perforations, or may have perforations in some areas. As an example, in the regions under the pad and/or adjacent to the pad, there may be full or partial thickness perforations in the holdfast. In other cases, there may be no perforations under or near the pad. By having no perforations under the pad, the medicament may be completely sealed within the chamber defined as the cavity formed between the pad and the protective cap. This seal may prevent migration of the medicament outside the chamber or evaporation of the medicament that may harden the medicament. The holdfast layer 106 may have different regions, including regions that house or support rigid or non-rigid structures that perform some function, and a grip region or tab that may make the device easier to grasp, apply and remove. The grip region may not have adhesive attached to it, enabling easier manipulation by the user. Other regions may include regions of more aggressive and less aggressive adhesive (e.g., more or less adhesive material), regions of hydrogel or hydrocolloid material (including adhesive hydrogels) to help prevent irritation from repeated or extended use. Tabs that may be part of (integral with) the holdfast material, or may also be formed separately, and may be made of different materials. The pad may be made of any biocompatible material. In some cases, it may be designed to wick fluids or blood. In other cases, it will not wick fluid, blood or medicament. In some cases, it completely blocks fluids from going through the pad, thus maintaining the medicament on the pad itself, without saturating the pad. Thus, in some cases, the pad or its top layer is impervious or relatively impervious to fluids and/or to medicaments, which may help maintain the medicament on the pad.

Figure 2:
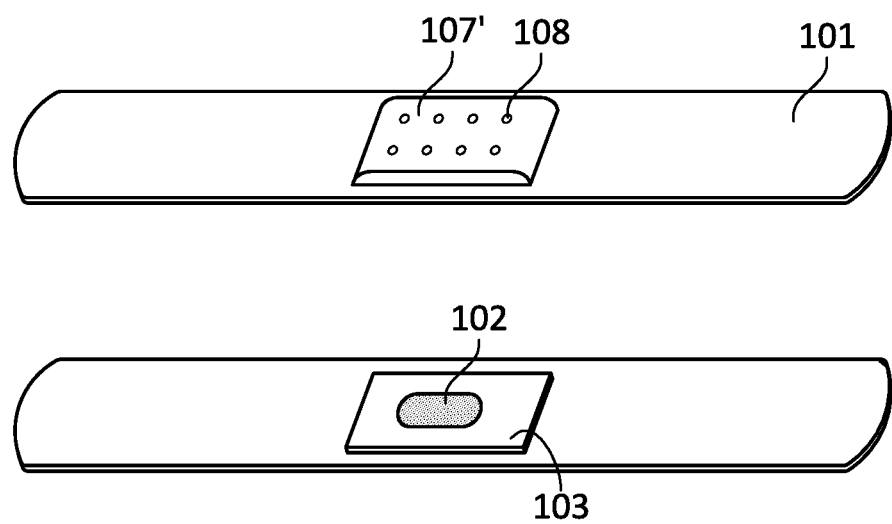
FIG. 2 is a different variation of the adhesive medical device shown in FIG. 1.

FIG. 2 shows a different variation of the adhesive device of FIG. 1. The protective cap 107' has one or more holes 108 that expose the pad and the medicament to air outside the protective cap. It is possible that the adhesive device itself may be sealed within an airtight package or chamber. In other cases, the package in which the adhesive bandage is contained may not be sealed or airtight. The provision of holes may allow the medicament to harden or soften as it is exposed to the surrounding air. In some variations (not shown) a thin layer of film may partly or completely protect and seal the underside of the protective cap to maintain the medicament within the protective cap and serve as a barrier between the medicament and the pad or holdfast. The user may be required to break this layer of film to release the medicament onto the pad for example.

FIG. 2 shows another variation of an adhesive medical apparatus (e.g., bandage). In FIGS. 1 and 2, the protective cap 107 and 107' may have a rounded, smooth shape. In other embodiments, the protective cap may have less rounded and more linear features. In still other embodiments, the protective cap may we wavy, symmetric or asymmetric, or may have uneven features. As shown in these figures, the protective cap is formed continuously with the liner 101 (i.e., both the protective cap and liner are integrated), which serves to both protect the adhesive and the medicament until the subject applies the adhesive device. By having a single integrated piece comprising the protective cap and liner, it is easier and quicker for the user to apply the device. Further, it will be more convenient for the user to dispose of a single, larger piece than two or three separate smaller pieces (if the liner was separate from the protective cap). One purpose of the protective cap is to prevent the medicament (which may be viscous, liquid, semi-liquid or semi-viscous) from moving or migrating beyond the pad. Such movement of the medicament may otherwise be expected to happen during storage (especially when the device is stored on its side or upside down) or during transport of the adhesive device, and which may be worsened by exposure to temperature extremes, including high temperatures. Additionally, high humidity or repeated vibration (as might be seen in distribution the product from the manufacturer to the store or to the consumer's home) may also promote the movement of medicament beyond the pad. Thus, a key role of the protective cap may be to ensure non-movement of the medicament prior to the use of the adhesive device. As mentioned previously, there may also be a need to seal the medicament on top of the pad and to minimize exposure to the external environment (e.g., air) so that the optimal properties of the active and inactive ingredients of the medicament are maintained as long as possible. Thus, the addition of the protective cap may be important to maximize shelf life of the adhesive device.

Figure 3A:
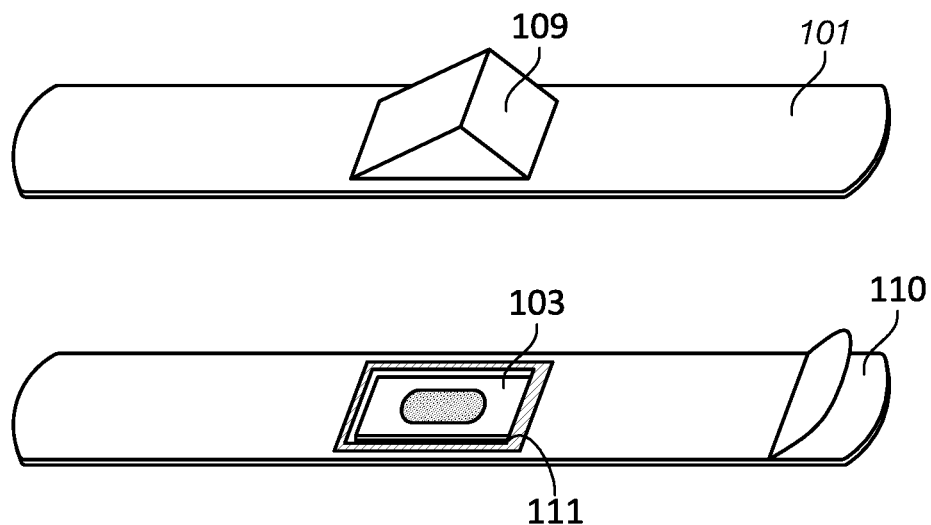
FIGS. 3A and 3B are different variations of the adhesive medical device shown in FIG. 1.

In FIG. 3A, the protective cap 109 has a more dimensional, pyramidal shape. Also in this variation, a removable tab 110 is attached to one or both sides of the holdfast, to enable the user to handle the device without touching the adhesive. An additional adhesive ring 111 comprising double sided adhesive is shown circling the pad, providing a potentially more robust and definitive seal for the protective cap, to help prevent migration of the medicament from beyond the pad area and to promote an air tight seal. This double-sided adhesive may be stickier or have greater adhesive properties than surrounding adhesive on other parts of the adhesive layer.

Figure 3B:
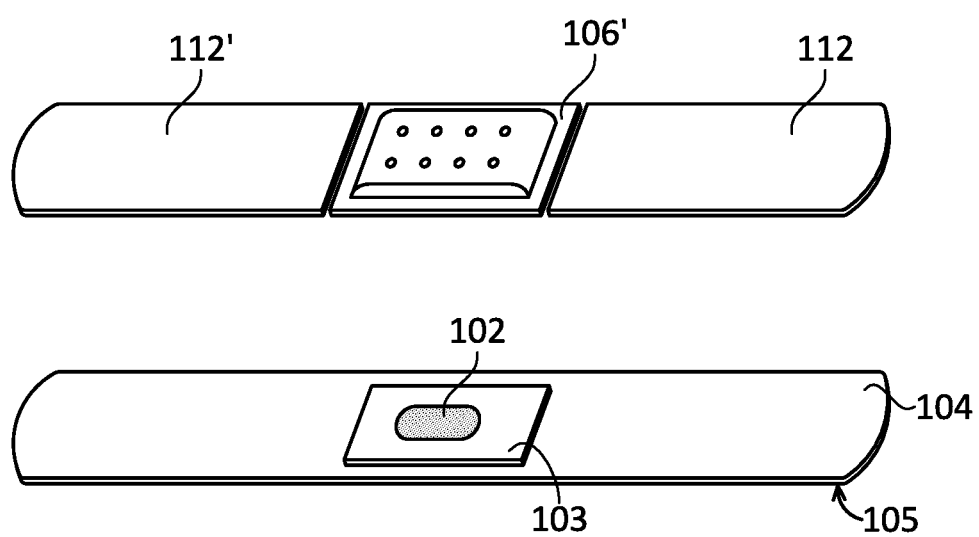

In FIG. 3B, a top perspective view of an adhesive device is provided (the upper region of the device is again shown above the lower region in a semi-exploded view as in FIGS. 1-3). The device in FIG. 3B is similar to that in FIG. 1, except that that the liners 112 and 112' are now separate from the protective cap 106'. In this case, the user could peel off both liners and the protective cap independently prior to application of the adhesive device.

FIG. 4A provides top perspective views of an adhesive device that is a variant of the embodiment shown in FIG. 1. In this embodiment, the liner 101 and protective cap 107 are integrated into single piece. A separate liner 101' is also shown. On the left, the device is shown prior to removal of the combined liner and protective cap. On the right, the liners and protective cap have been removed, exposing the medicament 102 on the pad 103. Note that the protective cap has served to contain the medicament on the pad 103 and keep it away from the surrounding adhesive layer.

Figure 4E:
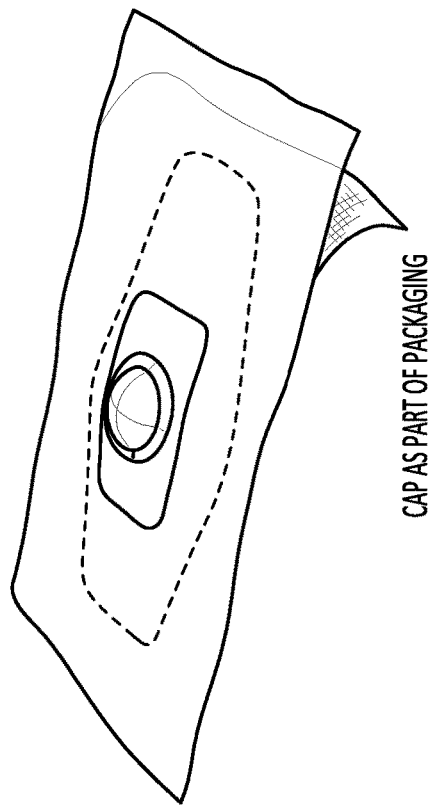
FIG. 4E is an adhesive medical device with a protective cap.

FIG. 4B is a top perspective view of the device shown in FIG. 4A. FIG. 4C is a top perspective view of a BAND-AID brand antibiotic adhesive bandage with a roughly square shaped protective cap affixed to the liner to prevent migration of the antibiotic film beyond the pad. FIG. 4D is a top perspective drawing of the device previously described in FIG. 4C. In some variants (not shown), the adhesive layer near the base of the protective cap region (where the protective cap attaches to the adhesive layer) may be more sticky (or in some cases, less adhesive or sticky) than the rest of the adhesive layer present on the device. This variable level of stickiness may allow a more definitive seal between the protective cap and the adhesive layer (compared to the seal between the rest of the liner and the adhesive layer), preventing migration of the medicament off the pad. FIG. 4E is a top down perspective view of a device in which the protective cap is integrated into the packaging or liner.

Figure 4G:
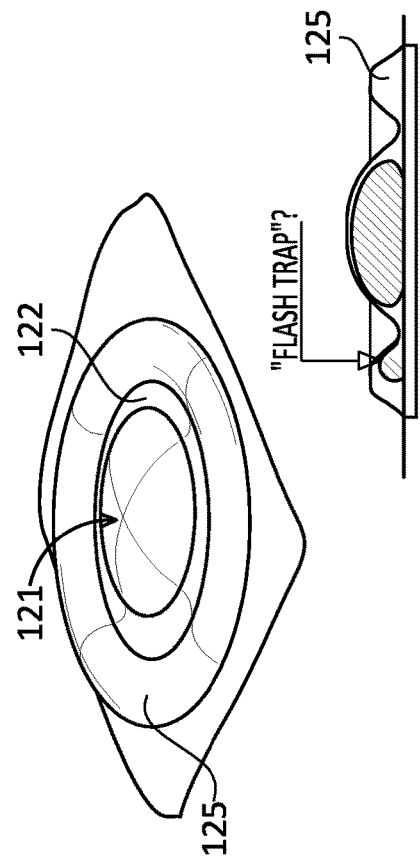
FIGS. 4F-4H are top down views of alternate designs of protective caps.
Figure 4D:
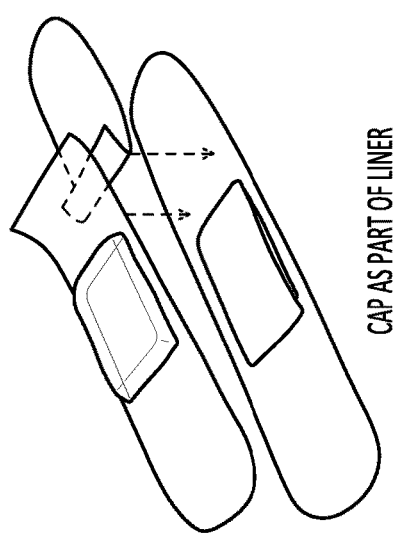
Figure 4F:
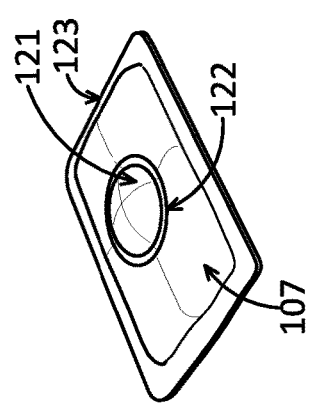

FIG. 4F is a close-up view of the protective cap 107, which comprises a convex dome 121 that serves to contain the medicament onto the pad (not shown) of the device. A containment ring 122 is seen at the base of the convex dome. This containment ring tightly or semi-tightly apposes the pad of the device, serving as a physical barrier preventing the movement or migration of the medicament off the pad. This containment ring generally provides a complete barrier around the pad, though in some cases, there may be fenestrations or holes within the containment ring that allows some movement of medicament outside the ring.

FIG. 4G is a variant of the protective cap seen in prior examples. In this case, the convex dome 121 is surrounded by the containment ring 122, which in turn is surrounded by an overflow chamber 125, which serves as a "flash trap" to capture and/or contain any medicament or other material that leaks or otherwise migrates from the convex dome underneath the containment ring 122.

Figure 4H:
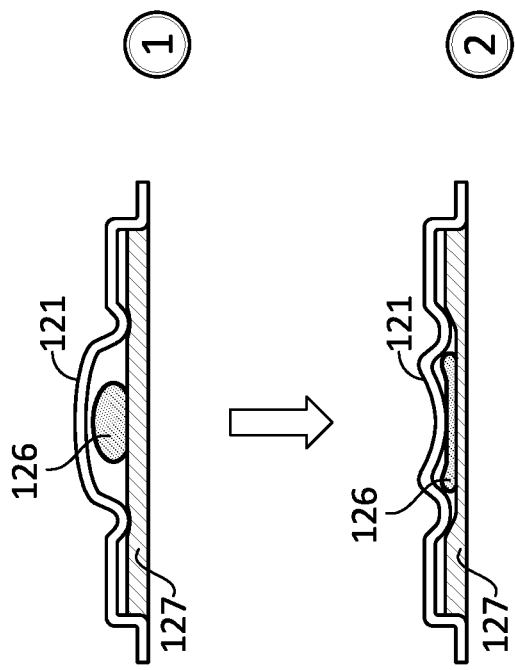

FIG. 4H is top down view of another embodiment of the protective cap in which the convex dome can be "snapped" into a second, deployed configuration, in which the dome is now concave and displaced in the direction of the pad (not shown). This "snapping" action may produce an audible or softly audible "click" that is meant to engage the user. Further, the displacement of the dome in the direction of the pad serves to spread the medicament previously contained within or on the underside of the dome onto the pad area.

Figure 4I:
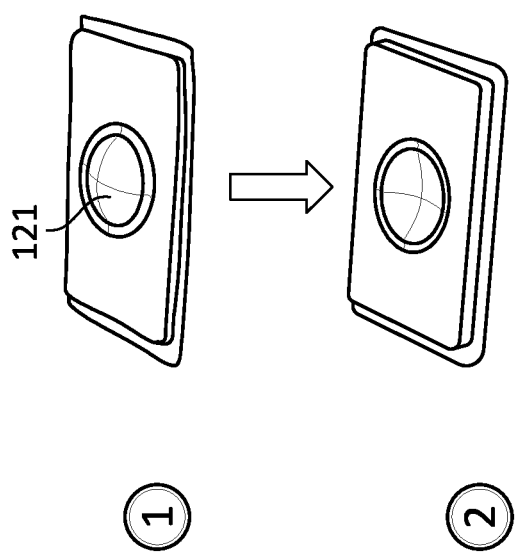
FIGS. 4I-4K are cross sectional views of protective caps.

FIG. 4I shows the protective cap in the pre-deployed (above figure) and deployed (lower figure) states. Clearly seen is the spreading of the medicament 126 across the pad 127 after the protective cap has been pressed or displaced by the user.

Figure 4K:
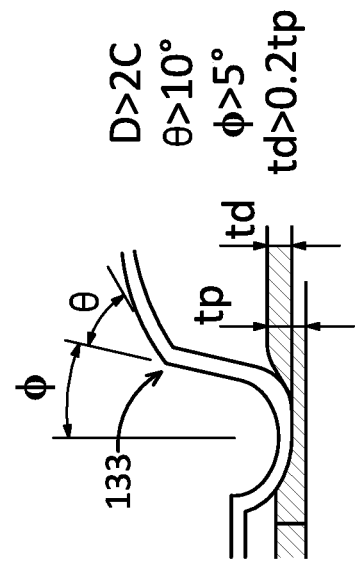
Figure 4J:
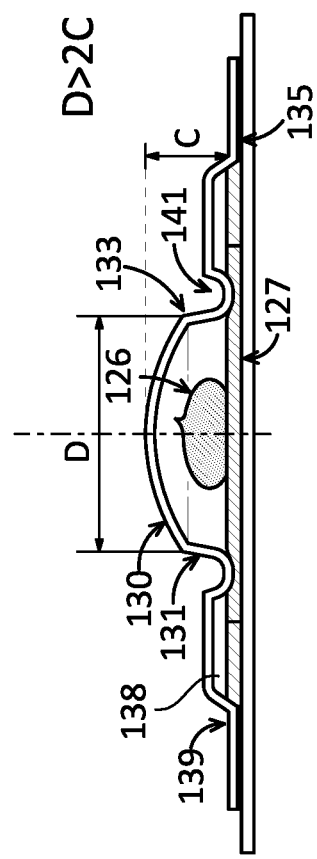

FIG. 4J is a more-detailed cross sectional view of the device shown in FIG. 4I. The protective cap comprises a top zone 130 which inflects sharply at transition area 133, leading to downward zone 131. This transition area is important as it enables a "bi-stable" configuration of the protective cap. That is, the protective cap assumes only one of two preferred configurations, pre-deployed and deployed as described in FIG. 4I. Again, the protective cap serves to protect the medicament 126. The cap is tightly apposed again and presses down against the pad 127 at pinch zone 141. Further away from center of the protective cap is an overflow chamber 138 which circumferentially surrounds the periphery of the pad and is intended to capture or contain medicament that gotten through or around the pinch zone 141. An extra adhesive zone 135 serves to securely attach and/or seal the edges 139 of the protective cap to the device. This extra adhesive zone may be more or less sticky than adhesive elsewhere on the device as it is intended to secure and/seal the protective cap tightly onto the device and facilitates the pinch zone 141 providing sufficient force to seal the medicament 126 within the central portions of the protective cap.

FIG. 4K shows a more detailed view of the protective cap shown in FIG. 4J. Several recommended geometric parameters are shown including various angles defined by the top zone and downward zone. These parameters generally may be defined by the manufacturing process used. In the case of in-line forming of plastic sheet in a web converting process for example, the distance D is greater than two times the height of the cap C as shown in FIG. 4. Additionally, the angle Θ is generally greater than 10 degrees to help create a "bi-stable cap" that is capable of "snapping" and creating an audible sound and sensation that can be felt or discerned by the user's finger. Further the angle Φ is generally greater than 5 degrees as smaller angles would be significantly harder to form using available manufacturing processes. Finally, as shown, the thickness of the pad is at least 20% of the total thickness of the device (wherein the thickness of the device is defined as the sum of thicknesses of the adhesive substrate and pad).

Figure 4L:
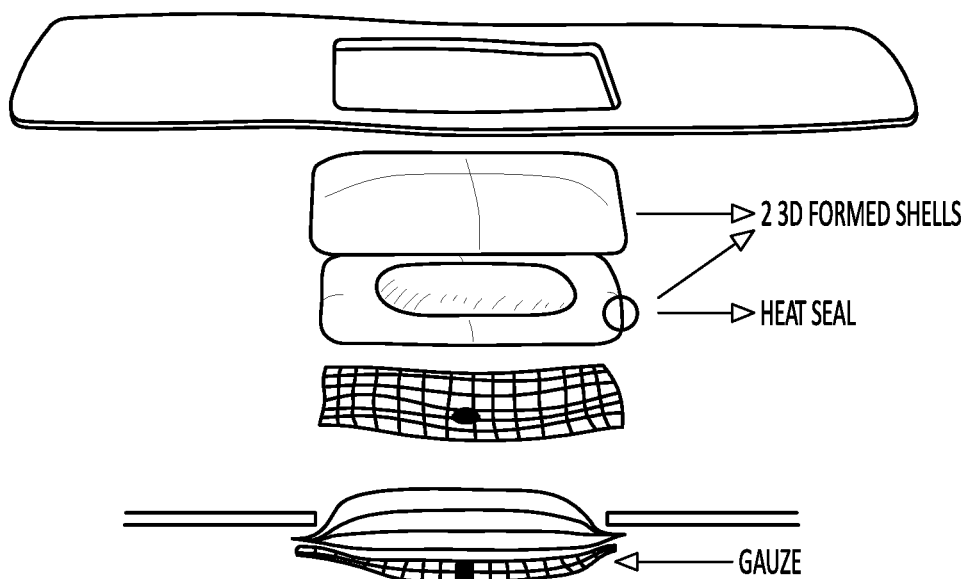
FIGS. 4L and 4M are exploded views of adhesive medical devices with protective caps.

FIG. 4L shows an exploded view of an alternate construction of an adhesive device comprising a 3D formed shell which may be heat sealed to the pad or other portion of the device as well as a gauze portion.

Figure 4M:
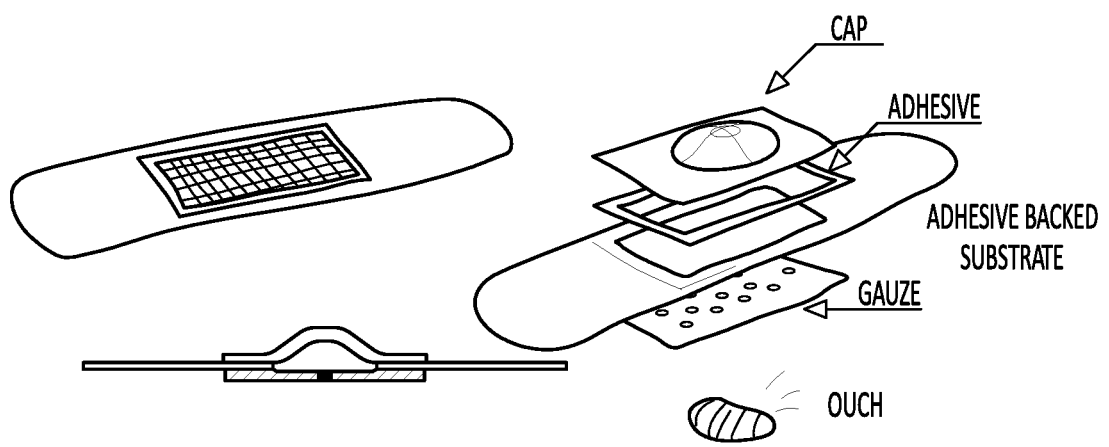

FIG. 4M shows another exploded view of a different embodiment comprising a protective cap, adhesive substrate and gauze, which is designed to protect a wound on the user. A medicament may or may not be present in this device.

Figure 5:
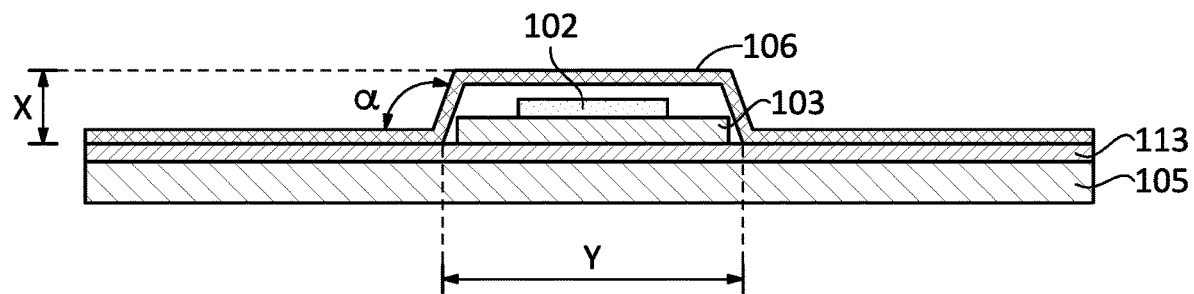
FIGS. 5 and 6 are cross-sectional views of the adhesive medical device shown in FIG. 1.

FIG. 5 shows a cross sectional view of the device in FIG. 1. The adhesive substrate 105 is attached to a double sided adhesive 113 which is itself removably attached to the protective cap 106 which has an integrated liner. The protective cap 106 serves to protect the medicament 102 that has been dispensed onto the pad 103. The protective cap 106 has linear elements and corners in this example. The distance X represents the height of the protective cap 106 which is measured from the top of the adhesive 113 to the top of the protective cap 106. The distance Y represents the length or width of the protective cap 106 measured at the base of the protective cap 106. Generally, measurements of length, width and circumference at the base of the protective cap 106 (or base of the barrier cap (which will be defined later) or base of any other rigid portion of the adhesive devices described herein) begin and end where the protective cap/barrier cap/other rigid portion deflects, bends or is shaped away from the adhesive layer 113 as is shown in FIG. 5.

Figure 6:
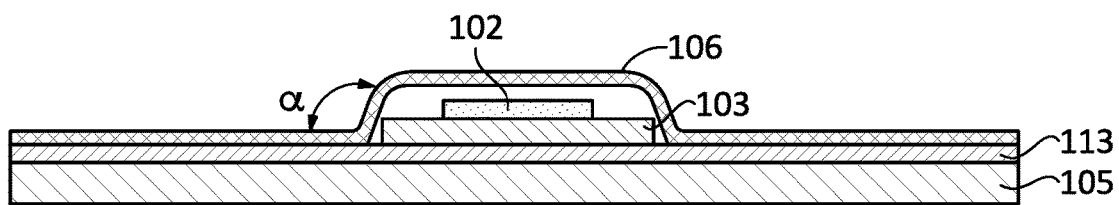

In FIG. 6, a cross sectional view of another embodiment of the adhesive device is shown, this time with a protective cap and liner that is curved, and not linear (straight-angled) as is shown in FIG. 5.

Figure 7:
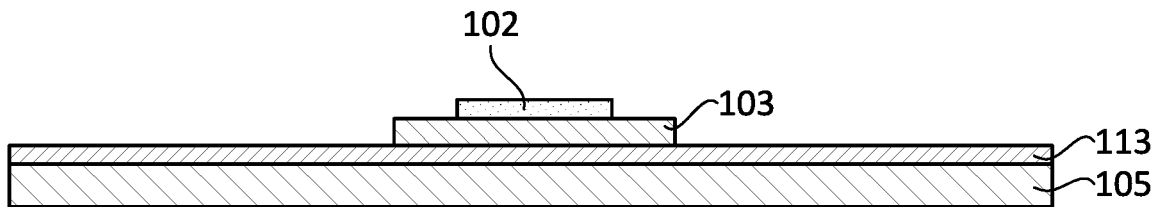
FIG. 7 is a cross-sectional view of the adhesive medical device prior to application onto the user.

FIG. 7 is a cross sectional view of an adhesive device as shown in FIG. 5 or 6 after the protective cap has been removed, exposing the medicament on the pad, prior to application of the device by the subject.

Figure 8:
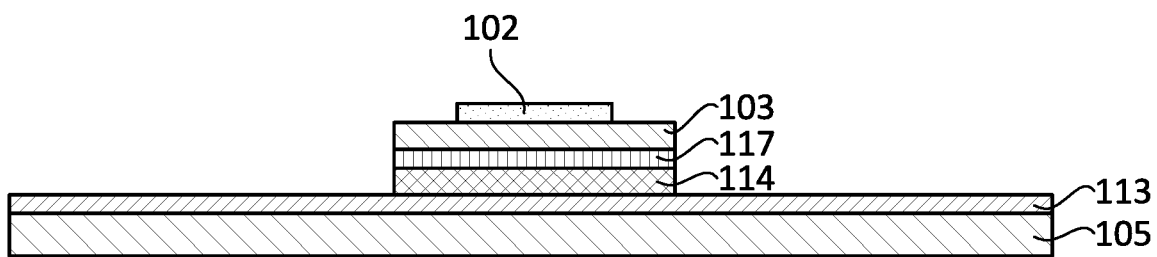
FIG. 8 is a different variation of the adhesive medical device shown in FIG. 7.

FIG. 8 is a cross sectional view of the adhesive device shown in FIG. 5 or 6 after the protective cap has been removed, exposing the medicament 102 on the pad 103, and prior to application of the device by the subject. In FIG. 8, there is an additional barrier layer 114 and an additional double-sided adhesive 117 present. The barrier layer 114 may prevent the medicament from seeping or penetrating or traversing through the pad and into the adhesive 113 and adhesive substrate 105. Thus, the barrier layer 114 may serve as a seal between the medicament and the out portions of the device.

Figure 9A:
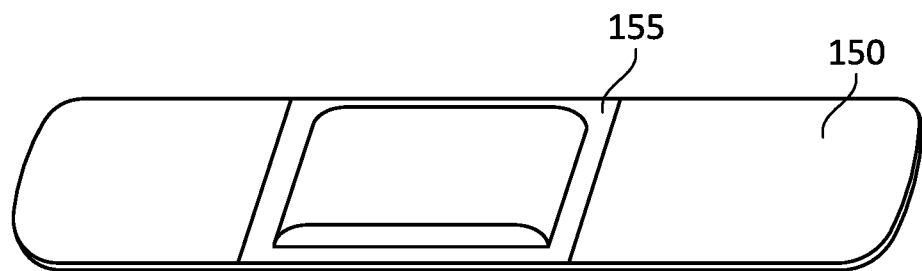
FIGS. 9A and 9B illustrate top down and exploded view, respectively, of an adhesive medical device.

FIG. 9A is a top perspective view of an adhesive medical device comprising an adhesive holdfast 150 and a barrier cap 155. This device is may be used to treat wounds (especially painful ones), bed sores, and burns. The barrier cap 155 provides a rigid protective barrier that protects and prevents harm to the wound as it heals. The barrier cap 155 may have one or more small or large holes, which may provide exposure of the wound to air. In other cases, no holes or perforations are present in the barrier cap 155. A gauze, foam or other soft substance which may have hemostatic properties, may be held within barrier cap 155, either as part of the device or may be inserted by the user or healthcare provider. A medicament may also be present within the barrier cap 155.

Figure 9B:
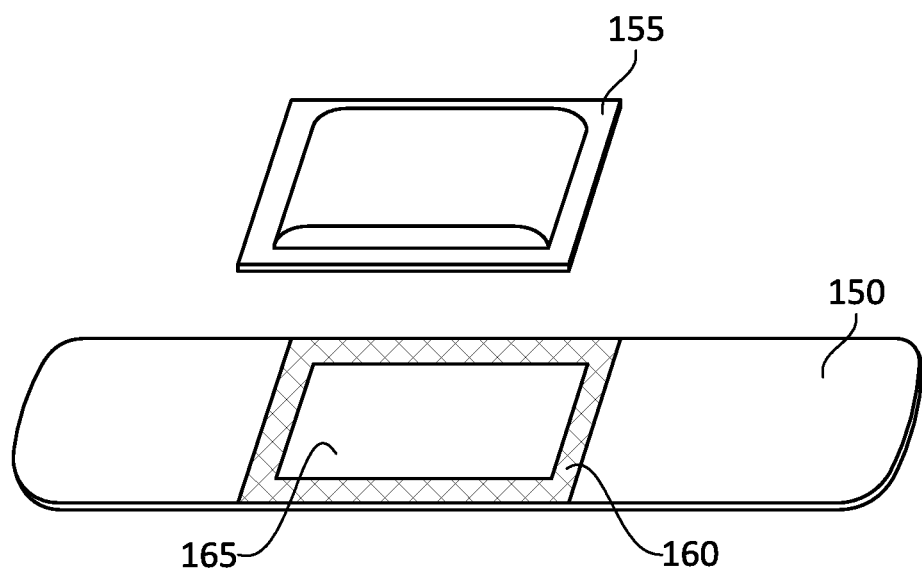

FIG. 9B is a top perspective view of the adhesive medical device of FIG. 9A in which the barrier cap 155 has been removed from the rest of the device to demonstrate the construction of the adhesive device. An opening 165 is seen within the adhesive holdfast (through the adhesive layer and the adhesive substrate layer). A double-sided adhesive 160 is shown attached to the adhesive holdfast and serves to attach and seal the barrier cap 155. Not shown in FIG. 9B is a liner which is present along the entire underside of the adhesive holdfast 150, and covers the opening 165.

Figure 9C:
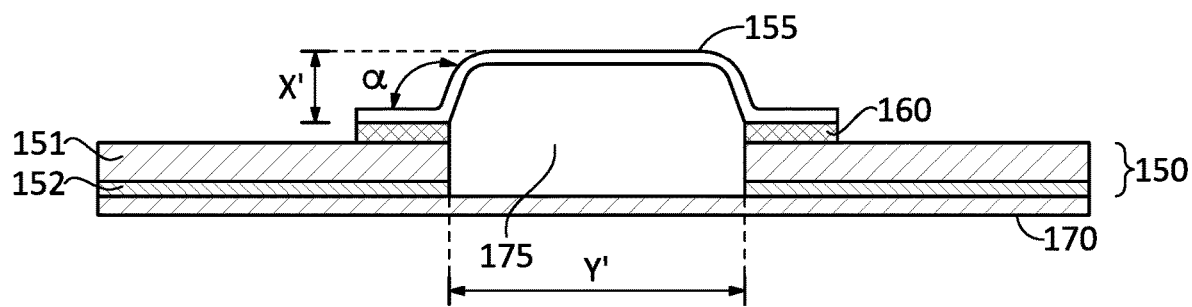
FIGS. 9C and 9D illustrate cross sectional views of the adhesive medical device shown in FIGS. 9A and 9B.

FIG. 9C illustrates a cross sectional view of the device shown in FIGS. 9A and 9B. The adhesive substrate 150 is shown, comprising the adhesive substrate 151 and the adhesive 152. The liner 170 is shown on the underside of the device. The barrier cap 155 is attached via the double sided adhesive 160 to the adhesive substrate. A chamber 175 is seen which is empty. The angle α (the angle between the outer edge plane of the barrier cap and the wall of the barrier cap) is also shown. The distance X' represents the height of the barrier cap 155 which is measured from the top of the adhesive 160 to the top of the barrier cap 155. The distance Y' represents the length or width of the barrier cap 155 measured at the base of the barrier cap 155. Generally, measurements of length, width and circumference at the base of the barrier cap 155 (or base of the protective cap 106 (defined earlier) or base of any other rigid portion of the adhesive devices described herein) begin and end where the protective cap/barrier cap/other rigid portion deflects, bends or is shaped away from the adhesive layer 160 as is shown in FIG. 9C.

Figure 9D:
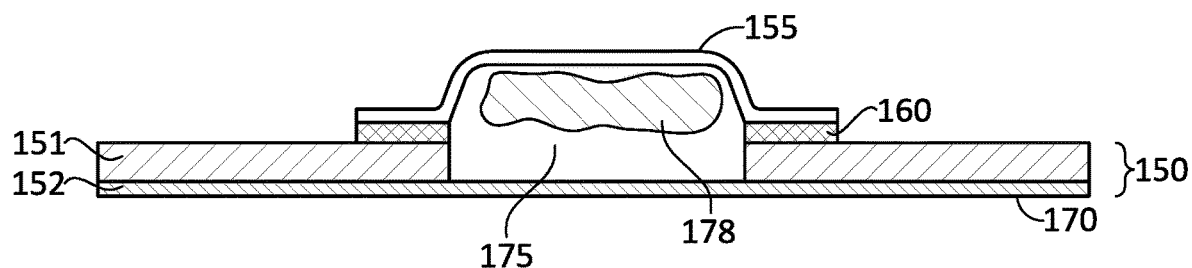

FIG. 9D shows the device of FIG. 9C in which the chamber 175 is filled with a medicament. In general, chamber 175 can be filled with a medicament 178, or a soft substance like gauze, sodium polyacrylate, foam or other hemostatic compound, or both a medicament and a gauze, etc. In some embodiments, a mesh, filter or other porous or semi-porous material (not seen in FIG. 9D) may be present, attached on top or below double sided adhesive 160 or on top of or below adhesive 152, in both cases traversing the opening that defines chamber 175. The purpose of the mesh or filter is to help partly contain the medicament or gauze, etc. within the barrier cap and/chamber 175 to help modulate or slow its transit or exposure to the subject's skin.

The angle α seen in FIGS. 5-6 and FIG. 9C will be generally greater than 90° and less than 180°, more specifically between 90-95°, between 95-100°, between 100-105°, between 105-110°, between 110-115°, between 115-120°, between 120-125°, between 125-130°, between 130-135°, between 135-140°, between 140-145°, between 145-150°, between 150-155°, between 155-160°, between 160-165°, between 165-170°, between 170-175°, or between 175-180°. More preferably, the angle α will be between 92-122° which is a convenient range to enable forming of protective cap (or barrier cap) during web converting while creating a suitable height of the protective cap or barrier cap to allow it to contain the pad and medicament.

In general, in any of the 3D structures (e.g., caps, cover, protective cap, barrier cap, protective cover, vacuum cap, etc.) described herein all of the walls may have angle with respect to the perpendicular direction relative to the base plane of the structure. For example, all of the walls of the 3D structure may be at an angle of between about 58 degrees and 88 degrees relative to the plane formed by the outer (peripheral) baser region of the structure. As mentioned above, this outer base region may have a larger wall thickness compared to all of the walls forming the 3D structure (e.g., projecting up from this base region).

The height of the protective cap 106 in FIGS. 5 and 6, may refer to the distance between the top of the adhesive layer 113 and the top of the protective cap 106 (and the height of the barrier cap in FIG. 9C, which may refer to the distance between the top of the adhesive 160 and the top of the barrier cap 155) may generally be between about 0.1 mm to 3.5 cm, in some variations between 0.3 mm and 1.0 cm, in some variations between about 0.5 mm and about 5.0 mm and in some variations between about 1.0 mm and about 3.5 mm.

The ratio of the maximum length of the protective cap/barrier cap (measured on the inside at the base of the protective cap/barrier cap in a direction that is parallel to the adhesive holdfast in the figures) to the height of the protective cap/barrier cap is generally greater than 1:1, more specifically greater than 2:1, or greater than 3:1, though in some cases where the protective/barrier cap is much longer than wide, this ratio my be less than 1:1 or less than 1:2. The maximum length of the protective/barrier cap is defined as the maximum distance between any two points measured at the base of the inside of the protective/barrier cap. In other words, this is the maximum internal distance or dimension measured at the base of the protective/barrier cap. This definition applies to any shape of the protective/barrier cap (or any other 3D component in an other device described herein) whether it is circular, oval, triangular, square, rectangular, or other polygonal shape or non-polygonal shape.

The ratio of the minimum length of the protective cap/barrier cap (measured on the inside at the base of the protective cap/barrier cap in a direction that is parallel to the adhesive holdfast in the figures) to the height of the protective cap/barrier cap is generally greater than 1:1, more specifically greater than 2:1, or greater than 3:1. The minimum length of the protective/barrier cap is defined as the minimum distance between any two points measured at the base of the inside of the protective/barrier cap. In other words, this is the minimum internal distance or dimension measured at the base of the protective/barrier cap. This definition applies to any shape of the protective/barrier cap whether it is circular, oval, triangular, square, rectangular, or other polygonal shape or non-polygonal shape. In some variations, because of limitations of in-line forming during the web converting process, the height of the protective cap/barrier cap may be limited by the length, width and/or circumference of the base of the protective cap/barrier cap. In some variations, the ratio of the height of the protective cap/barrier cap relative to the area of the opening (surface area) may be less than about 0.50 (e.g., less than about 0.45, less than about 0.4, less than about 0.35, less than about 0.30, less than about 0.25, less than about 0.2). In some variations, e.g., depending on the shape of the opening, it may be more accurate to describe the height in terms of the total distance of the perimeter (or circumference) of the opening. The terms perimeter or circumference both mean the total linear distance measured along the inside of a closed curve measured at the base of the protective cap/barrier cap. As defined herein, the terms perimeter and circumference may apply to any closed curve and need not be limited to circular shapes. For example, the maximum height of the protective cap/barrier cap may be a function of the length of the perimeter of the opening formed. Further, the height of the cap/cover may be within about 95%, within about 90%, within about 85%, within about 80%, within about 75%, within about 70%, within about 65%, within about 60%, within about 55%, within about 50%, within about 45%, within about 40%, within about 35%, within about 30%, within about 25%, within about 20%, within about 15%, within about 10%, within about 5% etc. of the length of the perimeter of the opening.

The thickness of the protective cap or barrier cap in these and other embodiments may be uniform, mostly uniform, somewhat variable or variable, which may be defined by the manufacturing methods used and relative tolerances that are possible. The thickness of this protective cap/barrier cap and/or liner may be less than about 0.01 mm, between about 0.01 mm and about 0.1 mm, between about 0.1 mm and about 0.2 mm, between about 0.2 mm and about 0.3 mm, between about 0.3 mm and about 0.4 mm, between about 0.4 mm and about 0.5 mm, between about 0.5 mm and about 0.6 mm, between about 0.6 mm and about 0.7 mm, between about 0.7 mm and about 0.8 mm, between about 0.8 mm and about 0.9 mm, between about 0.9 mm and about 1.0 mm, between about 1.0 mm and about 1.1 mm, between about 1.1 mm and about 1.2 mm, between about 1.2 mm and about 1.3 mm, between about 1.3 mm and about 1.4 mm, between about 1.4 mm and about 1.5 mm, between about 1.5 mm and about 1.6 mm, between about 1.6 mm and about 1.7 mm, between about 1.7 mm and about 1.8 mm, between about 1.8 mm and about 1.9 mm, between about 1.9 mm and about 2.0 mm, between about 2.0 mm and about 2.1 mm, between about 2.1 mm and about 2.2 mm, between about 2.2 mm and about 2.3 mm, between about 2.3 mm and about 2.4 mm, between about 2.4 mm and about 2.5 mm, between about 2.5 mm and about 2.6 mm, between about 2.6 mm and about 2.7 mm, between about 2.7 mm and about 2.8 mm, between about 2.8 mm and about 2.9 mm, between about 2.9 mm and about 3.0 mm.

Thickness of plastic sheets to be formed during web converting into protective caps, barrier caps, or any other plastic or formed component in another device described herein may be measured in inches or mm (e.g., 1 inch is approximately 25.4 mm). For example, plastic sheets made of any material described herein (including polycarbonate, polyethylene, acrylics or polyethylene terephthalate in many cases) may be 0.0025" (0.0635 mm), 0.005" (0.127 mm) or 0.01" (0.254 mm) or 0.015" (0.381 mm) or 0.02" (0.508 mm) or 0.03" (0.763 mm) or 0.04" (1.016 mm) or 0.05" (1.27 mm) or other thicknesses. As further examples, barrier caps may have thicknesses of 0.005" (0.127 mm) or 0.01" (0.254 mm), protective caps (including those that "snap" or have bistable configurations, may have thicknesses of 0.005" (0.127 mm) or 0.01" (0.254 mm), negative pressure therapy device plastic caps may have thicknesses of 0.01" (0.254 mm) or 0.015" (0.381 mm), ostomy wafers may have flared cone thicknesses of 0.02" (0.508 mm), intraosseous access securement devices may have plastic hub thicknesses of 0.02" (0.508 mm), and surgical wound protector barrier caps may have thicknesses of 0.01" (0.254 mm). As described previously, the thickness of any or all of these plastic components may be variable.

Regions of the protective cap and barrier cap may have a thickness that is different from other regions of the protective cap and barrier cap, especially at regions of curvature or where regions have been stretched during the forming process. For example, the walls of the protective cap or barrier cap (that extend away from the generally planar adhesive substrate) may be thinner or thicker than the rest of the protective cap/barrier cap. As one example, by being thinner than the rest of the protective cap/barrier cap, this portion of the device may be more transparent than the rest of the protective cap/barrier cap, enabling the user to see the pad and/or medicament on the pad. These walls may be primarily linear as seen in FIG. 5 or may be curved as is seen in FIG. 6. Though the terms protective cap and barrier cap are used primarily in these descriptions of material choice, thickness, and geometries (including lengths, widths, heights, perimeters, angles, rations, etc.), these parameters specified herein also apply to or any other 3D component in an other device described herein, including by not limited to wound therapy devices, ostomy wafers, IV stabilization devices, intraosseous access devices.

Figure 9E:
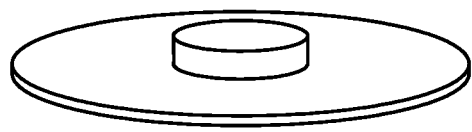
FIGS. 9E and 9F are variants of the devices shown in FIGS. 9A and 9B.
Figure 9F:
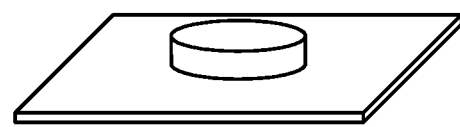

FIGS. 9E and 9F illustrates different shapes and sizes of the devices previously described in FIGS. 9A-D. The adhesive and/or barrier caps shapes can be any polygonal shape including square, rectangle, circle, oval, triangle or variants or modifications thereof. Non-polygonal shapes or irregularly shaped barrier caps and adhesive shapes may also find use.

Figure 9G:
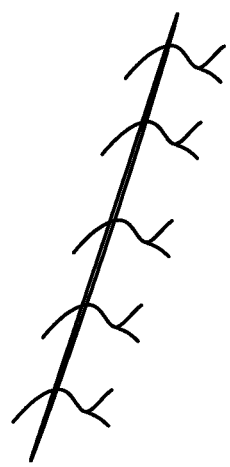
FIG. 9G is an illustration of a surgical wound.
Figure 9H:
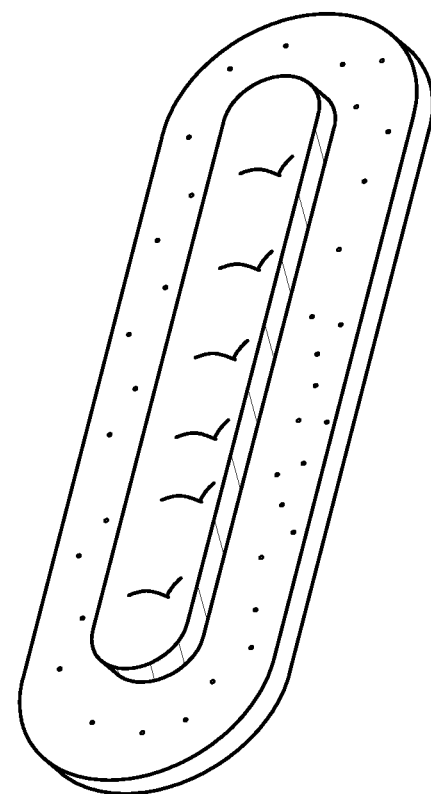
FIG. 9H is an illustration of a medical device that has been applied to the wound.

FIG. 9G shows an incision site wound as might be seen after surgery. FIG. 9H shows an adhesive medical device with construction similar to that of FIGS. 9C and 9D that has been placed on top of the wound to protect the wound and promote healing. A medicament such as an antibiotic or petroleum jelly may be present in the chamber, providing a moist environment for wound healing. The device shown in FIG. 9G. and other devices with a barrier cap offer several benefits in protecting a wound. First, the barrier cap which is semi-rigid or fully rigid helps stabilize the wound/incision site as the rigid structure that surrounds the wound helps to keep the wound edges together and generally reduces movement of the wound's surfaces as it heals. This promotes wound healing. The barrier cap may have a transparent barrier cap which enables the user and healthcare provider to monitor the healing progress and confirm that the wound is not infected or inflamed. This would minimize the requirement to keep removing and reapply wound dressings to visualize healing of the wound FIGS. 9I and 9J show different embodiments of protective adhesive devices that were described previously. FIG. 9K shows a side view (top drawing) of the device shown in FIG. 9J and a cross sectional view (bottom drawing) of the same device.

FIG. 9L is a photograph of the device shown in FIG. 9J. The liner is seen through the transparent cap. Transparent, non-transparent, opaque, colored or non-colored caps may find use.

FIG. 9M shows various geometric parameters of devices such as those seen in FIGS. 9A-9L.

FIGS. 9N and 9O are a top view and photograph of similar adhesive devices. FIG. 9P shows a side view of another adhesive device that serves to protect a user's wound. Another photograph of a different embodiment is shown in FIG. 9Q. Any shape or emblem or logo may be imprinted or formed into the plastic cap of this embodiment or any other device described herein. Various geometric parameters are depicted in FIG. 9R. In some embodiments, any of the plastic caps described herein may be applied to currently available adhesive bandages which generally comprise a liner, adhesive layer (onto which a pad is affixed), and adhesive substrate. The cap may be applied to the top side of the adhesive substrate using an round, oval or ring of double-sided adhesive.

Figure 9T:
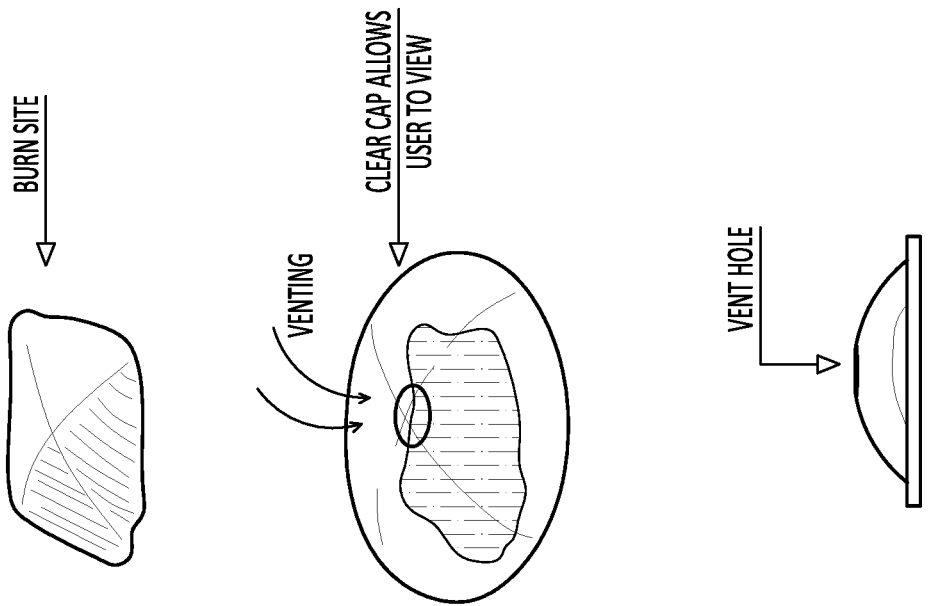
FIGS. 9S and 9T are adhesive medical devices with protective features.
Figure 9S:
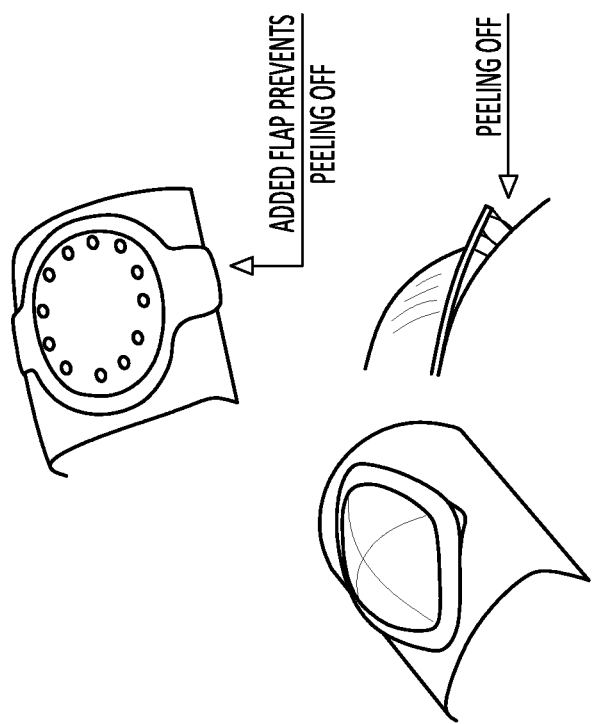

FIG. 9S shows a top view of an adhesive medical device that protects wounds on moveable surfaces such as a finger. An extra adhesive flap is provided that ensures that the device remains attached to the skin, even during movement.

FIG. 9T offers multiple views of an adhesive device that protects a burn. There is a clear cap that allows the user or healthcare provider to monitor the progression of wound healing. An optional vent hole or series of vent holes may provide exposure to ambient air which may help with wound healing.

FIG. 9U shows alternate cap designs. FIG. 9V shows additional cap designs including those meant to be flexible during a user's movement.

Figure 9W:
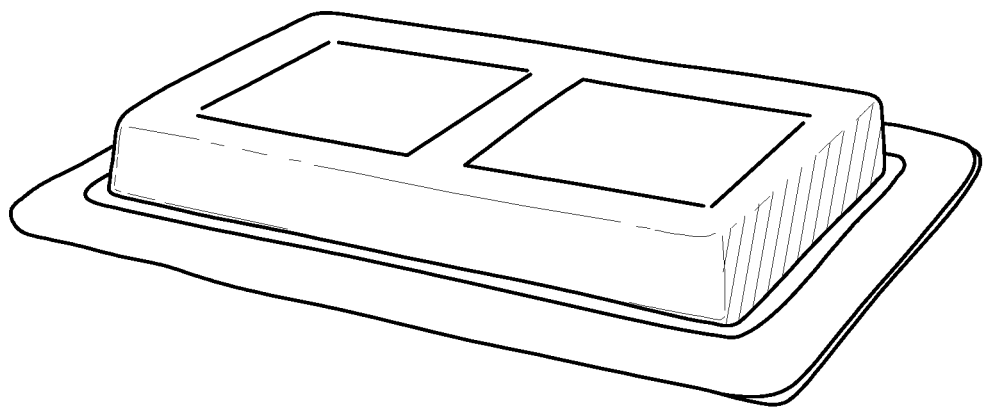
FIGS. 9W and 9X illustrate devices with caps that include windows.
Figure 9X:
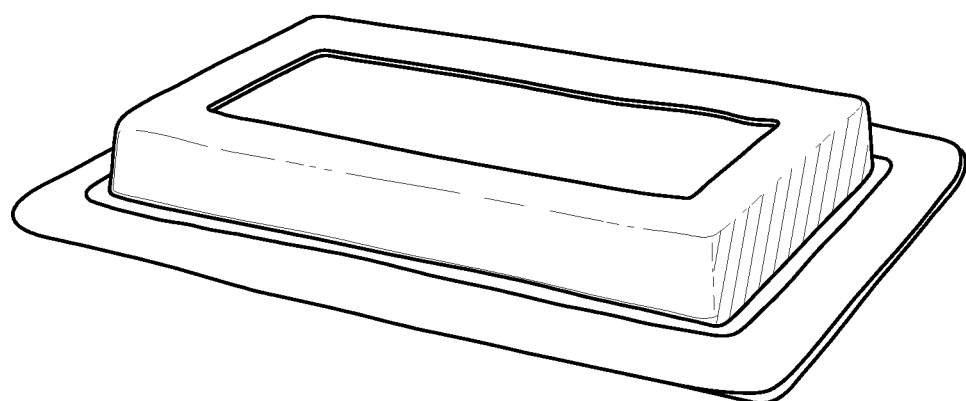

FIGS. 9W and 9X show devices with barrier caps that include openings or windows. One or more windows may be incorporated into the cap design. These windows allow the healthcare provide or the user to administer topical medications including but not limited to any of the medicaments previously listed. In some cases, 2-octyl cyanoacrylate or n-butyl-2 cyanoacrylate (such as Dermabond or Indermil or any other medical cyanoacrylates) may be applied through these windows and onto the skin, to close the wound. By adding a rigid or semi-rigid cap around the wound, it keeps the wound edges together, allowing the cyanoacrylate or skin glue to effectively bond or cure or dry. This may be especially helpful during application of the medical cyanoacrylate as the healthcare provider's gloves frequently will become stuck to themselves or to the patient's skin during application of the medical cyanoacrylate. This also addresses a major issue with applying medical cyanoacrylates and other similar skin care products, namely that the wound edges separate during application of the product. Thus, the subject device improves the performance of medical cyanoacrylates. Further, the device prevents the user (especially children) from picking at the dried medical cyanoacrylate or the wound which may cause the separation of the edges of the wound and poor wound healing. Furthermore, the device can reduce tension on the skin in otherwise high tension areas, which might otherwise lead to re-opening of the wound. In other cases, the device may prevent friction or abrasion to the healing wound site. In some cases, a device with no windows (such as those shown in FIGS. 9I and 9J) may be applied on top of the wound after the medical cyanoacrylate has dried, to protect the site during showering and bathing, until the dried adhesive has sloughed naturally.

Figure 10B:
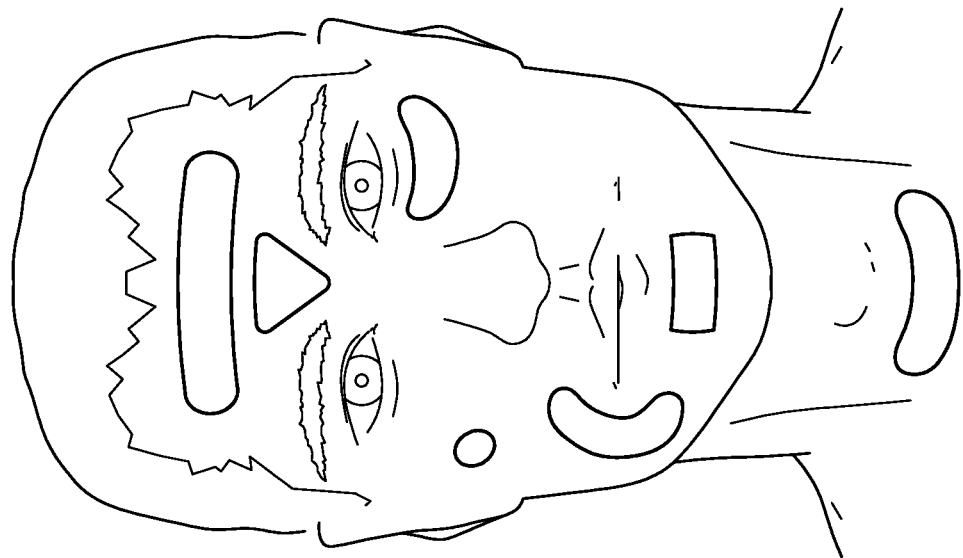
FIG. 10B shows different shape variations for adhesive medical devices for application to the face.
Figure 10A:
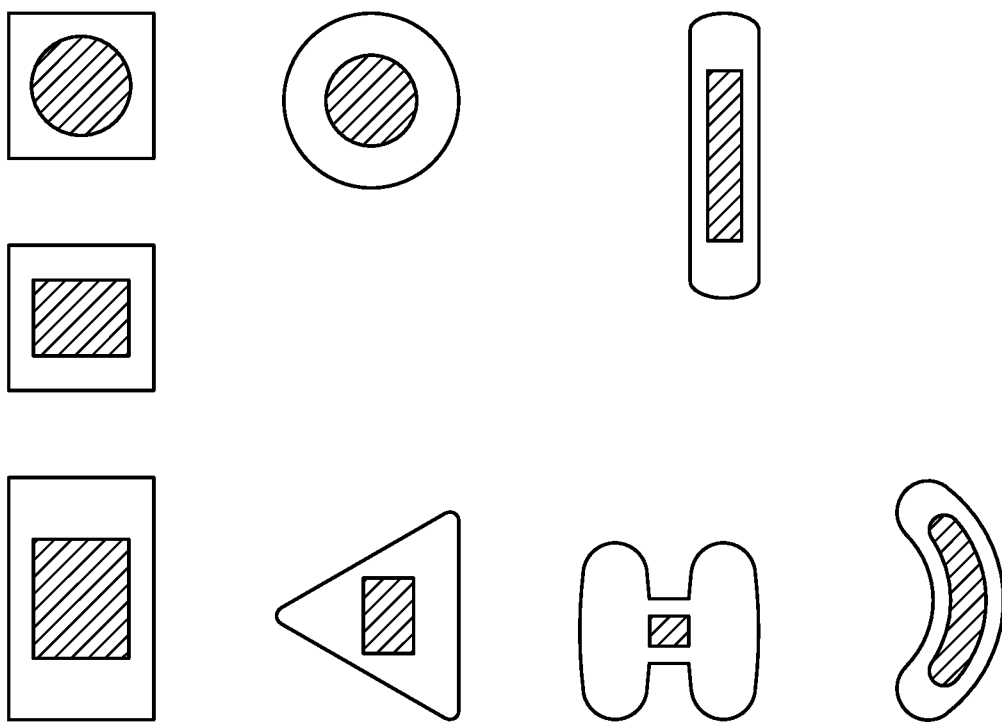
FIG. 10A shows different shape variations for adhesive medical devices.

FIG. 10A shows different shape variations of adhesive devices with pads. Medicament (not shown) may be applied on any of the devices shown. The holdfast shape may be a circle, square, rectangle, oval, rhomboid, trapezoid, pentagon, hexagon, semi-circle, or any polygonal or shape listed above. The pad shape (and corresponding shape of the protective cap) may be circle, square, rectangle, oval, rhomboid, trapezoid, pentagon, hexagon, semi-circle, or any polygonal or shape listed above. Any shape combination of holdfast and pad and/or protective cap may be used. Different, non-standard shapes may also find use, especially when such shapes are adapted to be secured on an anatomical body part including the finger, hand, arm, leg, trunk, buttocks, back, heal, toe ankle, wrist, elbow, shoulder, knee or the like. The adhesive devices may have lengths of approximately 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm and widths of approximately 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm. Total device circumference or the summation of edge lengths may be approximately 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 51 cm, 52 cm, 53 cm, 54 cm, 55 cm, 56 cm, 57 cm, 58 cm, 59 cm, 60 cm, 61 cm, 62 cm, 63 cm, 64 cm, 65 cm, 66 cm, 67 cm, 68 cm, 69 cm, or 70 cm.

FIG. 10B shows several holdfast shapes that are well suited for application on face, including on or around the eyes, nose, mouth, ears, brow, chin, etc.

Figure 11:
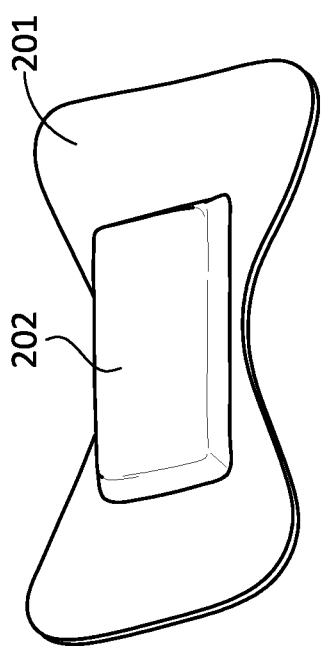
FIG. 11 is a different variation of an adhesive medical device that can be applied to the toes or fingers.

FIG. 11 shows one example of a liner 201 and protective cap 202 of an adhesive device that is designed to administer medicament to a finger or toe. The protective cap 202 is roughly symmetrically placed in this figure, although asymmetric location of the cap (and thus any pad that it protects) either along the width or length of the device is possible. In this example, the protective cap and liner are integrated into a single component. The protective cap and liner component may be made using in line forming methods or injection molding as described herein.

Figure 12:
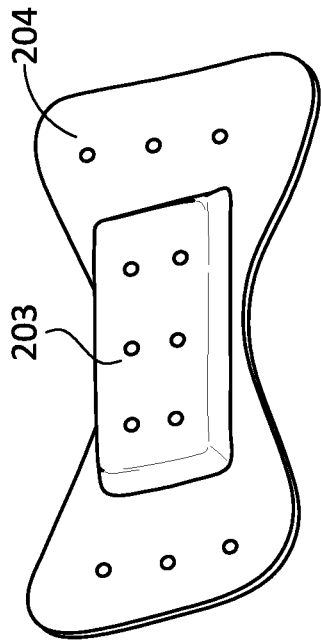
FIG. 12 is a variation of the adhesive medical device shown in FIG. 11.

FIG. 12 illustrates a different embodiment of the protective cap 203 and liner 204 in which multiple holes are located in either or both structures. These holes in the protective cap may enable exposure of the medicament to air which may serve to harden or otherwise condition the medicament prior to its use by the subject.

Figure 13:
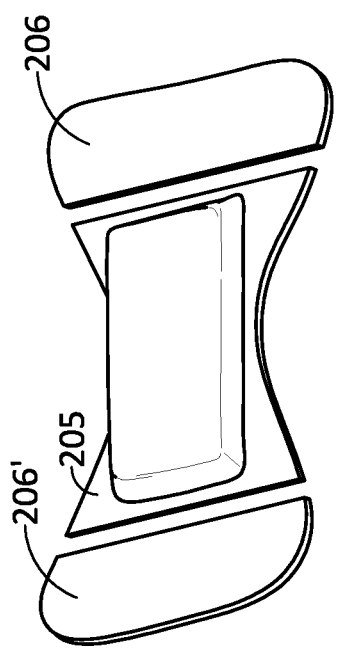
FIG. 13 is another variation of the adhesive medical device shown in FIG. 11.

FIG. 13 shows another embodiment of the protective cap 205 and liners 206 and 206' which in this case are symmetrically placed. In this embodiment, the protective cap and liners are three separate components, as opposed to the unitary construction previously described.

Figure 14:
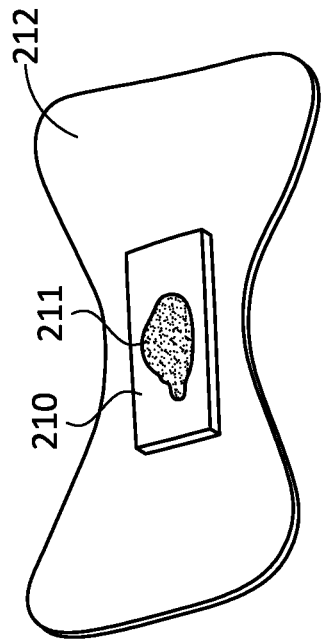
FIG. 14 shows the adhesive medical device shown in FIG. 11 prior to application onto a user.

FIG. 14 illustrates the holdfast 212 and pad 210 and medicament 211 for an adhesive device, whose corresponding protective caps and liners were shown in FIGS. 12 and 13. The pad is roughly symmetrically placed in this embodiment. In other embodiments, that pad may be off-center in either of the two axes. This shape of the adhesive device is suited to application of medicament to the nails of either the fingers or toes.

Protective and Barrier Caps

The protective caps and barrier caps seen in FIGS. 1-6, FIG. 9, FIGS. 11-13 (and the vacuum caps and all other plastic 3D pieces or components to be described below) may share similar physical features and may be manufactured using similar techniques. The protective caps may protect a medicament after the time of manufacturing until the device is applied by a subject. As such, it may protect the medicament during transport and storage of the adhesive device. The barrier caps may generally protect the subject's wound after application, and may also contain a medicament. The protective cap and barrier cap can be made and applied through a variety of manufacturing methods. For example, they may be injection molded in-line (within the manufacturing line) or off-line and then fed one at a time or more than one at a time via a bowl feeder to be applied to the adhesive device. In many cases, the adhesive device may be manufactured through a web converting process in which reams of material (adhesive substrate, adhesive layer, liners, plastic sheet and the like) are fed and then cut and joined using processes that are well known to those skilled in the art. The plastic sheet may be formed (e.g., cold formed, thermoformed, heated then formed) during the web converting process and then cut in the appropriate shape and accurately placed on the moving or locally stationary web. The width (defined as the shortest distance across a polygonal shape) of the protective cap/barrier cap may be the same width as the adhesive substrate. In FIG. 1, for example, the width of the protective cap and cover (liner) may be identical or nearly identical in dimensions as the underlying adhesive substrate and adhesive. In other cases, the dimensions of the protective cap/barrier cap (which may include the liner) may exceed the width or length dimensions of the adhesive substrate and adhesive by approximately 0.05 mm, by approximately 0.10 mm, by approximately 0.15 mm, by approximately 0.20 mm, by approximately 0.25 mm, by approximately 0.30 mm, by approximately 0.35 mm, by approximately 0.40 mm, by approximately 0.45 mm, or by approximately 0.50 mm. The protective cap/barrier cap and/or liner shall be placed on the adhesive substrate and adhesive so that any edge of the protective cap/barrier cap and/or liner is approximately 0.05 mm, approximately 0.10 mm, approximately 0.15 mm, approximately 0.20 mm, approximately 0.25 mm, approximately 0.30 mm, approximately 0.35 mm, approximately 0.40 mm, approximately 0.45 mm, or approximately 0.50 mm from the edge of the adhesive substrate and adhesive on which it is placed. Accuracy of this placement during the web converting process or other processes may be accomplished using vision systems that may use optics (e.g., optical sensors, lasers, etc.) and devices that are not in registration can be rejected in an automated or manual process. The protective cap/barrier cap should be placed symmetrically or substantially symmetrically to the adhesive and/or adhesive substrate to help ensure that the subject views the product as a quality product.

The protective cap/barrier cap may be made from a variety of materials that are conducive to injection molding or in-line forming during a web converting process. These materials include but are not limited to polycarbonate and polyethylene (including high density polyethylene). The protective cap/barrier cap may be any color and may be transparent, opaque or variably opaque. Choice of color and opacity of the protective cap/barrier cap may be important to protect the medicament from light or other elements which may affect the quality or longevity of the medicament. The choice of color may be cosmetic in nature. For example, the protective or barrier cap can be any color such as blue, red, green, yellow or the like and various shading or gradations in coloring are possible for cosmetic and non-cosmetic reasons. For example, novel adhesive bandages that have a blue barrier cap may be produced, which may appeal to children of fashion-conscious adults. In some cases, the material used in the cap (such as some plastics) may partially or completely block ultraviolet light, which may help with wound healing, scar prevention or may help prevent discoloration of the wound/skin as it heals. Writing or other marking may be provided on the protective cap/barrier cap or any other part of the adhesive device including the adhesive substrate or liner. Laser cutting, die cutting or other cutting method may be used to cut the protective cap/barrier cap or any other part of the adhesive device, providing novel features or cosmetic benefits. In some cases, the protective or barrier cap may be shaped into a functional or whimsical shape, such as child-friendly shapes or the shapes of various cartoon characters, bugs, sporting goods, or other shapes that may appeal to children or adults. The protective or barrier cap may be made from thermochromatic materials that change color with heat. Importantly, the edges of the protective cap/barrier are not sharp and are not likely to cut or otherwise harm a user.

FIG. 15 shows an adhesive device that is shaped to administer medicament to a toe, including an adhesive holdfast 212 and a pad 210 that is centrally located. The medicament is not shown in this figure but would be dispensed on the pad 210. The various dimensions of the adhesive device are labeled. Length A' is typically between about 2 cm and about 20 cm, for example, between about 3 cm and about 14 cm and more specifically between about 4 cm and about 10 cm. Length A' may be approximately 3.0.cm, 3.5 cm, 4.0 cm, 4.5 cm, 5.0 cm, 5.5 cm, 6.0 cm, 6.5 cm, 7.0 cm, 7.5 cm, 8.0 cm, 8.5 cm, 9.0 cm, 9.5 cm, 10.0 cm, 10.5 cm, 11.0 cm. Length B' is typically between about 1 cm and about 12 cm, more specifically between about 2 cm and about 10 cm and most specifically between about 3 cm and about 6 cm. Length B' may be approximately 2.0 cm, 2.5 cm, 3.0 cm, 3.5 cm, 4.0 cm, 4.5 cm, 5.0 cm, 5.5 cm, 6.0 cm, 6.5 cm, 7.0 cm, 7.5 cm, 8.0 cm, 8.5 cm, 9.0 cm, 9.5 cm, and 10.0 cm. Length C' is typically between about 1.0 cm and about 9.0 cm, more specifically between about 2.0 cm and about 6.0 cm and most specifically between about 2.0 cm and about 5.0 cm. Length C' may be approximately 2.0 cm, 2.5 cm, 3.0 cm, 3.5 cm, 4.0 cm, 4.5 cm, 5.0 cm, 5.5 cm, and 6.0 cm. Length D' is typically between about 0.5 cm and about 6.0 cm, more specifically between about 0.75 cm and about 5.0 cm and most specifically between about 1.0 cm and about 3.0 cm. Length D' may be approximately 1.0 cm, 1.5 cm, 2.0 cm, 2.5 cm, 3.0 cm, 3.5 cm, 4.0 cm, 4.5 cm, 5.0 cm, 5.5 cm, and 6.0 cm. Length E' is typically between about 0.75 cm and about 10 cm, more specifically between about 1.0 cm and about 6.0 cm and most specifically between about 1.5 cm and about 5.0 cm. Length E' may be approximately 1.0 cm, 1.5 cm, 2.0 cm, 2.5 cm, 3.0 cm, 3.5 cm, 4.0 cm, 4.5 cm, and 5.0 cm. The shape shown has been optimized to enable delivery of medicament directly to the nail, nail bed, under the nail bed, and surrounding finger or toe tissue to promote a medical benefit. For example, such a device in which the medicament is an anti-fungal ointment may be used to treat nail fungus. The device would ideally provide medicament to all parts of the nail and nail bed to maximize therapeutic benefit. Other embodiments of devices may be used to treat heal cracks with various moisturizers and other medicaments such as urea.

FIG. 16 illustrates the adhesive device 302 of FIGS. 14 and 15 placed on the subject's toe 300. The nail 301 is shown completely covered by the adhesive device. Not shown is the medicament which is covers the nail 301 to provide therapeutic benefit.

FIG. 17 shows an embodiment of an adhesive device designed to adhere to the subject's skin and to protect various wires 403 (which may be part of other medical devices/sensors as might be seen in the wards or ICU of a hospital) through the use of a protective cover 402 and an adhesive holdfast 401. The tunnel created by the protective cover provides a conduit for these wires and protects the wires from damage or lowers the likelihood the wires will be inadvertently pulled or displaced by the subject or others. The cross-section shown is triangular; rectangular, hemi-circular/hemi-oval, or any other appropriate shaped cross-section (or combination of shapes) may be used. The protective cover 402 maybe bent, curved, or bendable (e.g., having accordion sides) or the like.

FIGS. 18A and 18B show an adhesive medical device that provides negative pressure wound therapy to a subject's wound to promote faster healing and less scarring. FIG. 18A shows the device in an inactivated state. The adhesive holdfast 502 (which may be a hydrocolloid) adheres the device to the skin in close apposition to the wound 501. The pad 503 in this case optionally has holes or fenestrations 504, though in some embodiments fenestrations are not present. A vacuum cap 505 is seen in a non-activated state, in which the wound is exposed to ambient environmental pressure (non-negative). Double-sided adhesive 508 is attached to the vacuum cap 505 and to the adhesive holdfast 502.

In FIG. 18B, the vacuum cap 505 has been displaced in a direction towards the wound and air in the chamber 507 has been displaced outside the chamber 507 through the pressure relief element 506. In some cases, the pressure relief element 506 is a valve or serves a similar purpose of a valve, namely allowing air to be evacuated out of the chamber when the vacuum cap 505 is pressed down and preventing or minimizing flow of air back into the chamber. This allows a negative pressure to be created and maintained (the device is now in an activated state). This negative pressure may be in the 0-200 mm Hg range, more specifically in the 10-150 mm Hg range, and in some variations in the 40-150 mm Hg range. The level of negative pressure generated by the device may be variable. When the device returns to an inactivated state (after a period of seconds, several minutes, 5-10 minutes, 10-15 minutes, 15-30 minutes, 30-45 min, 45-60 min, 1-2 hours, 2-3 hours, 3-4 hours, 4-5 hours, 5-6 hours, 6-9 hours, 9-12 hours, 12-15 hours, 15-18 hours) then the user can press the vacuum cap again to again create negative pressure within the chamber. Such a device may be worn for hours or days before being replaced.

Figure 18C:
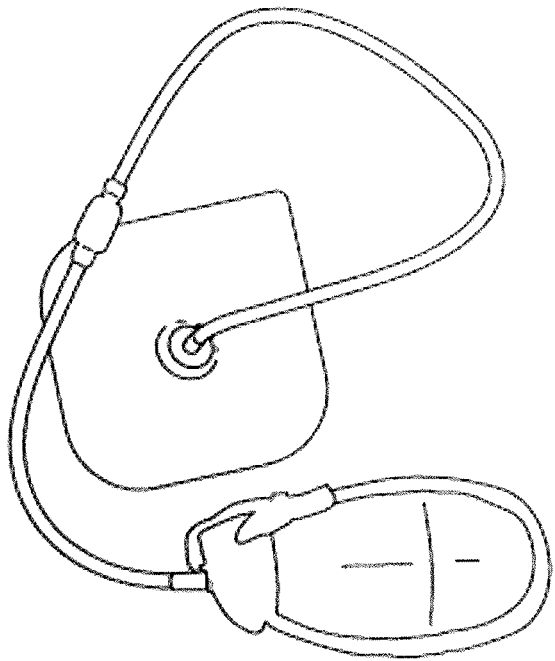
FIGS. 18C and 18D illustrate a negative pressure wound therapy system.
Figure 18D:
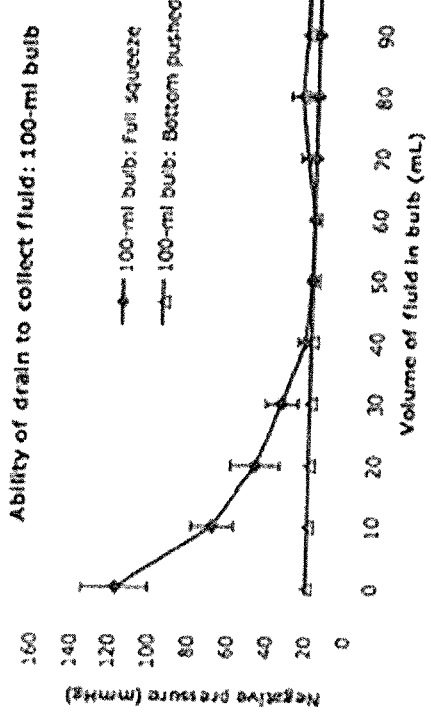

In some embodiments, such as those shown in FIGS. 18C and 18D, a small external suction device (such as pipet bulb or other type of bulb suction) may be used to provide ongoing negative pressure or to create negative pressure sporadically. These external suction devices may include bulb suction devices similar to those used to drain chest and abdominal wounds after surgery.

Figure 18E:
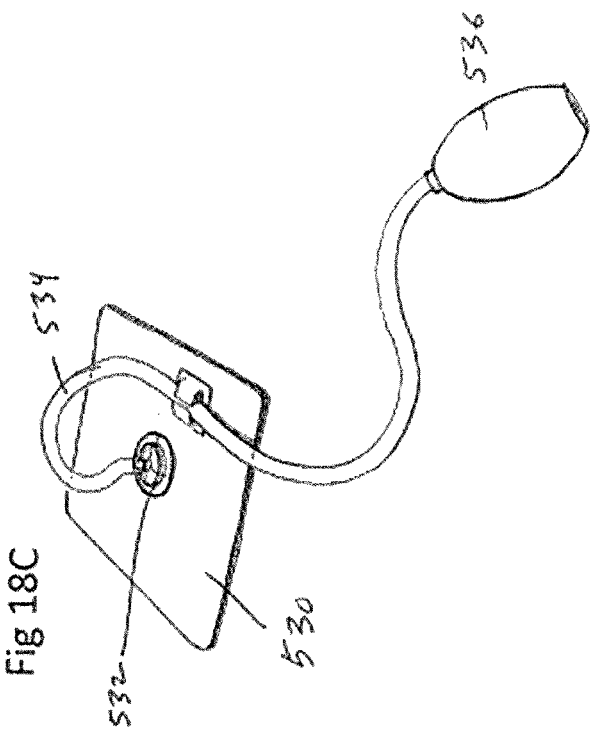
FIG. 18E shows the pressure profile of a manually actuated vacuum source.

As shown in FIG. 18C, negative pressure wound therapy devices generally comprise an absorbent pad or other wound dressing 530 (such as a hydrocolloid), a plastic cap 532 and tubing 534 that connects to a vacuum source, in this case, a manually-actuated bulb suction device 536. A bulb suction device 536 may have capacities between 50 ml and 2000 ml and more preferably between (and including 100 ml and 500 ml). Capacities of 100 ml, 150 ml, 200 ml, 300 ml, 400 ml and 500 ml may find use. Representative negative pressures created by a 100 ml bulb as a function of bulb volume is shown in FIG. 18E. Generally, it has been shown in the medical literature that negative pressures between 40-150 mm Hg are useful in the treatment of wounds. In use, a bulb suction device may need to be pressed (and negative pressure re-generated) and/or fluid drained on an intermittent basis, for example every few hours.

Figure 18F:
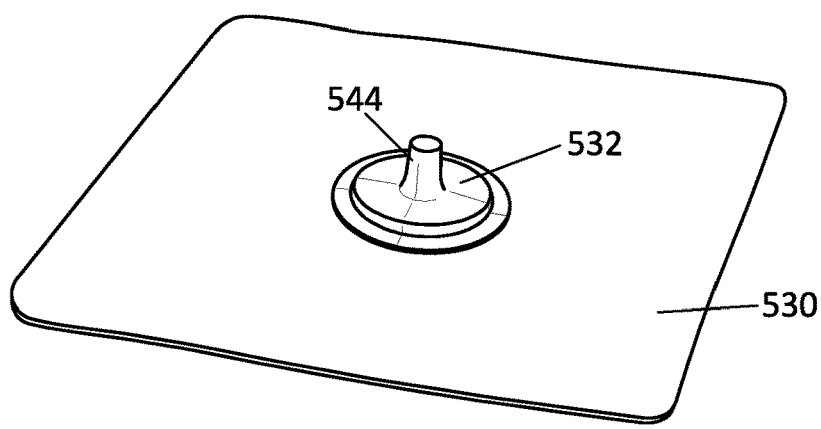
FIGS. 18F-18L illustrate various views of a dressing that may be used for negative pressure wound therapy.

As shown in FIG. 18F, the plastic cap 532 may contain one or more ports including, for example, a approximately perpendicularly-projecting adapter 544 that connects the plastic cap to medical grade tubing (not shown) which enables fluid (air) communication between the wound and the vacuum source. In many cases, there may be a foam or gauze or other absorbent wound interface layer that is placed within the wound of the patient or on top of the patient's skin or wound, thus serving as a partial or complete barrier between the device and the patient. In some cases, the pad or gauze or other absorbent feature is part of the device, for example attached to the underside of the holdfast (such as hydrocolloid or the like). In some cases, the base of the cap can be round, oval, semi-oval, curved, rectangular, square or other geometrical shape. As the plastic cap extends away from the user's skin, the cap may assume a conical or tapering three-dimensional shape, which has an opening which can be attached to tubing that connects to the vacuum source. In some cases, a view port may be present on or within the cap to enable the patient or healthcare provide to assess the healing of the wound and/or confirm the wound is not infected. In other cases, the entire plastic cap may be transparent or enable view of the healing of the wound.

In some embodiments, the negative pressure wound device (including any and all components such as the tubing or bulb or other fluid collection means) may be held or attached to the patient's body (such as their leg or foot) through the use of an attachment means such as tape, gauze, Velcro, strap or the like.

The plastic cap 532 generally has a leak-proof seal to the adhesive substrate 530. It also may contain a port or adapter to connect to the vacuum source. This connection to the vacuum source may be through a press fit seal, or other means of connection that is commonly known in the art. The plastic cap or plastic cover may also contain one or more other ports—a port to remove waste exudate into a waste receptacle or reservoir, a port to add water, saline, antibiotic or other fluid to the wound area, and/or a viewing area or port that provides a visual indication of the progress of the wound healing.

This cap may be cone shaped and may be manufactured smaller or larger to be sized for specific wound sizes or common wound locations. For example, it may be sized particularly for a common spot for diabetic ulcers on the foot or there may be child or adult sizes. The plastic cap generally is located on top of the hole within the adhesive substrate (or holdfast), allowing the fluid transmission of negative pressure to the wound.

Figure 18G:
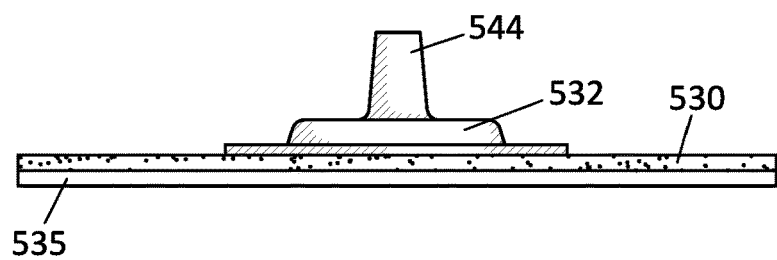

FIG. 18G shows a slide view of the negative pressure wound therapy dressing. The plastic cap 532 is shown, including the adapter 544 which has a tapering shape as it projects away from the skin surface. The adhesive substrate 530 is shown attached to the liner 535.

Figure 18H:
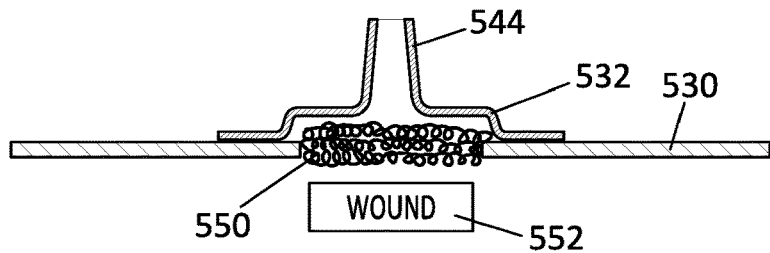

FIG. 18H shows a cross sectional view of the device shown in FIG. 18G. The liner has been removed and foam 550 is seen between the plastic cap and the wound 552. In this case, the foam 550 has been sucked into the chamber within the plastic cap 532 due to the negative pressure created by the device. In this example, the opening in the adhesive substrate 530 is approximately the same size as the base of the plastic cap 532. In other cases, the length of the opening in the adhesive substrate is smaller than the length of the opening at the base of the plastic cap (defined by the internal dimensions of the cap). This ratio between the length/diameter of the opening in the adhesive substrate 530 to the length/diameter of the base of the plastic cap 532 (defined by the internal dimensions of the cap) is generally less than 1:10, less than 1:9, less than 1:8, less than 1:7, less than 1:6, less than 1:5, less than 1:4, less than 1:3, less than 1:2, less than 1:1.

Figure 18I:
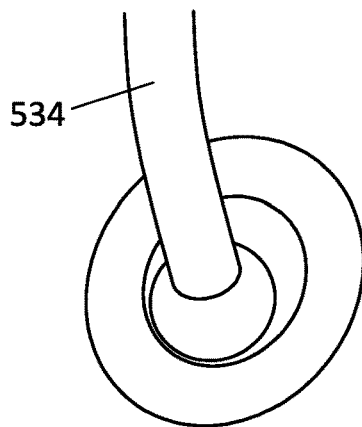
Figure 18J:
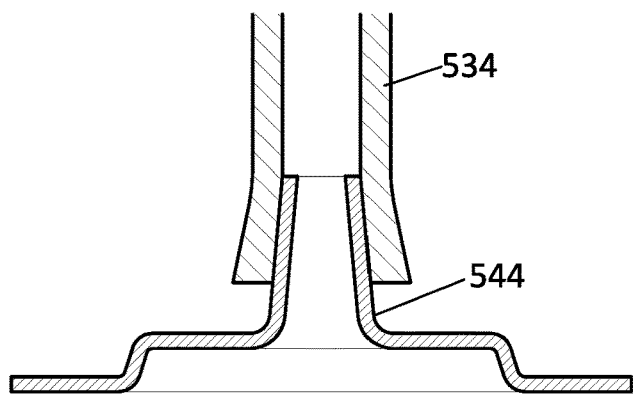

FIG. 18I shows the tubing 534 attached to the plastic cap via the adapter. FIG. 18J shows a cross sectional view of this attachment, in this case using a press fit between the tubing 534 and the adapter 544.

The cap may be raised and/or have a hollow space within it. The height and shape of the plastic cap may be limited by the manufacturing process used (i.e. forming during web converting). The cap may be made out of any variety of common plastics, such as ABS, PC/ABS, PVC, polypropylene, polyethylene, polycarbonate, or others, or could contain, be impregnated with, be adhered to, be coated with, or be manufactured out of any variety of biologically compatible materials, such as PEG, PLA, PGA, PLGA, hydrogels, etc. The plastic cap 532 may additionally contain a hub for the purposes of aspirating wound exudate and other liquids from the wound. An additional tube and suction source may be applied in order to remove this exudate from underneath the occlusive dressing and drain it into a waste container. Leak prevention mechanisms may be designed into any of the parts described in this invention. Less than 10 mL of exudate is expected per day for many patients with diabetic ulcers, though in some cases, this may be significantly more, especially for other disease states.

As described previously, the device contains tubing between the plastic cap and the vacuum source, which may be made from any medical grade, biocompatible material. The tubing may additionally lock or seal onto the source of the vacuum via a Luer lock or similar standard sealing system, or it may press fit into an inlet sized to make a seal at that connection. The tubing material is generally non reactive to and/or compatible with normal medical device sterilization.

An additional adapter or locking mechanism may be added to the tubing, in order to separate the tubing portion in two parts: a reusable section with in which the tubing connects to the vacuum source, and a disposable section that attaches to the wound dressing/absorbent pad and is attached to the plastic cap as described previously. This additional adapter could be any quick release adapter/locking mechanism such that the disposable wound dressing section could be taken off, thrown away, and the wound dressing replaced and reconnected to the vacuum source. The adapter material can undergo normal medical device sterilization.

The device shown in FIG. 18F may be used with any source of vacuum, including self-actuating suction bulbs as shown in FIGS. 18C and 18D, or may be used with any commercially-available vacuum sources, including those made by companies such as Kinetic Concepts, Smith and Nephew, Spiracur and the like. Thus, sources of the vacuum may include manual power, that are self-powered, or that use electrical power, i.e. a portable suction pump, plastic bellows, a manual suction bulb, or wall suction as is provided by medical providers or hospitals. In some embodiments, a filter may be used in the device assembly in order to prevent or reduce the amount of microbes, exudate, or any contamination from the wound site from reaching the vacuum pump. This filter may be in any position between the vacuum pump and an exudate collection container, or in the tubing itself.

This therapy can be utilized continuously over a period of a few minutes to a few days, or can be used intermittently throughout therapy for wound healing. The vacuum source may pull a pressure between −40 and −150 mm Hg, but may be optimized to −75 and −125 mm Hg. Consistent pressure may be maintained until the patient interrupts it, it may be variable, or it may slowly return to zero, thus triggering the patient to reset it. In some embodiments, the device may make use of valves or other viable methods of pressure modulation in order to reduce or increase the amount of negative pressure delivered to the wound. The device may be configured to provide any suitable or desired level of negative pressure at any suitable or desired frequency.

In some embodiments, the device may be configured such that air can only flow through the device or parts of the device in one direction, in order to maximize efficiency of the vacuum applied. This could be designed by using one way valves or other methods.

Figure 18K:
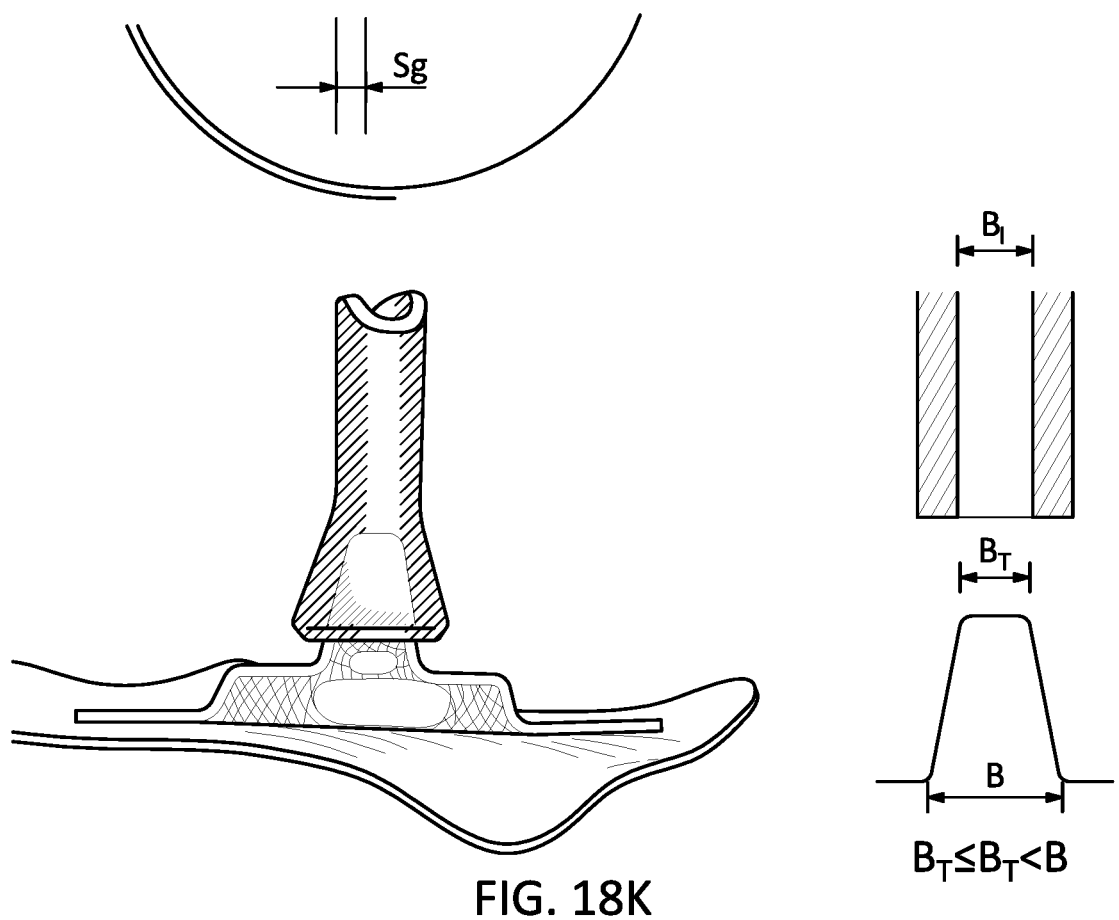

The construction and geometry of the vacuum cap may be similar to that of the protective cap and barrier cap that were previously described. This includes the angle α and the various dimensional attributes that were previously described for protective and barrier caps. In some embodiments, as shown in FIG. 18K, the geometric dimensions of the plastic cap (namely the adapter portion of the plastic cap which is shown with a conical shape) designed to facilitate a press fit interface with the tubing. In this example, the diameter of the top of the cone is equal to or smaller than the inner diameter of the tubing to which it is attached. This helps to create a press fit and/or seal between the plastic cap and tubing.

Figure 18L:
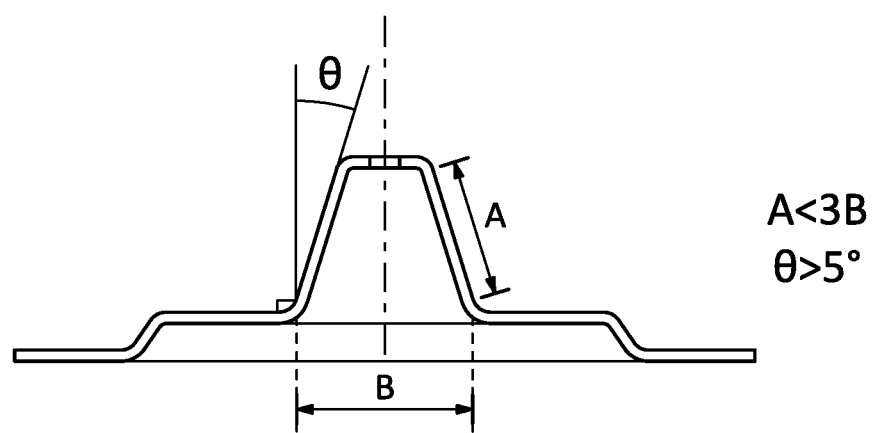

In FIG. 18L, the relative ratio of the length of the adapter portion of the plastic cap ("A") to the internal diameter of the base of the adapter portion of the plastic cap ("B") is defined. Generally A<3B. In some cases, A<2B and in still other cases, A may be approximately equal to B. These relative ratios may be defining by the forming process as well as the materials used and whether heat has been applied. Further, the angle Θ as defined within FIG. 18L is generally greater than 5 degrees, as this makes the forming process easier.

Figures 18M, 18N:
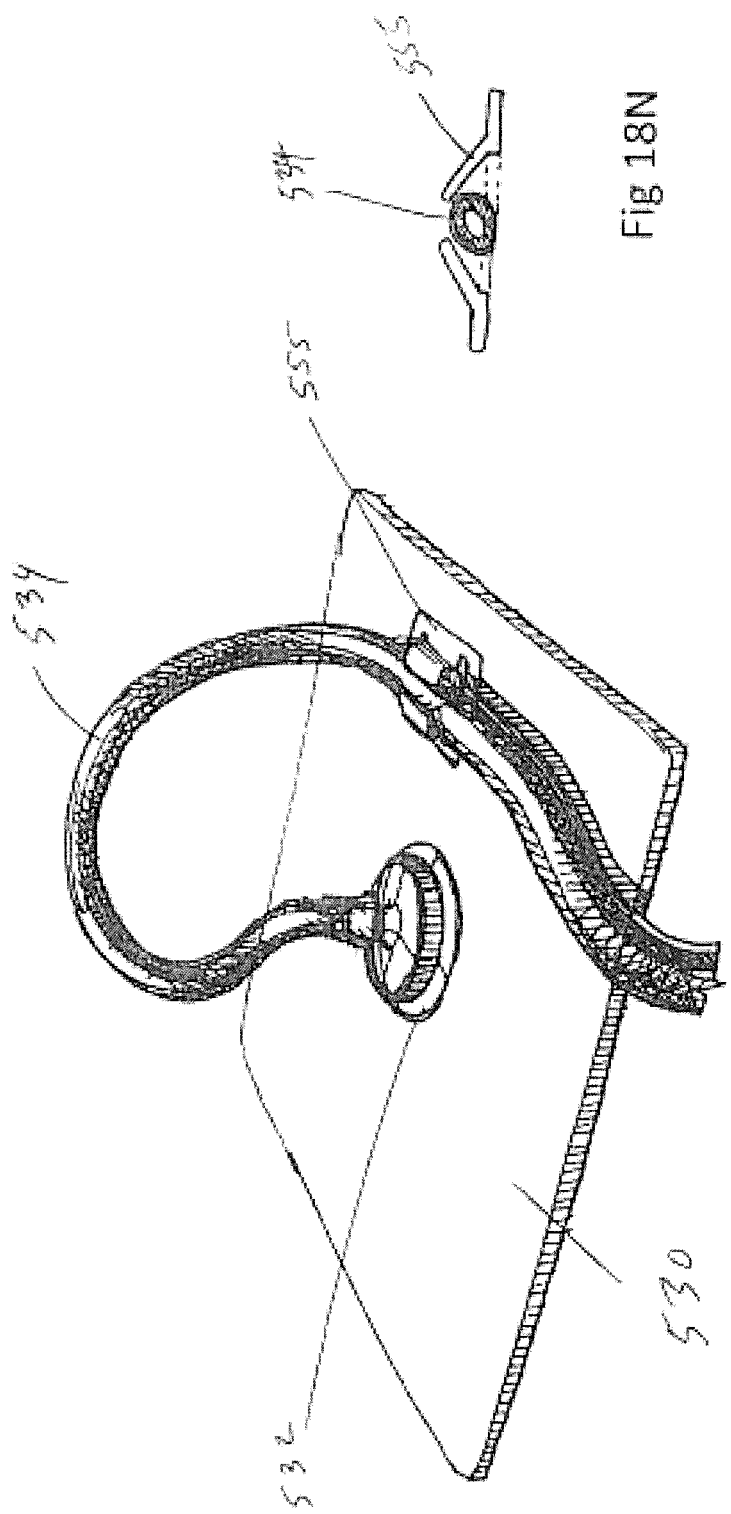

FIG. 18M shows another embodiment of the negative pressure wound therapy device in which the tubing 534 is stabilized onto the adhesive substrate 530 by tubing attachment means 555. A cross sectional view of tubing attachment means 555 is seen in FIG. 18N, in which tubing 534 is seen secured within the tubing attachment means 555. Attaching the residual tubing in such a manner makes it less likely for the tubing to be unintentionally pulled off the plastic cap 532, and helps to keep the tubing in a more orderly state.

Alternate embodiments of tubing attachment means is shown in FIGS. 18O and 18P. The method of securing the tubing within the tubing attachment means is shown in FIG. 18Q. An alternative method of securing the tubing is shown in FIGS. 18R and 18S, prior to insertion of the tubing. The device shown here may have a living (or integral hinge) along its path. FIGS. 18T and 18U show the tubing attachment means after the tubing has been inserted. FIG. 18V shows the insertion of the tubing in the tubing attachment means and FIGS. 18W and 18X show a side and top view respectively. FIG. 18Y shows different embodiments of the previously described plastic cap, including one with ridges to afford improved rigidity or strength. FIG. 18Z shows a sequential manufacturing method of forming the plastic cap comprising the first step of forming a relatively smaller (shallower) cap, followed by step of creating a much larger cap, followed by a third step of forming a cap that is an intermediate size between the caps formed after the first and second forming steps.

Figure 19A:
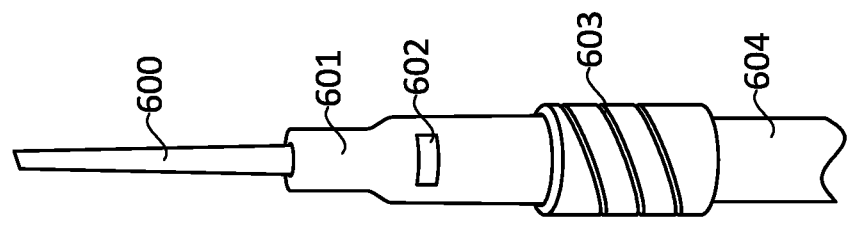

FIG. 19A shows a standard (prior art) IV catheter that has a insertion tube 600 which extends in the subject's vein, a plastic hub 601, a locator 602 located on the plastic hub, a connection region 603 and tubing 604 which may be connected to an IV bag for example.

Figure 20:
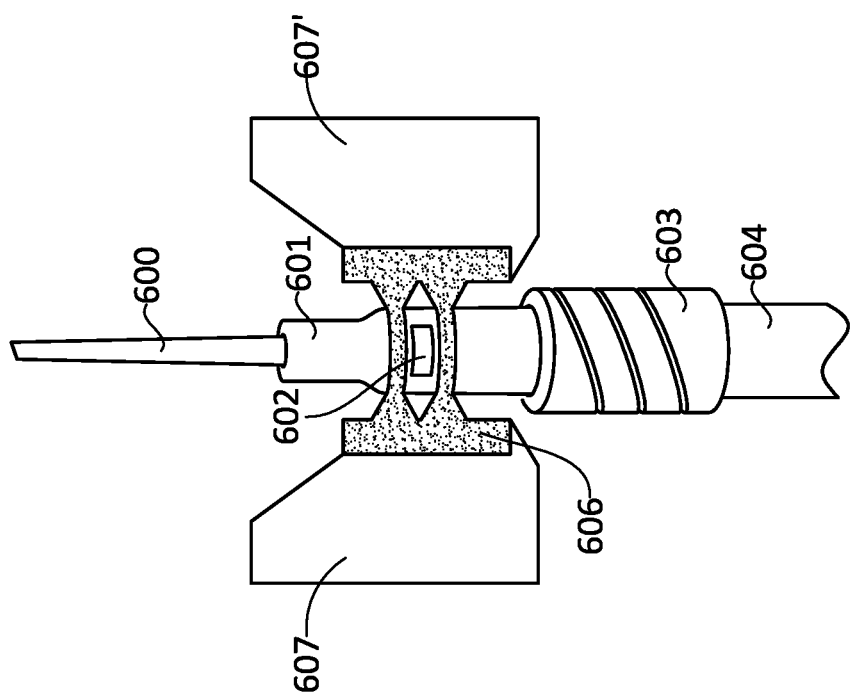
FIGS. 19A and 20 illustrate an adhesive medical devices designed to stabilize an IV catheter.

FIG. 20 illustrates a subject device that is designed to stabilize an IV catheter such as the one shown in FIG. 19A. The IV stabilization device has adhesive holdfasts 607 and 607' which are located on either side of the plastic hub 601. A fixator 606 releaseably surrounds the locator 602, thereby preventing or minimizing the potential for movement of the plastic hub and insertion tube. In some embodiments, the fixator has a secure press fit with the locator 602, leading to a snap fit. In other embodiments, the fit is less tight, but still secure enough to prevent significant movement of the plastic hub 601 and insertion tube 600.

FIG. 21A shows a cross-sectional view of the IV catheter stabilization device of FIG. 20. The adhesive holdfast in this case comprises both an adhesive substrate layer 612 and adhesive 611 that is in contact with the liner 610. The fixator 606 is attached using a double sided adhesive 613 which connects the fixator 606 and the adhesive substrate 612. The angles β and σ are generally >90 degrees. More specifically, σ may be between about 90-95 degrees, between about 95-100 degrees, between about 100-105 degrees, between about 105-110 degrees, between about 110-115 degrees, between about 115-120 degrees, between about 120-125 degrees, between about 125-130 degrees, between about 130-135 degrees, or between about 135-140 degrees. More specifically, β may be between about 90-95 degrees, between about 95-100 degrees, between about 100-105 degrees, between about 105-110 degrees, between about 110-115 degrees, between about 115-120 degrees, between about 120-125 degrees, between about 125-130 degrees, between about 130-135 degrees, or between about 135-140 degrees.

FIG. 21B illustrates a variant of the device shown in FIGS. 20 and 21A wherein the double sided adhesive 613 extends into the fixator 606. This double-sided adhesive is intended to securely fasten the plastic hub of the IV catheter (not shown). IV stabilization devices that offer both the physical securement of the fixator 606 onto the locator 602 (as described in FIG. 20 and FIG. 21A) and the use of double sided adhesive to secure the plastic hub (as described in FIG. 21B) are also possible.

FIG. 21C illustrates a cross sectional view of another embodiment of an IV catheter securement device, this time intended to secure "butterfly type" IV catheters. As can be seen in FIG. 21C, the wing 655 of the IV catheter insertion device has been secured within the attachment region 650 that is attached via double-sided adhesive layer 651 to the adhesive substrate 670 which in turn is attached via adhesive layer 680 to the removeable liner 690.

FIG. 21D is a top down view of the butterfly type catheter that has been secured when its wings 655 were slid under tabs 656, 657, 658, 659, 660, and 661 of the attachment region 650 of the IV catheter stabilization device. All of the IV catheter and other catheter securement devices can prevent significant movement of the catheter even when exposed up to 2 pounds, up to 4 pounds, up to 6 pounds, up to 8 pounds, up to 10 pounds, up to 12 pounds, up to 14 pounds, up to 16 pounds of force.

Figure 21F:
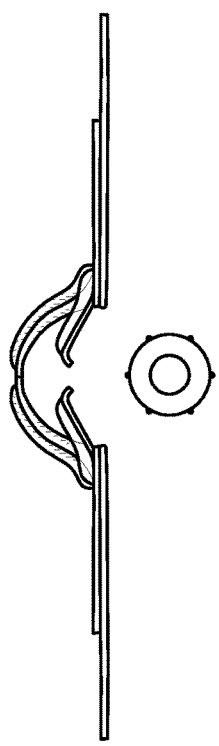
FIGS. 21E-21J illustrate various adhesive medical devices that are designed to stabilize IV catheters.
Figure 21H:
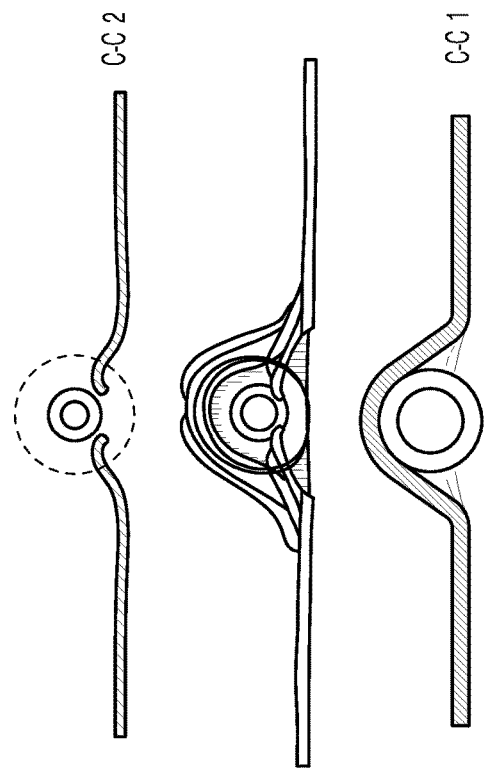
Figure 21E:
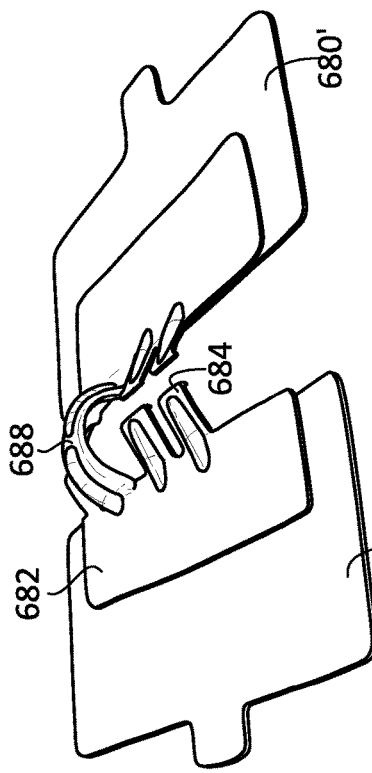

FIG. 21E illustrates a subject device that is designed to stabilize an IV catheter. Adhesive substrates 680 and 680' are attached to wings 682 that attach to each adhesive substrate on either side. Hub lock 688 is snapped on top of the IV hub (not shown) and projections 684 abut the bottom of the IV tubing (not shown). Ridges are present on hub lock 688 and projections 684 to provide necessary rigidity to the formed plastic parts that may otherwise be too flexible to stabilize the IV hub from moving. FIG. 21F shows a cross sectional view of the device previously described in FIG. 21F.

Figure 21G:
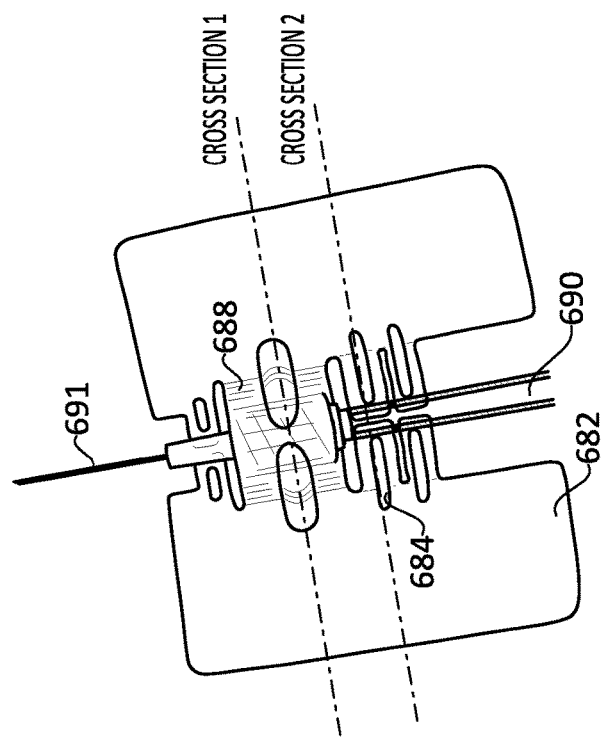
Figure 21I:
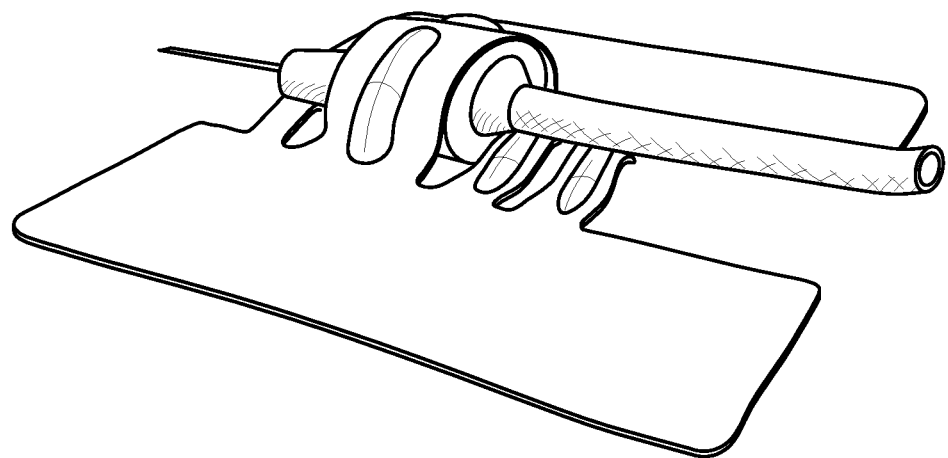

FIG. 21G shows a top view of the IV stabilization device shown in FIG. 21E, this time with an IV catheter and IV extension kit in place. The catheter hub is clearly seen snugly secured within the hub lock 688. Also seen is the IV catheter indwelling component 691 and the IV extension set tubing 690. Again, projections 684 can be seen. Various cross sectional views of the device seen in FIG. 21G are seen in FIG. 21H. A side profile view is seen of the device in FIG. 2H.

Figure 21J:
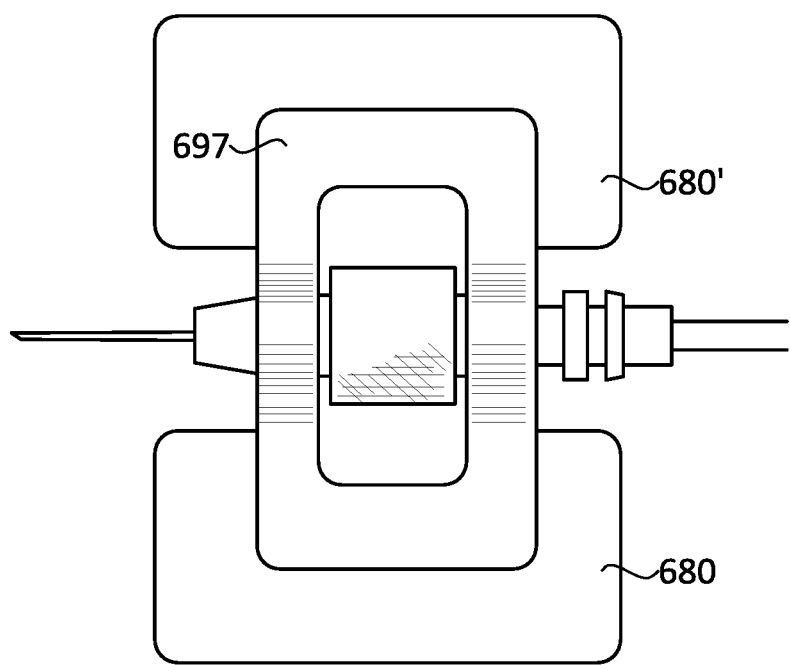
Figure 21K:
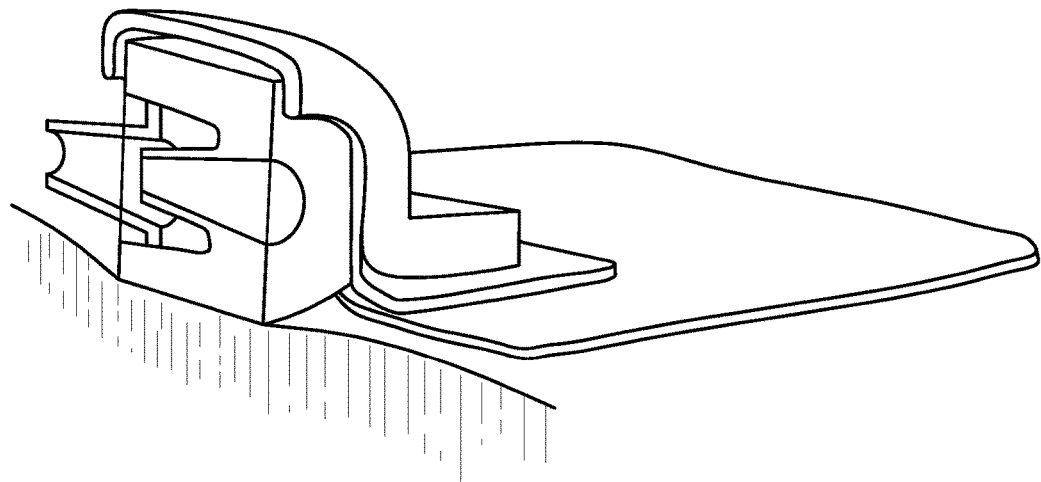
FIGS. 21K and 21L illustrate an IV stabilization device.
Figure 21L:
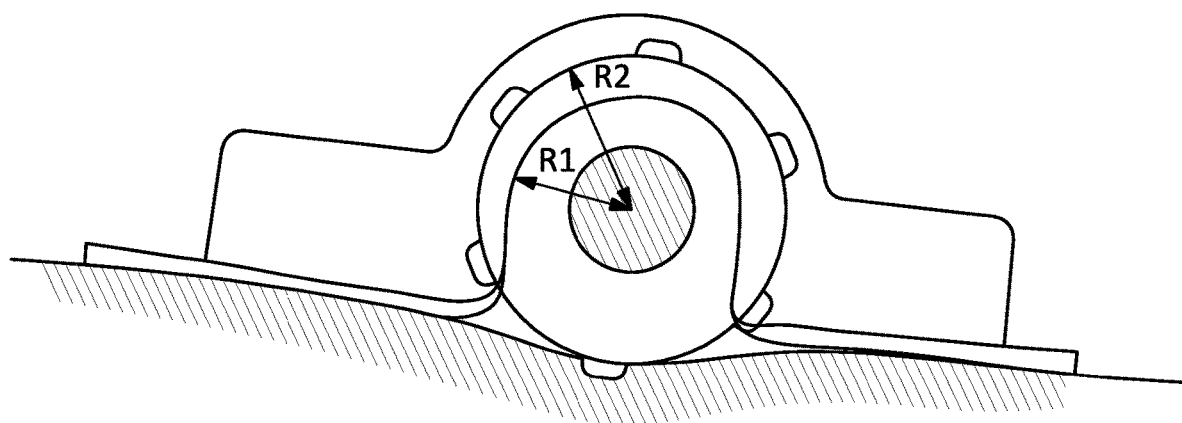
Figure 21O:
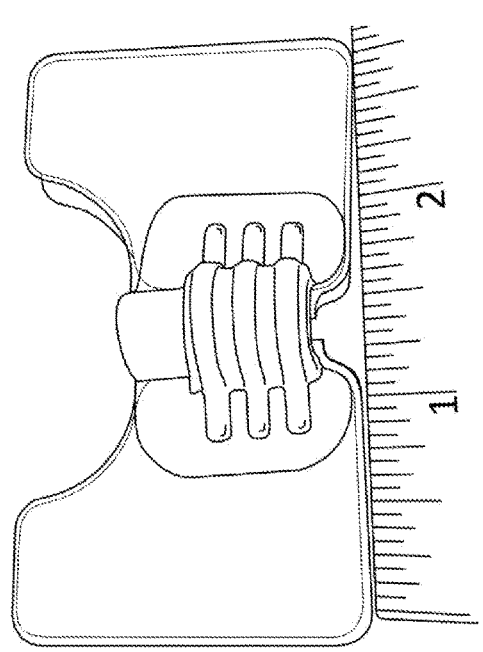
FIGS. 21M-21P show another embodiment of a IV securement device

Additionally, another embodiment of an IV stabilization device is seen in FIG. 21J, in which a plastic hub securement means 697 surrounds the IV catheter hub preventing it from movement. The hub securement means is attached on either side to the adhesive substrates 680 and 680'. FIGS. 21K and 21L show another embodiment of the IV stabilization device.

Figure 21P:
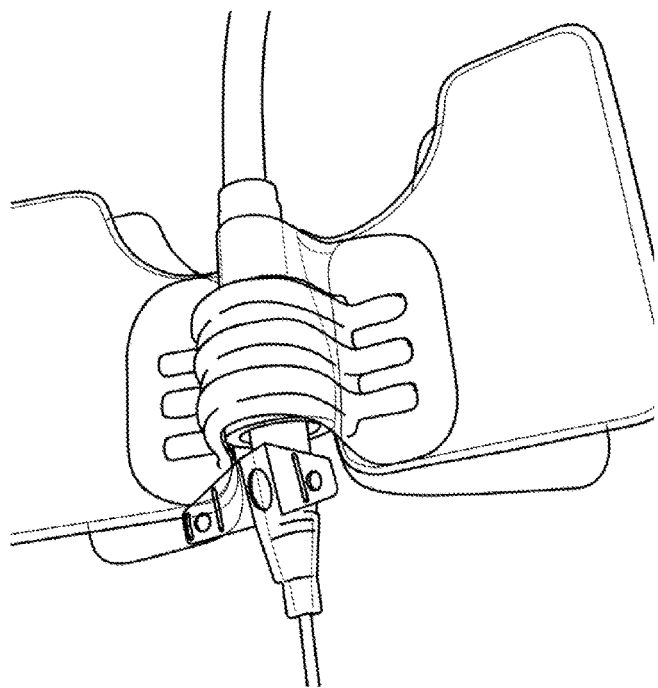
Figure 21M:
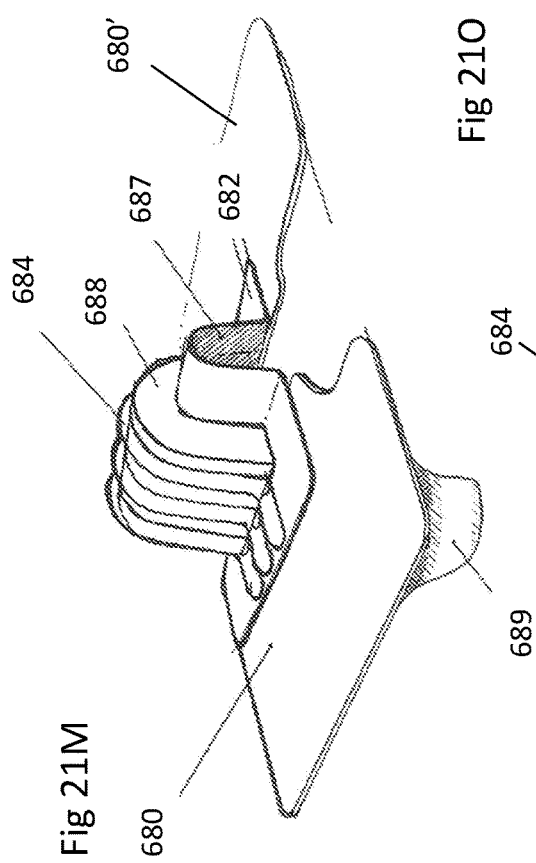

FIGS. 21M, 21N, 21O and 21P show another embodiment of an IV stabilization device. In this example, the device includes an IV hub capture region having a hub lock 688 and a planar base region 682. The hub lock and base are integral, meaning that they are formed of the same material. The hub lock region extends up into a tunnel-like shape having an elongate length with regions of different heights, including ribbed regions 684. An axially middle region of the lock ("tunnel") has a greater height than the narrower end regions on either end of the tunnel, as shown in FIG. 21M. The ribbed regions extend onto the base region and may provide structural support (e.g., enhancing rigidity). The entire structure of the base and hub lock may be formed of a single planar material that can be pressed or stamped as described above.

Figure 21N:
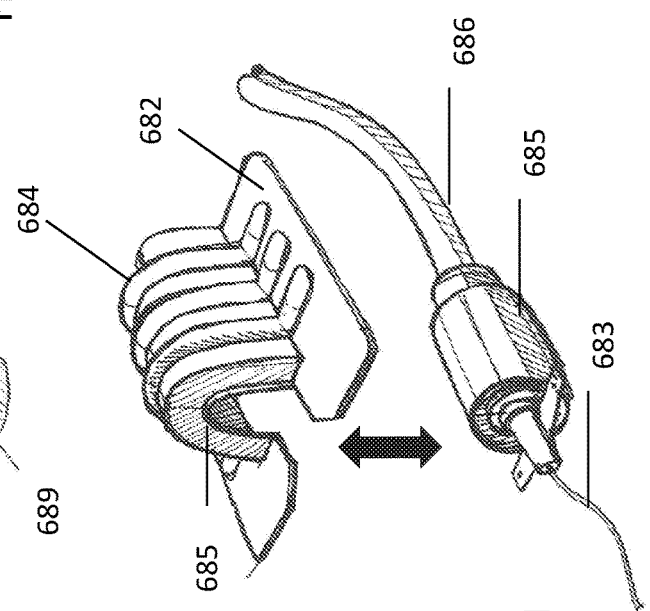

In the example shown in FIGS. 21M-21P, a pair of adhesive substrates 680 and 680' are attached to the planar substrates 682 on either side of the hub lock 688. These regions 682 may be referred to as wings. The hub lock 688 is shown with ribs or projections 684 providing structural rigidity. In some variations, rather than outwardly projecting ribs (e.g., having a greater height in the channel/tunnel through the hub lock), the ribs may be inwardly projecting, having a lower height in the channel/tunnel through the hub lock. Distal exit port 687 of the hub lock can be positioned over, to surround an extension set tubing that could then be connected to an IV bag, for example. In FIGS. 31M-21P, a removable liner 689 can also be seen over the adhesive. This liner can be removed to place the device against a patient or structure (e.g., after placing it over the IV hub). FIG. 21N shows a device having an IV hub capture region including a hub lock 688, planar base regions on either side (wings) 682, and a proximal port 685. The device may be positioned on top of an IV catheter 683, as shown, where the catheter includes a catheter hub 685 and IV extension 686. In some cases, the hub lock may be designed to "snap" onto the hub, providing a tactile and auditory confirmation to the user that the securement device has been applied appropriately. The geometry of the hub lock 688 may be either semi-circular or oval in cross section thorough the tunnel region (e.g., transverse to the long axis of the channel), with oval or non-circular cross-sections potentially providing more comfort as it may provide less downward force on the hub (and therefore less downward force on the skin of the user). Further, proximal port 685 may have a flat or substantially flat end (as opposed to having a "tunnel" that may be present on the distal end (distal exit port 687). This flat end of proximal port 685 provides clearance for the wings or other feature of the IV catheter 683 that might otherwise be obstructed if the proximal port 685 was not flat or otherwise designed with a means of accommodating such wings. For example, in some variations, the opening forming into the hub lock region 685 may have a height that is less than the height within the channel/tunnel through the hub lock region, but extends less than a few mm in the longitudinal axis of the channel (e.g., less than 5 mm, less than 4 mm, less than 3 mm, less than 2 mm, less than 1 mm, etc.). In contrast the opposite entrance, distal exit port 687, into the tunnel region may include a 'roof' region that extends in the longitudinal axis of the channel at a lower height than the mid-region of the channel for a distance of greater than the extent of the proximal exit port height, e.g., greater than a few mm (e.g., greater than 3 mm, 5 mm, 6 mm, 7 mm, 8 mm, 9 mm, 10 mm etc.)

Figure 22:
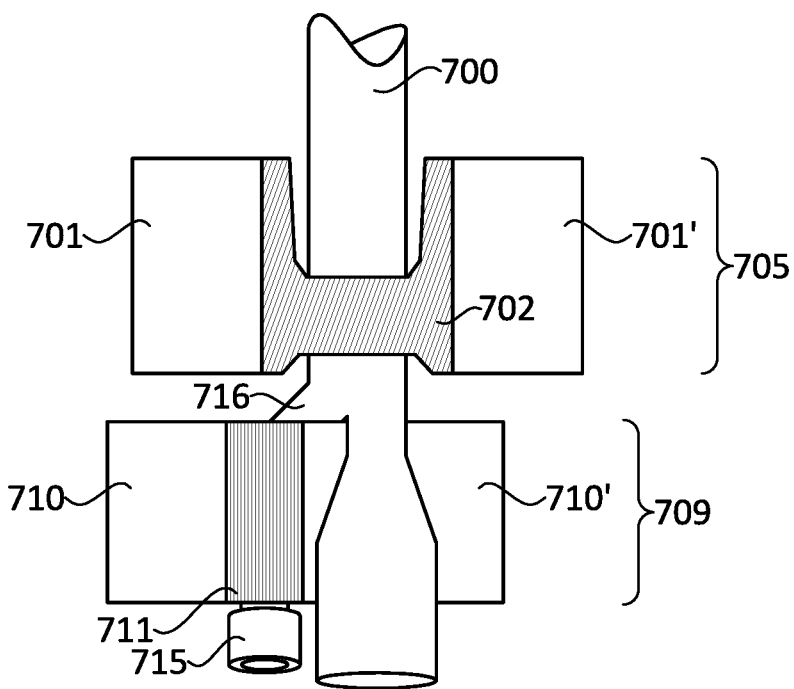
FIG. 22 shows an adhesive medical device designed to stabilize a urinary catheter.

FIG. 22 illustrates an adhesive medical device 705 designed to help stabilize a urinary (Foley) catheter. The catheter 700 is shown. A first adhesive stabilization device has adhesive holdfasts 701 and 701' and a fixator 702 that is securely connected to the adhesive holdfasts 701 and 701'. A catheter 700 is shown being stabilized by the fixator that is generally made from a rigid material. This rigid material may be made through a web converting process. In this case, upward movement of the catheter is prevented as the increased width of the catheter at its branch 716 will abut the fixator 702. A second adhesive stabilization device 709 is shown attached to the lower portion of the urinary catheter. Adhesive holdfasts 710 and 710' are shown securely attached to the fixator 711. A hub 715 is also shown. The adhesive stabilization device 709 prevents the upward movement of the catheter as the hub abuts the fixator 711. Downward movement of the catheter will be prevented as the branching 716 of the catheter abuts the fixator, preventing such movement.

Figure 23:
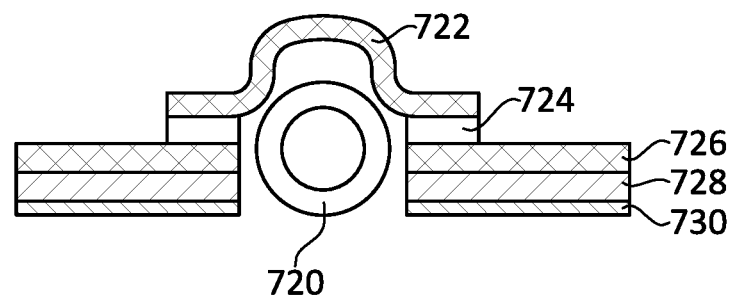
FIG. 23 shows a cross-sectional view of the medical device in FIG. 22 after application to the subject.

FIG. 23 shows a cross section view of both of the adhesive stabilization devices shown in FIG. 22. The adhesive holdfast comprises two layers, the adhesive layer 728 and the adhesive substrate layer 726, to which a double-sided adhesive 724 is attached. Also attached to the double-sided adhesive 724 is the fixator 722 that releaseably secures the urinary catheter 720 restricting its movement. A liner 730 can also be seen, which protects the adhesive layer 728 prior to application to the subject. The liner 730 can have many configurations, including ones in which it bends upon itself, to make it easier for the user to remove the backing or to apply the adhesive stabilization device. The fixators described in the prior paragraph are generally rigid or semi-rigid and are formed though a web converting manufacturing process. Many of the thickness, dimensional and material attributes previously described for the protective caps and barrier caps also apply to the fixators, as they are all created via similar manufacturing processes. Other embodiments of related devices may be used to stabilize drains in other body locations such as biliary, abscess, feeding tube, naso-gastric or naso-enteric, or nephrostomy applications.

Figure 24A:
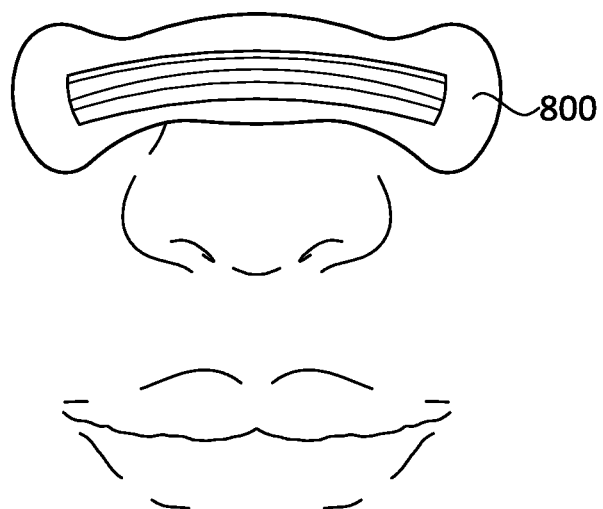
FIG. 24A illustrates a nasal dilator strip applied to the subject's nose.
Figure 24B:
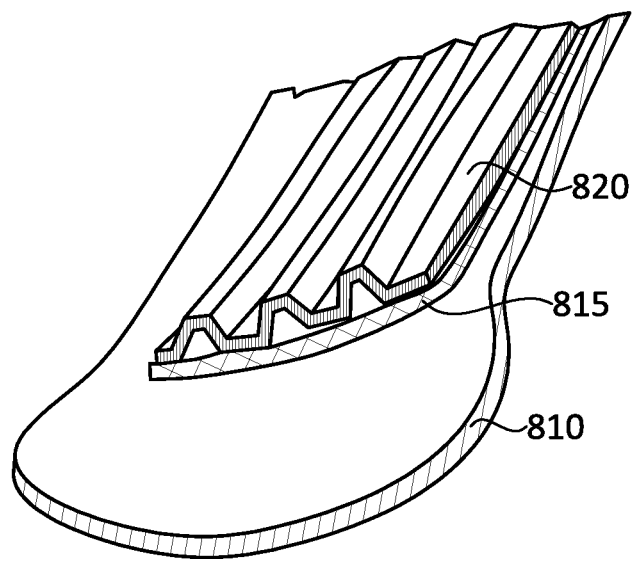
FIGS. 24B and 24C show sectional views of the device shown FIG. 24A.
Figure 24C:
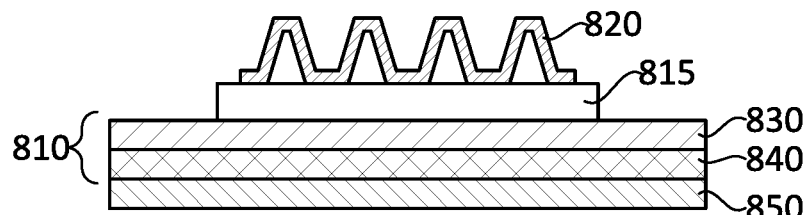

FIG. 24A illustrates a nasal strip 800 designed to dilate the nasal passageways to treat allergies, snoring, or the like. FIG. 24B shows a close of view of the device 800. Multiple ridges 820 are attached via adhesive 815 to the holdfast 810. The ridges which are generally made of plastic provide stability to the device. FIG. 24C illustrates a cross sectional view of the nasal strip 800 in which the ridges can be seen. The addition of ridges on top of the nasal strip is to promote increased force generation of the nasal strip as it pulls on the outside of the nose, thereby increase nasal patency and improving airflow through the nose. In some cases, the nasal strip may be pre-shaped or pre-formed (for example, the ridges may be pre-formed) to fit on top of the nose (i.e. the device may have a natural curve and not be flat as shown). By having a pre-curved shape, the device may be more comfortable to wear than a device that is substantially linear prior to application to the subject. Efficacy may also be improved as a result.

The ridges of this nasal strip may assume any shape including straight, mostly straight, wavy, curvy, or the like. FIG. 24D shows a cross section of one embodiment of the nasal strip. Additional embodiments are shown in FIGS. 24E-G. FIGS. 24F and 24G show devices that have been pre-shaped during the manufacturing process.

Figure 24H:
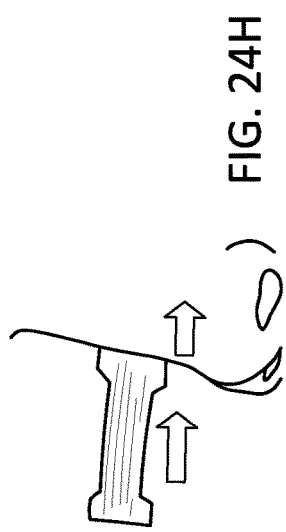
FIGS. 24H-24J illustrate the application of a splint device such as the one shown in FIG. 24E applied to a subject's nose.
Figure 24I:
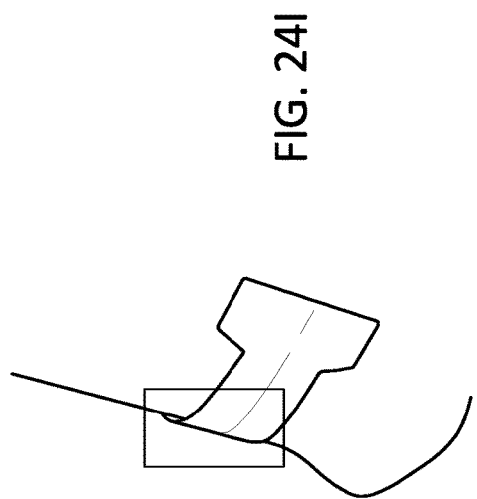
Figure 24J:
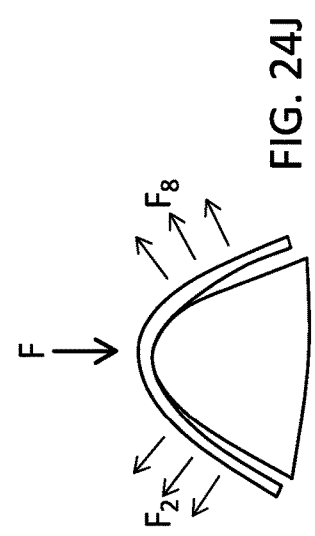
Figure 24D:
FIG. 24D shows a side view of a splint device such as the one shown in FIG. 24A.
Figure 24E:
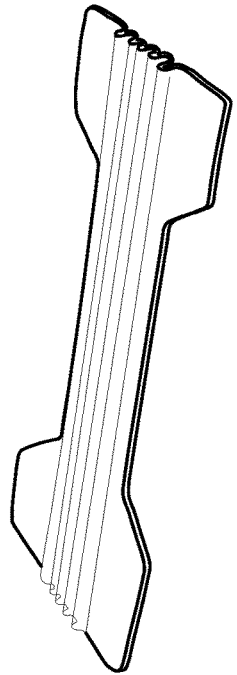
FIGS. 24E-24G show side perspective views of different variations of splint devices such as the one shown in FIG. 24A.
Figure 24F:
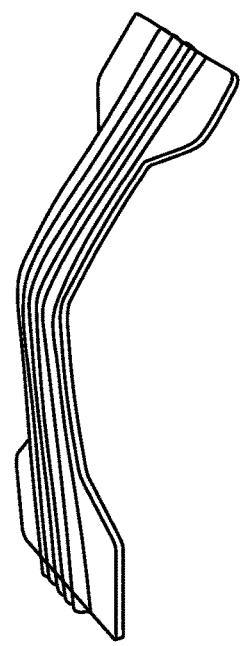
Figure 24G:
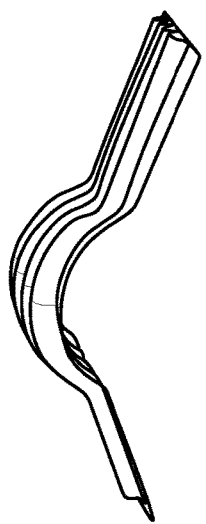

The subject nasal devices are attached to the exterior of the nasal passages as shown in FIG. 24H. Compared to other currently available nasal devices, the subject devices exert less pressure on the bridge of the nose (as shown in FIG. 24I) compared to currently available devices as there is less orthogonal force applied to the nose compared with other devices that do not have a 3D formed plastic component as shown in FIG. 24J.

Figure 24K:
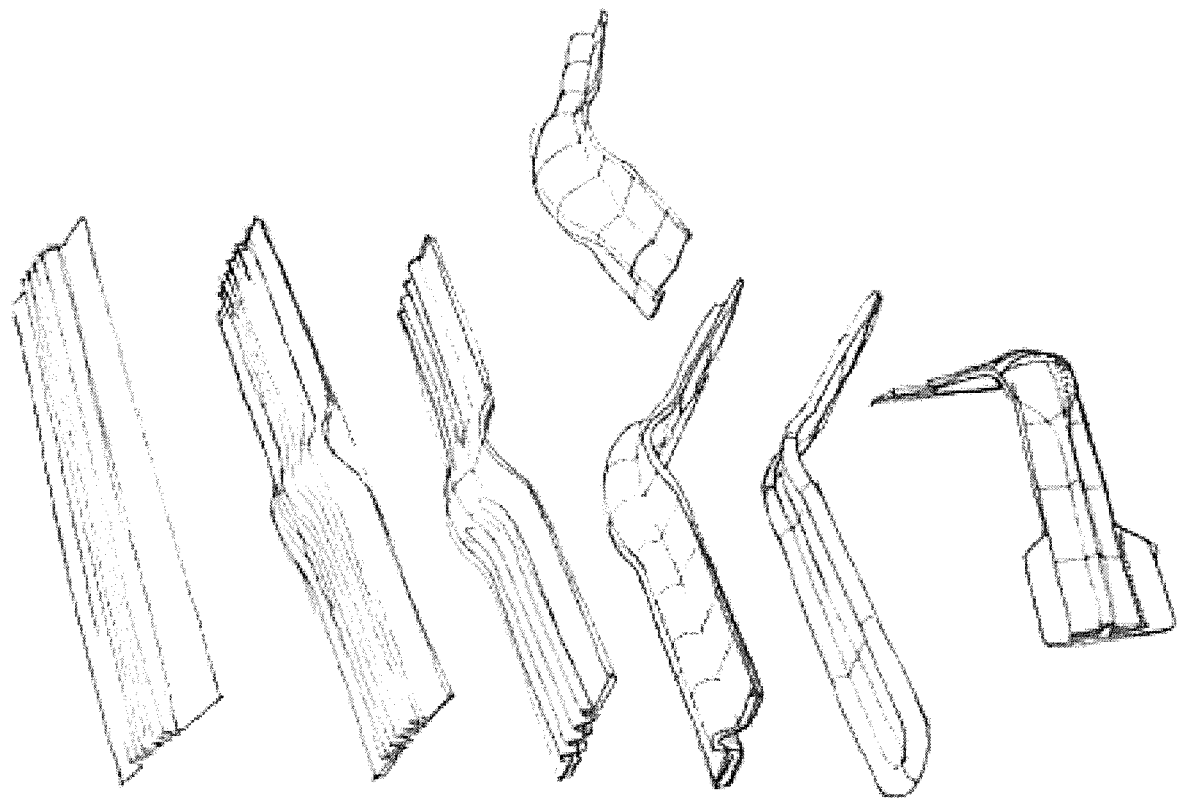
FIG. 24K shows side perspective views of various nasal splint devices.
Figure 24L:
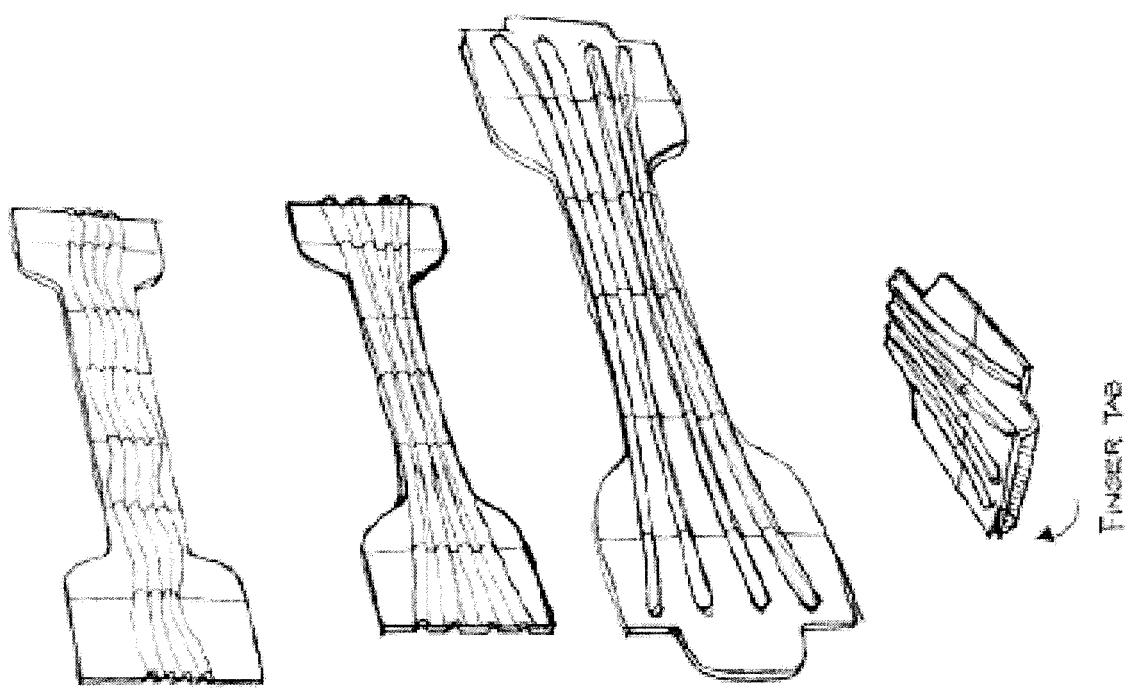

FIG. 24K shows alternative embodiments of the subject nasal devices. FIG. 24L shows further embodiments of the subject nasal devices in which the ridges are not uniformly straight. In some cases, the ridges are generally straight near the central portion of the device only to flare or diverge further away from the central portion of the device which may improve its ability to dilate or maintain patency of the nasal passages. In some cases, the plastic (or other material that provides structural support or increased rigidity) may be formed in such a way as to create a tab that allows application or removal of the device. Currently available devices can be difficult to remove from the skin of the user, so the use of such a tab that is raised or otherwise easy for the user to grasp would allow easier removal of the device. This tab could be made from the same formed material as the ridges as one example. In other cases, the tab and the ridge may be made from separate materials. FIG. 24M shows an additional nasal strip embodiment.

FIG. 24N shows a nasal strip with a formed 3D component that is curved. Removal tabs 865 are designed to help enable the user to remove the nasal strip after use. Removal tabs 865 may be planar or substantially planar compared with the body of the formed 3D portion of the nasal strip or may be formed at an angle of between approximately 1-5 degrees, between approximately 5-10 degrees, between approximately 10-15 degrees, between approximately 15-20 degrees, between approximately 20-25 degrees, between approximately 25-30 degrees, between approximately 30-35 degrees, between approximately 35-40 degrees, between approximately 40-45 degrees, between approximately 45-50 degrees, between approximately 50-55 degrees, between approximately 55-60 degrees, and so on (relative to the central body region). The removal tab(s) may be on one side or both sides of the device and may project outward from the remainder of the 3D formed piece a distance between approximately 0.5-1.0 mm, between approximately 1.0-1.5 mm, between approximately 1.5-2.0 mm, between approximately 2.0-2.5 mm, between approximately 2.5-3.0 mm, between approximately 3.0-3.5 mm, between approximately 3.5-4.0 mm, between approximately 4.0-4.5 mm, between approximately 4.5-5.0 mm, between approximately 5.0-5.5 mm and so on. The removal tab may be attached to the adhesive holdfast (though in some variation it is not attached to the adhesive holdfast) and it may have an adhesive layer. In some variations the removal tab(s) do not include an adhesive layer. The device shown in FIG. 24N may optionally have a slight bend across its length which may help enable placement of the centrally on top of the nose (e.g., over the bridge of the nose).

FIG. 24O shows another embodiment of a curved nasal strip in which central removal tab 866 is located centrally or substantially centrally on the device. Central removal tab may be located on top of the bridge of a user's nose (not shown). In use, the user's fingers would hold the removal tab (or place her finger or finger nail under the removal tab) and pull the tab in a direction substantially orthogonal to the skin, or pull the tab substantially downward (or both) to remove the device. A central removal tab 866 may be more comfortable to use than side removal tabs, as the skin below the central removal tab is more closely attached to the underlying bone of the nose than the skin on the side of the nose (closer to the nares). The central removal tab may be symmetrically (as shown) or asymmetrically (not shown) positioned relative to the midline of the device. Further, a logo or other embossed feature may be formed into the central removal tab or any other part of the 3D formed component. The removal tabs described herein are generally attached to the rest of the 3D formed part or may be integrally formed with the rest of the body of the device (e.g., a uni-body construction) although in some cases, the removal tab may be a separate component. In some cases, the removal tab may be an extension of the adhesive holdfast (not labeled) without an underlying adhesive layer.

Figure 24P:
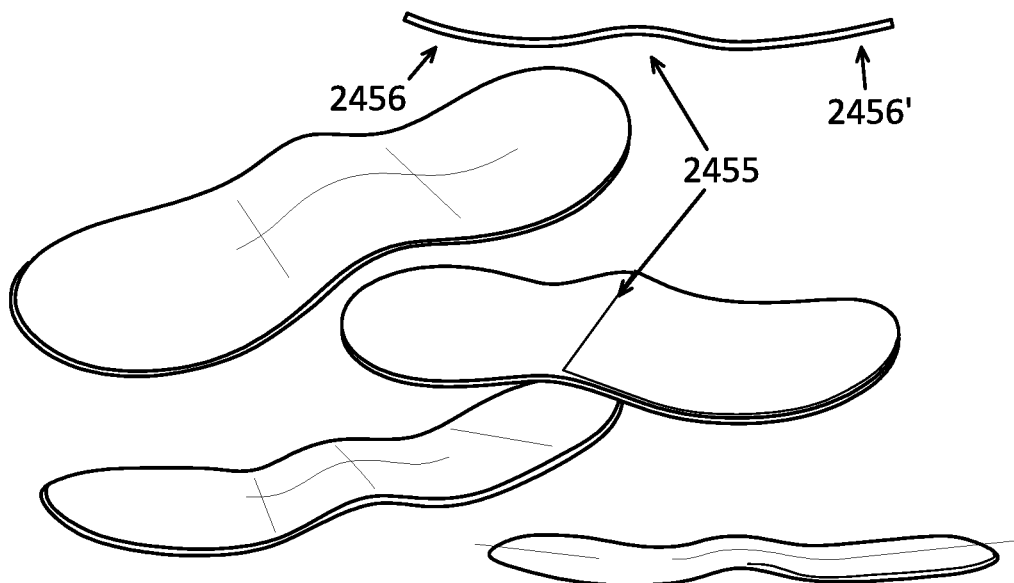
Figure 24Q:
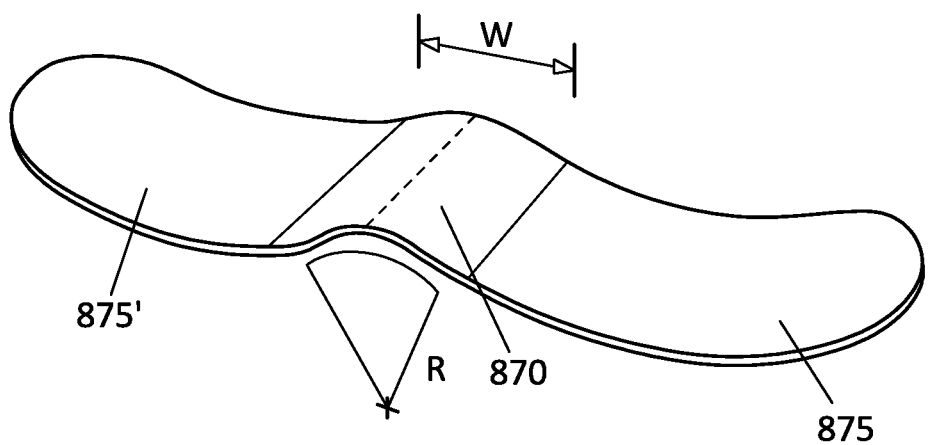
Figure 24R:
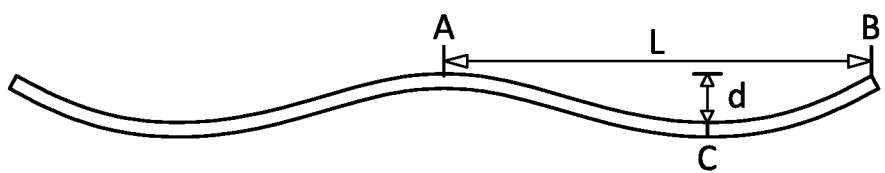

FIG. 24P shows another embodiment of a nasal strip with multiple bends or curves across its length. The central curve 2455 may help with central placement on the nose and the lateral bends 2456 may offer increased mechanical advantage in holding the nares and nasal valve open. The curves also offer aesthetic benefits. FIGS. 24Q and 24R show additional views of the device of FIG. 24P.

FIG. 24Q shows a nasal strip with a center section 870 that is curved to form a convex surface (relative to the upper surface of the long body of the device) which may be positioned to contact the ridge of the nose first during application. To ensure even contact with the nose, the center section 870 may have a positive curvature with a radius (denoted R) of between about 10-20 mm and the width of this section (denoted W) that is less than 15-20 mm. The relatively small width may provide a clear registration area for the user to align to the ridge of the nose, especially in poorly lit settings or when the user is drowsy. More specifically, radius R should be approximately less than or equal to 5 mm, between 5-6 mm, between 6-7 mm, between 7-8 mm, between 8-9 mm, between 9-10 mm, between 10-11 mm, between 11-12 mm, between 12-13 mm, between 13-14 mm, between 14-15 mm, between 15-16 mm, between 16-17 mm, between 17-18 mm, between 18-19 mm, between 19-20 mm, between 20-21 mm, between 21-22 mm, between 22-23 mm, between 23-24 mm, between 24-25 mm, or more than or equal to about 25 mm. Width W should be less than or equal to 10 mm, between approximately 10-11 mm, between 11-12 mm, between 12-13 mm, between 13-14 mm, between 14-15 mm, between 15-16 mm, between 16-17 mm, between 17-18 mm, between 18-19 mm, between 19-20 mm, between 20-21 mm, between 21-22 mm, between 22-23 mm, between 23-24 mm, between 24-25 mm or more than or equal to about 25 mm.

Lateral sections 875 and 875' in FIG. 24Q are located on either side of center section 870 and may be concave (relative to the upper surface of the long axis of the device) in many cases, although in some cases may be flat or substantially flat. The mechanism for pulling the outer surface of the nose outward (and thereby opening the nasal valve and/or nares) may be exerted by the formed plastic of the body springing back towards a straight configuration after elastic deformation. In order to apply adequate pulling force to expand the nasal nares and/or nasal passages, the lateral sections 875 and 875' may be adapted so that they don't bow downward excessively (e.g., they are not too concave). By not being excessively concave, although as mentioned above, they may be slightly concave, device (and specifically the lateral sections) of the device may flex adequately and contact the nose in a tensioned state before springing back, thereby opening the nasal passages. FIG. 24R shows a cross-section of the nasal strip device shown in FIGS. 24Q and 24R, with three locations across the length of the nasal strip labeled A, B and C. A is the center ridge, B is the lateral edge and C the lowest point on the concave curve formed at the two side of the device. If a line is drawn connecting A to B, as shown in FIG. 24R, which defines a length AB, the normal or orthogonal distance of point C from this line is shown as length "d". The ratio of d:AB should preferably not exceed 1:6 to maximize opening of the user's nasal passages. In some cases, d:AB is between approximately 1:2 and 1:3, between approximately 1:3 and 1:4, between approximately 1:4 and 1:5, between approximately 1:5 and 1:6, between approximately 1:6 and 1:7, between approximately 1:7 and 1:8, between approximately 1:9 and 1:10, between approximately 1:10 and 1:11, between approximately 1:11 and 1:12, between approximately 1:12 and 1:13, between approximately 1:13 and 1:14, between approximately 1:14 and 1:15 between approximately 1:15 and 1:16 and so forth.

Figure 24S:
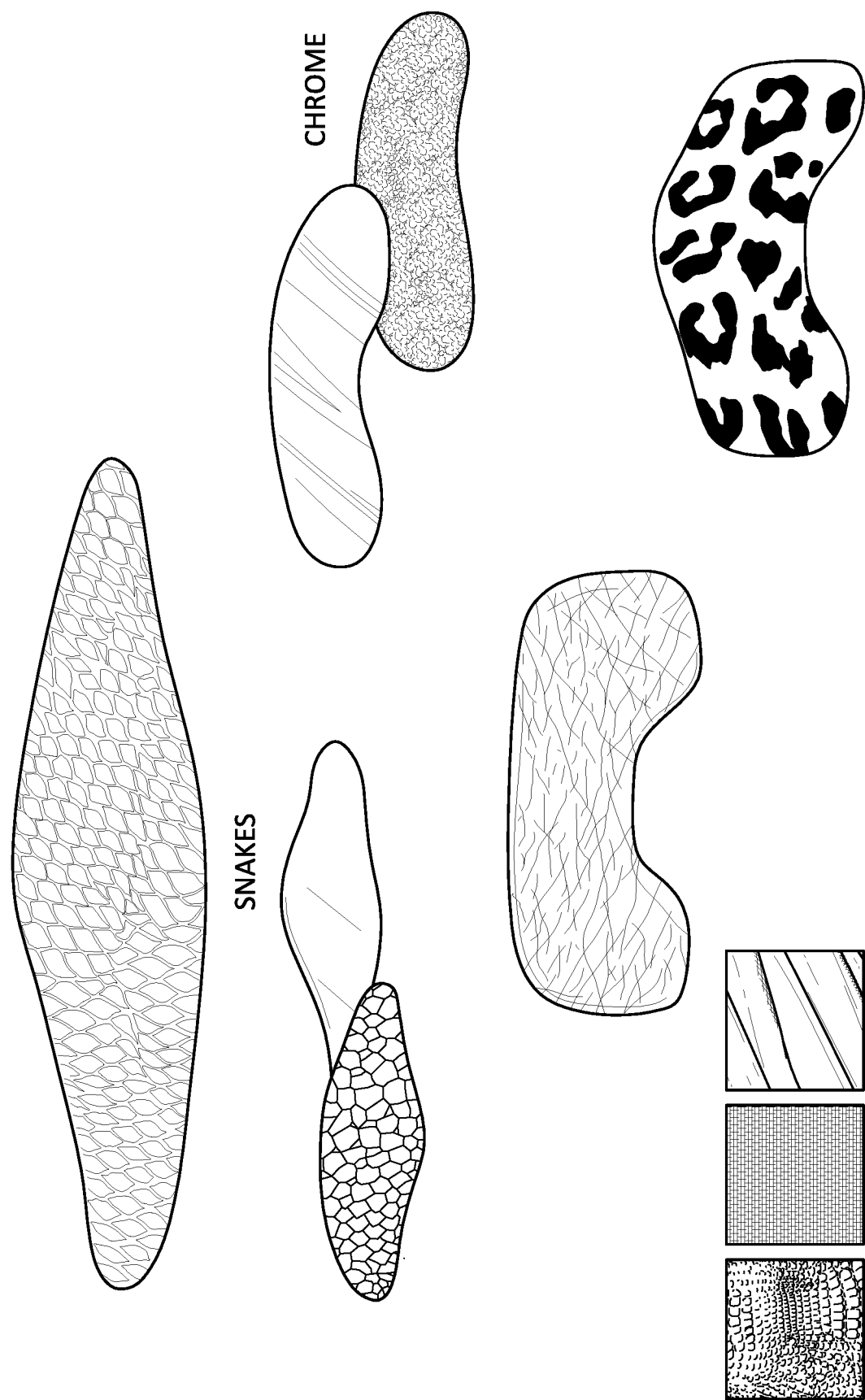

In general the preformed shapes of the nasal strips described herein are particularly significant. As discussed above, the elongate body of the nasal device may be relatively rigid. In addition, any of these devices may also include additional textures or structural (e.g., stiffening) elements. For example, FIG. 24S illustrates several embodiments of nasal strips in which a pattern or texture is formed into the 3D formed piece. Further, any of these devices may include colors or surface ornamentation. For example, a variety or colors are possible. Any of the nasal strips described herein may have a 3D formed component that has one or more curves of bends to help facilitate placement or improve performance.

Figure 25A:
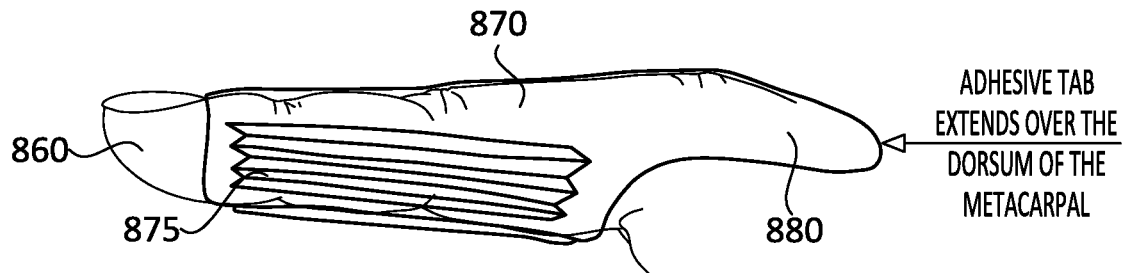
FIGS. 25A and 25B show side and top views of an adhesive device to splint a subject's finger.
Figure 25B:
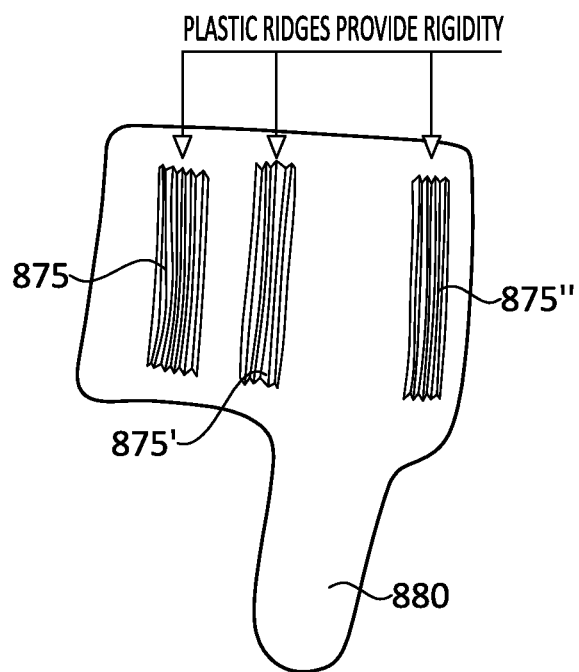

FIG. 25A illustrates a novel finger splint for a finger 860. Such a device would be helpful for a subject with a broken or sprained finger or otherwise seeking to prevent of limit movement of a finger or toe. Multiple ridges 875 are seen attached to the holdfast 870. A projection of holdfast 880 is seen extending proximally onto the hand, providing extra support. FIG. 25B shows a series of plastid ridges 875, 875', and 875" which when the splint is applied on a subject's finger, provide significant support, prevent finger flexion and promoting healing. A cross sectional image of this novel finger splint would be similar to the cross sectional image show in FIG. 24C. Other shapes for various splints for the body may find use, including splints for any joint in the human body, especially for "smaller joints" on the limbs, on the hands or feet, fingers or toes, wrists or ankle.

FIG. 26A illustrates the (prior art) placement of an intraosseous needle into the bone marrow of a subject. FIG. 26B shows a top view of an intraosseous needle securement device. The holdfast 900 can be seen, as can a lattice 902 (which is generally made of thin plastic). Centrally located is the plastic hub 904, in the middle of which is the opening 910. On the sides of the plastic hub are ridges 908 which are added to increase stability of the plastic hub which may otherwise be too flimsy to secure an intraosseous needle. FIG. 26C illustrates a side view of the device shown in FIG. 26B. A liner 912 has been added in close proximity to the holdfast 900, the holdfast comprising both an adhesive layer and a substrate layer.

FIGS. 27A and 27B are illustrations of various ridges, ribs, and/or struts that may be added to any plastic cap, hub, barrier cap, or other plastic or formed component described in this application. These ridges and ribs may provide increased rigidity to any of the devices show in any of the figures. Without these ridges of ribs, the subject devices may not be strong enough to perform their intended function. Further, as many or all of the plastic three dimensional pieces described herein are intended to be created in-line during the converting process, they are likely to be stretched and may have areas of weakness that may have a tendency to buckle and/or break. The addition of ridges and ribs can significantly reduce the likelihood of buckling or breaking.

Figure 28D:
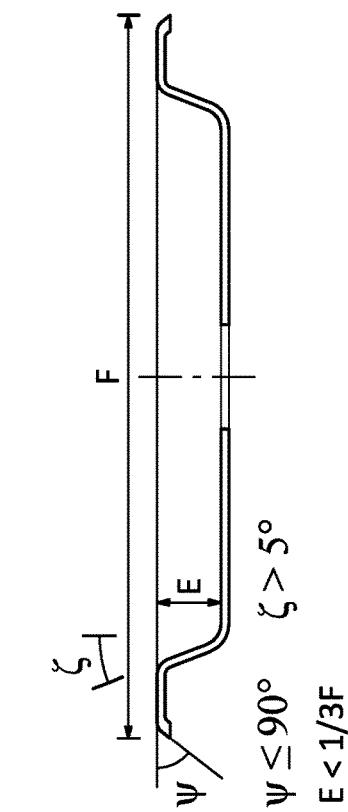
Figure 28C:
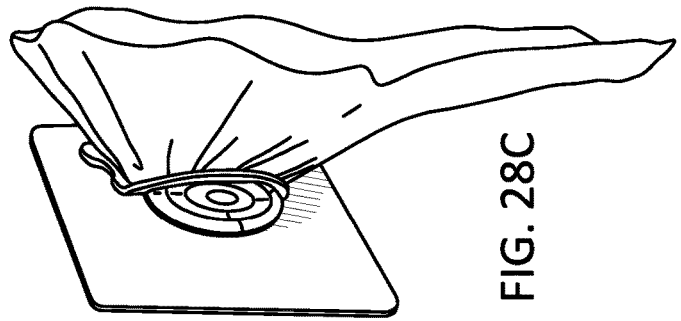
Figure 28B:
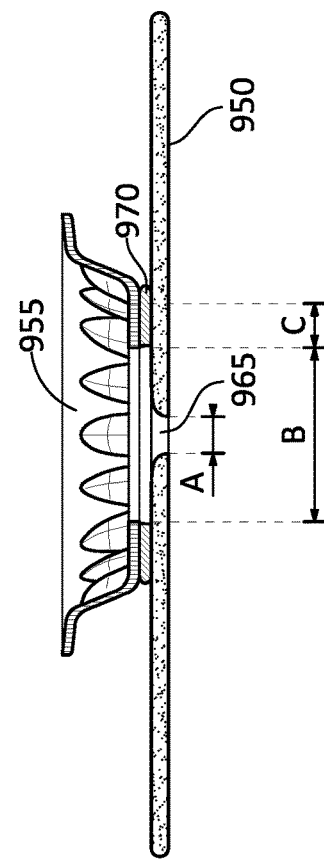
Figure 28A:
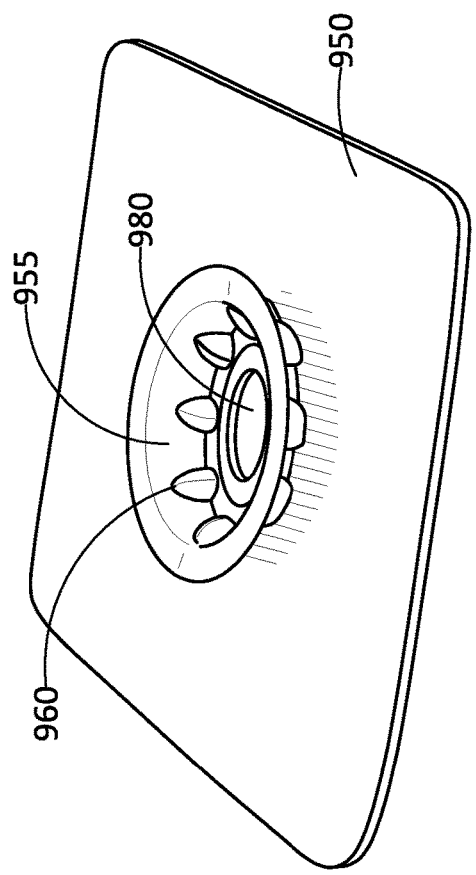

FIG. 28A is the top view of an ostomy (wafer) device. Holdfast 950 can be seen, onto which is securely fixed a flared cone 955 that has internal ridges 960. Not shown are optional external ridges on the outer surface of the flared cone 955. The ostomy "wafer" illustrated in FIG. 28A can be attached removably to an ostomy bag as is seen in FIG. 28C.

FIG. 28B is a cross-sectional view of the device shown in FIG. 28A. A double-sided adhesive 970 is shown securely adhering the flared cone 955 to the holdfast 950. In this drawing the liner is now shown. An opening 965 within the holdfast is shown, allowing the passage of stool. The diameter of opening 965 is defined as length "A". This opening 965 can subsequently be further expanded or shaped by the user to adapt to his or her ostomy size and shape. The hole 980 within the center of the flared cone 955 has a diameter "B". In general, B>A in length. In some cases, B>1.5A, B>2A, B>2.5A, B>3A, B>3.5A, or B>4A. Further, the length C, which is defined as the length in which base of the flared cone 955 is in contact with the holdfast 950, is between approximately 2 and 3 mm, between approximately 3 and 4 mm, between approximately 4 and 5 mm, between approximately 5 and 6 mm, between approximately 6 and 7 mm, between approximately 7 and 8 mm, or between approximately 8 and 9 mm. Ample contact between the base of the flared cone 955 is important as it provides necessary rigidity and securement to the device.

Figure 28E:
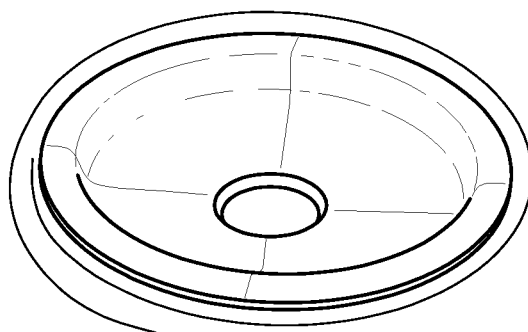
Figure 28F:
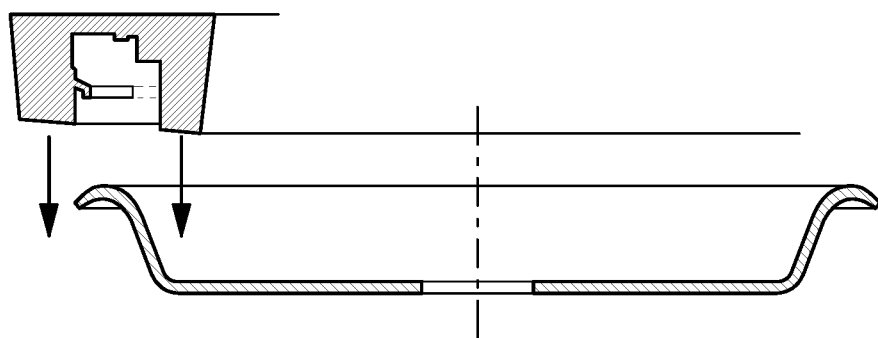
Figure 28G:
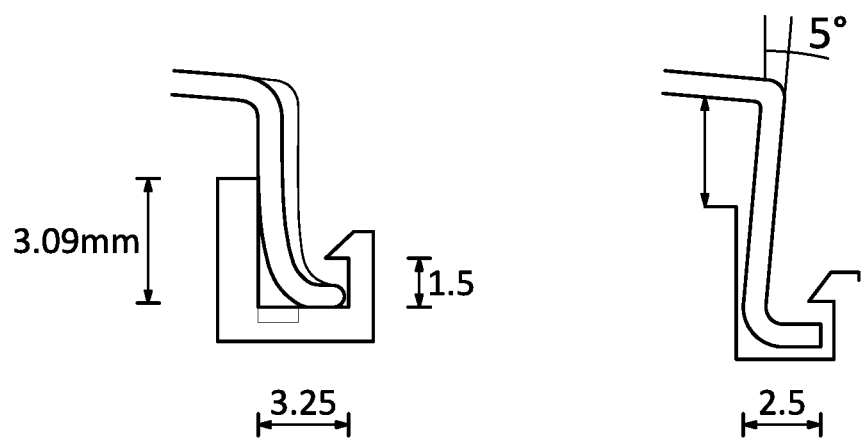

FIG. 28D shows some added dimensions of the flared cone of the ostomy device and important geometric parameters that both provide ample rigidity and are manufacturable using in line forming during a web converting process. FIG. 28E, shows an alternative embodiment of the ostomy flared cone, as does FIG. 28F. Finally, FIG. 28G illustrates details that allow the flared cone to be securely connected with the ostomy bag. The ostomy devices (including ostomy wafers) may have flange diameter sizes of 1.5 inch (38.1 mm), 1.25 inch (31.75 mm), 1.75 inch (44.45 mm), 2.25 inch (57.15 mm), 2.5 inch (63.5 mm), and 2.75 inch (69.85 mm) and the like, including intermediate sizes. Also described herein are adhesive securement devices including a shaped (e.g., formed) layer of material that includes channels/guides and/or capture regions for gathering and/or securing a catheter, and particularly a peripherally inserted central catheter (PICC). For example, a PICC may be a thin, soft, flexible tube used as an intravenous (IV) line; treatments, such as IV medications, can be given though a PICC, and blood for laboratory tests can also be withdrawn from a PICC. A PICC may have multiple lumens, e.g., for adding/withdrawing different solutions. The proximal end of a PICC (the non-inserted end) may therefore have multiple lines feeding into the lumen of the PICC. A PICC may include an anchor which provides structural support for the PICC and may be where the single catheter tube may bifurcate into one or more tubes. In some cases this PICC anchor may have a "wing" having holes for sutures to be placed.

Described herein are adhesive securement devices for use with a PICC that is formed of a (a "PICC adhesive securement device") that include one or more guides for individually holding/securing multiple lines of the PICC. These adhesive PICC line guide devices may also include a lock, clasp, or holder that may be integrally formed from the body of the device and may hold the one or more lines of the PICC in place.

For example, a PICC line guide device with a clamp may include a base that is formed to include a plurality of projections (e.g., posts, channels, rims, etc.) forming a guide, and also includes an arm (e.g., clasp arm) configured to bend over and secure one or more lines (or two or more lines) of the PICC against the base. The base and/or arm may also include an adhesive material. For example, adhesive material on the base may secure the device to the patient, while adhesive material on the arm (or in some variations on the opposite side of the base) may secure the one or more lines of the PICC against the base, within the guide formed by the projections. A PICC line guide device may also be adapted so that any anchor (e.g., wings) on the PICC attach to the base. The PICC anchor may engage one or more projections extending from the base; these anchor-interfacing projections may be separate from, or may be the same as, the guide projections for separating, securing and/or guiding one or more of the lines of the PICC. An anchor may also be secured by the arm.

FIGS. 29A-29E illustrate one variation of a PICC securement device. In FIGS. 29A and 29B, a PICC securement device (line guide device) is shown comprising a plurality of (e.g., four) rigid or semi-rigid post-like projections 2901 formed from a rigid or semi-rigid base that is itself attached to an adhesive holdfast layer that can attach to the patient. As shown in FIG. 29C, an arm (configured as an adhesive flap) 2903 is wrapped on top of the lines (tubings) 2905 of the catheter and attached to the adhesive holdfast layer, thereby securing the catheter to the patient's body. The arm in this example is formed as a hinged or flexible portion of the base 2908 of the device. Any of the devices (including the PICC-securing devices described) may include a liner or release liner coving the adhesive material, and configured to be manually removed.

FIGS. 29D and 29E show an alternative embodiment of a PICC securement device in which multiple projections 2911 are formed from a rigid or semi-rigid base 2915 which is itself attached to an adhesive holdfast layer. In this example, release liners are used to protect the adhesive regions (on the base and on the arm) until the device is applied, as illustrated in FIG. 29E. In FIGS. 29A-29E, the devices shown may secure in particular the multiple lines of a PICC and may keep them organized, which may advantageously prevent pulling on the PICC and/or tangling, confusion or interference with different PICC lines. Alternatively, in some variations one or more of the posts (e.g., 2911) may be replaced with a hook or C-shaped region, such as the hook region shown in FIG. 45A or the like. In some variations, the hook or C-shaped region may be a living hinge that can bend or be bent over a tube being held by the device to lock the tube in place. In some embodiments, a locking mechanism is present on the device.

FIG. 29F shows another embodiment of a PICC securement device in which the PICC device (not shown) fits securely into the device using one or more snaps 2934 that are part of the fixation means 2932 which is itself attached to adhesive holdfast 2930. This structure, including the projecting snaps, may be formed using any of the techniques described herein, including in particular the stamping/pressing techniques. For example, the projecting snaps 2934 may be initially formed as a region having angled sides, as shown in FIG. 29G. The putative snap may then be formed from this region by cutting (e.g., laser cutting) from above. Each of the sides to be removed (region 2936) is formed at an angle of greater than 90° relative to the flat base region 2940, so that a laser may be positioned above the device and used to cut out the region 2936, leaving behind an opening 2938, forming the snap region.

In some devices described herein, an alignment guide may be present. For example, an alignment guide may comprise a visual alignment guide that a subject can look at to align the device (e.g., in a mirror). For example, the device may be marked by a shape, a text, or a color, to help align the device with a location on the body include the ear canal or ostomy site. In some variations, at least a region of the device may be transparent or opaque. In some variations, the alignment guide is a tactile alignment guide. A tactile alignment guide may be felt by the subject. For example, the alignment guide may be a ring, ridge, bump, post, or the like. An alignment guide may be a cone or conical region.

In some variations, the device may further include a support frame. The support frame may be removable and/or removably attached to another portion of the device including the adhesive substrate, the adhesive layer or another portion of the device including rigid portions of the device that may be made from plastic. For example, the support frame may support the device, including the holdfast region of the device, and be completely or partially removable after the device has been applied to the subject. In some variations, the support frame remains on the device after application. The support frame may serve to make application of the device easier or to prevent the holdfast from unintentionally attaching to itself, to another portion of the device or to the subject. As mentioned, any of these devices may also include a support frame. In some variations, the support frame is a support frame layer.

Methods of Making/Manufacturing adhesive devices

Different manufacturing methods including web converting may be used to make the adhesive devices described herein. Multiple layers may be laminated together using heat, pressure or adhesives either alone or in combination. Methods may include cutting, laser cutting, die cutting, jet cutting, or the like. In some variations, thermoforming or cold forming may be used either as part of a continuous process or as part of a multi-step process. In some variations, casting, molding or injection molding may be used. In some variations, silicone or thermoplastic urethane may be used in any or all parts of the subject devices. Mesh may be used in any or all parts of the device, serving as a filter or other role. For example, the mesh may be formed of nylon or other fibrous materials. In some variations, it may be beneficial to use materials that are relatively stiff. Exemplary meshes may include: molded polypropylene plastic mesh (e.g., 0.0140" thickness), precision woven nylon mesh (31.2 openings per inch×31.2 openings per inch), precision woven nylon mesh (80×80), precision woven polypropylene mesh (69×69), filter mesh, precision woven nylon mesh (198×198), PTFE diamond mesh, precision woven polyester mesh (109×109), precision woven polyester mesh (45.7×45.7).

Portions of the adhesive medical devices may be assembled or joined together using adhesive (e.g., by using the adhesive substrate region of the adhesive holdfast), by compression, laminating, by welding, by heat staking, heat sealing, gluing, or press fitting. Ultrasonic or laser welding may also be used. The adhesive or layers of adhesive may cut before, after or during the process of combining them through the aforementioned processes. In some cases, the unneeded portions of adhesive or adhesive layers may be cut against (kiss cut) the liner they are cast on or a process liner. After cutting the liners may be removed carrying the unneeded portions of adhesive or adhesive layers with them.

The devices described herein may be continuously fabricated, batch fabricated, or fabricated by hand. In particular, the layered devices described herein may be fabricated by sequentially adding and processing multiple layers to form the final device and then packaging the final device. A layer may be pre-processed by cutting, trimming, forming, stamping etc., or otherwise modifying it. Processing may be performed by layering strips or sheets corresponding to the different layers, and cutting or stamping the devices out of the strips or sheets after they have been at least partially assembled. The various operations may be combined into single tools or in multiple tools and aligned or registered to one another using a closed loop system and/or PID controller in and automated, semi-automated or manual system. The adhesive holdfast layer may be formed by, for example, cutting a continuous strip of shapes. A three dimensional portion of the device (such as the barrier cap, protective or fixator) may be thermoformed or cold formed and then cut and accurately placed or transferred on the moving web. A three dimensional portion of the device may be formed and connected to the device in-line as part of a continuous process or formed in a separate process and then attached in a subsequent process. A three dimensional portion of the device may be delivered in a continuous roll of material or individually (e,g, in a bowl feeder) and picked and placed onto a moving roll.

Three dimensional forming, and particularly forming in combination with or as part of web processing may be used in fabrication of the apparatuses described herein. For example, a film of polymeric (e.g., plastic) material may be stamped, pressed, pushed, vacuum formed or otherwise deformed or molded as a step in the web processing of the device. In some variations the formed portion may include a metallic material (e.g., aluminum) that can be deformed with the material and also operate as a barrier for water and oxygen. Forming may be done without any heat applied (i.e. cold forming) or with heat applied (i.e. thermoforming). Heat may be applied in various ways including, heating the material which is to be formed before it reaches the forming tool, heating the forming tool or both pre-heating the material and the forming tool. Annealing may also be done after forming to give the finished shape the desired physical properties.

In some variations the formed material may be used to form three-dimensional shapes, e.g., a cover, protective cap, barrier cap, protective cover, vacuum cap, etc., and may be web processed along with the other layers, in particular the layer(s) forming the adhesive holdfast and any backing layer(s). In one example, the apparatus may be formed by a continuous process in which a web (sheet) of plastic material from which the cover or cap (e.g. protective cap) is to be formed is cold-formed by stamping to form a chamber or cavity having a desired dimension. After forming chambers on the sheet, it may be combined (while aligned) with an adhesive layer. In some variations, the adhesive layer may be at least partially cut (e.g. by stamping or the like) to remove internal regions. The adhesive layer may also be pre-applied to a backing layer on one side. In some variations the adhesive layer forming the holdfast region (including an adhesive and adhesive substrate) may be formed as a preliminary web that is then sequentially or simultaneously combined with other webs, including a formed web forming a cap or cover.

In one variation of a method for forming an adhesive bandage having a medicament may be performed by a combined cold forming or thermoforming and web processing technique. For example, the adhesive substrate may be combined with the adhesive to form a first web. An additional web forming the pad to which a medicament may be applied (including applied during the fabrication process), pre-applied, or the like, may be cut and placed onto the adhesive side of the first web. A layer of plastic material that is initially flat may then be cold-formed to form the cover/chambers and placed (e.g. rolled) over the pad and medicament. In some cases, heated dies are used to form the plastic sheets. In some cases, the medicament may be applied or deposited into the protective cap or barrier cap or other chamber formed during the manufacturing process. This medicament can be deposited on to/into a cap/chamber/blister when the web that is receiving the medicament is facing upward or downward. The combined webs may then be finally cut to form bandages as shown in FIGS. 1 and 5, or other variations. In particular, rotary die cutting may be used, and automatic eye registration may be used to ensure that cutting, laminating, printing or other processes are aligned appropriately to provide the desired tolerances.

In some variations, a cold-forming or thermoforming technique may be used in combination with the web processing in which individual layers (webs) are cut before placement and/or after placement against other webs. The placement maybe accurate to within a tolerance of less than about 1.0 mm, less than about 0.1 mm, less than about 0.05 mm, less than about 0.01 mm, less than about 0.005 mm, less than about 0.001 mm.

Another example of a continuous fabrication process including cold forming or thermoforming may be used to form a bandage including a protective region (cap) such as those shown in FIGS. 9A-9C. In one example, the bandage may be formed by placing cut layers of adhesive and/or adhesive substrate on a liner layer (forming an opening in the adhesive substrate/adhesive) and an additional layer of double-sided tape or adhesive around the opening, then applying cold or thermo formed covers/caps that have been cut to size, over the openings and secured by the double-sided tape or adhesive. As mentioned above, the steps of forming, cutting and placing may be arranged so that the process can be continuously (and in some cases automatically) performed.

FIG. 30 is a flowchart summarizing how the instant devices may be manufactured using web converting methods. First, raw materials may enter the manufacturing process, generally in the form of sheets wound on rolls. The unwinding process unrolls the material, including the adhesive, substrate, liner or combinations thereof. A nip roller may be used during this stage to create and maintain tensioning of the web of materials, and may use independent servo motor control to accurately maintain tensioning. Alternatively, a nip roller may be used during other parts of the process. In fact, a nip roller may be used during any or all of the parts of the process shown in FIGS. 29A-29E. As one example, the nip roller may be used towards the end of the manufacturing process (in addition to near the start) to ensure that adequate tensioning has been maintained in the process.

Next, the holdfast (or any or all of its components) may be kiss-cut and any extra waste material may be separated and rewound for subsequent disposal. The cut pattern is generally optimized to minimize wastage of materials. A punch or other tool may be used to create holes in the holdfast or liner or both. Alternatively, a laser may be used to create a hole or to etch a feature or writing onto the device. Slit cutting (using a rotary cutting tool for example) and spreading of the web (using spreading rollers) may then be completed. Spreading can happen in the cross-web direction and in machine direction, which may be helpful in minimizing use or wastage of incoming material. The adhesive device may be transferred to new liner if desired. The liner may be folded or slit to ease in the removal of the device.

Precise cutting and island placing of fabric (such as the pad of a BAND-AID) or other material may then be completed, accomplished though the use of a servo-controlled process. A nip roller may be used at this point to press the pad onto the adhesive holdfast. Next the plastic sheet may be formed, through the use of cold forming or thermoforming. This may occur using a rotary die tool, with male and female components. In some cases, vacuum and or heat may be utilized to enable the forming process. In other cases, vacuum and heat are not required. A step-and-repeat process (during the forming process) may be utilized. A step-and-repeat process can permit the utilization of a standard die set (i.e. not rotary) which may allow for tighter tolerances. In other cases, a step-and-repeat process is not used, which may increase the speed of production and number of units that can be produced in a given time period. In some cases, sequential molds with identical, similar, different or variable shapes may find use. An annealing step may be added after forming. A step and repeat process, where a moving web is stopped and then indexed, may also be used in conjunction with a continuous web converting process. Where the step and repeat portion of the web is fed into an accumulator or multiple rollers or pulleys that index closer and further from one another as the step and repeat web is fed in. The web may then be fed or pulled from the accumulator at a steady continuous rate.

In general, 0.1-0.3 mm PET and polycarbonate are preferred materials for inline forming operations to make the devices described herein, although other materials listed herein may also be used.

The difficulty in forming certain 3D features will vary significantly from device to device. Some important parameters to consider include the relative depth of a given feature compared to its surrounding base of material (which may include width, length, circumference and perimeter of the base which has already been discussed herein). This may be referred to as the "depth of draw" and this has been discussed previously in depth in the sections related to the protective and barrier cap. For example, it is preferred that the "aspect ratio" which is defined as the ratio of width (either short width or long width) to height (defined as the highest deflection from the base) shall generally not exceed 1:2. Certain exceptions are possible by increase the complexity of the forming operation. Other parameters to consider include edge sharpness and material thickness.

Some products may require alignment of multiple cut features in the product at different locations (also know as registration). Registration capabilities with currently available equipment at high speeds is typically +/−0.030 which means that the position of the formed plastic components may vary in position by that amount during manufacturing. Challenges with registration may be minimized by building all of the cut features into the same tool.

Regarding packaging, packaging may be done inline with cold seal pouch film to minimize cost. Tabs or other three dimensional features (including those made from formed plastic) may potentially become flattened during packaging as cold sealing is typically done by running the product and material between two rollers, one steel and the other rubber. One solution is to provide relief on of these rollers of other tools to accommodate a 3D part being passed through the line, to minimize the potential for damage to the product.

In some cases, a medicament is dispensed or injected into the cavity or depression formed during the earlier described forming process. The depression may be downward facing so that the liquid/fluid ointment is held in place by gravity. Next, the formed plastic piece may be cut using a cutting tool, die or laser. The formed plastic piece can then be accurately placed on the moving web. A vision system may be used to aid in alignment or to identify processing defects. Adhesives may be used to securely fix the plastic formed piece to the holdfast, although in other cases, heat sealing or other bonding methods may find use.

At this point, the individual "final product" may be cut (via die cutting or the like) using controlled cutting techniques under the control of a vision system. Additional inspection/machine vision testing may be completed to ensure quality of the product, including confirming the accurate placement of the pad, pad size, patch (or holdfast) size and any other feature such as the location and size/height of the formed plastic piece. Defective pieces may be removed from the line automatically or manually. The vision system may also provide registration feedback to the cut-out die station or other parts of the manufacturing system. A bullnose may also be used to remove any air prior to packaging. Final inspection of the part (visual or otherwise) or testing of an individual part may or may not be required.

The device can then be placed into the packaging and the packing sealed and cut into individual packaging. Various heat settings, pressure settings or dwell time of sealing may be modified to ensure a good seal. A slit cutting tool may be helpful to create multiple lanes of packaged product. A take away conveyor with reject gate or compressed air may be used to remove defective product. Next, cartoning and case packing may be completed. Any and all parts of this process may be interchanged with any other part. Other parts of the process may be deleted or not used if not appropriate. Some parts of the process may be repeated one or more times. The process may be broken into multiple steps which may be performed at different times or on different pieces of equipment.

Regarding packaging, any appropriate packaging technique may be used. As an example, cold sealing or heat sealing may find use. Foil or film packaging or other pouching may be used, which may help prevent evaporation of the medicament. Specialized packing such as a flat bed reciprocating packager may find use.

Converter speeds may achieve 30 feet/minute and packaging speeds may achieve 40 feet/minute. In some cases, the fabricating of the product and the packaging operation may be separate processes. In other cases, they may be connected, part of a seamless single operation or manufacturing line.

Returning to the figures, FIGS. 31A and 31B illustrate another embodiment of an IV securement device. An adhesive holdfast may be attached using adhesive 3108 which is attached to bottom securement door 3104 which is connected in turn to top securement door 3102. This device includes a living hinge located between the bottom securement door 3104 and top securement door 3102. The Luer lock, also known as the hub, (not shown) can be captured in between the bottom securement door 3104 and top securement door 3102 when the device is in the closed position (not shown).

In FIG. 31B, the proximal a port 3105 (which faces towards the site of insertion into the body) of the bottom securement door 3104 has an opening with a cross sectional area that is larger than the cross sectional area of the opening of the distal port 3106. Further, the proximal port 3105 has a smaller tunnel length (which may be zero) than that of the distal port 3106 of bottom securement door 3104. The distal port abuts the hub prevent movement of the IV catheter and hub in the distal direction. The bottom securement door 3104 and the top securement door 3102 may be held together by a snap feature on one side. On the other side is a living hinge 3114. The device is designed to fit securely on the Luer lock (or hub) slightly the device is in the closed, deployed position (ie when the top and bottom securement door components are together). This provides both a snug fit on the Luer lock and provides a preload that takes up any slack on the snap.

Multiple ribs may be included to reinforce the cap's thin cross-section and provide stiffness and maintain the shape while forming. Additional ribs may be located adjacent to large features, terminating at the living hinge to ensure only the desired bending area is bent during folding. The top and bottom features are stamped or formed from a single sheet in one more forming steps (in the same station or across multiple stations). The snap features can be pre-cut or laser-cut post-forming.

FIGS. 31C-F show additional images of the device of FIGS. 31A and 31B.

FIGS. 32A,B,D and E illustrate a PICC/CVC (peripherally inserted central catheter/central venous catheter) securement device. In FIG. 32A, the adhesive holdfast 3200 and liner 3202 can be seen on both sides of the PICC anchor cap 3208. The PICC anchor cap 3208 is a rigid or semi-rigid, formed component that is placed on top of the rigid or semi-rigid PICC anchor (labeled as 3213 in FIG. 32C) which was previously described. The PICC anchor, which may or may not have wings fits at least partially firmly or firmly or in some cases snaps in firmly into the PICC anchor cap 3208. In this "top-down" type device, the PICC anchor cap 3208 is used to hold the PICC catheter securely and may or may not apply downward pressure on the PICC anchor against the patient's skin. The bifurcation area of the PICC anchor (where two or more tubes of the PICC emanate from the anchor—labeled as 3216 in FIG. 32C) is a relatively rigid and secure location to anchor the catheter. The PICC anchor cap has a bifurcation area 3206 (in this case for a PICC which bifurcates into two tubes—ie a "dual lumen PICC") which is designed to receive the bifurcation area of the PICC catheter. In some cases, the PICC anchor cap will have a silhouette or outline which substantially matches the outline of the PICC bifurcation area or the entirety of the PICC anchor including wings in some cases. A shallow anchor cap may apply relatively more pressure onto the PICC anchor and this pressure may be transferred to the user. A taller anchor cap may minimize downward pressure applied to the PICC anchor and thus the patient. Further, a taller anchor cap may secure the PICC catheter more securely as the PICC catheter is less likely to be able to slide under the PICC anchor cap. PICC anchor abutment 3207 can also be seen and helps to prevent the PICC catheter from moving in the distal direction (away from the insertion site).

FIG. 32B shows an exploded view of the device shown in FIG. 32A. In this case, the liner 3202 folds onto itself although in other embodiments, the liner may be a single layer. A double-sided adhesive 3218 is shown which attaches the adhesive holdfast 3200 to the PICC anchor cap 3208. Also seen is small cutout 3220 which enables the wings of the PICC catheter (not shown) to be placed within the PICC anchor cap 3208 without being obstructed by the double-adhesive during placement. FIGS. 32D and 32E show finished prototypes of the devices shown in FIGS. 32A and 32B.

Figure 32G:
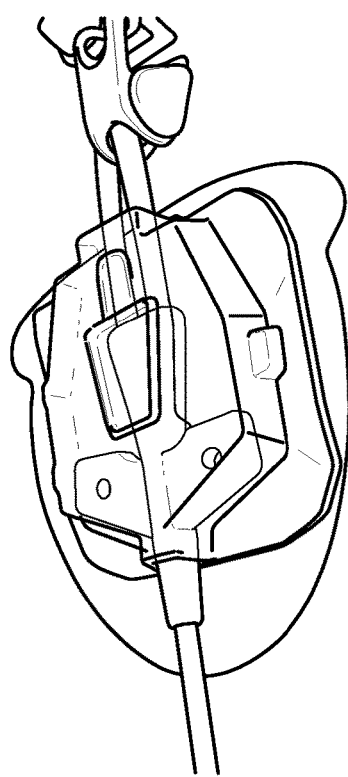
Figure 32H:
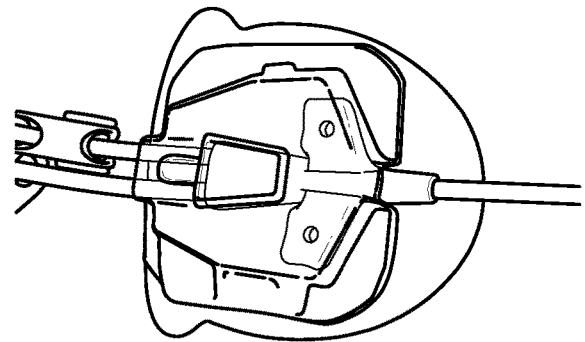
Figure 32F:
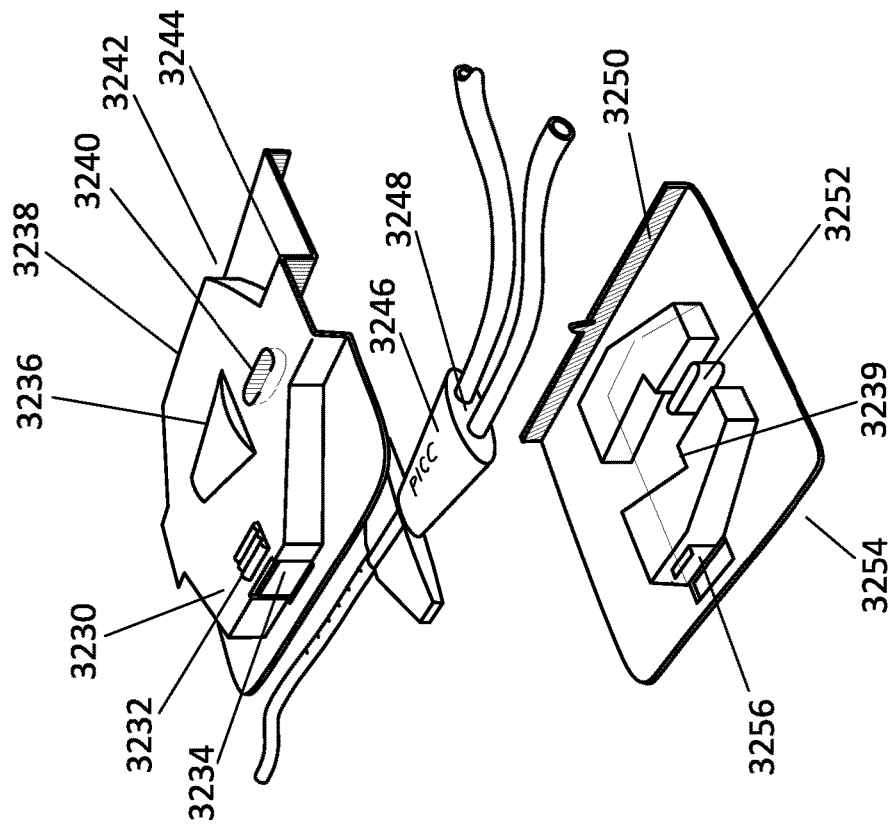

In FIGS. 32F-H, another embodiment of a PICC securement device is illustrated, this time featuring a living hinge. In this embodiment, the PICC anchor 3246 is captured or secured from both the top securement door 3238 and bottom securement door 3254 of the securement device. A living hinge 3250 is seen connecting the top securement door 3238 and bottom securement door 3254, allowing the device to open and close around the PICC anchor. There may be high friction between the PICC anchor and the glossy formed plastic material (such as polycarbonate) used for the securement device which helps secure the PICC anchor into the PICC securement device. The securement device (including the top and bottom securement doors) may be slightly undersized relative to the PICC anchor so the PICC anchor is very secure upon closing/locking of the device.

On the bottom securement door 3254, several formed features capture the base of the PICC anchor preventing it from moving up/down or side to side. The PICC bifurcation area (defined above) where two or more tubes emanate from the PICC anchor is held in place by one or more projections 3252 and 3240 that are formed from either the top securement door 3238, the bottom securement door 3254 or both. These projections help prevent movement of the PICC anchor, especially in the distal direction (away from the insertion site). Further, abutment 3239 also prevents this distal movement of the PICC anchor. The wing of the PICC anchor may also fit into a recess that is preferably formed into the bottom securement door, again to help prevent the PICC from bring pulled out distally.

The top securement door 3238 exerts continuous downward pressure and keeps the PICC anchor from being displaced out of the device. The proximal end of the cap 3230 also constrains the wing from being pulled in the direction of the insertion site. Ribs or ridges can be placed in one or several locations on the top securement door 3238 and bottom securement door 3254 including next to large formed features such as 3242 or on or near large flat surfaces to maintain flatness (and reduce warping of formed parts).

Snap 3256 and cutout 3234 are present in the securement device and hold the top and bottom halves together in the closed position. One or more snaps or cutouts may be on the top anchor or the bottom anchor door or both. Closure of the device is facilitated by formed corrugations 3232 which the user's fingers press down on to engage the snap. These corrugations may also increase the rigidity of the snap area, providing structural support for the entire device.

Figure 32J:
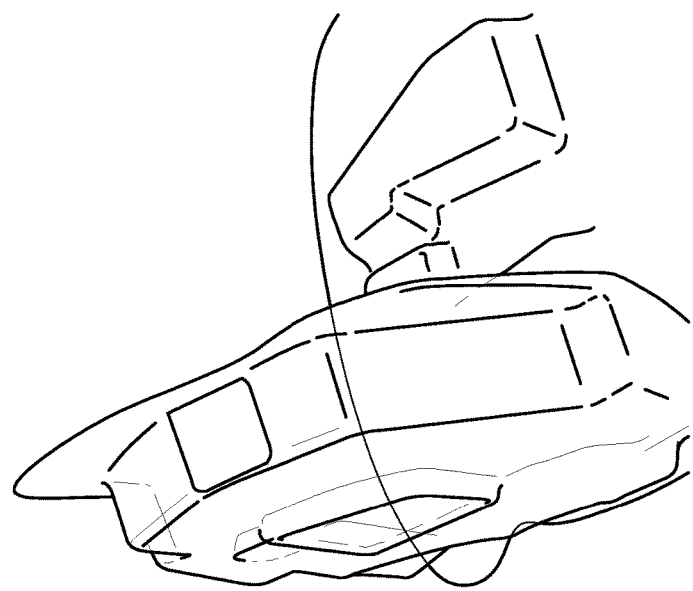
Figure 32K:
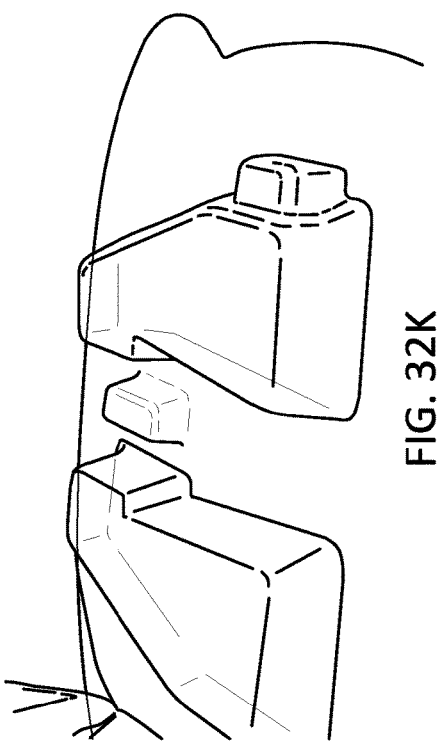
Figure 32I:
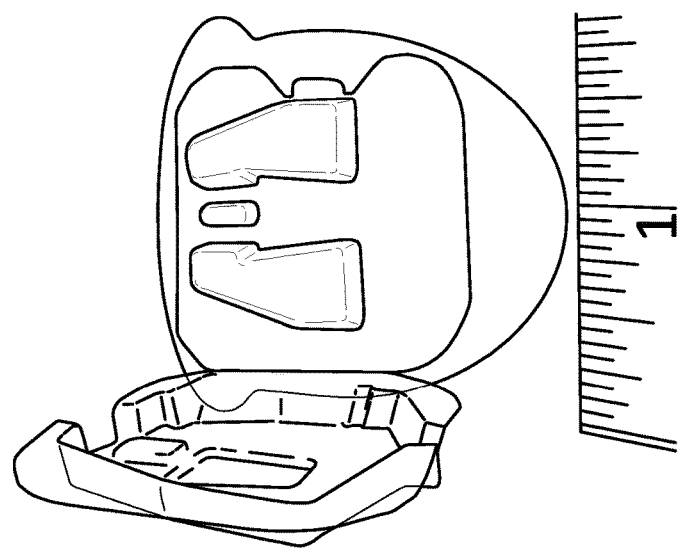

FIGS. 32I-K are images of prototypes of the devices described in FIGS. 32F-H.

Preventing Warping of Formed 3D Parts

Any of the device described herein may include one or more features, including structural features (e.g., creases, patterned wrinkles and/or raised patterns) to help prevent warping and allow the surface to lay flat. In general, particularly when forming flat sheets of material into the 3D structures described herein by pressing or stamping, flat sheets have a tendency to warp during the pressing/forming process, depending on material properties, material thickness, mold configuration, temperature of dies, number of dies and their sequence, depth of draw, etc. During die pressing, the die may not be able to maintain a flat shape because the die may only deform the plastic within an elastic range. The material may spring back or return to a warped shape after the die is released as the residual stresses in the adjacent formed features start "pulling on" the flat area. This warping phenomena is illustrated in FIG. 33A. In this case, a 3D structure 3305 was formed by the pressing/stamping technique described herein, however warping of previously flat sections 3307 of the plastic sheet occurred.

In some variations, otherwise flat surfaces (e.g., horizontal surfaces) may therefore be patterned to prevent or limit the warping. In general, a raised pattern may be formed in the horizontal regions (e.g., base regions), as illustrated in FIGS. 33B and 33C. In FIGS. 33B and 33C, the otherwise flat, horizontal surfaces of the device have been press formed (e.g. at the same time, before or after forming the rest of the 3D structure(s) of the device) to create shallow ribs running along flat areas that give it a frame of rigidity. In FIG. 33B, the lattice structure is generally square and in 33C, the lattice structure is generally triangular. Ribs such as 3302 can be seen in both figures and their addition may help maintain flatness of material that may otherwise warp. Further, ribs or ridges may be applied wherever extra strength is required or when large flat areas are present. In general, the raised pattern (including intersecting ribs as shown in FIGS. 33B and 33C) may project above or below the 'neutral' height of the sheet being formed by no more than about 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 m, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, etch. In particular, the height of the raised regions may be less than 2 mm. The actual height may depend on the location of other formed features and the extent of flat features. Elongate, and in some variations interconnecting and/or intersecting projections (ribs) may project enough to provide some stiffness or rigidity to the flat surface (e.g., a rim region, or wing region around a device) but may be short or shallow enough not to interfere with the operation of the projecting region. In addition, the spacing between projections (ribs) may be larger or smaller, depending on the desired stiffness. For example, a preferred rib height to distance between ribs may be larger than 1:8, larger than 1:7, larger than 1:6, larger than 1:5, larger than 1:4, larger than 1:3 or larger than 1:2 depending on application. Generally, the closer the space, the stiffer the overall ('flat') region may be, depending also on the shape of the projections. For example, the projections may have a curved cross-section (e.g., semi-circular or semi-ovoid) or polygonal cross-section (e.g., triangular, rectangular, etc.), etc.

In addition to the cross-sectional shape of the raised projections, the overall pattern of raised projections (e.g., ribs), may be configured to increase or decrease the stiffness. For example, a square lattice pattern as shown in 33B may provide stiffness in two general directions, but may allow warping in the diagonal directions (relative to the squares in the pattern) whereas triangular patterns (such as seen in FIG. 33C) do not. The choice of lattice geometry may also depend on the thickness of material, the depth of draw of nearby 3D shapes, the area of desired flat geometry and cosmetic concerns. Exemplary lattice geometries may include circular, triangular, rectangular, square, trapezoidal, pentagonal, hexagonal, heptagonal, octagonal, or any other polygonal geometry with equal or variable line segments. Asymmetric geometries may also be used. In general a shallow raised pattern of interconnected raised projections as described herein may extend over the majority of a surface (e.g., horizontal surface). Also, a combination of the above structures is also possible, including combinations of patterns and/or combinations of cross-sectional shapes. Further, variable raised projection heights (e.g., rib heights) may be used.

In some variations, these raised projections may be compressed or flattened during the fabrication technique to reduce the profile and/or modify the physical properties such as stiffness, of these otherwise flat regions. For example, after forming the projecting regions, they may be stamped flat or pressed (at an angle). This is illustrated in FIG. 33D. FIG. 33D shows a sequence of forming steps that may be used to produce a planar or substantially planar structure that neverless does not include warping that may otherwise occur when forming devices as described herein. In this example, the flat sheet is initially stamped to form the pattern, which may include a raised projection pattern on the horizontal regions. In the middle step shown in FIG. 33D, only the raised pattern is shown (additional 3D structures, such as projections 3305 shown in FIG. 33A, may also be included. These horizontal regions may then be mechanically flattened (or crushed) to form a flat (e.g., horizontal) surface that neverless includes a crushed pattern of the raised surface, as shown in FIG. 33D (bottom). In some cases, the same principle of sequential forming shown in 33D can be used to produce non-planar, substantially non-planar or other 3D formed structures with minimal warping. During the forming process, such as the process illustrated in 33D, it is possible to form ribs, and then crush them with a second pass to force plastic deformation into the final shape, which may be planar, substantially planar, non-planar, substantially non-planar or a combination thereof. The process of forming this crush pattern may result in a pattern in which flattened raised structures are apparent on these horizontal surfaces; the flattened raised structures may overlap against each other in and/or adjacent to the formerly raised regions.

Draft and Radius Control:

FIG. 34 shows a 3D formed part, with two different radii of curvature marked, "r" and "R". When forming less complex or less deep features, a draft of approximately 3 degrees, approximately 4 degrees, approximately 5 degrees, approximately 6 degrees, or approximately 7 degrees may be used. For deeper and/or more complex features, a draft of approximately 8 degrees, approximately 9 degrees, approximately 10 degrees, approximately 11 degrees, approximately 12 degrees, or approximately 13 degrees may be used. Compound curves may increase the chances of plastic warping during forming and may create fold marks on the plastic. Sharp angles on vertically-oriented edges should ideally be avoided as a sharp tool may slice through the plastic being formed. Adding a fillet (e.g., a band or ribbon region around the structure) that is about 0.5 mm or greater to these edges may be beneficial.

In some variations, ribs or ridges may be positioned around the sides of some or all of the large features being formed. For example, ribs or ridges may be approximately 1 mm wide, approximately 2 mm wide, approximately 3 mm wide, or approximately 4 mm wide to support the sides of large features. As mentioned above, shallow projections on the flat surfaces (e.g., interconnecting patterns) may be used (e.g., approximately 2 mm wide/1.5 mm tall ribs) to add rigidity. At the base of isolated tall and thin features a fillet radius of between about 0.2 mm to 0.8 mm may be used, more ideally between 0.3 mm and 0.6 mm and most ideally between 0.4 mm and 0.5 mm should be added to the base to help material flow.

To facilitate forming, a radius of 0.25-0.75 mm, more ideally from 0.35-0.65 mm and most ideally between 0.45 and 0.5 mmm on horizontal edges is adequate for features 3 to 6 mm thick. For shallower features it may be beneficial to reduce the gap locally between the dies, reduce the fillet radius to 0.15-0.35 mm, more ideally from 0.2 mm-0.3 mm and most ideally to approximately 0.25 mm and possibly design bend angles to be 5 to 10 degrees sharper than seen on the features to compensate for the material springing back. Shallow features generally require sharper bends to form.

Forming with Progressive Dies:

Any of the structures described herein may be formed by the stamping techniques described herein. In particular, any of these devices may be formed by a plurality of repeated stamping steps (e.g. progressive, overlapping stamping) which may help shape and form the devices. For example, a relative taller feature may be formed using a series of forming steps with different dies or the same die that progressively forms the feature into its final shape. This may include one step, two steps, three steps or four steps or more all of which may happen on single tool or single station of the press or across two or more tools or stations. This is illustrated in FIGS. 35A and 35B. In general, the press-forming (e.g., stamping) techniques described herein may alter not only the height (z) of regions of a sheet of material to form a 3D structure, but iterative stamping (press forming) may also be used to modify the base size (x,y) of the sheet.

In practice, the multiple stamping steps may be built into a single die/tool with several spring loaded and/or static forming features that engage the material at the same time with various spring coefficients or at different times during the forming process. This may be done with forming features in one or both sides of the tool that form material and then are removed as following forming features are engaged. In some variations the forming features may be male or female molds, male/male, or female/female, and may be on the same tool.

In some variations, the forming techniques described herein may extend the structures being formed out of the plane of the material (e.g., in the z direction) without substantially changing the size of the plane. Alternatively, the size of the plane (in x,y) may be changed as the height of the projecting structures(s) is changed.

For example, in FIG. 35A, the first forming step (first image on left) leads to an intermediate piece that has a certain depth and width. In the second forming step, the piece becomes deeper (taller) but retains approximately the same width at the base. A third forming step produces a taller final piece that is deeper and maintains roughly a similar width of the bases as after the first and second forming steps. Thus, this process shows the progressive increase in one dimension during sequential forming steps.

Alternatively, FIG. 35B demonstrates a sequence of forming processes in which the width of the structure (and the width of the base region) is changed with sequential presses, forming the projection region. The first forming step leads to an intermediate piece that has a first depth and width. The second forming step (in the middle of FIG. 35B) then leads to the forming of a deeper (taller) intermediate piece, but in this case, the width 3509 at the bases has decreased. In the final forming step of the example of FIG. 35B, the piece is formed to become maintain the same depth (although in come cases, it may be formed to become deeper) and again, the width at the base has again decreased compared to the previous forming step. Thus, FIG. 35B shows how a sequence of forming steps may lead to intermediate or final formed pieces that can have either increasing lengths in some dimensions and decreasing lengths in other dimensions. The benefit of progressive (over the same region of material) forming operations is to enable a deeper draw or more delicate or complex 3D structures, while minimized cracking of the plastic being formed and/or warping. Additionally, sequential forming operations also provides the additional benefit of more uniform thickness of the formed material, ensuring more uniform strength throughout all portions of the 3D formed part.

FIG. 35C shows difference sizes and shapes of formed 3D structures. In this case, the depth of feature "A" is less than feature "C" which is less than feature "B". In general, features with depth of "A" are fairly simple to form, as the depth of draw is relatively small and the base is not too small. Feature "C" is considerably more difficult to form than feature "A" as its depth is significantly larger with less of a relative increase in the width of the base. Forming feature "C" is thus more difficult and the piece is more likely to break during forming and/or there may be variable thickness of material (and therefore strength) at different locations of the feature. Feature "B" is in fact easier to form than feature "C" as the opening (or lack or material) under the curve enable easier forming. In a similar manner, creating one or more "steps" within the formed material can allow the forming of relatively deep 3D formed structures. The iterative forming (stamping/pressing) steps described above may be used to form any of these types of structures, but may be particularly useful in forming structures such as "C" in which the structure extends from the base to a relatively tall height around the entire circumference of the structure.

In operation, any of these structures may be formed in rapid succession (e.g., stamp or pressing steps) or they may be formed with a delay between steps. The stamps may include an alignment guide to help align them between stamps/pressing steps; in some variations the previously stamped shape may be used as an alignment guide. In some variations a pressed alignment guide shape may be formed during an earlier step to be used for alignment during a later step.

Any of the variations described herein may include a living hinge. For example, FIGS. 36A-F illustrate various embodiments of living hinge mechanisms that find use in the subject devices. FIGS. 36 A and B show a planar sheet that has a series of grooves or lines with decreased thickness that are arranged in a parallel manner. As shown in 36B, the plastic sheet now has the ability to bend along this joint, thus serving as a living hinge. These grooves of indentations can be formed into the plastic during manufacturing. When forming a living hinge using the web conversion (e.g., moving web) technique as described herein, the axis of the living hinge may be in the direction of the web movement. Alternatively, in some variations the axis of the living hinge may be in a direction perpendicular to the web movement.

FIG. 36C uses many small perforations to weaken the plastic, allowing the plastic bend on itself, again serving as a living hinge. These perforations may be created during web converting through the use of a laser cutter or cutting tool or other die. FIG. 36D uses multiple bends or small cutouts (which can be removed using a die or using a laser cutter) to enable bending. FIGS. 36 E and F show alternative embodiments of living hinges. In some cases, it may be necessary to reinforce areas with ribs where bending is undesirable.

Other alternative means of creating a living hinge mechanism include creating numerous parallel cuts that soften the material, thereby enabling bending or using multiple parallel half depth cuts, again with the goal of enabling multiple bending of the plastic. In addition, the top and bottom piece can be formed in two sheets then stacked on top of each other then glued together at the hinge location. This provides a hinge that has the tendency to close instead of staying open.

As shown in FIG. 36F, to achieve a 180 degree bend, a combination of more gentle bends 3610 and a step down 3620 may help achieve the benefits of a living hinge.

Snap/Locking Mechanisms

FIGS. 37A-O illustrate various snap/locking mechanism, for example those that could be incorporated in a living hinge securement devices, or to otherwise connect two structures together (even if not formed of the same piece and connected by a hinge). The first type, seen in FIG. 37A shows an independent boss 3700 which is formed and then cut (with a laser cutter, e.g., from a vertical or non-vertical direction) to yield a smaller boss 3710 with an undercut created post-forming. As mentioned above, the outwardly sloping face 3705 enables such laser cutting of the undercut. A completely vertical face would be more difficult to cut using a laser cutter mounted above the converting line. In other cases, the undercut is formed by pre-cutting the material or cutting post-forming. Thus, in general, any of the walls of the structures formed, and particularly those having cut-out regions, may be configured to allow cutting from above, and particularly laser cutting, but having an angle that is greater than 90° relative to the horizontal (flat) base or plane of the device. For example in FIG. 37A, the wall to be cut 3705 is at an angle of between about 91° and 97° with the base region. In general, the walls to be cut or trimmed may be formed at an angle of greater than 91°, such as greater than 92°, 93°, 94°, 95°, 96°, 97°, 98°, 99°, 100°, 101°, 102°, 103°, 104°, 105°, 110°, etc., when measured up from the horizontal plane of the base. Thus, looking down on the wall from above or below the base, the wall includes a portion of the surface against which the laser cutter may engage to cut the edge.

Figure 37B:
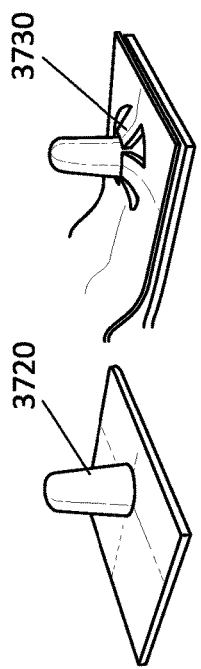

In a separate embodiment, shown in FIG. 37B, there is a straight boss 3720 with a separate part that overlaps the boss which has short flaps 3730. The flaps self-lock onto the boss when pulled the other way due to friction and its steep angle relative to the surface. In come cases, the straight boss may have grooves (not shown) into which the flaps may fit. The boss may be approximately 4-7 mm tall and 3 mm wide at the top, drafted at 3 degrees or less from vertical. The flaps may be approximately be 2.5 mm long and interfere with the boss by 0.5-0.7 mm with a sharp cut edge. To release the latch the flaps are forced to flip downwards. Thus the length of the flap and interference controls how much force is needed.

Figure 37C:
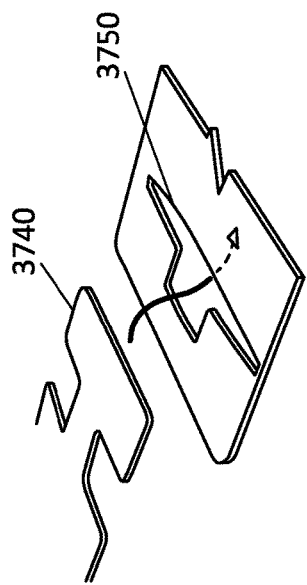

In FIG. 37C, a separate embodiment involving a simple tab 3740 and hole 3750 is shown. In FIG. 37D, another embodiment for the locking mechanism is shown.

FIG. 37E shows some images of the necessary geometries needed to optimize such locking mechanisms. The length of the underside of the hook 3780 should have ample clearance that is roughly 3-5 times the thickness of the material being formed to account for warping of the female part and cut tolerances. In FIG. 37F, the snap should have a slanted undercut 3777 of between 10-35 degrees relative to the horizontal plane. The slack should be taken up by applying a preloading force either by the material's natural elasticity or by making the PICC or IV cavity slightly interfere with the catheter. The latter provides the added benefit of keeping the secured devices fit snugly when captured. Around the snap hook area, the hook should first be formed with a "shelf" feature which is then cut off, in order to maintain the hook's correct inner edge height.

FIG. 37F illustrates another embodiment of the locking mechanism. The front engagement 3781 generally has a generous draft of approximately 5 to 15 degrees; this enables having a bigger undercut. This provides a lead-in for snap 3781 that enables the snap to be designed with a deep engagement while still engaging easily. The cutout may cause the snap hook 3781 to weaken with the tendency to deform, therefore the area should be adequately strengthened by ribs 3785 and 3790 as shown in FIG. 37G. A pull tab 3789 can be added to aid releasing of the snap from the hook. The front edge 3786 and back edge 3788 of the snap receiver cut-out 3787 should be on a flat surface to aid cutting. In other cases, a laser cutter may be used to create the cutout, in which case the face from which cut-out 3787 is created should slope outward by at least 3 degrees or more to enable such lasercutting from a vertically mounted lasercutter. FIG. 37H shows a project or boss after forming and then after removing the cutout (for example by laser). FIGS. 37I-O show additional locking mechanisms comprising snaps and hooks.

FIGS. 38A and B show catheter securement devices capable of securing flexible catheters of various sizes and diameters. In FIG. 38A, the securement device has a formed 3D component 3805 which is attached to the adhesive holdfast 3807. Formed within formed 3D component 3805 is a central pillar 3810 which can be of any shape but preferentially is circular, around which a catheter is wound around using one or more turns. Catheter inlet 3812 and catheter outlet 3814 are both seen.

FIGS. 38B-D show several views of the same catheter securement device. In 38B, the adhesive holdfast 3820 can be seen, attached to 3D securement means 3840 which comprises a top securement door and bottom securement door (unlabeled) which are themselves connected via a living hinge mechanism 3860 which allows each door to pivot relative to the other. A locking mechanism is seen, comprising a projection 3865 which is formed from the bottom securement door and which fits within a cutout within top securement door.

FIG. 38C shows the device of FIG. 38B, now in an open state, in which the top securement door 3842 and bottom securement door 3835 have pivoted apart. FIG. 38D shows a cross sectional view of the device in FIGS. 38B and C showing the top securement door 3842, bottom securement door 3835, adhesive holdfast 3820 and liner 3880. In operation, the user would insert a flexible catheter, loop it around the central pillar 3810, close the top securement door 3842 so that it locks itself into the bottom securement door 3835 resulting in a audible "click" and tactile feedback, indicating the doors are locked and the catheter secured. The liner may be removed (and the securement device applied to the patient) either before or after the catheter has been placed into the securement device.

FIG. 39 illustrates an alternative means to secure the catheter within the securement device, specifically showing an alternative to the use of the central pillar within a living hinge device. Viewed from the top down, the catheter would be placed between one or more posts, and more preferably three or more posts. After placement of the catheter, the top securement door would again be locked into the bottom securement door as described previously in FIGS. 38B-D. FIG. 40 shows another means of securement, showing an alternative means of securing a catheter using series of linearly placed or substantially linearly placed projections that serve to receive a catheter and prevent its movement in any directions. This approach may involve press fitting the catheter into the projections without deforming the internal lumen of the catheter so much so that flow of fluids is substantially compromised or reduced.

FIG. 41 shows another tube or catheter securement device in which a formed tube holder 4103 is attached by a double sided adhesive (not shown) to adhesive holdfast 4110. Formed tube holder 4103 has two or more projections 4105 into which a tube or catheter is placed. The adhesive wrap 4210 is then placed over tube holder 4103 and secured against the adhesive holdfast 4110, thereby securing the tube or catheter onto the securement device and the patient's skin.

Figure 42C:
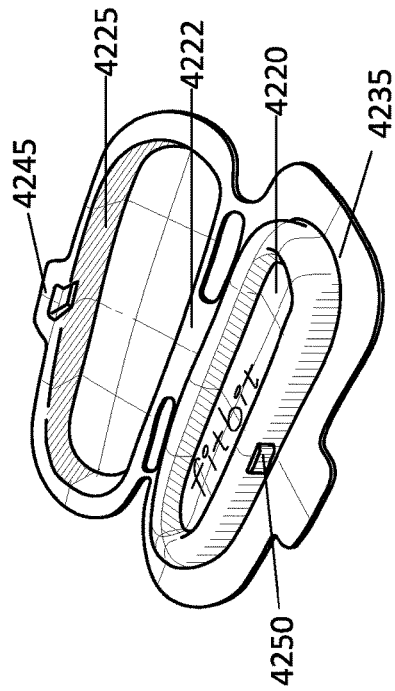
Figure 42D:
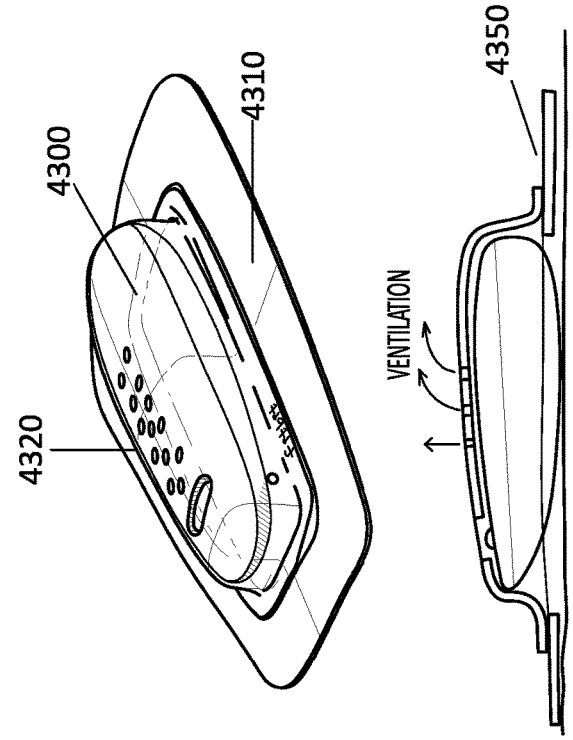
Figure 42A:
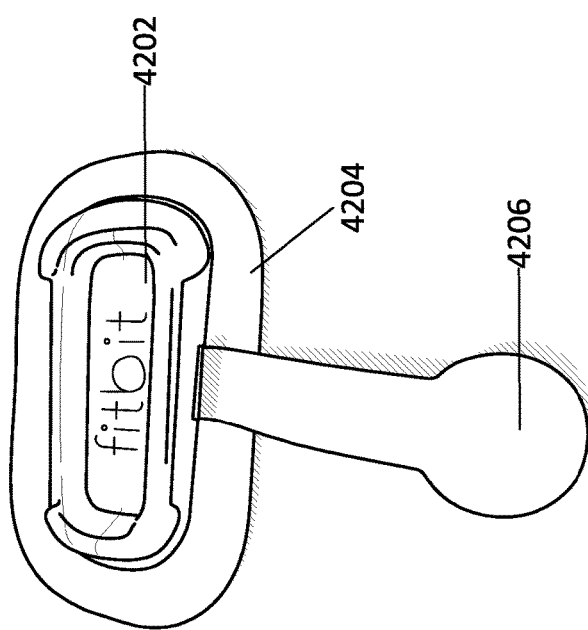
Figure 42B:
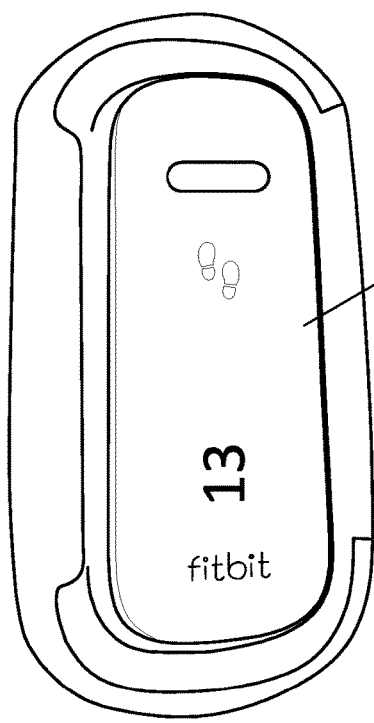

FIGS. 42A-C and FIG. 43 show devices used to secure various sensors including activity monitors and other health sensors to the body. FIG. 42A shows a holder of an activity monitor from Fitbit. One of the impediments to use of many activity monitors is that many people do not like to have watches or other instruments wrapped around or tethered to their wrist. The Fitbit One is an activity monitor that can be clipped onto the belt or other piece of clothing of the user.

The device shown in FIG. 42A provides another comfortable option to affix the activity monitor to the user or his clothing etc. In FIG. 42A, a formed 3D cradle 4202 is adhesively secured to an adhesive holdfast 4204. As shown in FIB. 42B, the activity monitor 4206 can then be placed onto the 3D cradle 4202. The liner is then then be removed from the adhesive wrap 4206 and the adhesive warp affixed to the activity monitor, the 3D cradle 4202 and/or the adhesive holdfast 4204 (and potentially the user or his clothing).

FIG. 42C shows another embodiment of an activity sensor. This embodiment shares similar features to other securement devices described herein, including the presence of a top securement door 4225, bottom securement door 4220 (on which the activity monitor sits), living hinge 4222, cutout 4245 and projection 4250. The rim 4235 that surrounds the bottom securement door 4220 is attached to the adhesive holdfast (not shown) using a double-sided adhesive. The operation of securement involves the user placing the activity monitor onto the bottom securement door 4220, closing the top securement door 4225 relative to the bottom securement door 4220 until they are locked together (a click sound may be audible). The liner may then be removed and the securement device (which now contains the activity monitor) may then be placed on to the user of her clothing. Alternatively, the device may be placed first onto the user or her clothes and then the activity monitory placed and secured within the securement device. The user may place this or any of the activity monitor securement device on any part of the body including the upper limb, lower limb, abdomen, thorax, head, neck, or pelvis. Preferred locations for placement include but are not limited to the wrist, forearm, or on the arm between the elbow and arm pit, including the inner or outer arm.

FIG. 42D shows another embodiment of an activity sensor securement device in which the activity monitor anchor 4300 surrounds and secures the activity monitor (unlabeled). One or more apertures 4320 may be present on the top, side or any location of the activity monitor anchor, to provide access to oxygen (for the battery for example) or to dissipate heat. A securement rim 4310 is attached to the activity monitor anchor (4300) and itself is attached by adhesive (not shown) to the adhesive holdfast 4350 which releasably secures the securement device (and activity monitor) to the user or her clothing.

FIG. 43 and FIG. 44 illustrate securement devices for the foley urinary catheter and other catheters with a branching structure. FIG. 43 shows a securement device that is "open". The bottom securement door 4400 is formed as other 3D components already described herein. Within the bottom securement door 4400 is a depressed region designed to hold the urinary catheter 4410. The urinary catheter 4410 branches into to smaller branches at branch point 4420 which is in close proximity to branch securement point 4430. Also seen is a cutout 4470 and projection 4460 which is located in the top securement door 4452. A living hinge 4450 is also included.

FIG. 44 shows a device that operates similarly as the one in FIG. 43. An adhesive holdfast 4485 is shown, onto which bottom securement door (unlabeled) is affixed. Ribs 4480 and living hinge 4490 are shown, along with top securement door 4475. This securement device is pictured in the closed state and operates in a similar as other securement devices described herein that feature living hinges.

Figure 45A:
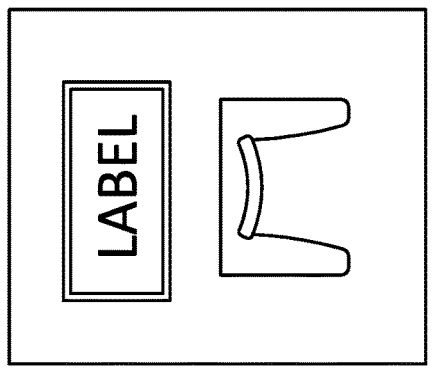
Figure 45E:
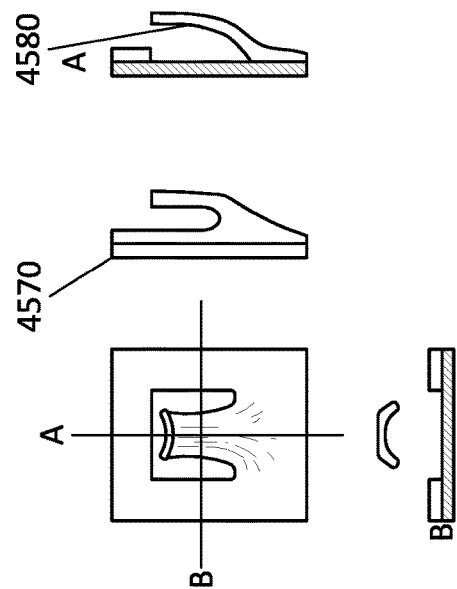
Figure 45B:
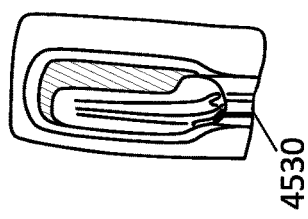

FIG. 45A illustrates a hook created using inline forming of 3D pieces, a process similar to other processes described herein. A circumferential rib 4510 (which may be partially or incompletely circumferential in some embodiments) is shown, surrounding a center cutout area 4520. A hook 4500 with hook ribs 4530 can also be seen. These ribs provide increased structural stability and durability to the hook. FIG. 45B shows a variant of the device shown in FIG. 45A in which the border (unlabeled) surrounding the entire hook device is raised. FIG. 45C shows the intermediate piece immediately after it has been formed in line. A laser cutter or die can be used to remove the cutout 4520 previously shown in FIG. 45A. The laser cutter will generally cut at an angle orthogonal to the moving web of material/product. As mentioned above, the material that is removed (located between the hook 4500 and circumferential rib 4510) is located on a gentle outwardly facing slope, with the laser cutter cutting out the excess material. In other words, face 4535 that from which the cutout is formed has a slope that is less than vertical. This slope may be 1-5 degrees from vertical, from 5-10 degrees from vertical, from 10-15 degrees from vertical, from 15-20 degrees from vertical, from 20-25 degrees from vertical, from 25-30 degrees from vertical, from 30-35 degrees from vertical, from 35-40 degrees from vertical, from 40-45 degrees from vertical, from 45-50 degrees from vertical, from 50-55 degrees from vertical, from 55-60 degrees from vertical, from 60-65 degrees from vertical, from 65-70 degrees from vertical, from 70-75 degrees from vertical, from 75-80 degrees from vertical, from 80-85 degrees from vertical, or from 85-90 degrees from vertical. The angle of the sloped faces may apply to any of the formed 3D components and devices described herein.

Figure 45D:
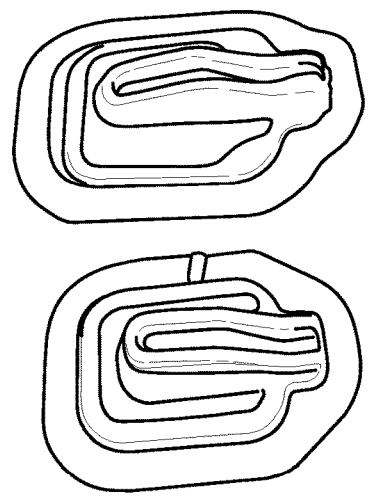
Figure 45C:
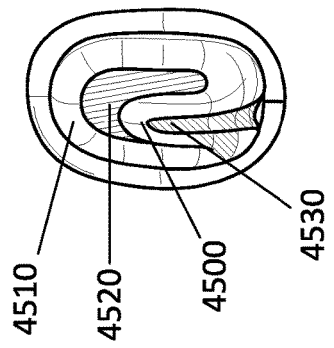
Figure 45F:
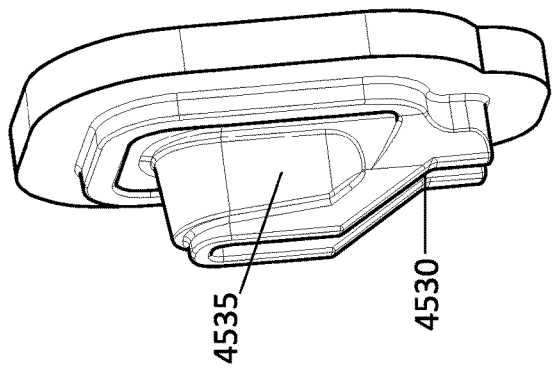

FIG. 45D are hook devices of different sizes similar to those described in FIGS. 45A-C. FIG. 45E illustrates another hook device that is held on a wall by an adhesive or magnet. Hooks like those shown in FIGS. A-E may be used to store keys, Christmas lights or other objects. In some cases, a separate label slot may also be present in the product. FIG. 45F illustrates the cross section of a hook device. Adhesive substrate 4570 and formed layer 4580 are both shown.

FIG. 46A-C show a series of "J hooks. The formed 3D piece is seen in FIG. 46A. The top portion of the device called the fixation portion 4600 attaches to the wall or other surface using an adhesive (not shown). A bend line 4605 can be seen, and may have a depressed or recessed portion that allows movement (pivoting along the axis) between the fixation portion 4600 and the hook region 4610. As mentioned, there is an adhesive layer under part or all of fixation portion 4600. Below the bend line 4605, there is generally less or no adhesive layer. The hook region is moveable. An optional "mouse hole cutout" can be seen as can a stiffening rib 4615 that are present on the fixation portion 4600 and/or the hook region 4610.

FIG. 46B shows a variant of the device seen in FIG. 46A. FIG. 46C shows another variant of the device shown in FIG. 46A, designed to hold cords or other objects.

FIG. 47 and FIG. 48 show other embodiments of devices that can be used for cord management or other purposes. Under the formed plastic pieces (and not shown) are the adhesive holdfast and/or liner. In some hook devices, the adhesive holdfast may or may not have a foam substrate or other substrate layer. That is, the only components of the device may be a plastic 3D formed piece and a double sided adhesive with liner.

FIGS. 49 and 50 are cord organizers that have a formed portion that is bendable due to the presence of corrugations. FIG. 51 is another embodiment of a cord organizer. FIG. 52A is a top down version of another cord organizer/hook device with a cross section view shown in FIG. 52B.

FIG. 53 is a holder device with a formed receptacle 5300 which is adhesively attached to an adhesive substrate 5310 which is in turn adhesively attached to the wall or other object. In some cases such as FIG. 53B, the only components of such a device include a formed receptacle 5300 and a double-sided adhesive (with removable liner) that attaches the formed receptacle 5300 to the wall for example.

FIG. 54 is another hook device which uses a web converted 3D formed piece along with a metal insert. An adhesive layer is present underneath the 3D formed piece.

FIG. 55 is a hook device which has a formed 3D piece featuring a living hinge. The flap portion of the device affixes to the wall using an adhesive layer. FIG. 56 is a variant of the device in FIG. 55 in which the adhesive layer is placed on the other side of the flap.

FIG. 57 is a cord organizer which uses a living hinge mechanism and locking mechanism as described previously. FIG. 58 is another embodiment of a cord management device, again using a living hinge and locking mechanisms.

FIG. 59 is another embodiment of a holder device in which the flap may be adhesively secured to the wall or other location.

FIGS. 60A and 60B are embodiments of hooks which are manufactured using processes that have been described herein.

FIG. 61 is a holder for paper or other planar or non-planar objects. In this case, there is a formed 3D anchor 6100, a hook 6130 and a cutout region 6120. This cutout region is cut from a formed, outwardly sloping wall, a process that has been described previously for other devices (including hooks) above. Also shown is an adhesive substrate 6110 which is larger than the anchor 6100. In some cases, the outer diameter of the anchor 6100 will be the same as or larger than the outer diameter of the adhesive substrate. In some cases, the only components of the device will be the plastic formed piece, a double-sided adhesive and liner.

FIG. 62 shows a device comprising a series of small hooks 6200 on a roll of adhesive substrate 6210 with a liner 6220. These small hooks 6200 are manufactured in an similar manner as other hooks described herein.

FIGS. 63-65 are simple clip devices designed to secure lightweight objects such as paper or the like. They comprise a formed plastic piece, a double-sided adhesive and a liner. A rib can be seen in FIG. 63. As with other hook devices and other devices described previously, after the step of 3D forming, an intermediate form will have been created, with an outwardly sloping wall of plastic present between the top of the hook 6310 and the base of the hook 6320. The angle of this outwardly sloping wall will be similar to what has been described previously. A laser cutter will then create the cutout, thereby creating the hook.

FIG. 66 is a self-adhesive holder that can be use as a business card holder or could be used for other household or office purposes.

FIG. 67 illustrates a self-adhesive means of mounting small objects. For example, this could involve using such a device in a scrapbook.

FIG. 68 shows a corner mounting product which can be used to place photographs in an album as one example. In some variations the corner mount may be used and/or adapted for use with a computer privacy screen.

FIG. 69 illustrates a nasogastric/orogastric tube securement device which is designed to be more secure and easier to apply than current methods that utilize tape. An additional benefit is reduced adhesive residue after removal than current methods. Current nasogastric tubes are time consuming to painful to place and require x-rays to confirm location after placement. Thus an effective securement device that prevents accidental dislodgement represents an improvement.

FIG. 70 illustrates an endotracheal tube securement device with an adhesive portion that attaches to both the patient's skin and the tube, as well as a formed plastic component designed to fit securely around the tube, matched to the outer diameter of the tube (though in some cases it may be oversized or undersized).

FIG. 71 shows a pull tab which may be flat or may be formed into a 3D configuration which is present between the adhesive and the skin for any portion of the devices described herein. The tab (which does not have adhesive between it and the skin) allows the user to easily begin removal of the device. Further, the pulling of the tab in the direction of the skin helps remove the device with less pain and potentially less residue after removal. This tab may be planar in portions or formed into a 3D shape in other portions. In many cases, the tab can be integrated into other 3D formed portions of the device as has been previously described in the nasal strips described herein.

FIG. 73 illustrates one example of a manufacturing process diagram that can be used for many of the products described herein including the nasal strips and securement devices in particular. In some cases, multiple forming stations may be required. In other cases, pouching of the product may happen in a separate location and may not be integrated into a single manufacturing line. In this example, there are four layers that may be run as part of the process, including the substrate (e.g., PETG), a transfer adhesive, a foam, and a liner.

FIG. 74 shows a device to secure tubing in which the tubing is slid under a clip and held in place by one or more projections created from formed plastic.

FIG. 75 illustrates another device to secure tubing comprising one or more fingers that hold the tubing against a surface such as the user's skin or furniture for example. The device may be bent to facilitate placement of the tube into the securement device.

FIG. 76 shows another tubing securement device in which the tubing is pressed into place.

FIG. 77 illustrates a device featuring a living hinge mechanism to secure tubing in place and shares features with other living hinge devices described herein.

FIG. 78 illustrates a tubing securement device in which formed plastic surrounding the tube and adhesive substrate (designed to wrap around the tubing) together helps prevent movement of the tubing.

FIGS. 79-80 illustrate alternative embodiments in which a formed plastic component in combination with an adhesive substrate that wraps around the tubing is used to keep the tubing secured.

FIGS. 81-82 illustrate securement devices to hold a nasogastric tube in place. Both devices have a 3D formed portion that is rigid or semi-rigid and surrounds and secures a nasogastric tube. This formed portion may have ridges to enhance stability or rigidity. The devices also have a flexible adhesive substrate layer that affixes the device to the user's nose or face.

Figure 83:
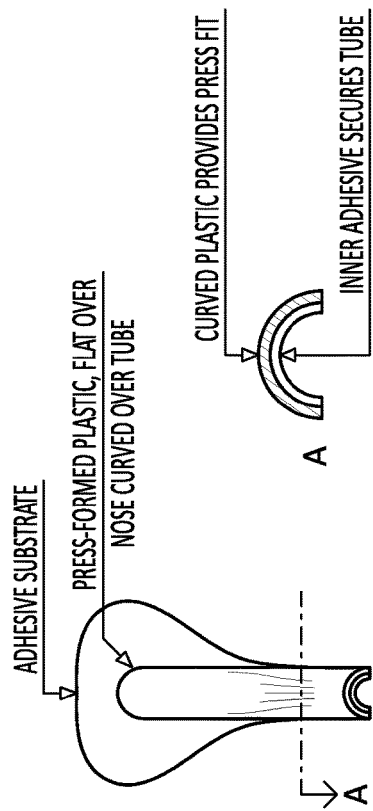

FIG. 83 shows different embodiments of how an adhesive substrate may wrap partly or completely around the tubing to hold it in place including different configurations and widths of the formed plastic portion.

FIG. 84 illustrates a tubing securement device that case be used to secure tubing to the user's face or other part of the body such as the leg (in the case of a urinary catheter for example).

FIG. 85 shows an embodiment of a securement device comprising a living hinge that secures tubing. The living hinge in this embodiment is similar to living hinges of other devices previously described.

FIG. 86 shows a tubing securement device that case be used to secure tubing, in which the formed component is located underneath the adhesive substrate.

FIG. 87 illustrates another embodiment of a tubing securement device that may comprise two adhesive layers.

FIG. 88 shows a securement device for endotracheal tubes comprising a formed component that at least partly covers the endotracheal tubing. The formed component has a slot for the placement of straps or other means of securing the device and/or the endotracheal tube.

Method of Use

Conditions that may be treated with the subject device include but are not limited to cuts, wounds, pressure ulcers, diabetic ulcers, burns, abrasions, surgical incisions, acne, psoriasis, allergic reactions, pain (including muscle pain, back pain and headache), cosmetic issues including wrinkles, nail fungus, skin fungus and other conditions. The devices may be used to treat humans or animals.

As previously mentioned, any of the layered adhesive devices described herein may be used to treat a variety of medical or non-medical conditions. A subject may apply the device to his or her skin. For example, the devices may be first removed from clean or sterile packaging. The devices described herein may be sized (e.g., child/adult, small, medium, large, etc.), or one-size-fits-all. Placement of an adhesive medical device may be done in front of a mirror or can occur without looking at a mirror, depending on the anatomic part of the body on which the device is being placed. A device having an adhesive holdfast with a protective cover may be prepared for application by first removing the protective cover, and then aligning the device (or alignment guide in some cases) with the body part or part of the skin being treated. The device may then be applied by pushing the adhesive holdfast against the skin or other body part to secure the device in communication with the body. In some cases, it gauze or other tape may be applied on top of the device and/or surrounding anatomic structures. After use, the device may be removed by peeling the adhesive holdfast away from the body/skin.

With regard to devices that provide negative pressure wound therapy, there may be several steps followed: 1. Applying a wound dressing/absorbent material to the wound itself, with or without saline and/or antibiotics (Examples of this include cutting a polyurethane foam to the size of the wound and placing it onto the wound, putting it in direct contact with the wound surface). 2. Applying the plastic cap and integrated dressing on the user's skin (on top of the wound). The initial absorbent material, plastic cap, and the area immediately surrounding the wound are now covered with an adhesive, fluid-and-air-tight cover film, such that a wound space is formed between cover film and wound base. The film adheres to the intact skin surrounding the patient's wound and closes the wound space around the edges of the plastic cap in a gas tight manner. 3. Connecting the vacuum source via the adapter or directly to the open end of exposed tubing stemming from the plastic cap. 4. Turning on, pumping, or otherwise activating the vacuum source. Initiating the negative pressure source generates a negative pressure in the wound space, i.e. in the space formed between the wound base and the plastic cap/double backed adhesive/hydrocolloid sealed top. 5. Turning off or otherwise inactivating the vacuum source. 6. Unlocking or otherwise removing the reusable vacuum pump and affiliated tubing section from the rest of the device. 7. Removing and replacing the disposable hydrocolloid/cap/adhesive/tubing/ports section. 8. Reconnecting the two sections to each other, and reengaging the vacuum.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath"

other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A medical device support apparatus having a three-dimensional shape, the apparatus comprising: a body portion comprising a sheet of material, the sheet of material having an elastic modulus of greater than 0.4 GPa, wherein the sheet of material is configured to be deformed from a flat plane to form: a base region extending in the flat plane, the base region having a first thickness; and a cavity region having one or more walls each having a thickness that is less than the first thickness, the cavity region at least partially surrounded by the base region, wherein the one or more walls of the cavity region extends out of the flat plane at an angle that is greater than 90° relative to an adjacent base region; and a plurality of ridges or a lattice pattern stamped into the sheet of material to enhance the stiffness of the apparatus wherein the body portion, base region, cavity region, and plurality of ridges or lattice pattern are part of a single monolithic portion of the sheet of material.

2. The apparatus of claim 1, further comprising an adhesive substrate portion coupled to at least a portion of the base region, wherein the adhesive substrate portion comprises a liner on a face opposite from the base region.

3. The apparatus of claim 1, wherein a volume of material in any section of a continuous portion of the base region bounded by an arbitrary shape projected on a plane that is parallel to the flat plane is approximately equal to or less than the volume of material in any section of a continuous portion of the cavity region bounded by the arbitrary shape in the plane.

4. The apparatus of claim 1, further comprising a cut-out section on a wall of the cavity region, wherein the wall is angled greater than 90° relative to the adjacent base region.

5. The apparatus of claim 1, wherein a ratio of a maximum length of the cavity region in the flat plane to a maximum depth of the cavity region perpendicular to the flat plane is greater than 2:1.

6. The apparatus of claim 1, wherein the angle of the one or more walls of the cavity region relative to the flat plane is greater than 90° and less than 180° relative to a portion of the base region adjacent to each of the one or more walls.

7. The apparatus of claim 1, wherein the base region forms a lip of greater than 0.5 mm around the cavity region.

8. The apparatus of claim 1, wherein the cavity region comprises the lattice pattern extending in parallel to the flat plane to enhance stiffness.

9. The apparatus of claim 1, wherein the cavity region comprises one or more surfaces having one or more edges, further wherein all of the surfaces of the cavity region have rounded edges.

10. The apparatus of claim 1, wherein the cavity region extends up from the base region by between about 1 mm and about 50 mm.

11. The apparatus of claim 1, wherein the sheet of material comprises a polycarbonate, a polyethylene, or polyethylene terephthalate.

12. The apparatus of claim 1, wherein the cavity region comprises a hub surrounded by the base region.

13. The apparatus of claim 1, further comprising an opening cut into a top of the cavity region.

14. The apparatus of claim 1, wherein the cavity region comprises the plurality of ridges extending at least partially up the one or more walls from the base region.

15. The apparatus of claim 14, wherein the plurality of ridges are arranged symmetrically around the cavity region.

16. A medical device support apparatus having a three-dimensional shape, the apparatus comprising: a body portion comprising a sheet of material, the sheet of material having an elastic modulus of greater than 0.4 GPa, wherein the sheet of material is configured to be deformed from a flat plane to form: a base region extending in the flat plane, the base region having a first thickness; and a cavity region encircled by the base region, the cavity region having one or more walls each having a thickness that is less than the first thickness, wherein the one or more walls of the cavity region extends out of the flat plane at an angle that is greater than 90° relative to an adjacent base region; and a plurality of ridges formed in the one or more walls and extending at least partially up the one or more walls from the base region to enhance the stiffness of the device, wherein the body portion, base region, cavity region, and plurality of ridges are part of a single monolithic portion of the sheet of material.

* * * * *